(12) United States Patent
Chen et al.

(10) Patent No.: US 7,314,887 B2
(45) Date of Patent: Jan. 1, 2008

(54) THROMBOPOIETIN ACTIVITY MODULATING COMPOUNDS AND METHODS

(75) Inventors: Jyun-Hung Chen, San Diego, CA (US); E. Adam Kallel, Escondido, CA (US); Thomas Lau, San Diego, CA (US); Matthew H. McNeill, San Clemente, CA (US); Todd A. Miller, San Marcos, CA (US); Bao N. Nguyen, San Diego, CA (US); Richard J. Penuliar, San Diego, CA (US); Dean P. Phillips, San Marcos, CA (US); Daniel A. Ruppar, San Antonio, TX (US); Lin Zhi, San Diego, CA (US); Jackline E. Dalgard, Del Mar, CA (US)

(73) Assignee: Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 11/256,572

(22) Filed: Oct. 21, 2005

(65) Prior Publication Data

US 2006/0116417 A1    Jun. 1, 2006

Related U.S. Application Data

(60) Provisional application No. 60/675,001, filed on Apr. 25, 2005, provisional application No. 60/621,879, filed on Oct. 25, 2004.

(51) Int. Cl.
*A61K 31/404* (2006.01)
*C07D 209/40* (2006.01)
(52) U.S. Cl. ..................... 514/418; 548/483
(58) Field of Classification Search ............ 514/418; 548/483
See application file for complete search history.

(56) References Cited

U.S. PATENT DOCUMENTS 1,792,355 A    2/1931    Boeniger (Continued)

FOREIGN PATENT DOCUMENTS

BE    653800    3/1965

(Continued)

OTHER PUBLICATIONS

Bains et al. "Silicon chemistry as a novel source of chemical diversity in drug design." *Current Opinion in Drug Discovery and Development*; 6(4):526-543 (2003).

(Continued)

*Primary Examiner*—Rebecca Anderson
*Assistant Examiner*—Jason M Nolan
(74) *Attorney, Agent, or Firm*—Knobbe, Martens, Olson & Bear LLP

(57) ABSTRACT

Disclosed herein are compounds of Formula (I), (II), and (III)

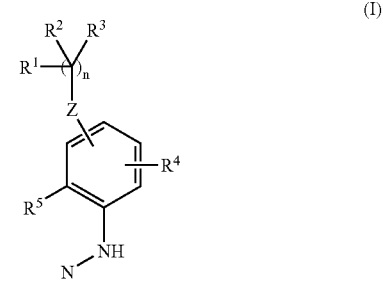

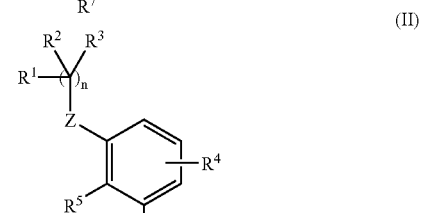

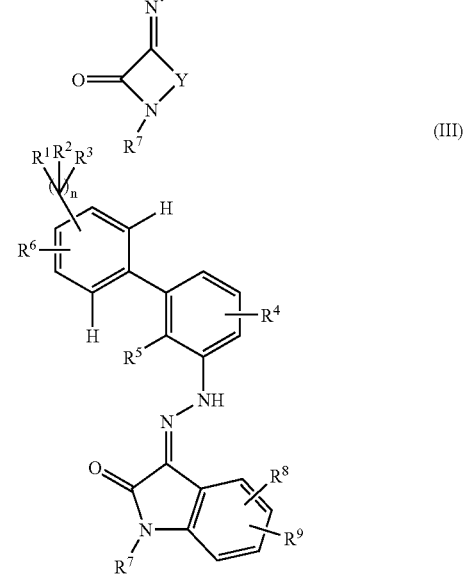

pharmaceutical compositions comprising the same, methods of modulating the activity a thrombopoietin receptor using the same, methods of identifying compounds as thrombopoietin receptor modulators, and methods of treating disease by administering a compound of the invention to a patient in need thereof.

37 Claims, No Drawings

U.S. PATENT DOCUMENTS

| | | |
|---|---|---|
| 3,148,192 A | 9/1964 | Velluz |
| 3,150,151 A | 9/1964 | Urbschaft et al. |
| 3,208,991 A | 9/1965 | Blout et al. |
| 3,718,678 A | 2/1973 | Farrand et al. |
| 3,754,857 A | 8/1973 | McKay |
| 3,966,900 A | 6/1976 | Hennart et al. |
| 4,322,533 A | 3/1982 | Lesher et al. |
| 4,451,398 A | 5/1984 | Patsch et al. |
| 4,720,304 A | 1/1988 | Ruff et al. |
| 5,001,229 A | 3/1991 | Franke et al. |
| 5,051,417 A | 9/1991 | Nadler et al. |
| 5,155,015 A | 10/1992 | Jimbo |
| 5,164,404 A | 11/1992 | Dahl et al. |
| 5,298,658 A | 3/1994 | Fabricius |
| 5,482,546 A | 1/1996 | Eida |
| 5,766,581 A | 6/1998 | Bartley et al. |
| 6,075,044 A | 6/2000 | Wang et al. |
| 6,448,238 B1 | 9/2002 | Shoichet et al. |
| 6,552,008 B1 | 4/2003 | Duffy et al. |
| 6,642,265 B1 | 11/2003 | Leungo et al. |
| 6,649,631 B1 | 11/2003 | Orme et al. |
| 6,670,387 B1 | 12/2003 | Luengo et al. |
| 6,720,345 B1 | 4/2004 | Luengo et al. |
| 6,875,786 B2 | 4/2005 | Duffy et al. |
| 6,964,701 B2 | 11/2005 | Foster et al. |
| 6,964,977 B2 | 11/2005 | Harris et al. |
| 7,026,334 B1 | 4/2006 | Takemoto et al. |
| 7,071,217 B2 | 7/2006 | Dickerson et al. |
| 7,105,529 B2 | 9/2006 | Davis et al. |
| 7,129,253 B2 | 10/2006 | Glennon et al. |
| 7,135,550 B2 | 11/2006 | Come |
| 7,160,870 B2 | 1/2007 | Duffy et al. |
| 2003/0229453 A1 | 12/2003 | Antonysamy et al. |
| 2004/0019190 A1 | 1/2004 | Erickson-Miller et al. |
| 2004/0024040 A1 | 2/2004 | Green et al. |
| 2004/0053299 A1 | 3/2004 | Delorme et al. |
| 2004/0058990 A1 | 3/2004 | Duffy et al. |
| 2004/0082626 A1 | 4/2004 | Takemoto et al. |
| 2004/0220146 A1 | 11/2004 | Freeman et al. |
| 2004/0253178 A1 | 12/2004 | Atwell et al. |
| 2005/0049267 A1 | 3/2005 | Suto et al. |
| 2005/0153977 A1 | 7/2005 | Sugasawa et al. |
| 2005/0234020 A1 | 10/2005 | Heerding |
| 2006/0069140 A1 | 3/2006 | Miyaji et al. |
| 2006/0084682 A1 | 4/2006 | Heerding et al. |
| 2006/0094694 A1 | 5/2006 | Owada et al. |
| 2006/0116417 A1 | 6/2006 | Chen et al. |
| 2006/0178518 A1 | 8/2006 | Moore |
| 2007/0105824 A1 | 5/2007 | Erickson-Miller et al. |

FOREIGN PATENT DOCUMENTS

| | | |
|---|---|---|
| DE | 193633 | 2/1907 |
| DE | 450819 | 10/1927 |
| DE | 4335623 | 4/1995 |
| EP | 0141067 | 8/1984 |
| EP | 0335237 | 3/1989 |
| GB | 1080864 | 8/1967 |
| GB | 2 168 347 A | 6/1986 |
| JP | 2-287457 | 11/1990 |
| JP | 2000-206645 | 7/2000 |
| JP | 2001-152055 | 5/2001 |
| JP | 2002-020641 | 1/2002 |
| JP | 2002-129072 | 5/2002 |
| JP | 2002-129073 | 5/2002 |
| JP | 2003-128946 | 5/2003 |
| JP | 2003-313450 | 11/2003 |
| JP | 2003-335972 | 11/2003 |
| JP | 2004-143118 | 5/2004 |
| WO | WO 01/21180 A1 | 3/2001 |
| WO | WO 01/89457 A2 | 11/2001 |
| WO | WO 03/037905 A1 | 5/2003 |
| WO | WO 03/082265 A2 | 9/2003 |
| WO | WO 03/103686 A1 | 12/2003 |
| WO | WO 2005/097119 A2 | 10/2005 |
| WO | WO 2005/107466 A1 | 11/2005 |
| WO | WO 2005/118551 | 12/2005 |
| WO | WO 2006/004545 | 1/2006 |
| WO | WO 2006/052936 A2 | 5/2006 |
| WO | WO 2006/076442 | 7/2006 |
| WO | PCT/US2007/00654 | 1/2007 |
| WO | WO 2007/062078 | 5/2007 |

OTHER PUBLICATIONS

Bartley et al. "Identification and Cloning of a Megakaryocyte Growth and Development Factor That Is a Ligand for the Cytokine Receptor Mpl." *Cell*; 77:1117-11124 (1994).

Basser et al. "Randomized, Blinded, Placebo-Controlled Phase I Trial of Pegylated Recombinant Human Megakaryocyte Growth and Development Factor With Filgrastim After Dose-Intensive Chemotherapy in Patients With Advanced Cancer." *Blood*; 89(9):3118-3128 (1997).

Cwirla et al. "Peptide Agonist of the Thrombopoietin Receptor as Potent as the Natural Cytokine". *Science*; 276:1696-1699 (1997).

Database Beilstein. Beilstein Institute for Organic Chemistry, Frankfurt-Main, DE; XP-002364395. Database accession No. BRN: 1499659; BRN: 1554046; BRN: 1554047.

Database Beilstein. Beilstein Institute for Organic Chemistry, Frankfurt-Main, DE; XP-002364396. Database accession No. BRN: 1513709.

Database Caplus Chemical Abstracts Service, Columbus, Ohio, US; XP-002364397 retrieved from STN accession No. 1978: 443178 Database accession No. 89: 43178.

de Sauvage et al. "Stimulation of megakaryocytopoiesis and thrombopoiesis by the c-Mpl ligand". *Nature*; 369:533-538 (1994).

Fanucchi et al. "Effects of Polyethylene Glycol-Conjugated Recombinant Human Megakaryocyte Growth and Development Factor on Platelet Counts After Chemotherapy for Lung Cancer." *New England J. Med.*; 336(6):404-409 (1997).

Kuter, David J. "Thrombopoietin: Biology and Clinical Applications." *The Oncologist*; 1:98-106 (1996).

Kuter et al. "The purification of megapoietin: A physiological regulator of Megakaryocyte growth and platelet production." *Proc. Natl. Acad. Sci.*; 91:11104-11108 (1994).

Lamb et al. "STAT protein complexes activated by interferon-γ and gp130 signaling molecules differ in their sequence preferences and transcriptional induction properties." *Nucleic Acids Research*; 23(16): 3283-3289 (1995).

Lok et al. "Cloning and expression of murine Thrombopoietin cDNA and stimulation of platelet production in vivo." *Nature*; 369: 565-568 (1994).

Metcalf, Donald. "Thrombopoietin—at last." *Nature*; 369:519-520 (1994).

Seidel et al. "Spacing of palindromic half sites as a determinant of selective STAT (signal transducers and activators of transcription) DNA binding and transcriptional activity." *Proc. Nat. Acad. Sci. USA*; 92: 3041-3045 (1995).

Tacke et al. "Sila-substitution—a useful strategy for drug design?" *New Series*; 10(4):191-197 (1986).

Vigon et al. "Molecular cloning and characterization of MPL, the human homolog of the v-mpl oncogene: Identfication of a member of the hematopoietic growth factor receptor superfamily." *Natl. Acad. Sci. USA*; 89:5640-5644 (1992).

Wendling et al. "c-MPL ligand as a humoral regulator of megakaryocytopoiesis." *Nature*; 369:571-574 (1994).

Wendling et al. "Mpl ligand or Thrombopoietin: Biological activities." *Biotherapy*; 10:269-77 (1998).

Abdel-Latif et al., "Reaction of Diazocompounds and Hydrazines on Indolin-2-one Derivatives", *Indian J. Chem.*, 1985, 24B(7), 775-777.

Abdel-Rahman et al., "Synthesis of some 1,2,4-Triazino [4,3-a] indole derivatives", *J. Indian Chem. Soc.*, 1991, 68(11), 621-624.

Abdel-Rahman et al., "Synthesis of Some New 2,3/2,4-Disubstituted-1,2,4-Trianzino [5,6-b] Indoles", *Asian J. Chem.*, 1992, 4(2), 364-371.

Alam et al., "Analytical studies of biologically active compounds-I: Quantitative Determination of Metabolies of 3-Substituted Isatin Derivatives by TLC", *Proc. Pakistan Acad. Sci.*, 1992, 29(2), 113-120.

Alam et al., "Biopharmaceutical Studies of 3-Substituted Isatin Derivatives", *Indian J. Exp. Biol.*, 1990, 28(10), 940-942.

Alam et al., "Electronic Spectra of Isatin Derivatives", *Proc. Pakistan Acad. Sci.*, 1987, 24(4), 337-348.

Ali, et al., "Analytical Studies on Biologically Active Compounds. Part II. Separation and Quantitation of Mixtures of Isatin Derivatives for Application to Metabolism Studies", *Pak. J. Sci. Ind. Res.*, 1995, 38(8), 330-332.

Aly, et al., "Synthesis and reactions of 1,3-dihydro-3-(3',5'-dioxo-2'H-1'-phenylpyrazolidene)-2h-indol-2-one", *Bull. Fac. Sci., Assuit Univ.*, 1996, 25(1-B), 25-33.

Aly, et al., "Reaction of 1-Acetyl-3-dicyanomethylene-1,3-dihydro-2H-indol-2-one with Some Nucleophilic Reagents: Synthesis of Some Indole and Quinoline Derivatives", *Heterocyclic Comm.*, 2000, 6(3), 249-252.

Amin, "Spectrophotometric Method for the Determination of Titanium in Soil, Geo-Chemical, Silicates Rock and Paint Samples", *Quim. Anal.*, 2002, 20, 217-222.

Amin, et al., "Simultaneous Spectrophotometric Determination of Thorium and Rare Earth Metals with Pyrimidine Azo Dyes and Cetylpyridinium Chloride", *Talanta*, 2001, 54(4), 611-620.

Atta et al., "β-Lactam Formation on Thin-Layer Chromatoplates", *Indian J. Chem*, 1979, 18B(5), 475-476.

Back et al., "Zusammenhange zwischen Konstitution von neutralziehenden Metallkomplexfarbstoffen, Verteilungsgleichgewichten zwischen flussigen Phasen und Farbegleichgewichten auf Polyamiden", *Helv. Chim. Acta*, 1959, 166, 1539-1553.

Ballantine et al., "Rearrangement and Cyclization in the Mass Spectra of a Series of Isatin Carbonyl Derivatives of Medicinal Interest. 2-Oxo-3-Indolinylidene Anils (N-Arylketimines), 2-Oxo-3-Indolinylidene Phenylhydrazones, 2-Oxo-3, 3-Bis (O-Diaminoaryl) Indolyl Derivatives and Their 2, 3-Quinoxaline Heterocyclic Analogues", *Organic Mass Spectrometry*, 1971, 5(8), 1003-1014.

Bauer, "Uber Oxalsaure-imidchloride", *Berichte der Deutschen Chemischen Gesellschaft*, 1907, 2650-2663.

Bauer, "Oxalic Acid Quinochlorides (II)", *Berichte der Deutschen Chemischen Gesellschaft*, 1909, 42, 2111-2118.

Beaton, et al., "Preparation and Hydrogen Bonding Studies of Phenylhydrazone Derivatives Of Alloxan: Crystal And Molecular Structure of Pyrimidine-2(1H),4(3H),5,6-tetraone 5-(2-nitrophenyl) hydrazone", *J. Chem. Soc., Perkin Trans. II:*, 1987, (4), 469-472.

Bogert et al., "Azo Derivatives of the Pyrimidines", *Proc. Natl. Acad. Sci.*, 1932, 18, 215-222.

Bramson, et al., Oxindole-Based Inhibitors of Cyclin-Dependent Kinase 2 (CDK2): Design, Synthesis, Enzymatic Activities, and X-ray Crystallographic Analysis, *J. Med. Chem.*, 2001, 44(25), 4339-4358.

Braun et al., "Isatin-4-Carbonsäure", *Berichte der Deutschen Chemischen Gesellschaft*, 1923, 2343-2347.

Buu-Hoi et al, "Carcinogenic Nitrogen Compounds. XIII. Benzacridines, benzacarbazoles, and Related Compounds Bearing Ethyl and Propyl Groups", *J. Chem. Soc.*, 1952, 4867-4869.

Buu-Hoi; et al,, "On New Isatines", *Bull. Soc. Chim. Fr.*, 1946, 586-587.

Cedere et al., "Reversible Inhibitors of Monomine Oxidase in the Indolinone Series", *Khimiki-Farmatsevticheskii Zhumal*, 1984, 18(5), 555-558.

Chan et al., "Barbituarate analogs of salazosulfanilamides", Khimiko-Farmatsevticheskii Zhurnal, 1973, 7(4), 26-30.

Chuaqui, et al., "Interaction Profiles of Protein Kinase-Inhibitor Complexes and Their Application to Virtual Screening", *J. Med. Chem.*, 2005, 48(1), 121-133.

Corsico Coda et al., "Copper (II) in Organic Synthesis. IV[1] Reaction of the Copper (II) Acetate Complex of Isatin-3-arylhydrazones with Dimethyl Acetylenedicarboxylate", *Tetrahedron*, 1985, 41(12), 2545-2555.

Coda et al., "The Copper (II) Acetate Complex of Isatin 3-Phenylhydrazones: An Unusual Role of Arylhydrazones as Ligands", *Gazz. Chim. Ital.*, 1985, 115(10), 549-553.

Congreve, et al., "Detection of Ligands From a Dynamic Combinatorial Library by X-ray Crystallography", *Angew. Chem., Int. Ed. Engl.*, 2003, 42(37), 4479-4482.

Costopanagiotis et al., "Application of Mass Spectrometry to the Analyses of Pharmaceuticals. Mass Spectra of Barbituric Acid Derivatives", *Mh. Chem.*, 1965, 96(6), 1800-1808.

Crippa et al., "Imesatins. II. New Developments and Clarification of Mayer's Synthesis", *Gazz. Chim. Ital.*, 1951, 81, 195-204.

Da Settimo et al., "Reactions of 2, 3-Dibromoindole Derivatives with Bromine and Other Oxidizing Agents", *J. Org. Chem.*, 1974, 39(14), 1995-1998.

Delimoge et al., "Simple Synthetic Routes to 5-(3,6-dihydro-2-oxo-2H-1,3,4-thiadiazin-5-yl)-1Hindole-2,3-diones and their derivatives", *J. Heterocycl. Chem.*, 1991, 28(6), 1525-1532.

Dessouki et al., Structural Investigation of Isatin-β -Arylhydrazone Derivatives by UV, IR, $^1$H NMR Spectra and PPP CI Calculations, *Spectrochimica Acta*, 1988, 44A(8), 849-851.

Di Carlo et al., "Synthesis and Properties of 1-Cyanoethylisatin", *J. Am. Chem. Soc.* 1945, 67, 199-201.

Dobrynin et al., "Relationship Between the Structure and the Cytotoxic Action of 3-Deriviatives of 1-Glycosylisatins", *Pharm. Chem. J.*, 1984, 18(12), 807-810.

Duffy et al. "Hydrazinonaphthalene and Azonaphthalene Thrombopoietin Mimics are Nonpeptidyl Promoters of Megakaryocytopoiesis." *J. Med. Chem.*, 2001, 44, 3730-3745.

Duffy et al. "Identification of a Pharmacophore for Thrombopoietic Activity of Small Nonpeptidyl Molecules. 1. Discovery and Optimization of Salicylaldehyde Thiosemicarbazone Thrombopoietin Mimics." *J. Med. Chem*, 2002, 45, 3573-3575.

Duffy et al. "Identification of a Pharmacophore for Thrombopoietic Activity of Small Nonpeptidyl Molecules.

2. Rational Design of Naphtha[1,2-d]imidazole Thrombopoietin Mimics." *J. Med. Chem*, 2002, 45, 3576-3578.

Dureja, et al., "Topochemical Models for Prediction of Cyclin-Dependent Kinase 2 Inhibitory Activity of Indole-2-ones", *J. Mol. Model.*, 2005, 11(6), 525-531.

Efremenko et al., "Azo-Coupling of 2,6-Di-tert-butyl-p-benzoquinone diazide with β-Dicarbonyl Compounds", *Bull. Acad. Sci. USSR Div. Chem. Sci.* (Engl. Transl.), 1971, 20, 2711-2712.

El Ashry et al., "Ring Expansion of Indoline-2,3-dione-3-phenylhydrazone to 3,1-Benzoxazine-2, 4(1H)-dione-4-phenylhydrazone", *Indian J. Chem*, 1978, 16B(11), 1036-1038.

Elguero et al, "Recherches dans la Serie des Azoles. XII.— Structure des Phenylazo-4 Pyrazolones-5", *Bull. Soc. Chim. Fr.*, 1966, 2990-2995.

Elguero et al., "The Tautomerism of Heterocycles", *Adv. Heterocycl. Chem. Spl. 1*, 321-339, Katritzky and Boulton eds., Academic Press, 1976, New York.

El-Shafei, et al., "Semi-Empirical Molecular Orbital Methods in the Design of Organic Colorants", *AATCC Review*, 2001, 23-26.

Erickson-Miller et al. "Discovery and characterization of a selective, nonpeptidyl thrombopoietin receptor agonist." *Experimental Hematology*, 2005, 33, 85-93.

Fadda, et al., "Synthesis of azodisperse dyes with pyridine ring for dyeing polyester fibres: Part II", *Indian Journal of Textile Research*, 1989, 14, 177-183.

Feher, et al., BHB: A Simple Knowledge-Based Scoring Function to Improve the Efficiency of Database Screening *J. Chem. Inf. Comput. Sci.*, 2003, 43(4), 1316-1327.

Ferrara, et al., "New Scoring Functions for Virtual Screening from Molecular Dynamics Simulations with a Quantum-Refined Force-Field (QRFF-MD). Application to Cyclin-Dependent Kinase 2", *J. Chem. Inf. Model.*, 2006, 46(1), 254-263.

Foye, et al., "The Preparation of Azopyrimidines and Their Metallized Derivatives", *J. Am. Pharm. Assoc.*, 1957, 46, 224-227.

Ganoub, "A Facile Approach to N-Heterocycles. The Reactions of Ylide Phosphoranes with Hydrazones", *Heterocycl. Commun.*, 2001, 7(2), 143-148.

Garg, et al., Potential Antidiabetics VIII: 4-Aryhydrazono-N'-guanylnitrate-3-methyl-2-pyrazolin-5-ones, 4-Arylazo-N'-guanylnitrate-3,5-dimethylpyrazoles, and 4-arylazo-N'-guanylnitrate-3,5-diphenylpyrazoles, *Journal of Pharmaceutical Sciences*, 1971, 60(2), 323-325.

Goldstein et al., "Specific Spot Test for Magnesium", *Mikrochim. Acta*, 1962, 50(1-2), 352-356.

Grandmougin et al., "Indigo. V. Halogenated Indigo and Derivatives", *Berrichte der Deutschen Chemischen Gesellschaft*, 1914, 47, 2365-2373.

Halberkann, "Abkömmlinge der Chininsäure", *Chem. Ber.*, 1921, 54(11), 3090-3107.

Haslinger, "Action of Ethylamine on Isatine. (II)", *Berichte der Deutschen Chemischen Gesellschaft*, 1908, 41, 1444-1453.

Hassan et al., Studies on Spiro Azetidinones and Spiro Thiazolidinones, III. Synthesis of Some New Spiro Azetidinones, Spiro Thiazolidinones, Bis-Azetidinones) and bis-thiazolidinones, *Z. Naturforsch*, 1979, 34b(4), 621-623.

Heller, "New Isomerisms in the Isatin Series. IV", *Chem. Ber*, 1920, 53B, 1545-1551.

Heller, "New Reduction Stage of the Nitro Group. III", *Chem. Ber*, 1910, 43, 2892-2899.

Heller, "On the Action of Dichloracetic Acid on Aniline and its Homologues. II", *Justus Liebigs Ann. Chem.*, 1908, 358, 349-373.

Heller, "Über die Einwirkung von Dichloressigsäure auf Anilin und Homologe", *Justus Liebigs Ann. Chem.*, 1910, 375, 261-288.

Helmy, "Spectrophotometric and Polarographic Behavior of 5-Phenyl azo-2,4,6-(1H,3H,5H)pyrimidinetrione in Aqueous Ethanolic Media", *Annali di Chimica*, 1996, 86(7-8), 369-380.

Hemmerich et al., "Synthesen in der Lumiflavinreihe", *Helv. Chim. Acta*, 1956, 39, 1242-1248.

Hihara, et al., "Photo-Oxidation of Pyrazolinylazo Dyes and Analysis of Reactivity as Azo and Hydrazone Tautomers Using Semiempirical Molecular Orbital PM5 Method", *Dyes and Pigments*, 2006, 69, 151-176.

Inagaki et al. "Induction of Megakaryocytopoiesis and Thrombocytopoiesis by JTZ-132, a Novel Small Molecule with Thrombopoietin Mimetic Activities." *Blood*, 2004, 104, 58-64.

Jones, et al., "The Structures of Some 5-Pyrazolones and Derived 4-Arylazo-5-Pyrazolones", *Tetrahedron*, 1963, 19, 1497-1507.

Joshi et al., "Synthesis, $^{19}$F NMR Spectral Studies and Antibacterial Evaluation of Some New Fluorine Containing Indole Derivatives", *J. Fluorine Chem.*, 1990, 48(2), 169-188.

Kalb, et al., "Untersuchungen in der Indigo-Gruppe, V.: 5.7.5'.7'-tetrajod-indigo, 5.6.7.5'.6'.7'-Hexajod-indigo und verwandte Verbindungen", *Chem. Ber.*, 1924, 57, 2105-2117.

Kamada, et al., "Absorption Spectra of Phenolazopyrazolones in Ionization State", *Nippon Kagaku Zasshi*, 1967, 88(8), 826-830.

Kamel et al., "Monoazo Metal Complex Forming Dyes. V. Dyes Derived from Isatin", *J. Chem. U. A. R.*, 1966, 9(2), 139-144.

Katritzky et al, "2-Chloro-3H-indol-3-one and its Reactions with Nucleophiles", *J.Heterocyclic Chem.*, 1989, 26(3), 821-828.

Kaul, et al., "NMR Spectra of Azophenols and Quinone Hydrazones", *Tetrahedron Lett.*, 1966, 32, 3897-3903.

Kaupp, et al., "Waste-Free Chemistry of Diazonium Salts and Benign Separation of Coupling Products in Solid Salt Reactions", *Chem. Eur. J.*, 2002, 8(6), 1395-1406.

Kitaev et al., "Study of the Structure and Reactivity of Nitrogen Containing Derivatives of Carbonyl Compounds Communication 30. Polarographic Investigation of Products of Combination of Diazonium Salts with 1,2-Diphenyl-3,5-dioxopyrazolidine, Its 4-Lydenes, and Barbituric Acid", *Russ. Chem. Bull.*, 1968, 17(5), 940-944.

Kondrashova et al., "Condensation of 4-(4-Hydroxycarbonylquinolin-2-yl)phenyldiazonium Chloride with $R^1CH_2R^2$ Compounds Containing the Activated-$CH_2$-Group", *Doklady Chemistry*, 2004, 398(1), 187-190.

Konstantinovic, et al., "UV/VIS spectrophotometric investigation of Schiff base in acid medium", *Physical Chemistry 2002, Proceedings of the International Conference on Fundamental and Applied Aspects of Physical Chemistry*, 6th, Belgrade, Yugoslavia, Sep. 26-28, 2002, 2 690-692.

Kroemer, et al., "Assessment of Docking Poses: Interactions-Based Accuracy Classification (IBAC) versus Crystal Structure Deviations", *J. Chem. Inf. Comput. Sci.*, 2004, 44(3), 871-881.

Lecher, et al., "The reactions of Arylhydrazines with Diketene and the Preparation of 1-Aryl-5-methyl-3-pyrazolones", *J. Am. Chem. Soc.*, 1944, 66 1959-1963.

Li, et al., "Structure-activity Relationship Study of Oxindole-based Inhibitors of Cyclin-Dependent Kinases Based on Least-Squares Support Vector Machines", *Analytica Chimica Acta*, 2007, 581(2), 333-342.

Maginnity et al., "Derivatives of o-, m- and p-Aminobenzotrifluoride", *J. Amer. Chem. Soc.*, , 1951, 73(8), 3579-3580.

Marcou, et al., "Optimizing Fragment and Scaffold Docking by Use of Molecular Interaction Fingerprints", *J. Chem. Inf. Model.*, 2007, 47(1), 195-207.

Martinet, "Syntheses Dans la Serie L'Indol, Homologues du Dioxindol et de L'Isatine", *Ann. Chim.* (Paris), 1919, (9)11, 85-111.

Martinet, et al., "Action de L'Oxime du Chloral sur les Amines Aromatiques;.Synthese D'Isatines", *Hebd. Seances Acad. Sci.*, 1921, 172, 1234-1236.

Massoud, "Synthetic Studies of Some New Derivatives Bearing Isatin Moiety", *Alex. J. Pharm. Sci.*, 2000, 14(1), 51-57.

Maysinger, et al., "Effects of Isatin N-Mannich Bases on HeLa cells", *Arzneim.-Forsch.*, 1980, 30(6), 932-935.

Meyer, "Dibromophenylisoxazolone et Derives", *C. R. Hebd. Seances Acad. Sci.*, 1912, 1511-1514.

Meyer, "Les Matieres Colorants Azoiques de la Phenylisoxazolone", *C. R. Hebd. Seances Acad. Sci.*, 1913, 1992-1995.

Meyer, "Sur les Matieres Colorants Azoiques de la Phenylisoxazolone", *Bull. Soc. Chim. Fr.*, 1913, 1030-1039.

Meyer, "Preparation et Proprietes de la Dibromo-4,4-phenylisoxazolone", *Ann. Chim.* (Paris), , 1914, 314-323.

Mossini, "Su Alcuni Nuovi Azoderivati Della p-Aminobenzosolfonamide", *Ann, Chimica farm.*, 1939 (Dez.) 47-53.

Mostafa, "Flame-atomic Absorption Spectrometric Determination of Chromium", *Analusis*, 1991, 19(10), 363-366.

Müller et al., "The Effects of Compounds Structurally Related to Isatin on the Monoamine Oxidase Activity of Mice Liver Homogenates", *Acta Biologica et Medica Germanica*, 1965, 14(2), 158-166.

Mustroph, "Blaue Azofarbstoffe auf der Basis von 3-Cyano-6-hydroxy-2-pyridonen", *Z. Chem.*, 1989, 29(11), 422-423.

Nesynov et al., "Arylation of monothiobarbituric acid by aryldiazonium salts", *Chem. Heterocycl. Compd.*, 1971, 7(9), 1271-1275.

Nishino, et al., "Azoic Diazo Components Containing Pyrazolone Ring", *Kogyo Kagaku Zasshi*, 1959, 62(4), 552-554.

Nishino, et al., "Azoic Diazo Components Containing Pyrazolone Ring", *Bulletin of the University of Osaka Prefecture, Series A*, 1959, 7, 79-84.

Nguyen, et al., "Synthesis and biological effects of some isatin derivatives", *Tap Chi Duoc Hoc*, 1998, 12, 8-10.

Oblak, et al., "In silico Fragment-Based Discovery of Indolin-2-one Analogues as Potent DNA Gyrase Inhibitors," *Bioorg. Med. Chem. Lett.*, 2005, 15(23), 5207-10.

Palluotto, et al., "Synthesis and Antibacterial Activity of Pyridazino[4,3-b] indole-4-carboxylic acids Carrying Different Substituents at N-2", *Il Farmaco*, 2002, 57(1), 63-69.

Parkes, et al., "Reactivity of the Methylene Group in Derivatives of Phenylacetic Acid", *J. Chem. Soc.*, 1938, 1841-1845.

Piscopo et al., "Studies On Heterocyclic Compounds: Indole-2,3-dione Derivatives. VII. Variously Substituted Hydrazones with Antimicrobial Activity", *Societa Italiana Biologia Sperimentale*, 1987, 63(9), 827-832.

Popp, "Synthesis of potential antineoplastic agents. XX. Compounds related to the 3-o-nitrophenylhydrazone of isatin", *J. Med. Chem.*, 1969, 12(1), 182-184.

Popp, "Potential Anticonvulsants. IX. Some Isatin Hydrazones and Related Compounds", *J. Heterocyclic Chem.*, 1984, 21(6), 1641-1645.

Potapova et al., "Biological Activity and Mechanism of Action of 1-Glycosylisatin-3-Thiosemicarbazones", *Khimiki-Farmatsevticheskii Zhumal*, 1984, 18(7), 785-790.

Radwan et al., "Synthesis of Diarylsulfides and Diarylsulfones Containing Pyrazoline, Isoxazoline, Pyrimidine and Condensed Phridazine Moieties", *Phosphorus, Sulfur and Silicon*, 1991, 63(3-4), 363-372.

Ram et al., "Pesticidal Mannich Bases Derived from Isatinimines", *J. Heterocyclic Chem.*, 1986, 23(5), 1367-1369.

Ram, "Application of nickel chloride to tea plants and control of blister blight", *Current Science*, 1961, 30, 57-58.

Rastelli, et al., "Discovery of New Inhibitors of Aldose Reductase from Molecular Docking and Database Screening", *Bioorg. Med. Chem.*, 2002, 10(5), 1437-1450.

Ressy et al., "Sur Les Preparations des Homologues de L'Isatine: Preparation de la Methyl-7-bromo-5-isatine", *Bull. Soc. Chim. Fr.*, 1923, (4)33, 637-640.

Revill et al., "Antithrombocytopenic Thrombopoietin Receptor Agonist", *Drugs of the Future*, 2006, 31(9), 767-770.

Ried et al., "Reactions with diazocarbonyl compounds. XXIX. Reaction of o-quinone diazides with active methylene compounds", *Justus Liebigs Ann. Chem*, 1968, 716, 190-1977.

Rupe, et al., "Das Phenylhydroxylamin-Derivat der Isatin-7-Carbonsäure",*Helv. Chim. Acta*, 1927, 10, 926-937.

Sakamoto et al., "N-[(N-Nitrosoarylamino) Methyl] Succinimide as A New Agent Generating Aromatic Diazotate", *Chem. Pharm. Bul.*, 1977, 25(4), 731-739.

Schoutissen, "Preparation des Derives du m-Dihydrazinobenzene en Partant de la Combinaison Tetrazonium du m-Diaminobenzene", *Recl. Trav. Chim. Pays-Bas*, 1933, 52, 869-873.

Schunck; et al., "Zur Kenntniss der Rothen Isomeren des Indigotins und Über Einige Derivate des Isatins", *Chem. Ber.*, 1895, 28(1), 539-547.

Sharma, "Dichloro Bis (Isatin β-Phenylhydrazone) Mercury (II)", *Current Science*, 1973, 42(3), 92.

Snavely, et al., "A study of the Structure of Hydrazones of Indole-2,3-dione and 1-Methylindole-2,3-dione with Nuclear Magnetic Resonance Spectroscopy", *J. Org. Chem.*, 1981, 46(13), 2764-2766.

Sokolowska, et al., "Synthesis and evaluation of organic pigments. 3. Studies Based on Nonmutagenic Twisted Benzidines", *Dyes and Pigments*, 2001, 48, 15-27.

Somoza, et al., "Rational Design of Novel Antimicrobials: Blocking Purine Salvage in a Parasitic Protozoan" *Biochemistry*, 1998, 37(16), 5344-5348.

Sridhar, et al., "Synthesis and Antibacterial Screening of Hydrazones, Schiff and Mannich Bases of Isatin Derivatives", *Eur. J. Med. Chem.*, 2001, 36(7-8), 615-625.

Sridhar, et al., "Synthesis, Characterization and Pharmacological Screening of Some Isatinoid Compounds", *Indian J. Chem., Sec. B*, 2002, 41B(3), 668-672.

Sridhar, et al., Anticonvulsant Activity of Hydrazones, Schniff and Mannich Bases of Isatin Derivatives, *European Journal of Pharmaceutical Sciences*, 2002, 16(3), 129-132.

Sridhar, et al., "Synthesis and Pharmacological Activities of Schiff Bases and Hydrazones of Isatin Derivatives", Indian Drugs, 2001, 38(4), 174-180.

Stahl, et al., "A Robust Clustering Method for Chemical Structures", *J. Med. Chem.*, 2005, 48(13), 4358-4366.

Stamm, "Zur Reaktion von Reaktivfarbstoffen mit Cellulose II. Natur der Bindung", *Helv. Chim. Acta*, 1963, 46, 3008-3019.

Summers et al., "Structure of 3-Alkyl-4-arylazoisoxazol-5-ones and Related Compounds", *J. Chem. Soc.*, 1965, 3312-3318.

Sumpter et al., "Study of Certain Brominated Derivatives of Oxindole", *J. Am. Chem. Soc.*, 1945, 67, 1656-1658.

Taha et al., "Isatin 3-Phenylhydrazone Complexes of Some Transition Metals", *J. Chem. U. A. R.*, 1970, 13(2), 227-230.

Terent'ev et al., "Preparation of Bromo-, .Nitro-, and Aminoindoles and Indolines", *J. Gen. Chem. USSR*, 1959, 29(8), 2504-2512.

Thomas, et al., "Protein Structures in Virtual Screening: A Case Study with CDK2", *J. Med. Chem.*, 2006, 49(1), 92-104.

Tirouflet et al., "Synthesis and Physicochemical Properties of Substituted Phthalonimides", *Compd. Rend.*, 1958, 246, 3255-3257.

Toda, "Absorption Spectra of 1-2 Chromium(III) Complexes", *Nippon Kagaku Zasshi*, 1968, 89(1), 29-32.

Tominaga, et al., "General Model for Estimation of the Inhibition of Protein Kinases Using Monte Carlo Simulations", *J. Med. Chem.*, 2004, 47(10), 2534-2549.

Tran, et al., "5-Fluoroisatin and Its Derivatives", *Tap Chi Duoc Hoc*, 1999, 11, 4-5.

Urbschat, "Azo Compounds with High Activity Against Leaf Fungi", *Angew. Chem.*, 1960, 72(24), 981-985.

Vine, et al., "In Vitro Cytotoxicity Evaluation of Some Substituted Isatin Derivatives", *Bioorg. Med. Chem.*, 2007, 15(2), 931-938.

Voronowa et al., "Polarographic Study of Azo derivatives of Barbituric and Thiobarbituric Acids", *J. Gen. Chem. USSR*, 1959, 29(9), 3083-3089.

Vottero, et al., "Inhibitors of Human Indoleamine 2,3-Dioxygenase Identifed With a Target-Based Screen in Yeast", *Biotechnol. J.*, 2006, 1(3), 282-288.

Wu, et al., SDOCKER: A Method Utilizing Existing X-ray Structures to Improve Docking Accuracy, *J. Med. Chem.*, 2004, 47(12), 3142-3148.

Wu, et al., "Discovery of a Novel Family of CDK Inhibitors with the Program LIDAEUS: Structural Basis for Ligand-Induced Disordering of the Activation Loop", *Structure*, 2003, 11(4), 399-410.

Yasuda, et al., "The Structure of 2-Pyrazolin-5-one Dyes", *J. Org. Chem.*, 1966, 31(6), 1722-1725.

Yamamoto, et al., "$^{15}$N NMR Study of Azo-Hydrazone Tautomerism of Some Water-soluble Dyes", *Dyes and Pigments*, 1989, 11, 173-177.

Olszewski, et al., "Potential Photoaffinity Labels for Tubulin. Synthesis and Evaluation of Diazocyclohexadienone and Azide Analogs of Colchicine, Combrestatin, and 3,4,5-Trimethoxybiphenyl", *J. Org. Chem.*, 1994, 59(15), 4285-4296.

International Search Report and Written Opinion for PCT/US2005/018924 dated Nov. 4, 2006.

International Search Report and Written Opinion for PCT/US2005/038055 dated Aug. 2, 2006.

Research, Development and License Agreement, dated Dec. 29, 1994, between SmithKline Beecham Corporation and Ligand Pharmaceuticals (with certain confidential portions omitted).

Invitation to Pay Additional Fees received in Intl. Application No. PCT/US2007/006547, mailed Aug. 17, 2007.

THROMBOPOIETIN ACTIVITY MODULATING COMPOUNDS AND METHODS

RELATED APPLICATIONS

The present application claims priority to the U.S. Provisional Patent Application Ser. No. 60/621,879, filed on Oct. 25, 2004, by Zhi et al., and entitled "THROMBOPOIETIN ACTIVITY MODULATING COMPOUNDS AND METHODS," and the U.S. Provisional Patent Application Ser. No. 60/675,001, filed on Apr. 25, 2005, by Zhi et al., and entitled "THROMBOPOIETIN ACTIVITY MODULATING COMPOUNDS AND METHODS," both of which are incorporated by reference herein in their entirety, including any drawings.

FIELD OF THE INVENTION

This invention relates to compounds that modulate one or more thrombopoietin activity and/or bind to thrombopoietin receptors; and to methods for making and using such compounds.

BACKGROUND

Thrombopoietin (TPO), also referred to as c-Mpl ligand, mpl ligand, megapoietin, and megakaryocyte growth and development factor, is a glycoprotein that has been shown to be involved in production of platelets. See e.g., Wendling, F., et. al., Biotherapy 10(4):269-77 (1998); Kuter D. J. et al., The Oncologist, 1:98-106 (1996); and Metcalf, Nature 369: 519-520 (1994). TPO has been cloned and its amino acid sequence and the cDNA sequence encoding it have been described. See e.g., U.S. Pat. No. 5,766,581; Kuter, D. J. et al., Proc. Natl. Acad. Sci., 91:11104-11108 (1994); de Sauvage F. V., et al., Nature, 369: 533-538 (1994); Lok, S. et al., Nature 369:565-568 (1994); and Wending, F. et al., Nature, 369: 571-574 (1994).

In certain instances, TPO activity results from binding of TPO to the TPO receptor (also called MPL). The TPO receptor has been cloned and its amino acid sequence has been described. See e.g., Vigon et al., Proc. Natl. Acad. Sci., 89:5640-5644 (1992).

In certain instances, TPO modulators may be useful in treating a variety of hematopoietic conditions, including, but not limited to, thrombocytopenia. See e.g., Baser et al. Blood 89:3118-3128 (1997); Fanucchi et al. New Engl. J. Med. 336:404-409 (1997). For example, patients undergoing certain chemotherapies, including but not limited to chemotherapy and/or radiation therapy for the treatment of cancer, may have reduced platelet levels. In certain instances, treating such patients with a selective TPO modulator increases platelet levels. In certain instances, selective TPO modulators stimulate production of glial cells, which may result in repair of damaged nerve cells.

Certain TPO mimics have been described previously. See e.g., WO 03/103686A1; and WO 01/21180.

SUMMARY OF THE INVENTION

In certain embodiments, the present invention provides a compound of Formula I:

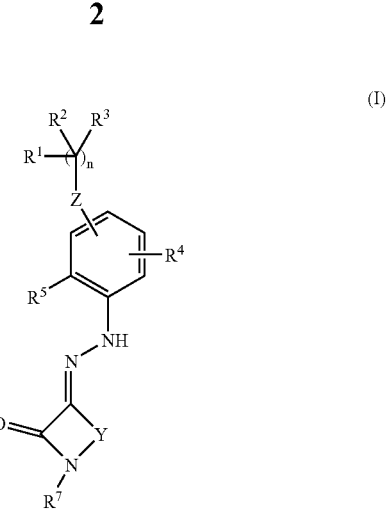

or a pharmaceutically acceptable salt, ester, amide, or prodrug thereof, wherein:

$R^1$ is selected from $CO_2R^{10}$, $CONR^{10}R^{11}$, $SO_3R^{10}$, and a carboxylic acid bioisostere;

$R^2$ and $R^3$ are each independently selected from null, hydrogen, $OR^{12}$, $NR^{12}R^{13}$, an optionally substituted $C_1$-$C_4$ aliphatic, an optionally substituted $C_1$-$C_4$ haloaliphatic, an optionally substituted $C_1$-$C_4$ heteroaliphatic, an optionally substituted ring, and $(CH_2)_m R^{14}$; or $R^2$ and $R^3$ taken together form an optionally substituted olefin; or $R^2$ and $R^3$ are linked to form an optionally substituted $C_3$-$C_8$ ring;

$R^4$ is selected from hydrogen, F, Cl, Br, $C_1$-$C_4$ aliphatic, $C_1$-$C_4$ haloaliphatic, $C_1$-$C_4$ heteroaliphatic, and a ring;

$R^5$ is selected from hydrogen, $OR^{10}$, $SR^{10}$, $NHR^{11}$, and $CO_2H$;

$R^6$ is selected from hydrogen, $OR^{12}$, $NR^{12}R^{13}$, F, Cl, Br, $C_1$-$C_4$ alkyl, $C_1$-$C_4$ haloalkyl, $C_1$-$C_4$ heteroalkyl, and a ring;

$R^7$ is selected from hydrogen, an optionally substituted $C_1$-$C_8$ aliphatic, an optionally substituted $C_1$-$C_8$ haloaliphatic, an optionally substituted $C_1$-$C_8$ heteroaliphatic, an optionally substituted $C_1$-$C_8$ heterohaloaliphatic, an optionally substituted ring, and $(CH_2)_m R^{14}$;

$R^{10}$ is selected from hydrogen, an optionally substituted $C_1$-$C_4$ aliphatic, $C_1$-$C_4$ haloaliphatic, $C_1$-$C_4$ heteroaliphatic, and a ring;

$R^{11}$ is selected from hydrogen, $SO_2R^{15}$, $C_1$-$C_4$ aliphatic, $C_1$-$C_4$ haloaliphatic, $C_1$-$C_4$ heteroaliphatic, and a ring;

$R^{12}$ and $R^{13}$ are each independently selected from hydrogen, an optionally substituted $C_1$-$C_4$ aliphatic, an optionally substituted $C_1$-$C_4$ haloaliphatic, an optionally substituted $C_1$-$C_4$ heteroaliphatic, an optionally substituted ring, and $(CH_2)_m R^{14}$; or one of $R^{12}$ and $R^{13}$ is an optionally substituted $C_2$-$C_6$ aliphatic or an optionally substituted ring and the other of $R^{12}$ and $R^{13}$ is null; or $R^{12}$ and $R^{13}$ are linked to form an optionally substituted $C_3$-$C_8$ ring;

$R^{14}$ is selected from an optionally substituted aryl and an optionally substituted heteroaryl;

$R^{15}$ is selected from hydrogen, $C_1$-$C_3$ aliphatic, $C_1$-$C_3$ haloaliphatic, and a ring;

Y is a 1-4 atom spacer comprising one or more groups selected from an optionally substituted $C_1$-$C_6$ aliphatic, an optionally substituted $C_1$-$C_6$ heteroaliphatic, an optionally substituted phenyl, an optionally substituted heteroaryl, an optionally substituted $C_3$-$C_5$ heterocycle, and an optionally substituted alicyclic, provided that Y is not —N=$CR^6$— orientated to form a dihydropyrazole;

Z is selected from:
- a 2-5 atom spacer selected from an optionally substituted $C_6$-$C_{10}$ aryl and an optionally substituted $C_1$-$C_8$ heteroaryl, and
- a 1-5 atom spacer of selected from an optionally substituted $C_1$-$C_6$ aliphatic, an optionally substituted $C_1$-$C_6$ heteroaliphatic, and an optionally substituted $C_1$-$C_6$ haloaliphatic;

m is 0, 1, or 2; and n is 0 or 1.

In certain embodiments, the invention provides a compound of Formula I or a pharmaceutically acceptable salt, ester, amide, or prodrug thereof, wherein:

$R^1$ is selected from $CO_2R^{10}$, $CONR^{10}R^{11}$, $SO_3R^{10}$, and a carboxylic acid bioisostere selected from tetrazole, $NHSO_2R^{15}$, $OC(S)NR^{10}R^{11}$, $SC(O)NR^{10}R^{11}$, and

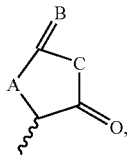

wherein A, B, and C are each independently selected from O, S, and N;

$R^2$ and $R^3$ are each independently selected from hydrogen, $OR^{12}$, $NR^{12}R^{13}$, an optionally substituted $C_1$-$C_4$ alkyl, an optionally substituted $C_1$-$C_4$ haloalkyl, an optionally substituted $C_1$-$C_4$ heteroalkyl, an optionally substituted ring, and $(CH_2)_mR^{14}$; or $R^2$ and $R^3$ taken together form an optionally substituted olefin; or $R^2$ and $R^3$ are linked to form an optionally substituted $C_3$-$C_8$ ring;

$R^4$ is selected from hydrogen, F, Cl, Br, $C_1$-$C_4$ alkyl, $C_1$-$C_4$ haloalkyl, $C_1$-$C_4$ heteroalkyl, and a non-aromatic ring;

$R^7$ is selected from hydrogen, an optionally substituted $C_1$-$C_8$ alkyl, an optionally substituted $C_1$-$C_8$ haloalkyl, an optionally substituted $C_1$-$C_8$ heteroalkyl, an optionally substituted $C_1$-$C_8$ heterohaloalkyl, an optionally substituted aromatic ring, and $(CH_2)_mR^{14}$;

$R^{10}$ is selected from hydrogen, an optionally substituted $C_1$-$C_4$ alkyl, $C_1$-$C_4$ haloalkyl, $C_1$-$C_4$ heteroalkyl, and a non-aromatic ring;

$R^{11}$ is selected from hydrogen, $SO_2R^{15}$, $C_1$-$C_4$ alkyl, $C_1$-$C_4$ haloalkyl, $C_1$-$C_4$ heteroalkyl, and a non-aromatic ring;

$R^{12}$ and $R^{13}$ are each independently selected from hydrogen, an optionally substituted $C_1$-$C_4$ alkyl, an optionally substituted $C_1$-$C_4$ haloalkyl, an optionally substituted $C_1$-$C_4$ heteroalkyl, an optionally substituted non-aromatic ring, and $(CH_2)_mR^{14}$; or one of $R^{12}$ and $R^{13}$ is an optionally substituted $C_2$-$C_6$ alkyl or an optionally substituted non-aromatic ring, and the other of $R^{12}$ and $R^{13}$ is null; or $R^{12}$ and $R^{13}$ are linked to form an optionally substituted $C_3$-$C_8$ ring;

$R^{15}$ is selected from hydrogen, $C_1$-$C_3$ alkyl, $C_1$-$C_3$ haloalkyl, and aryl;

Y is a 1-4 atom spacer comprising one or more groups selected from an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted phenyl, an optionally substituted heteroaryl, an optionally substituted $C_3$-$C_5$ heterocycle, an optionally substituted cycloalkyl, and an optionally substituted cycloalkenyl; and Z is selected from:
- a 2-5 atom spacer selected from an optionally substituted $C_6$-$C_{10}$ aryl and an optionally substituted $C_1$-$C_8$ heteroaryl, and
- a 1-5 atom spacer of selected from an optionally substituted $C_1$-$C_6$ alkyl, an optionally substituted $C_1$-$C_6$ heteroalkyl, an optionally substituted $C_1$-$C_6$ haloalkyl, an optionally substituted $C_2$-$C_6$ alkenyl, an optionally substituted $C_2$-$C_6$ heteroalkenyl, an optionally substituted $C_2$-$C_6$ haloalkenyl, an optionally substituted $C_2$-$C_6$ alkynyl, and an optionally substituted $C_2$-$C_6$ heteroalkyl.

In certain embodiments, the present invention provides a compound of Formula II:

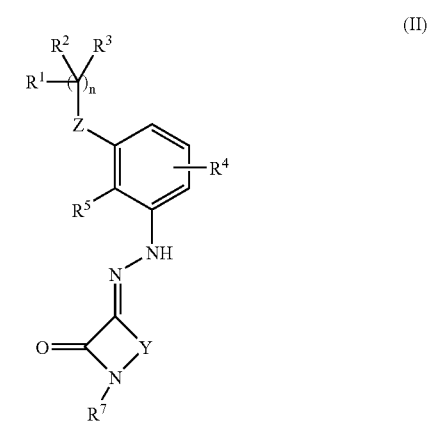

(II)

or a pharmaceutically acceptable salt, ester, amide, or prodrug thereof, wherein:

$R^1$ is selected from $CO_2R^{10}$, $CONR^{10}R^{11}$, $SO_3R^{10}$, and a carboxylic acid bioisostere;

$R^2$ and $R^3$ are each independently selected from null, hydrogen, $OR^{12}$, $NR^{12}R^{13}$, an optionally substituted $C_1$-$C_4$ aliphatic, an optionally substituted $C_1$-$C_4$ haloaliphatic, an optionally substituted $C_1$-$C_4$ heteroaliphatic, an optionally substituted ring, and $(CH_2)_m R^{14}$; or $R^2$ and $R^3$ taken together form an optionally substituted olefin; or $R^2$ and $R^3$ are linked to form an optionally substituted $C_3$-$C_8$ ring;

$R^4$ is selected from hydrogen, F, Cl, Br, $C_1$-$C_4$ aliphatic, $C_1$-$C_4$ haloaliphatic, $C_1$-$C_4$ heteroaliphatic, and a ring;

$R^5$ is selected from hydrogen, $OR^{10}$, $SR^{10}$, $NHR^{11}$, and $CO_2H$;

$R^6$ is selected from hydrogen, $OR^{12}$, $NR^{12}R^{13}$, F, Cl, Br, $C_1$-$C_4$ alkyl, $C_1$-$C_4$ haloalkyl, $C_1$-$C_4$ heteroalkyl, and a ring;

$R^7$ is selected from hydrogen, an optionally substituted $C_1$-$C_8$ aliphatic, an optionally substituted $C_1$-$C_8$ haloaliphatic, an optionally substituted $C_1$-$C_8$ heteroaliphatic, an optionally substituted $C_1$-$C_8$ heterohaloaliphatic, an optionally substituted ring, and $(CH_2)_m R^{14}$;

$R^8$ and $R^9$ are each independently selected from hydrogen, F, Cl, Br, $CO_2R^{10}$, $NO_2$, CN, $SO_2R^{10}$, $(CH_2)_m R^{14}$, $C_1$-$C_4$ aliphatic, $C_1$-$C_4$ haloaliphatic, $C_1$-$C_4$ heteroaliphatic, $C_1$-$C_4$ heterohaloaliphatic, and a ring;

$R^{10}$ is selected from hydrogen, an optionally substituted $C_1$-$C_4$ aliphatic, $C_1$-$C_4$ haloaliphatic, $C_1$-$C_4$ heteroaliphatic, and a ring;

$R^{11}$ is selected from hydrogen, $SO_2R^{15}$, $C_1$-$C_4$ aliphatic, $C_1$-$C_4$ haloaliphatic, $C_1$-$C_4$ heteroaliphatic, and a ring;

$R^{12}$ and $R^{13}$ are each independently selected from hydrogen, an optionally substituted $C_1$-$C_4$ aliphatic, an optionally substituted $C_1$-$C_4$ haloaliphatic, an optionally substituted $C_1$-$C_4$ heteroaliphatic, an optionally substituted ring, and $(CH_2)_m R^{14}$; or one of $R^{12}$ and $R^{13}$ is an optionally substituted $C_2$-$C_6$ aliphatic or an optionally substituted ring and the other of $R^{12}$ and $R^{13}$ is null; or $R^{12}$ and $R^{13}$ are linked to form an optionally substituted $C_3$-$C_8$ ring;

$R^{14}$ is selected from an optionally substituted aryl and an optionally substituted heteroaryl;

$R^{15}$ is selected from hydrogen, $C_1$-$C_3$ aliphatic, $C_1$-$C_3$ haloaliphatic, and a ring;

Q is selected from O and S;

X is selected from O, S, $NR^{10}$, and $CR^{10}R^{11}$;

Y is selected from:

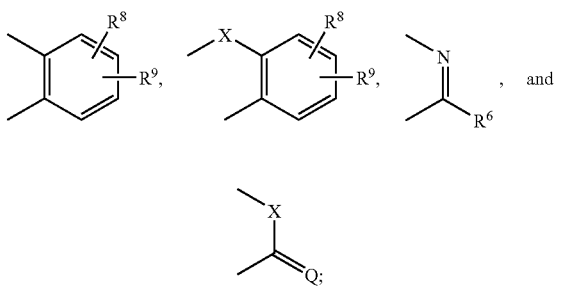

Z is selected from:
a 2-5 atom spacer selected from an optionally substituted $C_6$-$C_{10}$ aryl and an optionally substituted $C_1$-$C_8$ heteroaryl, and
a 1-5 atom spacer of selected from an optionally substituted $C_1$-$C_6$ aliphatic, an optionally substituted $C_1$-$C_6$ heteroaliphatic, and an optionally substituted $C_1$-$C_6$ haloaliphatic;

m is 0, 1, or 2; and
n is 0 or 1.

In certain embodiments, the invention provides a compound of Formula II or a pharmaceutically acceptable salt, ester, amide, or prodrug thereof, wherein:

$R^1$ is selected from $CO_2R^{10}$, $CONR^{10}R^{11}$, $SO_3R^{10}$, and a carboxylic acid bioisostere selected from tetrazole, $NHSO_2R^{15}$, $OC(S)NR^{10}R^{11}$, $SC(O)NR^{10}R^{11}$, and

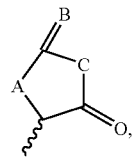

wherein A, B, and C are each independently selected from O, S, and N;

$R^2$ and $R^3$ are each independently selected from hydrogen, $OR^{12}$, $NR^{12}R^{13}$, an optionally substituted $C_1$-$C_4$ alkyl, an optionally substituted $C_1$-$C_4$ haloalkyl, an optionally substituted $C_1$-$C_4$ heteroalkyl, an optionally substituted ring, and $(CH_2)_m R^{14}$; or $R^2$ and $R^3$ taken together form an optionally substituted olefin; or $R^2$ and $R^3$ are linked to form an optionally substituted $C_3$-$C_8$ ring; or one of R2 or R3 is null and the other is $R^4$ is selected from hydrogen, F, Cl, Br, $C_1$-$C_4$ alkyl, $C_1$-$C_4$ haloalkyl, and $C_1$-$C_4$ heteroalkyl and a non-aromatic ring;

$R^7$ is selected from hydrogen, an optionally substituted $C_1$-$C_8$ alkyl, an optionally substituted $C_1$-$C_8$ haloalkyl, an optionally substituted $C_1$-$C_8$ heteroalkyl, an optionally substituted $C_1$-$C_8$ heterohaloalkyl, an optionally substituted aromatic ring, and $(CH_2)_m R^{14}$;

$R^8$ and $R^9$ are each independently selected from hydrogen, F, Cl, Br, $CO_2R^{10}$, $NO_2$, CN, $SO_2R^{10}$, $(CH_2)_m R^{14}$, $C_1$-$C_4$ alkyl, $C_1$-$C_4$ haloalkyl, $C_1$-$C_4$ heteroalkyl, $C_1$-$C_4$ heterohaloalkyl, and a ring;

$R^{10}$ is selected from hydrogen, an optionally substituted $C_1$-$C_4$ alkyl, $C_1$-$C_4$ haloalkyl, $C_1$-$C_4$ heteroalkyl, and a non-aromatic ring;

$R^{11}$ is selected from hydrogen, $SO_2R^{15}$, $C_1$-$C_4$ alkyl, $C_1$-$C_4$ haloalkyl, and $C_1$-$C_4$ heteroalkyl;

$R^{12}$ and $R^{13}$ are each independently selected from hydrogen, an optionally substituted $C_1$-$C_4$ alkyl, an optionally substituted $C_1$-$C_4$ haloalkyl, an optionally substituted $C_1$-$C_4$ heteroalkyl, an optionally substituted non-aromatic ring, and $(CH_2)_m R^{14}$; or one of $R^{12}$ and $R^{13}$ is an optionally substituted $C_2$-$C_6$ alkyl or an optionally substituted non-aromatic ring and the other of $R^{12}$ and $R^{13}$ is null; or $R^{12}$ and $R^{13}$ are linked to form an optionally substituted $C_3$-$C_8$ ring;

$R^{15}$ is selected from hydrogen, $C_1$-$C_3$ alkyl, $C_1$-$C_3$ haloalkyl, and aryl; and Z is selected from:
a 2-5 atom spacer selected from an optionally substituted $C_6$-$C_{10}$ aryl and an optionally substituted $C_1$-$C_8$ heteroaryl, and
a 1-5 atom spacer of selected from an optionally substituted $C_1$-$C_6$ alkyl, an optionally substituted $C_1$-$C_6$ heteroalkyl, an optionally substituted $C_1$-$C_6$ haloalkyl, an optionally substituted $C_2$-$C_6$ alkenyl, an optionally substituted $C_2$-$C_6$ heteroalkenyl, an optionally substituted $C_2$-$C_6$ haloalkenyl, an optionally substituted $C_2$-$C_6$ alkynyl, and an optionally substituted $C_2$-$C_6$ heteroalkyl.

In certain embodiments, the present invention provides a compound of Formula III:

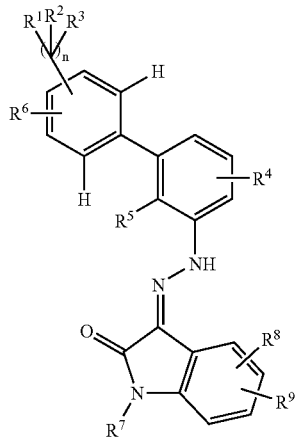

(III)

or a pharmaceutically acceptable salt, ester, amide, or prodrug thereof, wherein:
R¹ is selected from $CO_2R^{10}$, $CONR^{10}R^{11}$, $SO_3R^{10}$, and a carboxylic acid bioisostere;
$R^2$ and $R^3$ are each independently selected from null, hydrogen, $OR^{12}$, $NR^{12}R^{13}$, an optionally substituted $C_1-C_4$ aliphatic, an optionally substituted $C_1-C_4$ haloaliphatic, an optionally substituted $C_1-C_4$ heteroaliphatic, an optionally substituted ring, and $(CH_2)_m R^{14}$; or $R^2$ and $R^3$ taken together form an optionally substituted olefin; or $R^2$ and $R^3$ are linked to form an optionally substituted $C_3-C_8$ ring;
$R^4$ is selected from hydrogen, F, Cl, Br, $C_1-C_4$ aliphatic, $C_1-C_4$ haloaliphatic, $C_1-C_4$ heteroaliphatic, and a ring;
$R^5$ is selected from hydrogen, $OR^{10}$, $SR^{10}$, $NHR^{11}$, and $CO_2H$;
$R^6$ is selected from hydrogen, $OR^{12}$, $NR^{12}R^{13}$, F, Cl, Br, $C_1-C_4$ alkyl, $C_1-C_4$ haloalkyl, and $C_1-C_4$ heteroalkyl;
$R^7$ is selected from hydrogen, an optionally substituted $C_1-C_8$ aliphatic, an optionally substituted $C_1-C_8$ haloaliphatic, an optionally substituted $C_1-C_8$ heteroaliphatic, an optionally substituted $C_1-C_8$ heterohaloaliphatic, an optionally substituted ring, and $(CH_2)_m R^{14}$;
$R^8$ and $R^9$ are each independently selected from hydrogen, F, Cl, Br, $CO_2R^{10}$, $NO_2$, CN, $SO_2R^{10}$, $(CH_2)_m R^{14}$, $C_1-C_4$ aliphatic, $C_1-C_4$ haloaliphatic, $C_1-C_4$ heteroaliphatic, and $C_1-C_4$ heterohaloaliphatic;
$R^{10}$ is selected from hydrogen, an optionally substituted $C_1-C_4$ aliphatic, $C_1-C_4$ haloaliphatic, $C_1-C_4$ heteroaliphatic, and a ring;
$R^{11}$ is selected from hydrogen, $SO_2R^{15}$, $C_1-C_4$ aliphatic, $C_1-C_4$ haloaliphatic, $C_1-C_4$ heteroaliphatic, and a ring;
$R^{12}$ and $R^{13}$ are each independently selected from hydrogen, an optionally substituted $C_1-C_4$ aliphatic, an optionally substituted $C_1-C_4$ haloaliphatic, an optionally substituted $C_1-C_4$ heteroaliphatic, an optionally substituted ring, and $(CH_2)_m R^{14}$; or one of $R^{12}$ and $R^{13}$ is an optionally substituted $C_2-C_6$ aliphatic or an optionally substituted ring and the other of $R^{12}$ and $R^{13}$ is null; or $R^{12}$ and $R^{13}$ are linked to form an optionally substituted $C_3-C_8$ ring;

$R^{14}$ is selected from an optionally substituted aryl and an optionally substituted heteroaryl;
$R^{15}$ is selected from hydrogen, $C_1-C_3$ aliphatic, $C_1-C_3$ haloaliphatic, and a ring;
m is 0, 1, or 2; and
n is 0 or 1.

In certain embodiments, the invention provides a compound of Formula III or a pharmaceutically acceptable salt, ester, amide, or prodrug thereof, wherein:
R¹ is selected from $CO_2R^{10}$, $CONR^{10}R^{11}$, $SO_3R^{10}$, and a carboxylic acid bioisostere selected from tetrazole, $NHSO_2R^{15}$, $OC(S)NR^{10}R^{11}$, $SC(O)NR^{10}R^{11}$, and

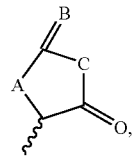

wherein A, B, and C are each independently selected from O, S, and N;
$R^2$ and $R^3$ are each independently selected from hydrogen, $OR^{12}$, $NR^{12}R^{13}$, an optionally substituted $C_1-C_4$ alkyl, an optionally substituted $C_1-C_4$ haloalkyl, an optionally substituted $C_1-C_4$ heteroalkyl, an optionally substituted ring, and $(CH_2)_m R^{14}$; or $R^2$ and $R^3$ taken together form an optionally substituted olefin; or $R^2$ and $R^3$ are linked to form an optionally substituted $C_3-C_8$ ring;
$R^4$ is selected from hydrogen, F, Cl, Br, $C_1-C_4$ alkyl, $C_1-C_4$ haloalkyl, $C_1-C_4$ heteroalkyl, and a non-aromatic ring;
$R^7$ is selected from hydrogen, an optionally substituted $C_1-C_8$ alkyl, an optionally substituted $C_1-C_8$ haloalkyl, an optionally substituted $C_1-C_8$ heteroalkyl, an optionally substituted $C_1-C_8$ heterohaloalkyl, an optionally substituted aromatic ring, and $(CH_2)_m R^{14}$;
$R^8$ and $R^9$ are each independently selected from hydrogen, F, Cl, Br, $CO_2R^{10}$, $NO_2$, CN, $SO_2R^{10}$, $(CH_2)_m R^{14}$, $C_1-C_4$ alkyl, $C_1-C_4$ haloalkyl, $C_1-C_4$ heteroalkyl, and $C_1-C_4$ heterohaloalkyl;
$R^{10}$ is selected from hydrogen, an optionally substituted $C_1-C_4$ alkyl, $C_1-C_4$ haloalkyl, $C_1-C_4$ heteroalkyl and a non-aromatic ring;
$R^{11}$ is selected from hydrogen, $SO_2R^{15}$, $C_1-C_4$ alkyl, $C_1-C_4$ haloalkyl, and $C_1-C_4$ heteroalkyl, and a non-aromatic ring;
$R^{12}$ and $R^{13}$ are each independently selected from hydrogen, an optionally substituted $C_1-C_4$ alkyl, an optionally substituted $C_1-C_4$ haloalkyl, an optionally substituted $C_1-C_4$ heteroalkyl, a non-aromatic ring, and $(CH_2)_m R^{14}$; or one of $R^{12}$ and $R^{13}$ is an optionally substituted $C_2-C_6$ alkyl or a non-aromatic ring, and the other of $R^{12}$ and $R^{13}$ is null; or $R^{12}$ and $R^{13}$ are linked to form an optionally substituted $C_3-C_8$ ring; and
$R^{15}$ is selected from hydrogen, $C_1-C_3$ alkyl, $C_1-C_3$ haloalkyl, and aryl.

In certain embodiments, a compound of Formula I, II, or III is a selective TPO modulator. In certain such embodiments, a compound of Formula I, II, or III is a TPO mimic.

In certain embodiments, the invention provides a selective TPO modulator. In certain embodiments, the invention provides a selective TPO receptor agonist. In certain embodiments, the invention provides a selective TPO receptor antagonist. In certain embodiments, the invention provides a selective TPO partial agonist. In certain embodiments, the invention provides a selective TPO receptor binding compound. In certain embodiments, the invention provides a TPO mimic. In certain embodiments, the invention provides a tissue-selective selective TPO modulator.

In certain embodiments, the invention provides methods for modulating a TPO activity. Certain such methods comprise contacting a cell with one or more compounds of the present invention. Such methods include, but are not limited to, contacting TPO and/or a TPO receptor with one or more compounds of the present invention.

In certain embodiments, the invention provides a method for identifying a compound that is capable of modulating TPO activity comprising contacting a cell capable of a TPO activity with a compound of the present invention and monitoring an effect on the cell. In certain such embodiments, the cell expresses a TPO receptor.

In certain embodiments, the invention provides methods of treating a patient comprising administering to the patient a compound of the present invention. In certain embodiments, such a patient suffers from thrombocytopenia. In certain embodiments, one or more compounds of the present invention are administered to a patient before, during or after chemotherapy, bone marrow transplantation, and/or radiation therapy. In certain embodiments, one or more compounds of the invention are administered to a patient suffering from aplastic anemia, bone marrow failure, and/or idiopathic thrombocytopenia. In certain embodiments, one or more compounds of the present invention are administered to a patient suffering from a disease of the nervous system. In certain embodiments, one or more compounds of the present invention are administered to patient suffering from amyotrophic lateral sclerosis, multiple sclerosis, or multiple dystrophy. In certain embodiments, one or more compounds of the present invention are administered to a patient with a nerve injury, including, but not limited to, a spinal cord injury.

In certain embodiments, the invention provides pharmaceutical compositions comprising one or more compounds of the present invention and a physiologically acceptable carrier, diluent, or excipient.

DETAILED DESCRIPTION OF THE PREFERRED EMBODIMENTS

It is to be understood that both the foregoing general description and the following detailed description are exemplary and explanatory only and are not restrictive of the invention claimed. Herein, the use of the singular includes the plural unless specifically stated otherwise. Herein, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definitions

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein for any purpose.

As used herein, the following terms are defined with the following meanings, unless expressly stated otherwise.

The term "selective binding compound" refers to a compound that selectively binds to any portion of one or more target.

The term "selective TPO receptor binding compound" refers to a compound that selectively binds to any portion of a TPO receptor.

The term "selectively binds" refers to the ability of a selective binding compound to bind to a target receptor with greater affinity than it binds to a non-target receptor. In certain embodiments, specific binding refers to binding to a target with an affinity that is at least 10, 50, 100, 250, 500, or 1000 times greater than the affinity for a non-target.

The term "target receptor" refers to a receptor or a portion of a receptor capable of being bound by a selective binding compound. In certain embodiments, a target receptor is a TPO receptor.

The term "modulator" refers to a compound that alters or elicits an activity. For example, the presence of a modulator may result in an increase or decrease in the magnitude of a certain activity compared to the magnitude of the activity in the absence of the modulator. In certain embodiments, a modulator is an inhibitor, which decreases the magnitude of one or more activities. In certain embodiments, an inhibitor completely prevents one or more biological activities. In certain embodiments, a modulator is an activator, which increases the magnitude of at least one activity. In certain embodiments the presence of a modulator results in a activity that does not occur in the absence of the modulator.

The term "selective modulator" refers to a compound that selectively modulates a target activity.

The term "selective TPO modulator" refers to a compound that selectively modulates at least one TPO activity. The term selective TPO modulator includes, but is not limited to "TPO mimic" which refers to a compound, the presence of which results in at least one TPO activity.

The term "selectively modulates" refers to the ability of a selective modulator to modulate a target activity to a greater extent than it modulates a non-target activity.

The term "target activity" refers to a biological activity capable of being modulated by a selective modulator. Certain exemplary target activities include, but are not limited to, binding affinity; signal transduction; enzymatic activity; transcription of one or more genes; the proliferation and/or differentiation of cells, including, but not limited to progenitor cells; generation of platelets; and alleviation of symptoms of a disease or condition.

The term "TPO activity" refers to a biological activity that results, either directly or indirectly from the presence of TPO. Exemplary TPO activities include, but are not limited to, proliferation and or differentiation of progenitor cells to produce platelets; hematopoiesis; growth and/or development of glial cells; repair of nerve cells; and alleviation of thrombocytopenia.

The term "thrombocytopenia" refers to a condition wherein the concentration of platelets in the blood of a patient is below what is considered normal for a healthy patient. In certain embodiments, thrombocytopenia is a platelet count less than 450,000, 400,000, 350,000, 300,000, 250,000, 200,000, 150,000, 140,000, 130,000, 120,000, 110,000, 100,000, 75,000, or 50,000 platelets per microliter of blood.

The term "receptor mediated activity" refers any biological activity that results, either directly or indirectly, from binding of a ligand to a receptor.

The term "agonist" refers to a compound, the presence of which results in a biological activity of a receptor that is the same as the biological activity resulting from the presence of a naturally occurring ligand for the receptor.

The term "partial agonist" refers to a compound, the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "aliphatic," alone or in combination, refers to a straight or branched chain comprising at least one carbon atom. Aliphatics include alkyls, alkenyls, and alkynyls. In certain embodiments, aliphatics are optionally substituted. Aliphatics include, but are not limited to, methyl, ethyl, propyl, isopropyl, butyl, isobutyl, tertiary butyl, pentyl, hexyl, ethenyl, propenyl, butenyl, ethynyl, butynyl, propynyl, and the like, each of which may be optionally substituted. As used herein, aliphatic is not intended to include cyclic groups.

The term "alkyl," alone or in combination, refers to a fully saturated aliphatic. In certain embodiments, alkyls are optionally substituted. In certain embodiments, an alkyl comprises 1 to 20 carbon atoms (whenever it appears herein, a numerical range, such as "1 to 20" or "$C_1$-$C_{20}$", refers to each integer in the given range; e.g., "$C_1$-$C_{20}$ alkyl" means that an alkyl group comprising only 1 carbon atom, 2 carbon atoms, 3 carbon atoms, etc., up to and including 20 carbon atoms). Examples of alkyls include, but are not limited to, methyl, ethyl, n-propyl, isopropyl, n-butyl, isobutyl, sec-butyl, tert-butyl, tert-amyl, pentyl, hexyl, heptyl, octyl and the like.

The term "alkenyl," alone or in combination, refers to an aliphatic having one or more carbon-carbon double-bonds. In certain embodiments, alkenyls are optionally substituted. Examples of alkenyls include, but are not limited to, ethenyl, propenyl, 1,4-butadienyl, and the like.

The term "alkynyl," alone or in combination, refers to an aliphatic having one or more carbon-carbon triple-bonds. In certain embodiments, alkynyls are optionally substituted. Examples of alkynyls include, but are not limited to, ethynyl, propynyl, butynyl, and the like.

The term "haloaliphatic," alone or in combination, refers to an aliphatic in which at least one hydrogen atom is replaced with a halogen atom. In certain embodiments in which two or more hydrogen atom are replaced with halogen atoms, the halogen atoms are all the same as one another. In certain such embodiments, the halogen atoms are not all the same as one another. Haloaliphatics include haloalkyls, haloalkenyls, and haloalkynyls. In certain embodiments, haloaliphatics are optionally substituted, in addition to the hydrogen/halogen substitution. The term "haloaliphatic" also includes perhaloaliphatic, in which all of the hydrogen atoms of the aliphatic are replaced by halogen atoms. Examples of perhaloaliphatic include trichloromethyl, pentacholorethyl, etc.

The term "heteroaliphatic," alone or in combination, refers to a group comprising an aliphatic and one or more heteroatoms. Certain heteroaliphatics are acylaliphatics, in which the one or more heteroatoms is not within an aliphatic chain. Heteroaliphatics include heteroalkyls, including, but not limited to acylalkys; heteroalkenyls, including, but not limited to, acylalkenyls; and heteroalkynyls, including, but not limited acylalkynyls. Examples of heteraliphatics include, but are not limited to, $CH_3C(=O)CH_2$—, $CH_3C(=O)CH_2CH_2$—, $CH_3CH_2C(=O)CH_2CH_2$—, $CH_3C(=O)CH_2CH_2CH_2$—, $CH_3OCH_2CH_2$—, $CH_3NHCH_2$—, and the like. In certain embodiments, heteroaliphatics are optionally substituted.

The term "heterohaloaliphatic" refers to a heteroaliphatic in which at least one hydrogen atom is replaced with a halogen atom. Heterohaloaliphatics include heterohaloalkyls, heterohaloalkenyls, and heterohaloalkynyls. In certain embodiments, heterohaloaliphatics are optionally substituted.

The term "olefin" refers to a C=C bond. The term "together form an olefin" refers to instances where two groups are bound to the same carbon atom and one of those two groups is =C and the other of those two groups is null. For example, if R' and R" in the structure below together form an olefin:

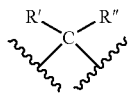

the resulting structure is:

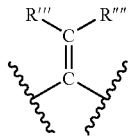

wherein R''' and R'''' represent hydrogen. Olefins may be optional substituted, in which case R''' and R'''' above are independently selected from hydrogen and an optional substituent.

The term "carbocycle" refers to a group comprising a covalently closed ring, wherein each of the atoms forming the ring is a carbon atom. Carbocylic rings may be formed by three, four, five, six, seven, eight, nine, or more than nine carbon atoms. Carbocycles may be optionally substituted.

The term "heterocycle" refers to a group comprising a covalently closed ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom. Examples of heterocycles include, but are not limited to the following:

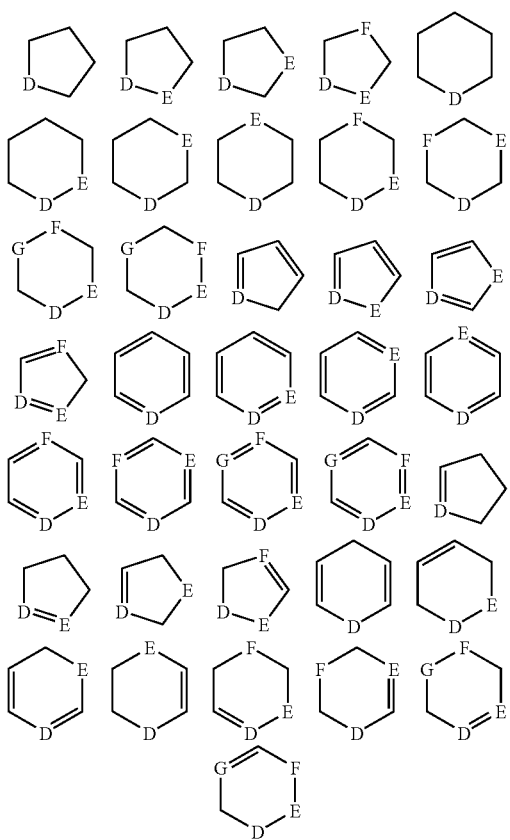

wherein D, E, F, and G independently represent a heteroatom. Each of D, E, F, and G may be the same or different from one another.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed planar ring having a delocalized π-electron system comprising $4n+2\pi$ electrons, where n is an integer. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfinyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic ring wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic heterocycle. Heteroaryl rings may be formed by three, four, five, six, seven, eight, nine, or more than nine atoms. Heteroaryls may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "non-aromatic ring" refers to a group comprising a covalently closed ring that is not aromatic.

The term "alicyclic" refers to a group comprising a non-aromatic ring wherein each of the atoms forming the ring is a carbon atom. Alicyclic rings may be formed by three, four, five, six, seven, eight, nine, or more than nine carbon atoms. In certain embodiments, alicyclics are optionally substituted. In certain embodiments, an alicyclic comprises one or more unsaturated bonds. Alicyclics include cycloalkyls, cycloalkenyls, and cycloalkynyls. Examples of alicyclics include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene. In certain embodiments, alicylcic rings are optionally substituted.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "arylalkyl" refers to a group comprising an aryl group bound to an alkyl group.

The term "ring" refers to any covalently closed structure. Rings include, for example, carbocycles (e.g., aryls and alicyclics), heterocycles (e.g., heteroaryls and non-aromatic heterocycles), aromatics (e.g., aryls and heteroaryls), and non-aromatics (e.g., alicyclics and non-aromatic heterocycles). Rings may be optionally substituted. Rings may form part of a ring system.

The term "ring system" refers to two or more rings, wherein two or more of the rings are fused. The term "fused" refers to structures in which two or more rings share one or more bonds.

The term "null" refers to a group being absent from a structure. For example, in the structure

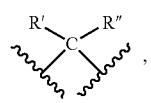

where in certain instances X is N, if X is N, one of R' or R" is null, meaning that only three groups are bound to the N.

The term "carboxylic acid bioisostere" refers to a group that is biologically equivalent to a carboxylic acid. For example, carboxylic acid bioisosteres include, but are not limited to, tetrazole, $NHSO_2R^{15}$, $OC(S)NR^{10}R^{11}$, $SC(O)NR^{10}R^{11}$, thiazolidinedione, oxazolidinedione, and 1-oxa-2,4-diazolidine-3,5-dione. In certain embodiments, a carboxylic acid bioisoster comprises the following structure:

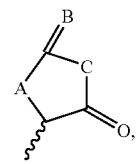

wherein A, B, and C are each independently selected from O, S, and N.

The term "spacer" refers to an atom or group of atoms that separate two or more groups from one another by a desired number of atoms. For example, in certain embodiments, it may be desirable to separate two or more groups by one, two, three, four, five, six, or more than six atoms. In such embodiments, any atom or group of atoms may be used to separate those groups by the desired number of atoms. In certain embodiments, spacers are optionally substituted. In certain embodiments, a spacer comprises an aliphatic. In certain embodiments, a spacer comprises atoms that are part of a ring.

Solely for the purposes of illustration, and without limiting the above definition, some examples of spacers are provided. Examples of 1-atom spacers include, but are not limited to, the following:

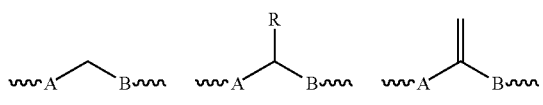

where A and B represent groups which are separated by the desired number of atoms. Examples of 2-atom spacers include, but are not limited to, the following:

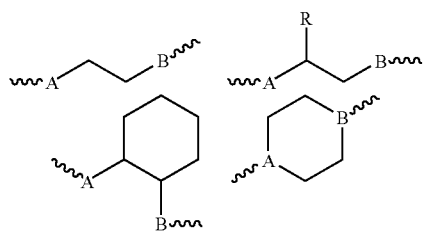

where A and B represent groups which are separated by the desired number of atoms. Examples of 3-atom spacers include, but are not limited to, the following:

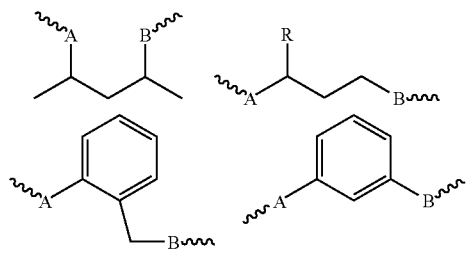

-continued

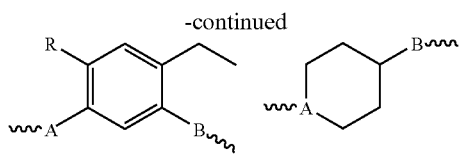

where A and B represent groups that are separated by the desired number of atoms.

In certain embodiments, a spacer separates atoms in a ring. For example, in the structure:

where Q is a 1-atom spacer, the resulting ring is a three-membered ring comprising A, B, and Q, where Q may be optionally substituted. An example of such a structure includes, but is not limited to:

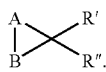

If Q is a 2-atom spacer, then a four-membered ring results; if Q is a three atom spacer, then a five-membered ring results; if Q is a four atom spacer, then a six-membered ring results; if Q is a five atom spacer, then a seven-membered ring results; if Q is a six atom spacer, then an eight-membered ring results; and so on. In certain embodiments, a spacer in a ring comprises a ring, such that the ring formed by the spacer and the ring comprised by the spacer are fused. For example, referring to the structure above where Q is a 3-atom spacer comprising a fused ring includes, but is not limited to, structures such as:

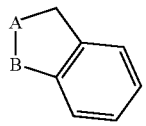

where the fused ring can be fused at any bond of the spacer. Such a fused ring may be optionally substituted and may be heterocyclic or carbocyclic.

As is evident from the above examples, the atoms of a spacer that create the desired separation may themselves be part of a group. That group may be, for example, an aliphatic, heteroaliphatic, haloaliphatic, heterohaloaliphatic, alicyclic, aryl, arylalkyl, heteroaryl, non-aromatic heterocycle, or substituted alkyl all of which are optionally substituted. Thus, the term "1-5 atom spacer" refers to a spacer that separates two groups by 1, 2, 3, 4, or 5 atoms and does not indicate the total size of the group that constitutes the spacer.

The term "linked to form a ring" refers to the circumstance where two atoms that are bound either to a single atom or to atoms that are themselves ultimately bound, are each bound to a linking group, such that the resulting structure forms a ring. That resulting ring comprises the two atoms, the atom (or atoms) that previously linked those atoms, and the linker. For example, if A and B below are "linked to form a ring"

the resulting ring includes A, B, the carbon atom to which both A and B are bound, and a linking group. Unless otherwise indicated, that linking group may be of any length and may be optionally substituted. Referring to the above example, resulting structures include, but are not limited to:

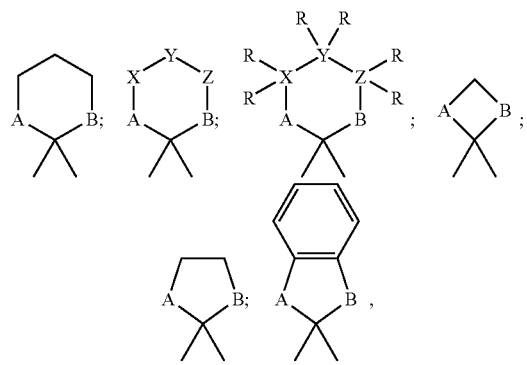

and the like.

In certain embodiments, the two atoms that are linked to form a ring are not bound to the same atom. For example, if A and B, below, are linked to form a ring:

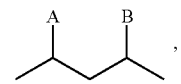

the resulting ring comprises A, B, the 3 carbon atoms that already link A and B, and a linking group. Examples of resulting structures include, but are not limited to:

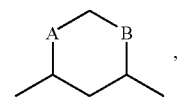

and the like.

The substituent "R" appearing by itself and without a number designation refers to a substituent selected from alkyl, cycloalkyl, aryl, heteroaryl (bonded through a ring carbon) and non-aromatic heterocycle (bonded through a ring carbon).

The term "O-carboxy" refers to a group of formula RC(=O)O—.

The term "C-carboxy" refers to a group of formula —C(=O)OR.

The term "acetyl" refers to a group of formula —C(=O)CH$_3$.

The term "trihalomethanesulfonyl" refers to a group of formula $X_3CS(=O)_2-$ where X is a halogen.

The term "cyano" refers to a group of formula —CN.

The term "isocyanato" refers to a group of formula —NCO.

The term "thiocyanato" refers to a group of formula —CNS.

The term "isothiocyanato" refers to a group of formula —NCS.

The term "sulfonyl" refers to a group of formula —S(=O)—R.

The term "S-sulfonamido" refers to a group of formula —S(=O)$_2$NR.

The term "N-sulfonamido" refers to a group of formula RS(=O)$_2$NH—.

The term "trihalomethanesulfonamido" refers to a group of formula $X_3CS(=O)_2NR-$.

The term "O-carbamyl" refers to a group of formula —OC(=O)—NR.

The term "N-carbamyl" refers to a group of formula ROC(=O)NH—.

The term "O-thiocarbamyl" refers to a group of formula —OC(=S)—NR.

The term "N-thiocarbamyl" refers to a group of formula ROC(=S)NH—.

The term "C-amido" refers to a group of formula —C(=O)—NR$_2$.

The term "N-amido" refers to a group of formula RC(=O)NH—.

The term "ester" refers to a chemical moiety with formula —(R)$_n$—COOR', where R and R' are independently selected from alkyl, cycloalkyl, aryl, heteroaryl (bonded through a ring carbon) and non-aromatic heterocycle (bonded through a ring carbon), where n is 0 or 1.

The term "amide" refers to a chemical moiety with formula —(R)$_n$—C(O)NHR' or —(R)$_n$—NHC(O)R', where R and R' are independently selected from alkyl, cycloalkyl, aryl, heteroaryl (bonded through a ring carbon) and heteroalicyclic (bonded through a ring carbon), where n is 0 or 1. In certain embodiments, an amide may be an amino acid or a peptide.

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

Unless otherwise indicated, the term "optionally substituted," refers to a group in which none, one, or more than one of the hydrogen atoms has been replaced with one or more group(s) are independently selected from: alkyl, heteroalkyl, haloalkyl, heteroholoalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives of amino groups. Such protective derivatives (and protecting groups that may form such protective derivatives) are known to those of skill in the art and may be found in references such as Greene and Wuts, above. In embodiments in which two or more hydrogen atoms have been substituted, the substituent groups may be linked to form a ring.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "pharmaceutical composition" refers to a pharmaceutical agent together with one or more inactive ingredient for pharmaceutical administration, such as a carrier, excipient, or the like.

The term "therapeutically effective amount" refers to an amount of a pharmaceutical agent or composition sufficient to achieve a desired therapeutic effect.

The term "prodrug" refers to an pharmaceutical agent that is converted from a less active form into a corresponding more active form in vivo.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g. compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

The term "tissue-selective" refers to the ability of a compound to modulate a biological activity in one tissue to a greater or lesser degree than it modulates a biological activity in another tissue. The biological activities in the different tissues may be the same or they may be different. The biological activities in the different tissues may be mediated by the same type of target receptor. For example, in certain embodiments, a tissue-selective compound may modulate receptor mediated biological activity in one tissue and fail to modulate, or modulate to a lesser degree, receptor mediated biological activity in another tissue type.

The term "monitoring" refers to observing an effect or absence of any effect. In certain embodiments, one monitors cells after contacting those cells with a compound of the present invention. Examples of effects that may be monitored include, but are not limited to, changes in cell phenotype, cell proliferation, receptor activity, or the interaction between a receptor and a compound known to bind to the receptor.

The term "cell phenotype" refers to physical or biological characteristics of a cell. Examples of characteristics that constitute phenotype included, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

The term "cell proliferation" refers to the rate at which cells divide. In certain embodiments, cells are in situ in an organism. In certain embodiments, cell are grown in vitro in a vessel. The number of cells growing in a vessel can be quantified by a person skilled in the art (e.g., by counting cells in a defined area using a microscope or by using laboratory apparatus that measure the density of cells in an appropriate medium). One skilled in that art can calculate cell proliferation by determining the number of cells at two or more times.

The term "contacting" refers to bringing two or more materials into close enough proximity that they may interact. In certain embodiments, contacting can be accomplished in a vessel such as a test tube, a petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may dead. Cells may or may not be intact.

Certain Compounds

Certain compounds that modulate one or more TPO activity and/or bind to TPO receptors play a role in health. In certain embodiments, compounds of the present invention are useful for treating any of a variety of diseases or conditions.

In certain embodiments, the present invention provides selective TPO modulators. In certain embodiments, the invention provides selective TPO receptor binding agents. In certain embodiments, the invention provides methods of making and methods of using selective TPO modulators and/or selective TPO receptor binding agents. In certain embodiments, selective TPO modulators are agonists, partial agonists, and/or antagonists for the TPO receptor.

In certain embodiments, the present invention relates to compounds of Formula I, II, or III:

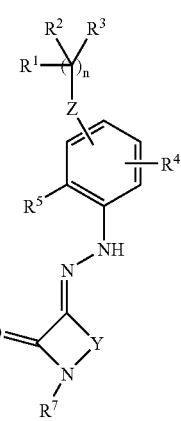

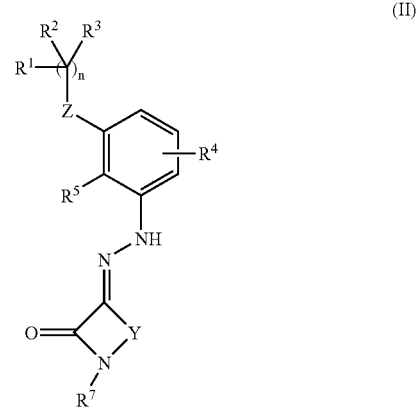

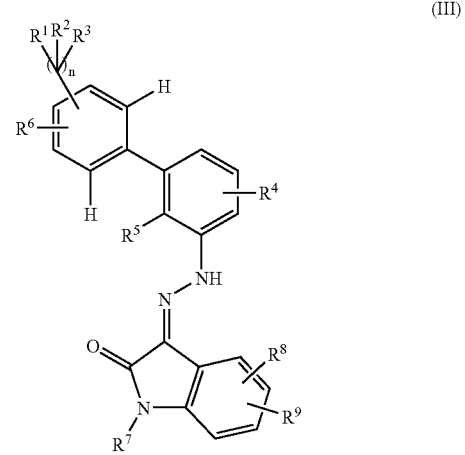

or a pharmaceutically acceptable salt, ester, amide, or prodrug thereof.

In certain embodiments, $R^1$ is selected from hydrogen, $CO_2R^{10}$, $CONR^{10}R^{11}$, $SO_3R^{10}$, and a carboxylic acid bioisostere. In certain embodiments in which $R^1$ is a carboxylic acid bioisostere, $R^1$ is selected from tetrazole, $NHSO_2R^{15}$, $OC(S)NR^{10}R^{11}$, $SC(O)NR^{10}R^{11}$, thiazolidinedione, oxazolidinedione, and 1-oxa-2,4-diazolidine-3,5-dione.

In certain embodiments, $R^2$ and $R^3$ are each independently selected from hydrogen, $OR^{12}$, $NR^{12}R^{13}$, an optionally substituted $C_1$-$C_4$ aliphatic, an optionally substituted $C_1$-$C_4$ haloaliphatic, an optionally substituted $C_1$-$C_4$ heteroaliphatic, $(CH_2)_m R^{14}$, an optionally substituted ring, and null. In certain such embodiments, $R^2$ and $R^3$ are each independently selected from an optionally substituted $C_1$-$C_4$ alkyl, an optionally substituted $C_1$-$C_4$ haloalkyl, an optionally substituted $C_1$-$C_4$ heteroalkyl. In certain embodiments, $R^2$ and $R^3$ taken together form an optionally substituted olefin. In certain embodiments, $R^2$ and $R^3$ are linked to form an optionally substituted $C_3$-$C_8$ ring. In certain such embodiments, $R^2$ and $R^3$ are linked to form an optionally substituted carbocycle, an optionally substituted heterocycle, an optionally substituted aromatic, or an optionally substituted non-aromatic ring. In certain such embodiments, $R^2$ and $R^3$ are linked to form an optionally substituted aryl, an optionally substituted heteroaryl, an optionally substituted alicyclic, or an optionally substituted non-aromatic heterocyclic. In certain embodiments, $R^2$ and $R^3$ are linked to form an optionally substituted aryl or an optionally substituted heteroaryl. In certain embodiments, $R^2$ and $R^3$ are linked to form an optionally substituted aryl. In certain embodiments, $R^2$ and $R^3$ are linked to form an aryl.

In certain embodiments, $R^4$ is selected from hydrogen, F, Cl, Br, optionally substituted $C_1$-$C_4$ aliphatic, optionally substituted $C_1$-$C_4$ haloaliphatic, optionally substituted $C_1$-$C_4$ heteroaliphatic, and an optionally substituted ring. In certain such embodiments, $R^4$ is selected from optionally substituted $C_1$-$C_4$ alkyl, optionally substituted $C_1$-$C_4$ haloalkyl, and optionally substituted $C_1$-$C_4$ heteroalkyl.

In certain embodiments, $R^5$ is selected from hydrogen, $OR^{10}$, $SR^{10}$, $NHR^{11}$, and $CO_2H$.

In certain embodiments, $R^6$ is selected from hydrogen, $OR^{12}$, $NR^{12}R^{13}$, F, Cl, Br, optionally substituted $C_1$-$C_4$ aliphatic, optionally substituted $C_1$-$C_4$ haloaliphatic, optionally substituted $C_1$-$C_4$ heteroaliphatic, and an optionally substituted ring. In certain such embodiments, $R^6$ is selected from optionally substituted $C_1$-$C_4$ alkyl, optionally substituted $C_1$-$C_4$ haloalkyl, and optionally substituted $C_1$-$C_4$ heteroalkyl. In certain embodiments, $R^6$ is selected from an optionally substituted carbocycle, an optionally substituted heterocycle, and optionally substituted aromatic, and an optionally substituted non-aromatic ring. In certain such embodiments, $R^6$ is selected from an optionally substituted aryl, an optionally substituted heteroaryl, an optionally substituted alicyclic, and an optionally substituted non-aromatic heterocyclic. In certain embodiments, $R^6$ is selected from an optionally substituted aryl and an optionally substituted heteroaryl. In certain embodiments, $R^6$ is selected from an optionally substituted aryl. In certain embodiments, $R^6$ is an aryl.

In certain embodiments, $R^7$ is selected from hydrogen, an optionally substituted $C_1$-$C_8$ aliphatic, an optionally substituted $C_1$-$C_8$ haloaliphatic, an optionally substituted $C_1$-$C_8$ heteroaliphatic, an optionally substituted $C_1$-$C_8$ heterohaloaliphatic, an optionally substituted ring, and $(CH_2)_m R^{14}$. In certain such embodiments, $R^7$ is selected from an optionally substituted $C_1$-$C_8$ alkyl, an optionally substituted $C_1$-$C_8$ haloalkyl, an optionally substituted $C_1$-$C_8$ heteroalkyl, and an optionally substituted $C_1$-$C_8$ heterohaloalkyl. In certain embodiments, $R^7$ is selected from an optionally substituted carbocycle, an optionally substituted heterocycle, and optionally substituted aromatic, and an optionally substituted non-aromatic ring. In certain such embodiments, $R^7$ is selected from an optionally substituted aryl, an optionally substituted heteroaryl, an optionally substituted alicyclic, and an optionally substituted non-aromatic heterocyclic. In certain embodiments, $R^7$ is selected from an optionally substituted aryl and an optionally substituted heteroaryl. In certain embodiments, $R^7$ is selected from an optionally substituted aryl. In certain such embodiments, $R^7$ is selected from an aryl ring optionally fused to one or more additional rings. In certain embodiments, $R^7$ is an aryl. In certain embodiments, $R^7$ is an optionally substituted phenyl ring.

In certain embodiments, $R^8$ and $R^9$ are each independently selected from hydrogen, F, Cl, Br, optionally substituted $C_1$-$C_4$ aliphatic, optionally substituted $C_1$-$C_4$ haloaliphatic, optionally substituted $C_1$-$C_4$ heteroaliphatic, optionally substituted $C_1$-$C_4$ heterohaloaliphatic, and an optionally substituted ring. In certain such embodiments, $R^8$ and/or $R^9$ is independently selected from optionally substituted $C_1$-$C_4$ alkyl, optionally substituted $C_1$-$C_4$ haloalkyl, optionally substituted $C_1$-$C_4$ heteroalkyl, and optionally substituted $C_1$-$C_4$ heterohaloalkyl. In certain embodiments, $R^8$ and/or $R^9$ is selected from an optionally substituted carbocycle, an optionally substituted heterocycle, and optionally substituted aromatic, and an optionally substituted non-aromatic ring. In certain such embodiments, $R^8$ and/or $R^9$ is selected from an optionally substituted aryl, an optionally substituted heteroaryl, an optionally substituted alicyclic, and an optionally substituted non-aromatic heterocyclic. In certain embodiments, $R^8$ and/or $R^9$ is selected from an optionally substituted aryl and an optionally substituted heteroaryl. In certain embodiments, $R^8$ and/or $R^9$ is selected from an optionally substituted aryl. In certain embodiments, $R^8$ and/or $R^9$ is an aryl.

In certain embodiments, $R^{10}$ is selected from hydrogen, optionally substituted $C_1$-$C_4$ aliphatic, optionally substituted $C_1$-$C_4$ haloaliphatic, optionally substituted $C_1$-$C_4$ heteroaliphatic, optionally substituted $C_1$-$C_4$ heterohaloaliphatic, an optionally substituted ring. In certain such embodiments, $R^{10}$ is selected from optionally substituted $C_1$-$C_4$ alkyl, optionally substituted $C_1$-$C_4$ haloalkyl, optionally substituted $C_1$-$C_4$ heteroalkyl, and optionally substituted $C_1$-$C_4$ heterohaloalkyl. In certain embodiments, $R^{10}$ is selected from an optionally substituted ring. In certain such embodiments, $R^{10}$ is selected from an optionally substituted carbocycle, an optionally substituted heterocycle, and optionally substituted aromatic, and an optionally substituted non-aromatic ring. In certain such embodiments, $R^{10}$ is selected from an optionally substituted aryl, an optionally substituted heteroaryl, an optionally substituted alicyclic, and an optionally substituted non-aromatic heterocyclic. In certain embodiments, $R^{10}$ is selected from an optionally substituted aryl and an optionally substituted heteroaryl. In certain embodiments, $R^{10}$ is selected from an optionally substituted aryl. In certain embodiments, $R^{10}$ is an aryl.

In certain embodiments, $R^{11}$ is selected from hydrogen, $SO_2R^{15}$, optionally substituted $C_1$-$C_4$ aliphatic, optionally substituted $C_1$-$C_4$ haloaliphatic, optionally substituted $C_1$-$C_4$ heteroaliphatic, optionally substituted $C_1$-$C_4$ heterohaloaliphatic, and an optionally substituted ring. In certain such embodiments, $R^{11}$ is selected from optionally substituted $C_1$-$C_4$ alkyl, optionally substituted $C_1$-$C_4$ haloalkyl, optionally substituted $C_1$-$C_4$ heteroalkyl, and optionally substituted $C_1$-$C_4$ heterohaloalkyl. In certain embodiments, $R^{11}$ is selected from an optionally substituted ring. In certain such embodiments, $R^{11}$ is selected from an optionally substituted carbocycle, an optionally substituted heterocycle, and optionally substituted aromatic, and an optionally substituted non-aromatic ring. In certain such embodiments, $R^{11}$ is selected from an optionally substituted aryl, an optionally substituted heteroaryl, an optionally substituted alicyclic, and an optionally substituted non-aromatic heterocyclic. In certain embodiments, $R^{11}$ is selected from an optionally substituted aryl and an optionally substituted heteroaryl. In certain embodiments, $R^{11}$ is selected from an optionally substituted aryl. In certain embodiments, $R^{11}$ is an aryl.

In some embodiments, $R^{12}$ and $R^{13}$ are each independently selected from hydrogen, optionally substituted $C_1$-$C_4$ aliphatic, optionally substituted $C_1$-$C_4$ haloaliphatic, optionally substituted $C_1$-$C_4$ heteroaliphatic, optionally substituted $C_1$-$C_4$ heterohaloaliphatic, an optionally substituted ring, and $(CH_2)_m R^{14}$. In certain such embodiments, $R^{12}$ and/or $R^{13}$ is independently selected from optionally substituted $C_1$-$C_4$ alkyl, optionally substituted $C_1$-$C_4$ haloalkyl, optionally substituted $C_1$-$C_4$ heteroalkyl, and optionally substituted $C_1$-$C_4$ heterohaloalkyl. In certain embodiments, $R^{12}$ and/or $R^{13}$ is selected from an optionally substituted carbocycle, an optionally substituted heterocycle, and optionally substituted aromatic, and an optionally substituted non-aromatic ring. In certain such embodiments, $R^{12}$ and/or $R^{13}$ is selected from an optionally substituted aryl, an optionally substituted heteroaryl, an optionally substituted alicyclic, and an optionally substituted non-aromatic heterocyclic. In certain embodiments, $R^{12}$ and/or $R^{13}$ is selected from an optionally substituted aryl and an optionally substituted heteroaryl. In certain embodiments, $R^{12}$ and/or $R^{13}$ is selected from an optionally substituted aryl. In certain embodiments, $R^{12}$ and/or $R^{13}$ is an aryl. In certain embodiments, one of $R^{12}$ or $R^{13}$ is a ring and the other of $R^{12}$ and $R^{13}$ is hydrogen.

In certain embodiments, $R^{12}$ and $R^{13}$ are linked to form an optionally substituted $C_2$-$C_8$ heterocycle. In certain embodiments, $R^{12}$ and $R^{13}$ are linked to form an optionally substituted $C_2$-$C_8$ heteroaryl. In certain embodiments, $R^{12}$ and $R^{13}$ are linked to form an optionally substituted $C_2$-$C_8$ non-aromatic heterocycle.

In certain embodiments, $R^{14}$ is selected from an optionally substituted ring. In certain such embodiments, $R^{14}$ is selected from an optionally substituted carbocycle, an optionally substituted heterocycle, and optionally substituted aromatic, and an optionally substituted non-aromatic ring. In certain such embodiments, $R^{14}$ is selected from an optionally substituted aryl, an optionally substituted heteroaryl, an optionally substituted alicyclic, and an optionally substituted non-aromatic heterocyclic. In certain embodiments, $R^{14}$ is selected from an optionally substituted aryl and an optionally substituted heteroaryl. In certain embodiments, $R^{14}$ is selected from an optionally substituted aryl. In certain embodiments, $R^{14}$ is an aryl.

In certain embodiments, $R^{15}$ is selected from hydrogen, optionally substituted $C_1$-$C_3$ aliphatic, optionally substituted $C_1$-$C_3$ haloaliphatic, and optionally substituted ring. In certain such embodiments, $R^{15}$ is selected from optionally substituted $C_1$-$C_3$ alkyl, and optionally substituted $C_1$-$C_3$ haloalkyl. In certain embodiments, $R^{15}$ is an optionally substituted aryl. In certain embodiments, $R^{15}$ is selected from an alkyl, a haloalkyl, an alicyclic, and an aryl. In certain embodiments, $R^{15}$ is selected from an optionally substituted ring. In certain such embodiments, $R^{15}$ is selected from an optionally substituted carbocycle, an optionally substituted heterocycle, and optionally substituted aromatic, and an optionally substituted non-aromatic ring. In certain such embodiments, $R^{15}$ is selected from an optionally substituted aryl, an optionally substituted heteroaryl, an optionally substituted alicyclic, and an optionally substituted non-aromatic heterocyclic. In certain embodiments, $R^{15}$ is selected from an optionally substituted aryl and an optionally substituted heteroaryl. In certain embodiments, $R^{15}$ is selected from an optionally substituted aryl. In certain embodiments, $R^{15}$ is an aryl.

In certain embodiments, Y is a 1, 2, 3, 4, 5, 7, or 8 atom spacer. In certain embodiments, Y is a 1-4 atom spacer selected from optionally substituted $C_1$-$C_6$ aliphatic and optionally substituted $C_1$-$C_6$ heteroaliphatic. In certain such embodiments, Y is a 1-4 atom spacer selected from optionally substituted $C_1$-$C_6$ alkyl, optionally substituted $C_1$-$C_6$ heteroalkyl, optionally substituted $C_2$-$C_6$ alkenyl, and optionally substituted $C_2$-$C_6$ heteroalkenyl.

In certain embodiments, Y is a 1-4 atom spacer comprising a ring. In certain such embodiments, Y is selected from optionally substituted phenyl, optionally substituted monocyclic heteroaryl, optionally substituted $C_3$-$C_5$ heterocycle, and optionally substituted alicyclic, including, but not limited to, optionally substituted cycloalkyl and optionally substituted cycloalkenyl.

In certain embodiments, Y is a 2-6 atom spacer comprising both (1) a ring selected from optionally substituted phenyl, optionally substituted monocyclic heteroaryl, optionally substituted $C_3$-$C_5$ heterocycle, and optionally substituted alicyclic and (2) 1-4 atoms selected from optionally substituted $C_1$-$C_6$ aliphatic, and optionally substituted $C_1$-$C_6$ heteroaliphatic.

In certain embodiments, Y is not —N=$CR^6$— orientated to form the dihydropyrazole. Thus, in such embodiments, the ring that includes Y cannot be:

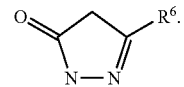

In certain embodiments, Y is selected from:

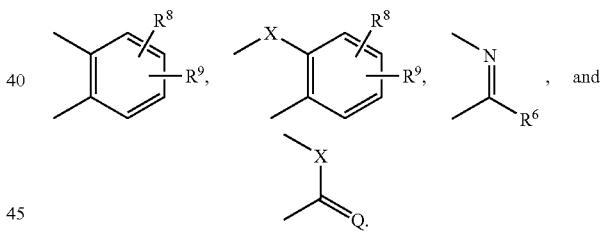

In certain embodiments, Q is selected from O and S.

In certain embodiments, X is selected from O, S, $NR^{10}$, and $CR^{10}R^{10}$;

In certain embodiments, Z is a 1 to 5 atom spacer. In certain embodiments, Z is a 2-5 atom spacer selected from an optionally substituted $C_6$-$C_{10}$ aryl and an optionally substituted $C_1$-$C_8$ heteroaryl. In certain embodiments, Z is a 1-5 atom spacer selected from an optionally substituted $C_1$-$C_6$ alkyl, an optionally substituted $C_1$-$C_6$ heteroalkyl, an optionally substituted $C_1$-$C_6$ haloalkyl, an optionally substituted $C_2$-$C_6$ alkenyl, an optionally substituted $C_2$-$C_6$ heteroalkenyl, an optionally substituted $C_2$-$C_6$ haloalkenyl, an optionally substituted $C_2$-$C_6$ alkynyl, and an optionally substituted $C_2$-$C_6$ heteroalkyl.

In certain embodiments, m is 0, 1, or 2.

In certain embodiments, n is 0 or 1. In embodiments in which n is 0, $R^1$ binds directly to Z and $R^2$ and/or $R^3$ are null, as appropriate. For example, if Z is a phenyl ring and n is 0, then $R^1$ binds directly to the phenyl ring and both $R^1$ and $R^2$ are null.

In embodiments in which two or more of a particular group are present, the identities of those two or more particular groups are selected independently and, thus, may be the same or different from one another. For example, certain compounds of the invention comprise two or more $R^{14}$ groups. The identities of those two or more $R^{14}$ groups are each selected independently. Thus, in certain embodiments, those $R^{14}$ groups are all the same as one another; in certain embodiments, those $R^{14}$ groups are all different from one another; and in certain embodiments, some of those $R^{14}$ groups are the same as one another and some are different from one another. This independent selection applies to any group that is present in a compound more than once.

One of ordinary skill in the art will recognize that the complete lists of possible identities for each above-listed group (all R groups, Y, Q, Z, m, and n) may be narrowed to provide shorter lists of possible identities. For example, since in certain embodiments $R^1$ is selected from hydrogen, $CO_2R^{10}$, $CONR^{10}R^{11}$, $SO_3R^{10}$, and a carboxylic acid bioisostere, it is to be understood that in certain embodiments, $R^1$ may be selected from $CO_2R^{10}$, $CONR^{10}R^{11}$, and $SO_3R^{10}$, because each of those possible identities is included on the longer list of possible identities. One of ordinary skill in the art will also recognize that broader terms include combinations of narrower terms, which may be substituted and selected. For example, in certain embodiments, $R^2$ is selected from an optionally substituted $C_1$-$C_4$ aliphatic. Because aliphatics include, but are not limited to, alkyls and alkenes, in certain embodiments, $R^2$ may be selected from an optionally substituted $C_1$-$C_4$ alkyl and an optionally substituted $C_1$-$C_4$ alkenyl. Similarly, in certain embodiments, $R^2$ is selected from an optionally substituted $C_2$-$C_3$ alkyl and an optionally substituted $C_2$-$C_4$ alkenyl, because those alkyls and alkenyls are included in the definition of $C_1$-$C_4$ aliphatics.

One of ordinary skill in the art will also understand that the above listed groups may be selected in any combination. For example, in certain embodiments, $R^1$ is selected from hydrogen, $CO_2R^{10}$, $CONR^{10}R^{11}$, $SO_3R^{10}$, and a carboxylic acid bioisostere; and $R^2$ is selected from hydrogen, $OR^{12}$, $NR^{12}R^{13}$, an optionally substituted $C_1$-$C_4$ aliphatic, an optionally substituted $C_1$-$C_4$ haloaliphatic, an optionally substituted $C_1$-$C_4$ heteroaliphatic, $(CH_2)_mR^{14}$, an optionally substituted ring, and null. Therefore, in certain embodiments, $R^1$ may be selected from hydrogen, and $CO_2R^{10}$; and at the same time $R^2$ may be selected from hydrogen, $OR^{12}$, $NR^{12}R^{13}$, and an optionally substituted $C_1$-$C_4$ aliphatic, because those lists of possible identities are included within the previous lists of possible identities. Such selection of combinations are included for all groups herein.

In certain embodiments, a compound of Formula I, II, or III is a selective TPO modulator. In certain embodiments, a compound of Formula I, II, or III is a selective TPO receptor agonist. In certain embodiments, a compound of Formula I, II, or III is a selective TPO receptor antagonist. In certain embodiments, a compound of Formula I, II, or III is a selective TPO receptor partial agonist. In certain embodiments, a compound of Formula I, II, or III is a tissue-specific selective TPO modulator. In certain embodiments, a compound of Formula I, II, or III is a selective TPO receptor binding compound. In certain embodiments, a compound of Formula I, II, or III is a TPO mimic.

In certain embodiments, the invention provides compounds including, but not limited to:

3'-{N'-[1-(3,4-Dimethyl-phenyl)-2-oxo-1,2-dihydro-indol-3-ylidene]-hydrazino}-2'-hydroxy-biphenyl-3-carboxylic acid (Compound 101);

2'-Hydroxy-3'-{N'-[2-oxo-1-(4-propyl-phenyl)-1,2-dihydro-indol-3-ylidene]-hydrazino}-biphenyl-3-carboxylic acid (Compound 102);

2'-Hydroxy-3'-{N'-[2-oxo-1-(4-ethyl-phenyl)-1,2-dihydro-indol-3-ylidene]-hydrazino}-biphenyl-3-carboxylic acid (Compound 103);

2'-Hydroxy-3'-{N'-[2-oxo-1-(4-trifluoromethoxy-phenyl)-1,2-dihydro-indol-3-ylidene]-hydrazino}-biphenyl-3-carboxylic acid (Compound 104);

3'-{N'-[1-(3-Fluoro-4-methoxy-phenyl)-2-oxo-1,2-dihydro-indol-3-ylidene]-hydrazino}-2'-hydroxy-biphenyl-3-carboxylic acid (Compound 105);

3'-{N'-[1-(3,4-Dimethyl-phenyl)-2-oxo-1,2-dihydro-indol-3-ylidene]-hydrazino}-2'-hydroxy-biphenyl-4-carboxylic acid (Compound 106);

2'-Hydroxy-3'-{N'-[2-oxo-1-(4-propyl-phenyl)-1,2-dihydro-indol-3-ylidene]-hydrazino}-biphenyl-4-carboxylic acid (Compound 107);

2'-Hydroxy-3'-{N'-[2-oxo-1-(4-ethyl-phenyl)-1,2-dihydro-indol-3-ylidene]-hydrazino}-biphenyl-4-carboxylic acid (Compound 108);

3'-{N'-[1-(4-tert-Butyl-phenyl)-2-oxo-1,2-dihydro-indol-3-ylidene]-hydrazino}-2'-hydroxy-biphenyl-3-carboxylic acid (Compound 109);

2'-Hydroxy-3'-{N'-[2-oxo-1-(4-trifluoromethyl-phenyl)-1,2-dihydro-indol-3-ylidene]-hydrazino}-biphenyl-3-carboxylic acid (Compound 110);

3'-[N'-(1-Benzyl-5-chloro-2-oxo-1,2-dihydro-indol-3-ylidene)-hydrazino]-2'-hydroxy-biphenyl-3-carboxylic acid (Compound 111);

3'-[N'-(1-Benzyl-5-methyl-2-oxo-1,2-dihydro-indol-3-ylidene)-hydrazino]-2'-hydroxy-biphenyl-3-carboxylic acid (Compound 112);

3'-[N'-(1-Benzyl-2-oxo-1,2-dihydro-indol-3-ylidene)-hydrazino]-2'-hydroxy-biphenyl-3-carboxylic acid (Compound 113);

2'-Hydroxy-3'-{N'-[2-oxo-1-(4-trifluoromethyl-phenyl)-1,2-dihydro-indol-3-ylidene]-hydrazino}-biphenyl-4-carboxylic acid (Compound 114);

3'-{N'-[1-(3,4-Dichloro-phenyl)-2-oxo-1,2-dihydro-indol-3-ylidene]-hydrazino}-2'-hydroxy-biphenyl-3-carboxylic acid (Compound 115);

2'-Hydroxy-3'-{N'-[1-(4-methyl-3-trifluoromethyl-phenyl)-2-oxo-1,2-dihydro-indol-3-ylidene]-hydrazino}-biphenyl-3-carboxylic acid (Compound 116);

3'-{N'-[1-(3-Fluoro-4-trifluoromethyl-phenyl)-2-oxo-1,2-dihydro-indol-3-ylidene]-hydrazino}-2'-hydroxy-biphenyl-3-carboxylic acid (Compound 117);

3'-{N'-[1-(3,5-Bis-trifluoromethyl-phenyl)-2-oxo-1,2-dihydro-indol-3-ylidene]-hydrazino}-2'-hydroxy-biphenyl-3-carboxylic acid (Compound 118);

3'-{N'-[3-(3,4-Dimethyl-phenyl)-4-oxo-2-thioxo-thiazolidin-5-ylidene]-hydrazino}-2'-hydroxy-biphenyl-3-carboxylic acid (Compound 119);

2'-Hydroxy-3'-{N'-[1-(4-isopropyl-phenyl)-2-oxo-1,2-dihydro-indol-3-ylidene]-hydrazino}-biphenyl-3-carboxylic acid (Compound 120);

3'-{N'-[1-(2-Fluoro-4-trifluoromethyl-phenyl)-2-oxo-1,2-dihydro-indol-3-ylidene]-hydrazino}-2'-hydroxy-biphenyl-3-carboxylic acid (Compound 121);

3'-{N'-[1-(2-Fluoro-4-methyl-phenyl)-2-oxo-1,2-dihydro-indol-3-ylidene]-hydrazino}-2'-hydroxy-biphenyl-3-carboxylic acid (Compound 122);

3'-{N'-[1-(4-Chloro-3-trifluoromethyl-phenyl)-2-oxo-1,2-dihydro-indol-3-ylidene]-hydrazino}-2'-hydroxy-biphenyl-3-carboxylic acid (Compound 123);

3'-{N'-[1-(4-Butyl-phenyl)-2-oxo-1,2-dihydro-indol-3-ylidene]-hydrazino}-2'-hydroxy-biphenyl-3-carboxylic acid (Compound 124);

3'-{N'-[1-(3-Fluoro-phenyl)-2-oxo-1,2-dihydro-indol-3-ylidene]-hydrazino}-2'-hydroxy-biphenyl-3-carboxylic acid (Compound 125);

2'-Hydroxy-3'-[N'-(2-oxo-1-m-tolyl-1,2-dihydro-indol-3-ylidene)-hydrazino]-biphenyl-3-carboxylic acid (Compound 126);

3'-{N'-[1-(4-Fluoro-phenyl)-2-oxo-1,2-dihydro-indol-3-ylidene]-hydrazino}-2'-hydroxy-biphenyl-3-carboxylic acid (Compound 127);

3'-[N'-(1-Benzyl-5-methoxy-2-oxo-1,2-dihydro-indol-3-ylidene)-hydrazino]-2'-hydroxy-biphenyl-3-carboxylic acid (Compound 128);

2'-Hydroxy-3'-{N'-[2-oxo-1-(3-trifluoromethyl-phenyl)-1,2-dihydro-indol-3-ylidene]-hydrazino}-biphenyl-3-carboxylic acid (Compound 129);

3'-{N'-[5-Chloro-1-(4-isopropyl-phenyl)-2-oxo-1,2-dihydro-indol-3-ylidene]-hydrazino}-2'-hydroxy-biphenyl-3-carboxylic acid (Compound 130);

3'-{N'-[6-Chloro-1-(4-isopropyl-phenyl)-2-oxo-1,2-dihydro-indol-3-ylidene]-hydrazino}-2'-hydroxy-biphenyl-3-carboxylic acid (Compound 131);

3'-{N'-[5-Fluoro-1-(4-isopropyl-phenyl)-2-oxo-1,2-dihydro-indol-3-ylidene]-hydrazino}-2'-hydroxy-biphenyl-3-carboxylic acid (Compound 132);

3'-{N'-[5-Methoxy-1-(4-isopropyl-phenyl)-2-oxo-1,2-dihydro-indol-3-ylidene]-hydrazino}-2'-hydroxy-biphenyl-3-carboxylic acid (Compound 133);

3'-{N'-[1-(3,4-Dimethyl-phenyl)-5-fluoro-2-oxo-1,2-dihydro-indol-3-ylidene]-hydrazino}-2'-hydroxy-biphenyl-3-carboxylic acid (Compound 134);

3'-{N'-[1-(4-Fluoro-3-trifluoromethyl-phenyl)-5-fluoro-2-oxo-1,2-dihydro-indol-3-ylidene]-hydrazino}-2'-hydroxy-biphenyl-3-carboxylic acid (Compound 135);

3'-{N'-[1-(3,5-Dichloro-phenyl)-5-fluoro-2-oxo-1,2-dihydro-indol-3-ylidene]-hydrazino}-2'-hydroxy-biphenyl-3-carboxylic acid (Compound 136);

3'-{N'-[1-(4-Propyl-phenyl)-6-chloro-2-oxo-1,2-dihydro-indol-3-ylidene]-hydrazino}-2'-hydroxy-biphenyl-3-carboxylic acid (Compound 137); and a pharmaceutically acceptable salt, ester, amide, or prodrug of any of those compounds. In certain embodiments, such compounds are selective TPO modulators.

In certain embodiments, the invention provides compounds including, but not limited to:

(±)-2'-Hydroxy-3'-(N'-{2-oxo-1-[4-(2,2,2-trifluoro-1-hydroxy-ethyl)-phenyl]-1,2-dihydro-indol-3-ylidene}-hydrazino)-biphenyl-3-carboxylic acid (Compound 138);

(±)-2'-Hydroxy-3'-(N'-{2-oxo-1-[4-(2,2,2-trifluoro-1-methoxy-ethyl)-phenyl]-1,2-dihydro-indol-3-ylidene}-hydrazino)-biphenyl-3-carboxylic acid (Compound 139);

2'-Hydroxy-3'-(N'-{2-oxo-1-[4-(2,2,2-trifluoro-ethyl)-phenyl]-1,2-dihydro-indol-3-ylidene}-hydrazino)-biphenyl-3-carboxylic acid (Compound 140);

3'-{N'-[1-(3,4-Dimethyl-phenyl)-4,5-dimethyl-2-oxo-1,2-dihydro-indol-3-ylidene]-hydrazino}-2'-hydroxy-biphenyl-3-carboxylic acid (Compound 141);

3'-{N'-[1-(3,4-Dimethyl-phenyl)-5-fluoro-4-methyl-2-oxo-1,2-dihydro-indol-3-ylidene]-hydrazino}-2'-hydroxy-biphenyl-3-carboxylic acid (Compound 142);

3'-{N'-[1-(3,4-Dimethyl-phenyl)-5-fluoro-6-methyl-2-oxo-1,2-dihydro-indol-3-ylidene]-hydrazino}-2'-hydroxy-biphenyl-3-carboxylic acid (Compound 143);

5-(4-{N'-[1-(3,4-Dimethyl-phenyl)-2-oxo-6-trifluoromethyl-1,2-dihydro-indol-3-ylidene]-hydrazino}-3-hydroxy-benzylidene)-thiazolidine-2,4-dione (Compound 144);

5-(4-{N'-[1-(3,4-Dimethyl-phenyl)-2-oxo-1,2-dihydro-indol-3-ylidene]-hydrazino}-3-hydroxy-benzylidene)-thiazolidine-2,4-dione (Compound 145);

3'-{N'-[1-(3,4-Dimethyl-phenyl)-4-fluoro-2-oxo-6-trifluoromethyl-1,2-dihydro-indol-3-ylidene]-hydrazino}-2'-hydroxy-biphenyl-3-carboxylic acid (Compound 146);

3'-{N'-[4-Chloro-1-(3,4-dimethyl-phenyl)-2-oxo-6-trifluoromethyl-1,2-dihydro-indol-3-ylidene]-hydrazino}-2'-hydroxy-biphenyl-3-carboxylic acid (Compound 147);

5-(4-{N'-[1-(3,4-Dimethyl-phenyl)-4-fluoro-2-oxo-6-trifluoromethyl-1,2-dihydro-indol-3-ylidene]-hydrazino}-3-hydroxy-benzylidene)-thiazolidine-2,4-dione (Compound 148);

5-(4-{N'-[4-Chloro-1-(3,4-dimethyl-phenyl)-2-oxo-6-trifluoromethyl-1,2-dihydro-indol-3-ylidene]-hydrazino}-3-hydroxy-benzylidene)-thiazolidine-2,4-dione (Compound 149);

3-(4-{N'-[1-(3,4-Dimethyl-phenyl)-2-oxo-6-trifluoromethyl-1,2-dihydro-indol-3-ylidene]-hydrazino}-3-hydroxy-phenyl)-acrylic acid (Compound 150);

1-(3,4-Dimethyl-phenyl)-3-{[2-hydroxy-4-(4-oxo-2-thioxo-thiazolidin-5-ylidenemethyl)-phenyl]-hydrazono}-6-trifluoromethyl-1,3-dihydro-indol-2-one (Compound 151);

1-(3,4-Dimethyl-phenyl)-4-fluoro-3-{[2-hydroxy-4-(4-oxo-2-thioxo-thiazolidin-5-ylidenemethyl)-phenyl]-hydrazono}-6-trifluoromethyl-1,3-dihydro-indol-2-one (Compound 152);

5-(3-{N-[1-(3,4-Dimethyl-phenyl)-2-oxo-6-trifluoromethyl-1,2-dihydro-indol-3-ylidene]-hydrazino}-2-hydroxy-benzylidene)-thiazolidine-2,4-dione (Compound 153);

3'-{N'-[5-Chloro-2-oxo-1-(4-propyl-phenyl)-1,2-dihydro-indol-3-ylidene]-hydrazino}-2'-hydroxy-biphenyl-3-carboxylic acid (Compound 154);

2'-Hydroxy-3'-{N'-[1-(4-methylsulfanyl-phenyl)-2-oxo-1,2-dihydro-indol-3-ylidene]-hydrazino}-biphenyl-3-carboxylic acid (Compound 155);

2'-Hydroxy-3'-{N'-[1-(4-methoxymethyl-phenyl)-2-oxo-1,2-dihydro-indol-3-ylidene]-hydrazino}-biphenyl-3-carboxylic acid (Compound 156);

(±)-2'-Hydroxy-3'-(N'-{2-oxo-1-[4-(2,2,2-trifluoro-1-hydroxy-1-methyl-ethyl)-phenyl]-1,2-dihydro-indol-3-ylidene}-hydrazino)-biphenyl-3-carboxylic acid (Compound 157);

3'-{N'-[5-Fluoro-1-(4-methyl-3-trifluoromethyl-phenyl)-2-oxo-1,2-dihydro-indol-3-ylidene]-hydrazino}-2'-hydroxy-biphenyl-3-carboxylic acid (Compound 158);

2'-Hydroxy-3'-(N'-{2-oxo-1-[4-(2,2,2-trifluoro-1-methoxy-1-methyl-ethyl)-phenyl]-1,2-dihydro-indol-3-ylidene}-hydrazino)-biphenyl-3-carboxylic acid (Compound 159);

3'-{N'-[1-(3,4-Dimethyl-phenyl)-6-fluoro-2-oxo-1,2-dihydro-indol-3-ylidene]-hydrazino}-2'-hydroxy-biphenyl-3-carboxylic acid (Compound 160);

3'-{N'-[6-Fluoro-1-(4-isopropyl-phenyl)-2-oxo-1,2-dihydro-indol-3-ylidene]-hydrazino}-2'-hydroxy-biphenyl-3-carboxylic acid (Compound 161);

3'-{N'-[1-(3,4-Dimethyl-phenyl)-2-oxo-5-trifluoromethyl-1,2-dihydro-indol-3-ylidene]-hydrazino}-2'-hydroxy-biphenyl-3-carboxylic acid (Compound 162);

3'-{N'-[6-Fluoro-2-oxo-1-(4-propyl-phenyl)-1,2-dihydro-indol-3-ylidene]-hydrazino}-2'-hydroxy-biphenyl-3-carboxylic acid (Compound 163);

2'-Hydroxy-3'-{N'-[2-oxo-1-(4-propyl-phenyl)-5-trifluoromethyl-1,2-dihydro-indol-3-ylidene]-hydrazino}-biphenyl-3-carboxylic acid (Compound 164);

3'-{N'-[4,5-Difluoro-1-(4-isopropyl-phenyl)-2-oxo-1,2-dihydro-indol-3-ylidene]-hydrazino}-2'-hydroxy-biphenyl-3-carboxylic acid (Compound 165);

2'-Hydroxy-3'-[N'-(2-oxo-1-piperidin-4-yl-1,2-dihydro-indol-3-ylidene)-hydrazino]-biphenyl-3-carboxylic acid (Compound 166);

3'-{N'-[5-Fluoro-1-(2-fluoro-4-methyl-phenyl)-2-oxo-1,2-dihydro-indol-3-ylidene]-hydrazino}-2'-hydroxy-biphenyl-3-carboxylic acid (Compound 167);

2'-Hydroxy-3'-[N'-(1-methyl-2-oxo-1,2-dihydro-indol-3-ylidene)-hydrazino]-biphenyl-3-carboxylic acid (Compound 168);

3'-[N'-(1-Cyclopentyl-2-oxo-1,2-dihydro-indol-3-ylidene)-hydrazino]-2'-hydroxy-biphenyl-3-carboxylic acid (Compound 169);

3'-{N'-[1-(3,4-Dimethyl-phenyl)-6-methyl-2-oxo-1,2-dihydro-indol-3-ylidene]-hydrazino}-2'-hydroxy-biphenyl-3-carboxylic acid (Compound 170);

2'-Hydroxy-3'-[N'-(2-oxo-1-phenyl-1,2-dihydro-indol-3-ylidene)-hydrazino]-biphenyl-3-carboxylic acid (Compound 171);

3'-[N'-(6-Fluoro-2-oxo-1-phenyl-2,3-dihydro-1H-indol-3-yl)-hydrazino]-2'-hydroxy-biphenyl-3-carboxylic acid (Compound 172);

3'-{N'-[1-(3,4-Dimethyl-phenyl)-6-isopropyl-2-oxo-1,2-dihydro-indol-3-ylidene]-hydrazino}-2'-hydroxy-biphenyl-3-carboxylic acid (Compound 173);

3'-{N'-[1-(3,4-Dimethyl-phenyl)-4-isopropyl-2-oxo-1,2-dihydro-indol-3-ylidene]-hydrazino}-2'-hydroxy-biphenyl-3-carboxylic acid (Compound 174);

3'-{N'-[1-(3,4-Dimethyl-phenyl)-2-oxo-6-trifluoromethyl-1,2-dihydro-indol-3-ylidene]-hydrazino}-4-fluoro-2'-hydroxy-biphenyl-3-carboxylic acid (Compound 175);

5'-Chloro-3'-{N'-[1-(3,4-dimethyl-phenyl)-2-oxo-6-trifluoromethyl-1,2-dihydro-indol-3-ylidene]-hydrazino}-4-fluoro-2'-hydroxy-biphenyl-3-carboxylic acid (Compound 176);

3'-{N'-[1-(3,4-Dimethyl-phenyl)-2-oxo-6-trifluoromethyl-1,2-dihydro-indol-3-ylidene]-hydrazino}-6-fluoro-2'-hydroxy-biphenyl-3-carboxylic acid (Compound 177);

3'-{N'-[1-(3,4-Dimethyl-phenyl)-4,5-difluoro-2-oxo-1,2-dihydro-indol-3-ylidene]-hydrazino}-2'-hydroxy-biphenyl-3-carboxylic acid (Compound 178);

3'-{N'-[1-(3,4-Dimethyl-phenyl)-2-oxo-6-trifluoromethyl-1,2-dihydro-indol-3-ylidene]-hydrazino}-2'-hydroxy-3-methyl-biphenyl-4-carboxylic acid (Compound 179);

3'-{N'-[1-(3,4-Dimethyl-phenyl)-2-oxo-6-trifluoromethyl-2,3-dihydro-1H-indol-3-yl]-hydrazino}-2-fluoro-2'-hydroxy-biphenyl-4-carboxylic acid (Compound 180);

3'-{N'-[1-(3,4-Dimethyl-phenyl)-4-fluoro-2-oxo-6-trifluoromethyl-2,3-dihydro-1H-indol-3-yl]-hydrazino}-4-fluoro-2'-hydroxy-biphenyl-3-carboxylic acid (Compound 181);

5'-Chloro-3'-{N'-[1-(3,4-dimethyl-phenyl)-4-fluoro-2-oxo-6-trifluoromethyl-1,2-dihydro-indol-3-ylidene]-hydrazino}-4-fluoro-2'-hydroxy-biphenyl-3-carboxylic acid (Compound 182);

3-[(3'-Carboxy-2-hydroxy-biphenyl-3-yl)-hydrazono]-1-(3,5-dimethyl-phenyl)-2-oxo-2,3-dihydro-1H-indole-6-carboxylic acid methyl ester (Compound 183);

3-[(3'-Carboxy-4'-fluoro-2-hydroxy-biphenyl-3-yl)-hydrazono]-1-(3,5-dimethyl-phenyl)-2-oxo-2,3-dihydro-1H-indole-6-carboxylic acid methyl ester (Compound 184);

3-[(3'-Carboxy-4'-fluoro-2-hydroxy-biphenyl-3-yl)-hydrazono]-1-(3,4-dimethyl-phenyl)-2-oxo-2,3-dihydro-1H-indole-6-carboxylic acid methyl ester (Compound 185);

3-[(3'-Carboxy-5-chloro-4'-fluoro-2-hydroxy-biphenyl-3-yl)-hydrazono]-1-(3,5-dimethyl-phenyl)-2-oxo-2,3-dihydro-1H-indole-6-carboxylic acid methyl ester (Compound 186);

3'-{N'-[1-(2-Cyano-thiophen-3-yl)-2-oxo-1,2-dihydro-indol-3-ylidene]-hydrazino}-2'-hydroxy-biphenyl-3-carboxylic acid (Compound 187);

2'-Hydroxy-3'-[N'-(2-oxo-1-thiophen-3-yl-1,2-dihydro-indol-3-ylidene)-hydrazino]-biphenyl-3-carboxylic acid (Compound 188);

3-[(3'-Carboxy-2-hydroxy-biphenyl-3-yl)-hydrazono]-1-(3,4-dimethyl-phenyl)-2-oxo-2,3-dihydro-1H-indole-6-carboxylic acid methyl ester (Compound 189);

3'-{N'-[1-(4-Chloro-3-trifluoromethyl-phenyl)-6-cyano-2-oxo-1,2-dihydro-indol-3-ylidene]-hydrazino}-2'-hydroxy-biphenyl-3-carboxylic acid (Compound 190);

5'-Chloro-3'-{N'-[6-cyano-1-(4-isopropyl-phenyl)-2-oxo-1,2-dihydro-indol-3-ylidene]-hydrazino}-4-fluoro-2'-hydroxy-biphenyl-3-carboxylic acid (Compound 191);

3'-{N'-[6-Cyano-1-(4-isopropyl-phenyl)-2-oxo-1,2-dihydro-indol-3-ylidene]-hydrazino}-4-fluoro-2'-hydroxy-biphenyl-3-carboxylic acid (Compound 192);

(±)-1-(3,4-Dimethyl-phenyl)-3-{[2-hydroxy-3'-(2,2,2-trifluoro-1-hydroxy-ethyl)-biphenyl-3-yl]-hydrazono}-6-methanesulfonyl-1,3-dihydro-indol-2-one (Compound 193);

3'-{N'-[6-Cyano-1-(4-isopropyl-phenyl)-2-oxo-1,2-dihydro-indol-3-ylidene]-hydrazino}-2'-hydroxy-biphenyl-3-carboxylic acid (Compound 194);

3'-{N'-[1-(3,4-Dimethyl-phenyl)-5-nitro-2-oxo-1,2-dihydro-indol-3-ylidene]-hydrazino}-2'-hydroxy-biphenyl-3-carboxylic acid (Compound 195);

3'-{N'-[1-(3,4-Dimethyl-phenyl)-6-methanesulfonyl-2-oxo-1,2-dihydro-indol-3-ylidene]-hydrazino}-2'-hydroxy-biphenyl-3-carboxylic acid (Compound 196);

3'-{N'-[6-Cyano-1-(3,4-dimethyl-phenyl)-2-oxo-1,2-dihydro-indol-3-ylidene]-hydrazino}-2'-hydroxy-biphenyl-3-carboxylic acid (Compound 197);

3'-{N'-[1-(5-Cyano-pyridin-3-yl)-2-oxo-1,2-dihydro-indol-3-ylidene]-hydrazino}-2'-hydroxy-biphenyl-3-carboxylic acid (Compound 198);

3'-[N'-(1-Furan-3-yl-2-oxo-1,2-dihydro-indol-3-ylidene)-hydrazino]-2'-hydroxy-biphenyl-3-carboxylic acid (Compound 199);

3'-[N'-(1-Benzo[1,3]dioxol-5-yl-2-oxo-1,2-dihydro-indol-3-ylidene)-hydrazino]-2'-hydroxy-biphenyl-3-carboxylic acid (Compound 200);

2'-Hydroxy-3'-{N'-[1-(3-methyl-thiophen-2-yl)-2-oxo-1,2-dihydro-indol-3-ylidene]-hydrazino}-biphenyl-3-carboxylic acid (Compound 201);

2'-Hydroxy-3'-[N'-(2-oxo-1-thiophen-2-yl-1,2-dihydro-indol-3-ylidene)-hydrazino]-biphenyl-3-carboxylic acid (Compound 202);

2'-Hydroxy-3'-{N'-[1-(4-isopropyl-phenyl)-2-oxo-6-trifluoromethyl-1,2-dihydro-indol-3-ylidene]-hydrazino}-biphenyl-3-carboxylic acid (Compound 203);

2'-Hydroxy-3'-{N'-[2-oxo-1-(4-propyl-phenyl)-6-trifluoromethyl-1,2-dihydro-indol-3-ylidene]-hydrazino}-biphenyl-3-carboxylic acid (Compound 204);

3'-{N'-[1-(4-Ethyl-phenyl)-5,7-difluoro-2-oxo-1,2-dihydro-indol-3-ylidene]-hydrazino}-2'-hydroxy-biphenyl-3-carboxylic acid (Compound 205);

3'-{N'-[1-(3,4-Dimethyl-phenyl)-5,7-difluoro-2-oxo-1,2-dihydro-indol-3-ylidene]-hydrazino}-2'-hydroxy-biphenyl-3-carboxylic acid (Compound 206);

3'-{N'-[5,7-Difluoro-2-oxo-1-(4-propyl-phenyl)-1,2-dihydro-indol-3-ylidene]-hydrazino}-2'-hydroxy-biphenyl-3-carboxylic acid (Compound 207);

3'-{N'-[5,7-Difluoro-1-(4-isopropyl-phenyl)-2-oxo-1,2-dihydro-indol-3-ylidene]-hydrazino}-2'-hydroxy-biphenyl-3-carboxylic acid (Compound 208);

3'-{N'-[1-(3,4-Dimethyl-phenyl)-2-oxo-6-trifluoromethyl-1,2-dihydro-indol-3-ylidene]-hydrazino}-2'-hydroxy-biphenyl-3-carboxylic acid (Compound 209);

3'-{N'-[1-(3,4-Dimethyl-phenyl)-6-ethyl-2-oxo-1,2-dihydro-indol-3-ylidene]-hydrazino}-2'-hydroxy-biphenyl-3-carboxylic acid (Compound 210);

3'-{N'-[1-(3,4-Dimethyl-phenyl)-6-methoxy-2-oxo-1,2-dihydro-indol-3-ylidene]-hydrazino}-2'-hydroxy-biphenyl-3-carboxylic acid (Compound 211);

3'-{N'-[5-Chloro-1-(3,4-dimethyl-phenyl)-2-oxo-6-trifluoromethyl-1,2-dihydro-indol-3-ylidene]-hydrazino}-2'-hydroxy-biphenyl-3-carboxylic acid (Compound 212);

3'-{N'-[1-(3,4-Dimethyl-phenyl)-6,7-dimethyl-2-oxo-1,2-dihydro-indol-3-ylidene]-hydrazino}-2'-hydroxy-biphenyl-3-carboxylic acid (Compound 213);

2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-2-methyl-propionic acid (Compound 214);

(−)-2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-propionic acid (Compound 215) and (+)-2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-propionic acid (Compound 215a);

(±)-(3'-{N'-[1-(3,4-Dimethyl-phenyl)-2-oxo-6-trifluoromethyl-1,2-dihydro-indol-3-ylidene]-hydrazino}-2'-hydroxy-5'-methyl-biphenyl-4-yl)-propionic acid (Compound 216);

(±)-2-(3'-{N'-[1-(3,4-Dimethyl-phenyl)-2-oxo-6-trifluoromethyl-1,2-dihydro-indol-3-ylidene]-hydrazino}-5'-fluoro-2'-hydroxy-biphenyl-4-yl)-propionic acid (Compound 217);

5-(4-{N'-[1-(3,4-Dimethyl-phenyl)-5,7-difluoro-2-oxo-1,2-dihydro-indol-3-ylidene]-hydrazino}-3-hydroxy-benzylidene)-thiazolidine-2,4-dione (Compound 218);

5-(4-{N'-[1-(4-Ethyl-phenyl)-5,7-difluoro-2-oxo-1,2-dihydro-indol-3-ylidene]-hydrazino}-3-hydroxy-benzylidene)-thiazolidine-2,4-dione (Compound 219);

5-(4-{N'-[5,7-Difluoro-2-oxo-1-(4-propyl-phenyl)-1,2-dihydro-indol-3-ylidene]-hydrazino}-3-hydroxy-benzylidene)-thiazolidine-2,4-dione (Compound 220);

5-(3-Hydroxy-4-{N'-[1-(4-isopropyl-phenyl)-2-oxo-6-trifluoromethyl-1,2-dihydro-indol-3-ylidene]-hydrazino}-benzylidene)-thiazolidine-2,4-dione (Compound 221);

5-(3-Hydroxy-4-{N'-[1-(4-isopropyl-phenyl)-2-oxo-5,7-difluoro-1,2-dihydro-indol-3-ylidene]-hydrazino}-benzylidene)-thiazolidine-2,4-dione (Compound 222);

3'-{N'-[1-(3,4-Dimethyl-phenyl)-2-oxo-6-trifluoromethyl-1,2-dihydro-indol-3-ylidene]-hydrazino}-5'-fluoro-2'-hydroxy-biphenyl-3-carboxylic acid (Compound 223);

5'-Chloro-3'-{N'-[1-(3,4-dimethyl-phenyl)-2-oxo-6-trifluoromethyl-1,2-dihydro-indol-3-ylidene]-hydrazino}-2'-hydroxy-biphenyl-3-carboxylic acid (Compound 224);

3'-{N'-[1-(3,4-Dimethyl-phenyl)-2-oxo-6-trifluoromethyl-1,2-dihydro-indol-3-ylidene]-hydrazino}-2'-hydroxy-5'-methyl-biphenyl-3-carboxylic acid (Compound 225);

2'-Hydroxy-3'-{N'-[2-oxo-6-trifluoromethyl-1-(4-trifluoromethyl-phenyl)-1,2-dihydro-indol-3-ylidene]-hydrazino}-biphenyl-3-carboxylic acid (Compound 226);

3'-{N'-[1-(4-Ethyl-3-methyl-phenyl)-2-oxo-6-trifluoromethyl-1,2-dihydro-indol-3-ylidene]-hydrazino}-2'-hydroxy-biphenyl-3-carboxylic acid (Compound 227);

3'-{N'-[1-(4-Chloro-3-trifluoromethyl-phenyl)-2-oxo-6-trifluoromethyl-1,2-dihydro-indol-3-ylidene]-hydrazino}-2'-hydroxy-biphenyl-3-carboxylic acid (Compound 228);

3'-{N'-[1-(3,5-Dimethyl-phenyl)-2-oxo-6-trifluoromethyl-1,2-dihydro-indol-3-ylidene]-hydrazino}-5'-fluoro-2'-hydroxy-biphenyl-3-carboxylic acid (Compound 229);

3'-{N'-[1-(3,4-Dimethyl-phenyl)-2-oxo-6-trifluoromethyl-1,2-dihydro-indol-3-ylidene]-hydrazino}-4,5'-difluoro-2'-hydroxy-biphenyl-3-carboxylic acid (Compound 230);

3'-{N'-[1-(3,5-Dimethyl-phenyl)-2-oxo-6-trifluoromethyl-1,2-dihydro-indol-3-ylidene]-hydrazino}-4,5'-difluoro-2'-hydroxy-biphenyl-3-carboxylic acid (Compound 231);

4,5'-Difluoro-2'-hydroxy-3'-{N'-[2-oxo-6-trifluoromethyl-1-(4-trifluoromethyl-phenyl)-1,2-dihydro-indol-3-ylidene]-hydrazino}-biphenyl-3-carboxylic acid (Compound 232);

3'-{N'-[1-(4-Fluoro-3,5-dimethyl-phenyl)-2-oxo-6-trifluoromethyl-1,2-dihydro-indol-3-ylidene]-hydrazino}-2'-hydroxy-biphenyl-3-carboxylic acid (Compound 233);

2'-Hydroxy-3'-{N'-[1-(4-methoxy-phenyl)-2-oxo-6-trifluoromethyl-1,2-dihydro-indol-3-ylidene]-hydrazino}-biphenyl-3-carboxylic acid (Compound 234);

3'-{N'-[1-(4-Fluoro-phenyl)-2-oxo-6-trifluoromethyl-1,2-dihydro-indol-3-ylidene]-hydrazino}-2'-hydroxy-biphenyl-3-carboxylic acid (Compound 235);

3'-{N'-[1-(3,5-Dimethoxy-phenyl)-2-oxo-6-trifluoromethyl-1,2-dihydro-indol-3-ylidene]-hydrazino}-2'-hydroxy-biphenyl-3-carboxylic acid (Compound 236);

3'-{N'-[1-(3,4-Dimethoxy-phenyl)-2-oxo-6-trifluoromethyl-1,2-dihydro-indol-3-ylidene]-hydrazino}-2'-hydroxy-biphenyl-3-carboxylic acid (Compound 237);

3'-{N'-[1-(3,5-Difluoro-phenyl)-2-oxo-6-trifluoromethyl-1,2-dihydro-indol-3-ylidene]-hydrazino}-2'-hydroxy-biphenyl-3-carboxylic acid (Compound 238);

5'-Fluoro-3'-{N'-[1-(4-fluoro-3,5-dimethyl-phenyl)-2-oxo-6-trifluoromethyl-1,2-dihydro-indol-3-ylidene]-hydrazino}-2'-hydroxy-biphenyl-3-carboxylic acid (Compound 239);

4,5'-Difluoro-3'-{N'-[1-(4-fluoro-3,5-dimethyl-phenyl)-2-oxo-6-trifluoromethyl-1,2-dihydro-indol-3-ylidene]-hydrazino}-2'-hydroxy-biphenyl-3-carboxylic acid (Compound 240);

2'-Hydroxy-3'-{N'-[1-(4-methoxy-3,5-dimethyl-phenyl)-2-oxo-6-trifluoromethyl-1,2-dihydro-indol-3-ylidene]-hydrazino}-biphenyl-3-carboxylic acid (Compound 241);

2'-Hydroxy-3'-{N'-[1-(4-hydroxy-3,5-dimethyl-phenyl)-2-oxo-6-trifluoromethyl-1,2-dihydro-indol-3-ylidene]-hydrazino}-biphenyl-3-carboxylic acid (Compound 242);

3'-{N'-[1-(4-Cyclohexyl-phenyl)-2-oxo-1,2-dihydro-indol-3-ylidene]-hydrazino}-2'-hydroxy-biphenyl-3-carboxylic acid (Compound 243);

2'-Hydroxy-3'-[N'-(2-oxo-1-pyridin-2-yl-1,2-dihydro-indol-3-ylidene)-hydrazino]-biphenyl-3-carboxylic acid (Compound 244);

2'-Hydroxy-3'-[N'-(2-oxo-1-pyridin-3-yl-1,2-dihydro-indol-3-ylidene)-hydrazino]-biphenyl-3-carboxylic acid (Compound 245);

3'-{N'-[1-(4-Ethyl-phenyl)-2-oxo-6-trifluoromethyl-1,2-dihydro-indol-3-ylidene]-hydrazino}-2'-hydroxy-biphenyl-3-carboxylic acid (Compound 246);

3'-{N'-[1-(4-Ethyl-phenyl)-4-fluoro-2-oxo-6-trifluoromethyl-1,2-dihydro-indol-3-ylidene]-hydrazino}-2'-hydroxy-biphenyl-3-carboxylic acid (Compound 247);

3-[(3'-Carboxy-2-hydroxy-biphenyl-3-yl)-hydrazono]-1-(3,5-dimethyl-phenyl)-2-oxo-2,3-dihydro-1-H-indole-5-carboxylic acid methyl ester (Compound 248);

3'-{N'-[1-(3-Chloro-4-methyl-phenyl)-2-oxo-6-trifluoromethyl-1,2-dihydro-indol-3-ylidene]-hydrazino}-2'-hydroxy-biphenyl-3-carboxylic acid (Compound 249);

5-(4-{N'-[1-(3,5-Dimethyl-phenyl)-2-oxo-6-trifluoromethyl-1,2-dihydro-indol-3-ylidene]-hydrazino}-3-hydroxy-benzylidene)-thiazolidine-2,4-dione (Compound 250);

2'-Hydroxy-3'-(N'-{2-oxo-1-[4-(4,4,4-trifluoro-butyl)-phenyl]-1,2-dihydro-indol-3-ylidene}-hydrazino)-biphenyl-3-carboxylic acid (Compound 251);

3'-{N'-[1-(3,5-Dimethyl-phenyl)-4-fluoro-2-oxo-6-trifluoromethyl-1,2-dihydro-indol-3-ylidene]-hydrazino}-2'-hydroxy-biphenyl-3-carboxylic acid (Compound 252);

3'-{N'-[1-(4-tert-Butyl-phenyl)-2-oxo-6-trifluoromethyl-1,2-dihydro-indol-3-ylidene]-hydrazino}-2'-hydroxy-biphenyl-3-carboxylic acid (Compound 253);

3'-{N'-[1-(3,4-Dimethyl-phenyl)-2-oxo-6-trifluoromethyl-1,2-dihydro-indol-3-ylidene]-hydrazino}-2'-hydroxy-biphenyl-4-carboxylic acid (Compound 254);

3'-{N'-[1-(3,4-Dimethyl-phenyl)-2-oxo-6-bromo-1,2-dihydro-indol-3-ylidene]-hydrazino}-2'-hydroxy-biphenyl-3-carboxylic acid (Compound 255);

3'-{N'-[1-(3,4-Dimethyl-phenyl)-2-oxo-6-trifluoromethyl-1,2-dihydro-indol-3-ylidene]-hydrazino}-3-fluoro-2'-hydroxy-biphenyl-4-carboxylic acid (Compound 256);

3'-{N'-[1-(3,5-Bis-trifluoromethyl-phenyl)-2-oxo-6-trifluoromethyl-1,2-dihydro-indol-3-ylidene]-hydrazino}-2'-hydroxy-biphenyl-3-carboxylic acid (Compound 257);

3'-{N'-[1-(3,4-Dichloro-phenyl)-2-oxo-6-trifluoromethyl-1,2-dihydro-indol-3-ylidene]-hydrazino}-2'-hydroxy-biphenyl-3-carboxylic acid (Compound 258);

3'-{N'-[1-(3,5-Dichloro-phenyl)-2-oxo-6-trifluoromethyl-1,2-dihydro-indol-3-ylidene]-hydrazino}-2'-hydroxy-biphenyl-3-carboxylic acid (Compound 259);

3-(4-{N'-[1-(3,5-Dimethyl-phenyl)-2-oxo-6-trifluoromethyl-1,2-dihydro-indol-3-ylidene]-hydrazino}-3-hydroxy-phenyl)-2-methyl-acrylic acid (Compound 260);

3-(4-{N'-[1-(3,4-Dimethyl-phenyl)-2-oxo-6-trifluoromethyl-1,2-dihydro-indol-3-ylidene]-hydrazino}-3-hydroxy-phenyl)-2-methyl-acrylic acid (Compound 261);

2'-Hydroxy-3'-[N'-(2-oxo-7-phenyl-1,2-dihydro-indol-3-ylidene)-hydrazino]-biphenyl-3-carboxylic acid (Compound 262);

3'-{N'-[1-(3,4-Dimethyl-phenyl)-2-oxo-6-trifluoromethoxy-1,2-dihydro-indol-3-ylidene]-hydrazino}-2'-hydroxy-biphenyl-3-carboxylic acid (Compound 263);

3'-{N'-[1-(3,4-Dimethyl-phenyl)-2-oxo-6-(1,1,2,2-tetrafluoro-ethoxy)-1,2-dihydro-indol-3-ylidene]-hydrazino}-2'-hydroxy-biphenyl-3-carboxylic acid (Compound 264);

3'-{N'-[1-(3,4-Dimethyl-phenyl)-5-methyl-2-oxo-1,2-dihydro-indol-3-ylidene]-hydrazino}-2'-hydroxy-biphenyl-3-carboxylic acid (Compound 265);

3'-{N'-[1-(4-Isopropyl-phenyl)-5-methyl-2-oxo-1,2-dihydro-indol-3-ylidene]-hydrazino}-2'-hydroxy-biphenyl-3-carboxylic acid (Compound 266);

3'-{N'-[1-(3,4-Dimethyl-phenyl)-6-phenyl-2-oxo-1,2-dihydro-indol-3-ylidene]-hydrazino}-2'-hydroxy-biphenyl-3-carboxylic acid (Compound 267);

3'-{N'-[1-(3-Trifluoromethyl-phenyl)-6-trifluoromethyl-2-oxo-1,2-dihydro-indol-3-ylidene]-hydrazino}-2'-hydroxy-biphenyl-3-carboxylic acid (Compound 268);

3'-{N'-[1-(4-Trifluoromethoxy-phenyl)-5-trifluoromethoxy-2-oxo-1,2-dihydro-indol-3-ylidene]-hydrazino}-2'-hydroxy-biphenyl-3-carboxylic acid (Compound 269);

3'-{N'-[1-(3,5-Dimethyl-phenyl)-6-trifluoromethyl-2-oxo-1,2-dihydro-indol-3-ylidene]-hydrazino}-2'-hydroxy-biphenyl-3-carboxylic acid (Compound 270);

3'-{N'-[1-(3-Trifluoromethyl-phenyl)-4,6-dimethyl-2-oxo-1,2-dihydro-indol-3-ylidene]-hydrazino}-2'-hydroxy-biphenyl-3-carboxylic acid (Compound 271);

3'-{N'-[1-(3-Trifluoromethyl-phenyl)-5,6-dimethyl-2-oxo-1,2-dihydro-indol-3-ylidene]-hydrazino}-2'-hydroxy-biphenyl-3-carboxylic acid (Compound 272);

3'-{N'-[1-(3,5-Dimethyl-phenyl)-6-trifluoromethyl-2-oxo-1,2-dihydro-indol-3-ylidene]-hydrazino}-2'-hydroxy-5'-chloro-4-fluoro-biphenyl-3-carboxylic acid (Compound 273);

3'-{N'-[1-(3,5-Dimethyl-phenyl)-6-trifluoromethyl-2-oxo-1,2-dihydro-indol-3-ylidene]-hydrazino}-2'-hydroxy-4-fluoro-biphenyl-3-carboxylic acid (Compound 274);

3'-{N'-[6-Chloro-1-(3,4-dimethyl-phenyl)-2-oxo-1,2-dihydro-indol-3-ylidene]-hydrazino}-2'-hydroxy-biphenyl-3-carboxylic acid (Compound 275);

3'-{N'-[5-Fluoro-2-oxo-1-(4-propyl-phenyl)-1,2-dihydro-indol-3-ylidene]-hydrazino}-2'-hydroxy-biphenyl-3-carboxylic acid (Compound 276);

3'-{N'-[5-Cyano-1-(3,4-dimethyl-phenyl)-2-oxo-1,2-dihydro-indol-3-ylidene]-hydrazino}-2'-hydroxy-biphenyl-3-carboxylic acid (Compound 277);

3'-{N'-[6-Chloro-1-(3,5-dimethyl-phenyl)-2-oxo-1,2-dihydro-indol-3-ylidene]-hydrazino}-2'-hydroxy-biphenyl-3-carboxylic acid (Compound 278);

4-Fluoro-3'-{N'-[1-(3-fluoro-4-methyl-phenyl)-2-oxo-6-trifluoromethyl-1,2-dihydro-indol-3-ylidene]-hydrazino}-2'-hydroxy-biphenyl-3-carboxylic acid (Compound 279); and a pharmaceutically acceptable salt ester, amide or prodrug of any of those compounds.

In certain embodiments, the invention provides compounds including, but not limited to:

3'-{N'-[1-(4-Chloro-3,5-dimethylphenyl)-2-oxo-6-trifluoromethyl-1,2-dihydroindol-3-ylidene]hydrazino}-2'-hydroxy-biphenyl-3-carboxylic acid (Compound 280);

3'-{N'-[1-(3,5-Dimethylphenyl)-4-fluoro-2-oxo-6-trifluoromethyl-1,2-dihydroindol-3-ylidene]hydrazino}-2'-hydroxybiphenyl-4-fluoro-3-carboxylic acid (Compound 281);

3'-{N'-[1-Benzo[1,3]dioxo-5-yl-2-oxo-6-trifluoromethyl-1,2-dihydroindol-3-ylidene]hydrazino}-2'-hydroxybiphenyl-3-carboxylic acid (Compound 282);

3'-{N'-[1-Benzo[1,3]dioxo-5-yl-2-oxo-6-trifluoromethyl-1,2-dihydroindol-3-ylidene]hydrazino}-2'-hydroxybiphenyl-2-fluoro-3-carboxylic acid (Compound 283);

3'-{N'-[1-(3,5-Dimethylphenyl)-2-oxo-6-trifluoromethyl-1,2-dihydroindol-3-ylidene]hydrazino}-2'-hydroxybiphenyl-2-hydroxy-3-carboxylic acid (Compound 284);

3'-{N'-[1-(3-Methoxycarbonylphenyl)-2-oxo-6-trifluoromethyl-1,2-dihydroindol-3-ylidene]hydrazino}-2'-hydroxybiphenyl-3-carboxylic acid (Compound 285);

3'-{N'-[1-(3-Methoxycarbonylphenyl)-2-oxo-1,2-dihydroindol-3-ylidene]hydrazino}-2'-hydroxybiphenyl-3-carboxylic acid (Compound 286);

3'-{N'-[7-Aza-1-(3,4-dimethylphenyl)-2-oxo-1,2-dihydroindol-3-ylidene]hydrazino}-2'-hydroxybiphenyl-3-carboxylic acid (Compound 287);

3'-{N'-[1-(3,5-Dimethylphenyl)-2-oxo-1,2-dihydroindol-6-trifluoromethyl-3-ylidene]hydrazino}-2'-hydroxybiphenyl-3-(2-methyl-2-propionic acid) (Compound 288);

3'-{N'-[1,3-N,N-Dimethylbarbitur-5-ylidene]hydrazino}-2'-hydroxybiphenyl-3-carboxylic acid (Compound 289);

3'-{N'-[1-N-(4-Trifluoromethylbenzyl)-2,8-dioxo-1,2,7,8-tetrahydroisoquinolin-7-ylidene]hydrazino}-2'-hydroxybiphenyl-3-carboxylic acid (Compound 290);

3'-{N'-[1-N-(4-Methylbenzyl)-2,8-dioxo-1,2,7,8-tetrahydroisoquinolin-7-ylidene]hydrazino}-2'-hydroxybiphenyl-3-carboxylic acid (Compound 291);

3'-{N'-[1-N-Benzyl-2,8-dioxo-1,2,7,8-tetrahydroisoquinolin-7-ylidene]hydrazino}-2'-hydroxybiphenyl-3-carboxylic acid (Compound 292);

3'-{N'-[1-N-(4-Trifluoromethylphenyl)-2,8-dioxo-1,2,7,8-tetrahydroisoquinolin-7-ylidene]hydrazino}-2'-hydroxybiphenyl-3-carboxylic acid (Compound 293);

3'-{N'-[1-N-(3-Trifluoromethylphenyl)-2,8-dioxo-1,2,7,8-tetrahydroisoquinolin-7-ylidene]hydrazino}-2'-hydroxybiphenyl-3-carboxylic acid (Compound 294);

3'-{N'-[1-N-(3,5-Dimethylphenyl)-2,8-dioxo-1,2,7,8-tetrahydroisoquinolin-7-ylidene]hydrazino}-2'-hydroxybiphenyl-3-carboxylic acid (Compound 295);

3'-{N'-[1-N-Phenyl-2,8-dioxo-1,2,7,8-tetrahydroisoquinolin-7-ylidene]hydrazino}-2'-hydroxybiphenyl-3-carboxylic acid (Compound 296);

3'-{N'-[1-N-(3,4-Dimethylphenyl)-2,8-dioxo-1,2,7,8-tetrahydroisoquinolin-7-ylidene]hydrazino}-2'-hydroxybiphenyl-3-carboxylic acid (Compound 297);

3'-{N'-[1-N-(3,4-Dimethylphenyl)-2-oxo-6-trifluoromethyl-1,2-dihydroindol-3-ylidene]hydrazino}-2'-fluorobiphenyl-3-carboxylic acid (Compound 298);

3-(3-{N'-[1-N-(3,4-Dimethylphenyl)-2-oxo-6-trifluoromethyl-1,2-dihydroindol-3-ylidene]hydrazino}-2-hydroxyphenyl)-2(Z)-propenoic acid (Compound 299);

3-(3-{N'-[1-N-(3,4-Dimethylphenyl)-2-oxo-4-fluoro-6-trifluoromethyl-1,2-dihydroindol-3-ylidene]hydrazino}-2-hydroxyphenyl)-2(Z)-propenoic acid (Compound 300);

5-(3-{N'-[1-(3,4-Dimethylphenyl)-2-oxo-4-fluoro-6-trifluoromethyl-1,2-dihydroindol-3-ylidene]hydrazino}-2-hydroxybenzylidene)thiazolidine-2,4-dione (Compound 301);

2-Chloro-3-(4-{N'-[1-(3,4-dimethylphenyl)-2-oxo-6-trifluoromethyl-1,2-dihydroindol-3-ylidene]hydrazino}-3-hydroxyphenyl)-2-propenoic acid (Compound 302);

2-Ethyl-3-(4-{N'-[1-(3,4-dimethylphenyl)-2-oxo-6-trifluoromethyl-1,2-dihydroindol-3-ylidene]hydrazino}-3-hydroxyphenyl)-2-propenoic acid (Compound 303);

1-N-Methyl-5-(4-{N'-[1-(3,5-dimethylphenyl)-2-oxo-6-trifluoromethyl-1,2-dihydroindol-3-ylidene]hydrazino}-3-hydroxybenzylidene)-1,3-diazolidine-2,4-dione (Compound 304);

5-(4-{N'-[1-(3,5-Dimethylphenyl)-2-oxo-6-trifluoromethyl-1,2-dihydroindol-3-ylidene]hydrazino}-3-hydroxybenzylidene)-1,3-diazolidine-2,4-dione (Compound 305);

2-Fluoro-3-(4-{N'-[1-(3,4-dimethylphenyl)-2-oxo-6-trifluoromethyl-1,2-dihydroindol-3-ylidene]hydrazino}-3-hydroxyphenyl)-2-propenoic acid (Compound 306);

(±)-2-Methoxy-3-(4-{N'-[1-(3,5-dimethylphenyl)-2-oxo-6-trifluoromethyl-1,2-dihydroindol-3-ylidene]hydrazino}-3-hydroxyphenyl)propanoic acid (Compound 307);

4-(3-{N'-[1-(3,4-dimethylphenyl)-2-oxo-6-trifluoromethyl-1,2-dihydroindol-3-ylidene]hydrazino}-2-hydroxyphenyl)butanoic acid (Compound 308);

3-(2-{N'-[1-(3,5-dimethylphenyl)-2-oxo-6-trifluoromethyl-1,2-dihydroindol-3-ylidene]hydrazino}-3-hydroxyphenoxy)propanoic acid (Compound 309);

4-(4-{N'-[1-(3,4-dimethylphenyl)-2-oxo-6-trifluoromethyl-1,2-dihydroindol-3-ylidene]hydrazino}-3-hydroxyphenyl)butanoic acid (Compound 310); and a pharmaceutically acceptable salt ester, amide or prodrug of any of those compounds.

In certain embodiments, the present invention provides any single compound selected from any of the above lists of compounds. In certain embodiments, the present invention provides any number and any combination of compounds selected from the above lists of compounds.

Certain compounds of the present inventions may exist as stereoisomers including optical isomers. The present disclosure is intended to include all stereoisomers and both the racemic mixtures of such stereoisomers as well as the individual enantiomers that may be separated according to methods that are known in the art or that may be excluded by synthesis schemes known in the art designed to yield predominantly one enantiomer relative to another.

Certain Synthesis Methods

In certain embodiments, certain compounds of the present invention can by synthesized using the following Schemes.

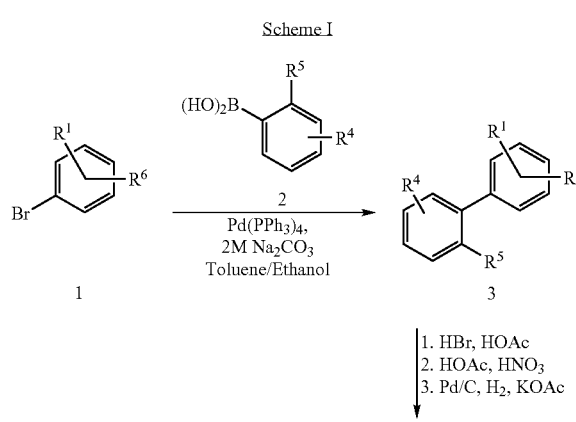

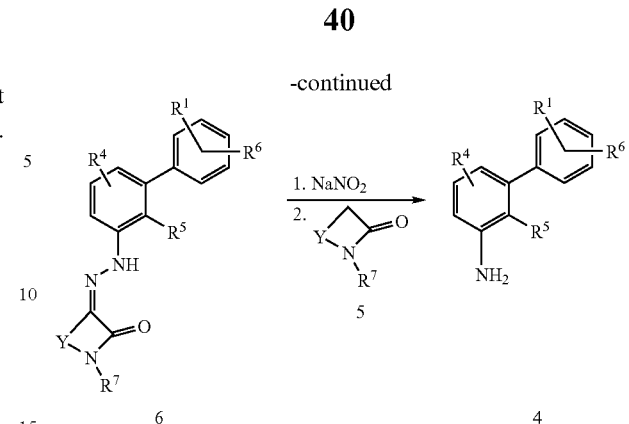

The process of Scheme I is a multi-step synthetic sequence that commences with the palladium catalyzed cross-coupling of a phenylboronic acid such as structure 2 and an aryl bromide such as structure 1 to form the biaryl structure 3. Deprotection of the methyl ether is followed by nitration and hydrogenation to give the biphenyl amino acid such as structure 4. The amino group is then diazotized under standard conditions and is treated with the appropriate coupling partner to give the final product of structure 6.

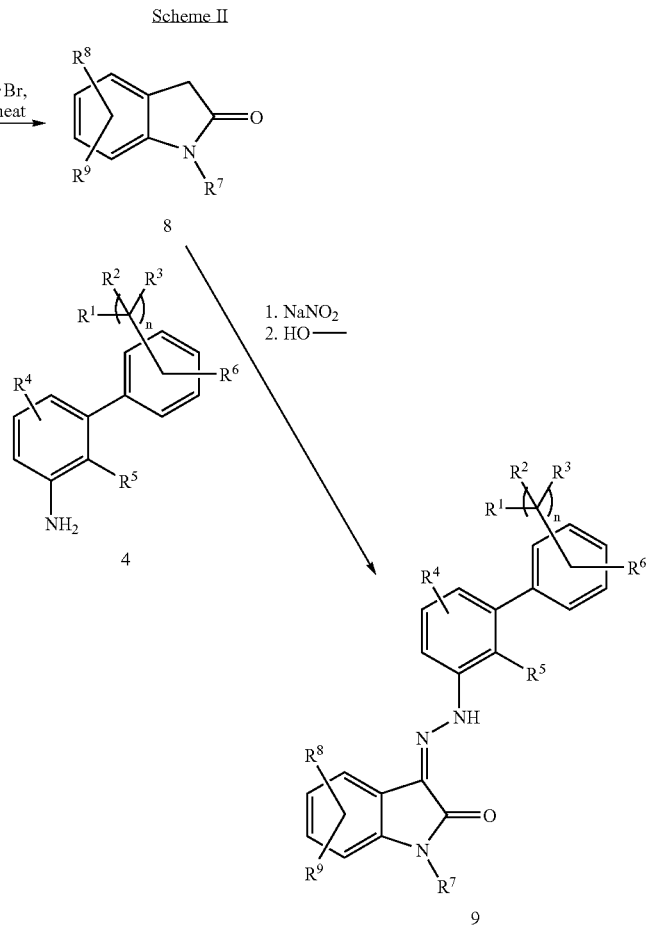

The process of Scheme II is a multi-step synthetic sequence that commences with the copper catalyzed cross-coupling of an oxindole such as structure 7 and an aryl or alkyl bromide to provide an N-substituted oxindole of structure 8. This is then followed by coupling the N-substituted oxindole with the diazonium salt of the biphenyl amino acid such as structure 4 to give the final product of structure 9.

Bn = CH$_2$Ph

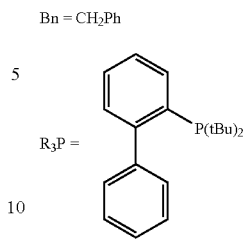

The process of Scheme III is a multi-step synthetic sequence that commences with the reductive amination of an aniline such as structure 10 with a benzaldehyde and conversion into the chloroacetanilide of structure 11 with chloroacetyl chloride. Palladium catalyzed ring closure gives the N-benzyl oxindole such as structure 12, which is then coupled to the diazonium salt of the biphenyl amino acid of structure 4 to give the final product of structure 9.

Scheme III

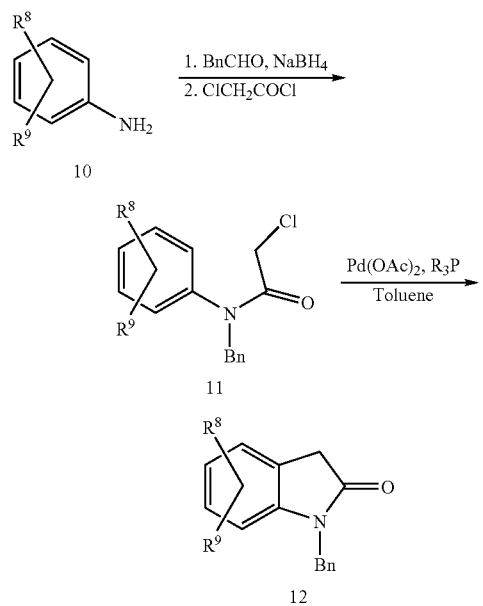

Scheme IV

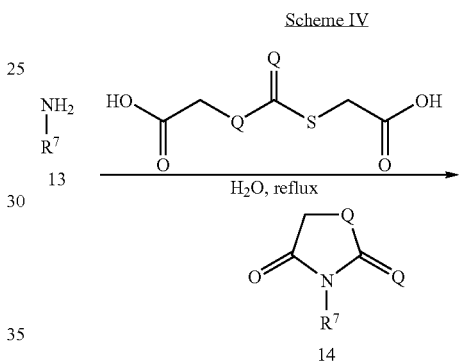

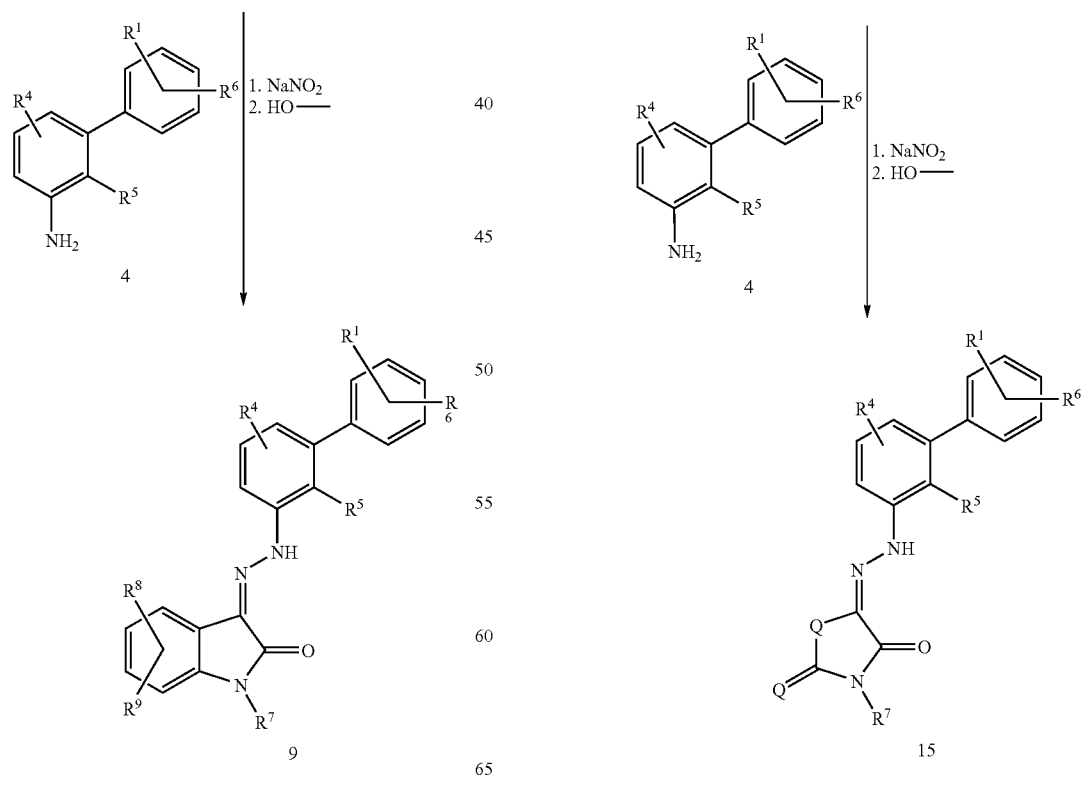

The process of Scheme IV is a multi-step synthetic sequence that commences with the conversion of an amine of structure 13 into an N-aryl rhodanine of structure 14 with bis(carboxymethyl)trithiocarbonate. The rhodanine is then coupled to the diazonium salt of the biphenyl amino acid such as structure 4 to give the final product of structure 15.

In certain embodiments, the invention provides a salt corresponding to a selective TPO modulator. In certain embodiments, the invention provides a salt corresponding to a selective TPO receptor binding agent. In certain embodiments, a salt is obtained by reacting a compound with an acid, such as hydrochloric acid, hydrobromic acid, sulfuric

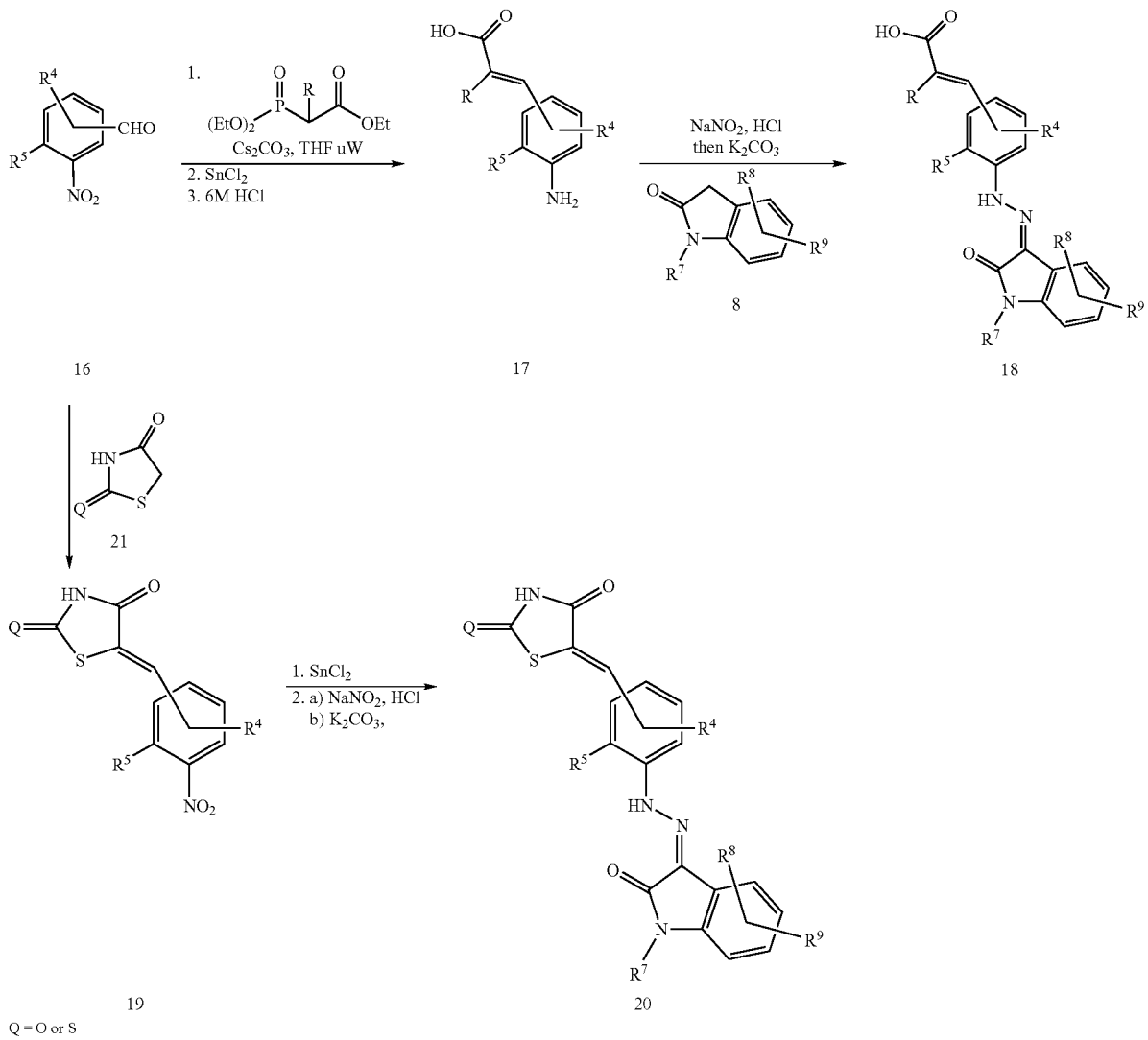

In Scheme V, a hyrdoxynitrobenzaldehyde such as structure 16 is converted into either a cinnamate such as structure 17 or thiazolidinedione derivative of structure 19. The requisite nitro-group is reduced and then converted into a diazonium salt and coupled to the corresponding N-aryl oxindole of structure 8 to give the final compound of structure 20.

One of skill in the art will recognize that analogous synthesis schemes may be used to synthesize similar compounds. One of skill will recognize that compounds of the present invention may be synthesized using other synthesis schemes. In certain embodiments, the invention provides a salt corresponding to any of the compounds provided herein.

acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as choline, dicyclohexylamine, N-methyl-D-glucamine, tris(hydroxymethyl)methylamine, 4-(2-hydroxyethyl)-morpholine, 1-(2-hydroxyethyl)-pyrrolidine, ethanolamine and salts with amino acids such as arginine, lysine, and the like. In certain embodiments, a salt is obtained by reacting a free acid form of a selective TPO modulator or selective TPO binding agent with multiple molar equivalents of a base, such as bis-sodium, bis-ethanolamine, and the like.

In certain embodiments, a salt corresponding to a compound of the present invention is selected from acetate, ammonium, benzenesulfonate, benzoate, bicarbonate, bisulfate, bitartrate, borate, bromide, calcium edetate, camsylate, carbonate, chloride, cholinate, clavulanate, citrate, dihydrochloride, diphosphate, edetate, edisylate, estolate, esylate, fumarate, gluceptate, gluconate, glutamate, glycollylarsanilate, hexylresorcinate, hydrabanine, hydrobromide, hydrochloride, hydroxynaphthoate, iodide, isethionate, lactate, lactobionate, laurate, magnesium, malate, maleate, mandelate, mucate, napsylate, nitrate, N-methylglucamine, oxalate, pamoate (embonate), palmitate, pantothenate, phosphate, polygalacturonate, potassium, salicylate, sodium, stearate, subaceatate, succinate, sulfate, tannate, tartrate, teoclate, tosylate, triethiodide, tromethamine, trimethylammonium, and valerate salts.

In certain embodiments, one or more carbon atoms of a compound of the present invention are replaced with silicon. See e.g., WO 03/037905A1; Tacke and Zilch, Endeavour, New Series, 10, 191-197 (1986); and Bains and Tacke, Curr. Opin. Drug Discov Devel. July:6(4):526-43(2003). In certain embodiments, compounds of the present invention comprising one or more silicon atoms possess certain desired properties, including, but not limited to, greater stability and/or longer half-life in a patient, when compared to the same compound in which none of the carbon atoms have been replaced with a silicon atom.

Certain Assays

In certain embodiments, compounds of the present invention may be used in a any of a variety of assays. For example, compounds of the present invention may be tested for potency as selective TPO modulators in a luciferase assay, such as those described in Lamb, et al., Nucleic Acids Research, 23: 3283-3289(1995) and/or Seidel et al., Proc. Nat. Acad. Sci. USA; 92: 3041-3045 (1995).

Certain compounds of the present invention may be used in in vitro proliferation and/or differentiation assays, such as those described by Bartley et al., Cell, 77: 1117-1124 (1994) and/or Cwirla, et al., Science, 276: 1696-1699 (1997).

Certain Pharmaceutical Compositions

In certain embodiments, at least one selective TPO modulator, or pharmaceutically acceptable salt, ester, amide, and/or prodrug thereof, combined with one or more pharmaceutically acceptable carriers, forms a pharmaceutical composition. Techniques for formulation and administration of compounds of the present invention may be found for example, in "Remington's Pharmaceutical Sciences," Mack Publishing Co., Easton, Pa., 18th edition, 1990.

In certain embodiments, a pharmaceutical composition comprising one or more compounds of the present invention is prepared using known techniques, including, but not limited to mixing, dissolving, granulating, dragee-making, levigating, emulsifying, encapsulating, entrapping or tabletting processes.

In certain embodiments, a pharmaceutical composition comprising one or more compounds of the present invention is a liquid (e.g., a suspension, elixir and/or solution). In certain of such embodiments, a liquid pharmaceutical composition comprising one or more compounds of the present invention is prepared using ingredients known in the art, including, but not limited to, water, glycols, oils, alcohols, flavoring agents, preservatives, and coloring agents.

In certain embodiments, a pharmaceutical composition comprising one or more compounds of the present invention is a solid (e.g., a powder, tablet, and/or capsule). In certain of such embodiments, a solid pharmaceutical composition comprising one or more compounds of the present invention is prepared using ingredients known in the art, including, but not limited to, starches, sugars, diluents, granulating agents, lubricants, binders, and disintegrating agents.

In certain embodiments, a pharmaceutical composition comprising one or more compounds of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition comprising one or more compounds of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition comprising one or more compounds of the present invention comprises one or more tissue-specific delivery molecules designed to deliver the one or more compounds of the present invention to specific tissues or cell types. For example, in certain embodiments, pharmaceutical compositions include liposomes coated with a tissue-specific antibody.

In certain embodiments, a pharmaceutical composition comprising one or more compounds of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition comprising one or more compounds of the present invention comprises a sustained-release system. A non-limiting example of such a sustained-release system is a semipermeable matrix of solid hydrophobic polymers. In certain embodiments, sustained-release systems may, depending on their chemical nature, release compounds over a period of hours, days, weeks or months.

In certain embodiments, a pharmaceutical composition comprising a compound of the present invention is prepared for oral administration. In certain of such embodiments, a pharmaceutical composition is formulated by combining one or more compounds of the present invention with one or more pharmaceutically acceptable carriers. Certain of such carriers enable compounds of the invention to be formulated as tablets, pills, dragees, capsules, liquids, gels, syrups, slurries, suspensions and the like, for oral ingestion by a patient. In certain embodiments, pharmaceutical compositions for oral use are obtained by mixing one or more compounds of the present invention and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more compounds of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more compounds of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, a pharmaceutical composition comprising one or more compounds of the present invention comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more compounds of the present invention is formulated as a prodrug. In certain embodiments, upon in vivo administration, a prodrug is chemically converted to the biologically, pharmaceutically or therapeutically more active form of the compound. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In certain embodiments, a pharmaceutical composition comprising one or more compounds of the present invention is useful for treating a conditions or disorders in a mammalian, and particularly in a human, patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., in the renal or cardiac area).

In certain embodiments, a pharmaceutical composition comprising one or more compounds of the present invention is administered in the form of a dosage unit (e.g., tablet, capsule, bolus, etc.). In certain embodiments, such dosage units comprise a selective TPO modulator in a dose from about 1 µg/kg of body weight to about 50 mg/kg of body weight. In certain embodiments, such dosage units comprise a selective TPO modulator in a dose from about 2 µg/kg of body weight to about 25 mg/kg of body weight. In certain embodiments, such dosage units comprise a selective TPO modulator in a dose from about 10 µg/kg of body weight to about 5 mg/kg of body weight. In certain embodiments, pharmaceutical compositions are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical composition.

In certain embodiments, the formulation, route of administration and dosage for a pharmaceutical composition of the present invention can be chosen in view of a particular patient's condition. (See e.g., Fingl et al. 1975, in "The Pharmacological Basis of Therapeutics", Ch. 1 p. 1). In certain embodiments, a pharmaceutical composition is administered as a single dose. In certain embodiments, a pharmaceutical composition is administered as a series of two or more doses administered over one or more days.

In certain embodiments, a pharmaceutical composition of the present invention is administered to a patient between about 0.1% and 500%, more preferably between about 25% and 75% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg of a compound of the present invention. In certain embodiments, a daily dosage regimen is administered as a single daily dose. In certain embodiments, a daily dosage regimen is administered as two, three, four, or more than four doses.

In certain embodiments, a pharmaceutical composition of the present invention is administered by continuous intravenous infusion. In certain of such embodiments, from 0.1 mg to 500 mg of a composition of the present invention is administered per day.

In certain embodiments, a pharmaceutical composition of the invention is administered for a period of continuous therapy. For example, a pharmaceutical composition of the present invention may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present invention at an amount sufficient to achieve a desired effect. In certain of such embodiments the plasma concentration is maintained above the minimal effective concentration (MEC). In certain embodiments, pharmaceutical compositions of the present invention are administered with a dosage regimen designed to maintain a concentration above the MEC for 10-90% of the time, between 30-90% of the time, or between 50-90% of the time.

In certain embodiments in which a pharmaceutical composition is administered locally, the dosage regimen is adjusted to achieve a desired local concentration of a compound of the present invention.

In certain embodiments, a pharmaceutical composition may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

In certain embodiments, a pharmaceutical composition is in powder form for constitution with a suitable vehicle, e.g., sterile pyrogen-free water, before use.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at the different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

Examples of pharmaceutical agents that may be co-administered with a pharmaceutical composition of the present invention include, but are not limited to, anti-cancer treatments, including, but not limited to, chemotherapy and radiation treatment; corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Certain Indications

In certain embodiments, the invention provides methods of treating a patient comprising administering one or more compounds of the present invention. In certain embodiments, such patient suffers from thrombocytopenia. In certain such embodiments, thrombocytopenia results from chemotherapy and/or radiation treatment. In certain embodiments, thrombocytopenia results bone marrow failure resulting from bone marrow transplantation and/or aplastic anemia. In certain embodiments thrombocytopenia is idiopathic. In certain embodiments, one or more compounds of the present invention are administered to a patient to in conjunction with harvesting peripheral blood progenitor cells and/or in conjunction with platelet apheresis. Such administration may be done before, during, and/or after such harvesting.

In certain embodiments, one or more compounds of the present invention are administered to a patient who suffers from a condition affecting the nervous system, including, but are not limited to, diseases affecting the nervous system and injuries to the nervous system. Such diseases, include, but not limited to, amyotrophic lateral sclerosis, multiple sclerosis, and multiple dystrophy. Injury to the nervous system include, but are not limited to spinal cord injury or peripheral nerve damage, including, but not limited to, injury resulting from trauma or from stroke. In certain embodiments, one or more compounds of the present invention are used to promote growth and/or development of glial cells. Such glial cells may repair nerve cells. In certain embodiments, compounds of the present invention are used to treat psychological disorders, including, but not limited to, cognitive disorders. In certain embodiments, one or more compounds of the invention are administered to enhance athletic performance.

EXAMPLES

The following examples, including experiments and results achieved, are provided for illustrative purposes only and are not to be construed as limiting the present invention.

Example 1

3'-{N'-[1-(3,4-Dimethyl-phenyl)-2-oxo-1,2-dihydro-indol-3-ylidene]-hydrazino}-2'-hydroxy-biphenyl-3-carboxylic acid (Compound 101)

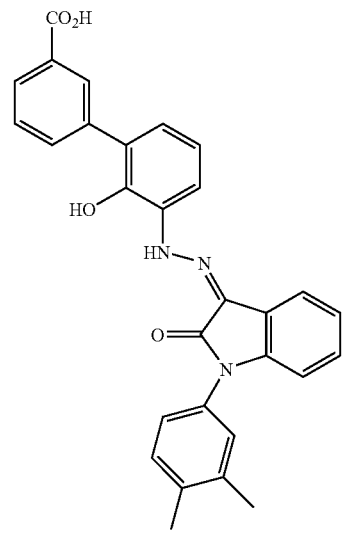

This compound was prepared as described in Scheme II. $^1$H NMR (500 MHz, DMSO-d$_6$) δ 13.07 (s, 1H), 13.03 (s, 1H), 9.26 (s, 1H), 8.12 (t, J=1.6 Hz, 1H), 7.94 (ddd, J=7.7, 1.6, 1.3 Hz, 1H), 7.79 (ddd, J=7.7, 1.6, 1.3 Hz, 1H), 7.73 (dd, J=7.9, 1.6 Hz, 1H), 7.72 (m, 1H), 7.60 (t, J=7.7 Hz, 1H), 7.35 (d, J=8.1 Hz, 1H), 7.30 (d, J=2.1 Hz, 1H), 7.28 (td, J=7.7, 1.3 Hz, 1H), 7.23 (dd, J=8.1, 2.1 Hz, 1H), 7.18 (td, J=7.7, 0.9 Hz, 1H), 7.11 (t, J=7.9 Hz, 1H), 7.00 (dd, J=7.9, 1.6 Hz, 1H), 6.85 (m, 1H), 2.31 (s, 3H), 2.30 (s, 3H).

Example 2

2'-Hydroxy-3'-{N'-[2-oxo-1-(4-propyl-phenyl)-1,2-dihydro-indol-3-ylidene]-hydrazino}-biphenyl-3-carboxylic acid (Compound 102)

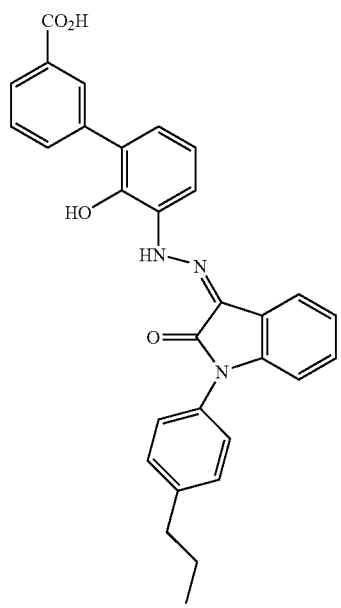

This compound was prepared as described in Scheme II. $^1$H NMR (500 MHz, DMSO-d$_6$) δ 13.07 (s, 1H), 13.03 (s, 1H), 9.27 (s, 1H), 8.11 (t, J=1.6 Hz, 1H), 7.94 (dt, J=7.7, 1.6 Hz, 1H), 7.79 (dt, J=7.7, 1.6 Hz, 1H), 7.73 (d, J=7.9 Hz, 1H), 7.73 (d, J=7.9 Hz, 1H), 7.60 (t, J=7.7 Hz, 1H), 7.44 (d, J=8.5 Hz, 2H), 7.41 (d, J=8.5 Hz, 2H), 7.29 (td, J=7.7, 1.3 Hz, 1H), 7.19 (td, J=7.7, 1.0 Hz, 1H), 7.11 (t, J=7.9 Hz, 1H), 7.00 (dd, J=7.7, 1.3 Hz, 1H), 6.87 (dd, J=7.7, 1.0 Hz, 1H), 2.66 (t, J=7.3 Hz, 2H), 1.66 (sext, J=7.3 Hz, 2H), 0.95 (t, J=7.3 Hz, 3H).

Example 3

2'-Hydroxy-3'-{N'-[2-oxo-1-(4-ethyl-phenyl)-1,2-dihydro-indol-3-ylidene]-hydrazino}-biphenyl-3-carboxylic acid (Compound 103)

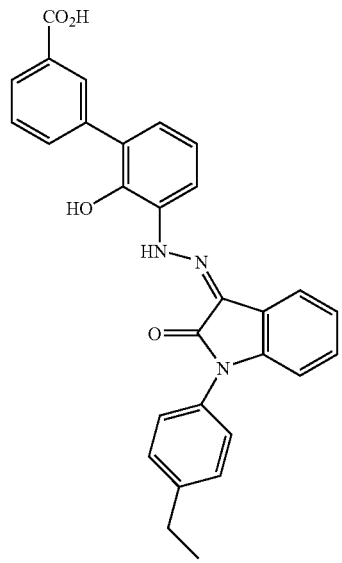

This compound was prepared as described in Scheme II. $^1$H NMR (500 MHz, DMSO-d$_6$) δ 13.06 (s, 1H), 13.03 (s, 1H), 9.27 (s, 1H), 8.11 (t, J=1.5 Hz, 1H), 7.94 (dt, J=7.8, 1.5 Hz, 1H), 7.79 (dt, J=7.8, 1.5 Hz, 1H), 7.73 (dd, J=7.8 Hz, 1H), 7.73 (dd, J=7.8 Hz, 1H), 7.60 (t, J=7.8 Hz, 1H), 7.45 (d, J=8.6 Hz, 2H), 7.43 (d, J=8.6 Hz, 2H), 7.29 (td, J=7.9, 1.0 Hz, 1H), 7.19 (td, J=7.9, 1.0 Hz, 1H), 7.11 (t, J=7.8 Hz, 1H), 7.00 (dd, J=7.9, 1.0 Hz, 1H), 6.87 (dd, J=7.9, 1.0 Hz, 1H), 2.71 (q, J=7.6 Hz, 2H), 1.25 (t, J=7.6 Hz, 3H).

Example 4

2'-Hydroxy-3'-{N'-[2-oxo-1-(4-trifluoromethoxy-phenyl)-1,2-dihydro-indol-3-ylidene]-hydrazino}-biphenyl-3-carboxylic acid (Compound 104)

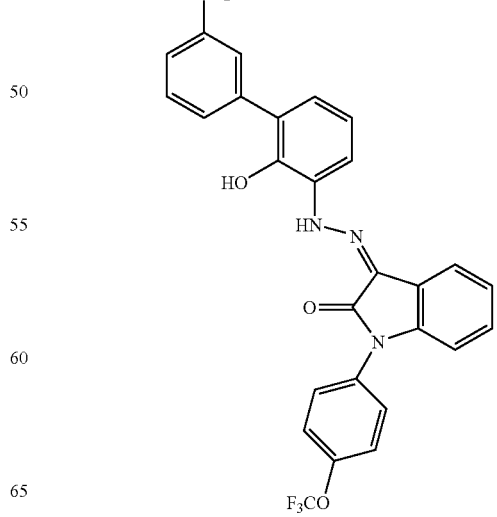

This compound was prepared as described in Scheme II. ¹H NMR (500 MHz, DMSO-$d_6$) δ 13.03 (s, 1H), 9.30 (s, 1H), 8.11 (t, J=1.8 Hz, 1H), 7.94 (ddd, J=7.8, 1.8, 1.2 Hz, 1H), 7.79 (ddd, J=7.8, 1.8, 1.2 Hz, 1H), 7.75 (dd, J=7.7, 1.0 Hz, 1H), 7.74 (dd, J=7.8, 1.6 Hz, 1H), 7.72 (d, J=8.9 Hz, 2H), 7.60 (t, J=7.8 Hz, 1H), 7.31 (td, J=7.7, 1.0 Hz, 1H), 7.22 (td, J=7.7, 1.0 Hz, 1H), 7.12 (t, J=7.8 Hz, 1H), 7.01 (dd, J=7.8, 1.6 Hz, 1H), 6.94 (dd, J=7.7, 1.0 Hz, 1H).

Example 5

3'-{N'-[1-(3-Fluoro-4-methoxy-phenyl)-2-oxo-1,2-dihydro-indol-3-ylidene]-hydrazino}-2'-hydroxy-biphenyl-3-carboxylic acid (Compound 105)

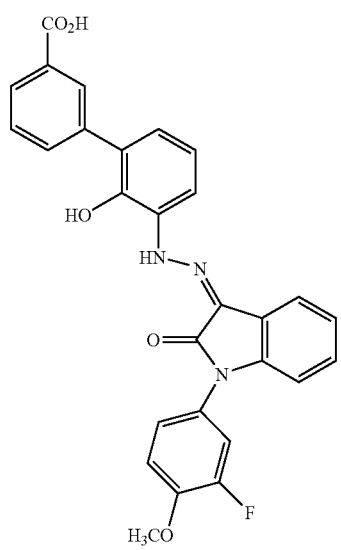

This compound was prepared as described in Scheme II. ¹H NMR (500 MHz, DMSO-$d_6$) δ13.03 (s, 1H), 9.28 (s, 1H), 8.12 (t, J=1.6 Hz, 1H), 7.94 (ddd, J=7.7, 1.6, 1.2 Hz, 1H), 7.79 (ddd, J=7.7, 1.6, 1.2 Hz, 1H), 7.74-7.71 (m, 2H), 7.60 (t, J=7.7 Hz, 1H), 7.50 (dd, J=12.3, 2.2 Hz, 1H), 7.38 (t, J=8.8 Hz, 1H), 7.35 (dd, J=8.8, 2.2 Hz, 1H), 7.29 (td, J=7.7, 1.0 Hz, 1H), 7.19 (td, J=7.7, 1.0 Hz, 1H), 7.11 (t, J=7.7 Hz, 1H), 7.00 (dd, J=7.7, 1.6 Hz, 1H), 6.87 (dd, J=7.7, 1.0 Hz, 1H), 3.93 (s, 3H).

Example 6

3'-{N'-[1-(3,4-Dimethyl-phenyl)-2-oxo-1,2-dihydro-indol-3-ylidene]-hydrazino}-2'-hydroxy-biphenyl-4-carboxylic acid (Compound 106)

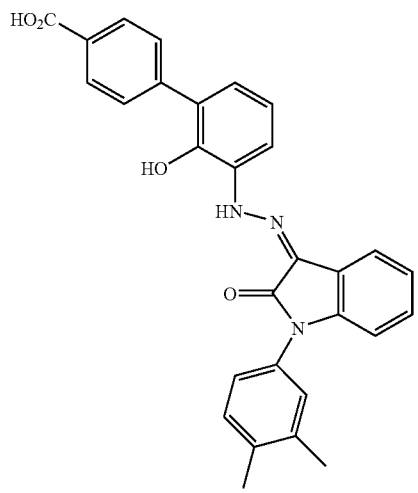

This compound was prepared as described in Scheme II. ¹H NMR (500 MHz, DMSO-$d_6$) δ 13.07 (s, 1H), 12.96 (s, 1H), 9.30 (s, 1H), 8.02 (d, J=8.4 Hz, 2H), 7.74 (dd, J=7.8, 1.6 Hz, 1H), 7.72 (dd, J=7.7, 1.0 Hz, 1H), 7.68 (d, J=8.4 Hz, 2H), 7.35 (d, J=8.0 Hz, 1H), 7.30 (m, 1H), 7.27 (td, J=7.7, 1.0 Hz, 1H), 7.23 (dd, J=8.0, 2.1 Hz, 1H), 7.18 (td, J=7.7, 1.0 Hz, 1H), 7.12 (t, J=7.8 Hz, 1H), 7.01 (dd, J=7.8, 1.6 Hz, 1H), 6.85 (dd, J=7.7, 1.0 Hz, 1H), 2.31 (s, 3H), 2.30 (s, 3H).

Example 7

2'-Hydroxy-3'-{N'-[2-oxo-1-(4-propyl-phenyl)-1,2-dihydro-indol-3-ylidene]-hydrazino}-biphenyl-4-carboxylic acid (Compound 107)

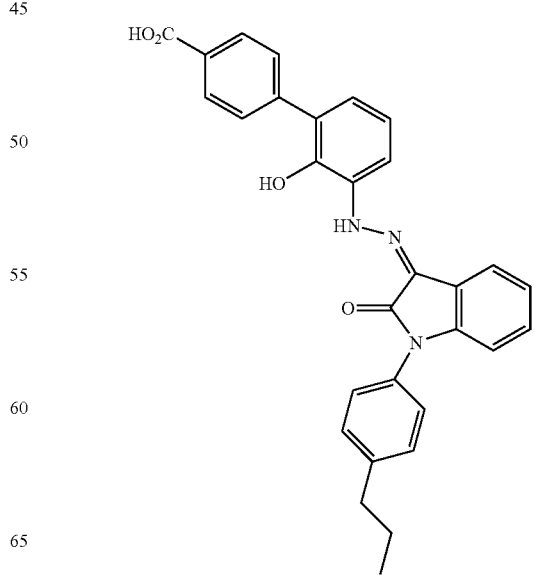

This compound was prepared as described in Scheme II. ¹H NMR (500 MHz, DMSO-d₆) δ13.06 (s, 1H), 12.96 (s, 1H), 9.31 (s, 1H), 8.02 (d, J=8.3 Hz, 2H), 7.75-7.72 (m, 2H), 7.68 (d, J=8.3 Hz, 2H), 7.44 (d, J=8.6 Hz, 2H), 7.41 (d, J=8.6 Hz, 2H), 7.29 (td, J=7.7, 1.0 Hz, 1H), 7.19 (td, J=7.7, 1.0 Hz, 1H), 7.12 (t, J=7.8 Hz, 1H), 7.01 (dd, J=7.8, 1.6 Hz, 1H), 6.87 (dd, J=7.7, 1.0 Hz, 1H), 2.66 (t, J=7.4 Hz, 2H), 1.66 (sext, J=7.4 Hz, 2H), 0.95 (t, J=7.4 Hz, 3H).

Example 8

2'-Hydroxy-3'-{N'-[2-oxo-1-(4-ethyl-phenyl)-1,2-dihydro-indol-3-ylidene]-hydrazino}-biphenyl-4-carboxylic acid (Compound 108)

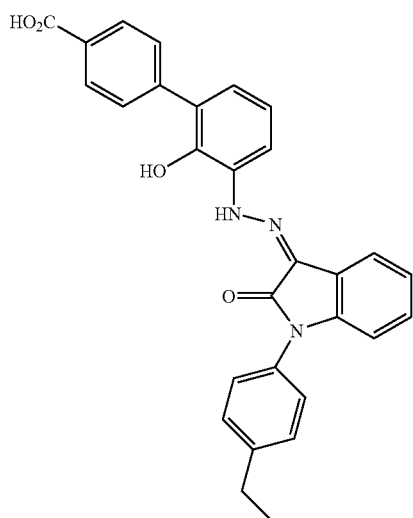

This compound was prepared as described in Scheme II. ¹H NMR (500 MHz, DMSO-d₆) δ13.21 (s, 1H), 8.47 (s, 1H), 8.11 (d, J=8.5 Hz, 2H), 7.79 (dd, J=7.8, 1.6 Hz, 1H), 7.76 (m, 1H), 7.68 (d, J=8.5 Hz, 2H), 7.47 (d, J=8.5 Hz, 2H), 7.45 (d, J=8.5 Hz, 2H), 7.29 (td, J=7.7, 1.1 Hz, 1H), 7.19 (td, J=7.7, 1.1 Hz, 1H), 7.12 (t, J=7.8 Hz, 1H), 7.02 (dd, J=7.8, 1.6 Hz, 1H), 6.92 (dd, J=7.7, 1.1 Hz, 1H), 2.75 (q, J=7.6 Hz, 2H), 1.29 (t, J=7.6 Hz, 3H).

Example 9

3'-{N'-[1-(4-tert-Butyl-phenyl)-2-oxo-1,2-dihydro-indol-3-ylidene]-hydrazino}-2'-hydroxy-biphenyl-3-carboxylic acid (Compound 109)

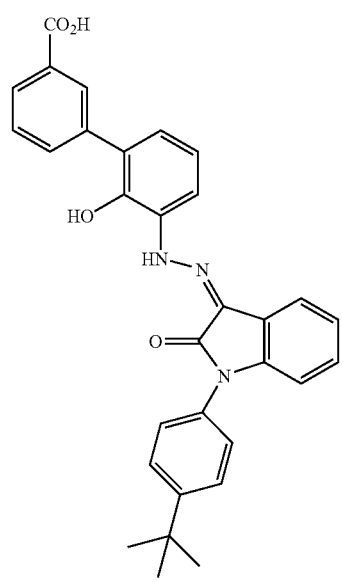

This compound was prepared as described in Scheme II. ¹H NMR (500 MHz, acetone-d₆) δ 13.22 (s, 1H), 8.20 (s, 1H), 8.02 (d, J=7.8 Hz, 1H), 7.80-7.74 (m, 3H), 7.64 (d, J=8.0 Hz, 2H), 7.58 (m, 1H), 7.48 (d, J=8.0 Hz, 2H), 7.29 (t, J=7.7 Hz, 1H), 7.19 (t, J=7.7 Hz, 1H), 7.11 (t, J=7.8 Hz, 1H), 7.00 (m, 1H), 6.92 (d, J=7.7 Hz, 1H), 1.38 (s, 9H).

Example 10

2'-Hydroxy-3'-{N'-[2-oxo-1-(4-trifluoromethyl-phenyl)-1,2-dihydro-indol-3-ylidene]-hydrazino}-biphenyl-3-carboxylic acid (Compound 110)

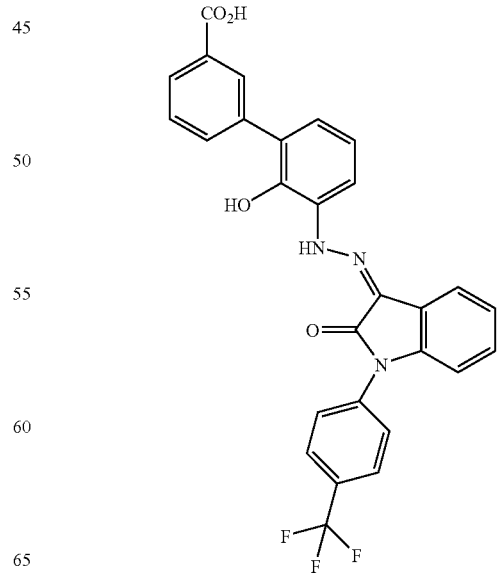

This compound was prepared as described in Scheme II.
¹H NMR (500 MHz, DMSO-d₆) δ 13.04 (s, 1H), 9.32 (s, 1H), 8.12 (t, J=1.5 Hz, 1H), 7.98 (d, J=8.5 Hz, 2H), 7.94 (dt, J=7.7, 1.5 Hz, 1H), 7.83 (d, J=8.5 Hz, 2H), 7.79 (dt, J=7.7, 1.5 Hz, 1H), 7.77 (d, J=7.8 Hz, 1H), 7.74 (dd, J=7.6, 1.2 Hz, 1H), 7.59 (t, J=7.7 Hz, 1H), 7.32 (td, J=7.6, 1.2 Hz, 1H), 7.24 (td, J=7.6, 1.2 Hz, 1H), 7.12 (t, J=7.8 Hz, 1H), 7.04 (d, J=7.8 Hz, 1H), 7.02 (dd, J=7.6, 1.2 Hz, 1H).

Example 11

3'-[N'-(1-Benzyl-5-chloro-2-oxo-1,2-dihydro-indol-3-ylidene)-hydrazino]-2'-hydroxy-biphenyl-3-carboxylic acid (Compound 111)

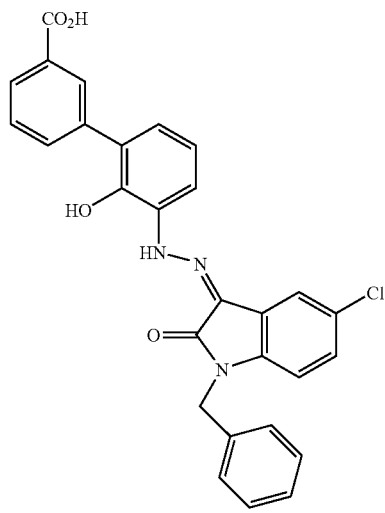

This compound was prepared as described in Scheme III.
¹H NMR (500 MHz, DMSO-d₆) δ 13.10 (s, 1H), 13.03 (s, 1H), 9.36 (s, 1H), 8.13 (t, J=1.7 Hz, 1H), 7.95 (ddd, J=7.7, 1.7, 1.3 Hz, 1H), 7.80 (ddd, J=7.7, 1.7, 1.3 Hz, 1H), 7.76 (dd, J=7.7, 1.6 Hz, 1H), 7.68 (d, J=2.1 Hz, 1H), 7.60 (t, J=7.7 Hz, 1H), 7.37-7.32 (m, 4H), 7.30 (dd, J=8.5, 2.1 Hz, 1H), 7.27 (m, 1H), 7.11 (t, J=7.7 Hz, 1H), 7.09 (d, J=8.5 Hz, 1H), 7.03 (dd, J=7.7, 1.6 Hz, 1H), 5.05 (s, 2H).

Example 12

3'-[N'-(1-Benzyl-5-methyl-2-oxo-1,2-dihydro-indol-3-ylidene)-hydrazino]-2'-hydroxy-biphenyl-3-carboxylic acid (Compound 112)

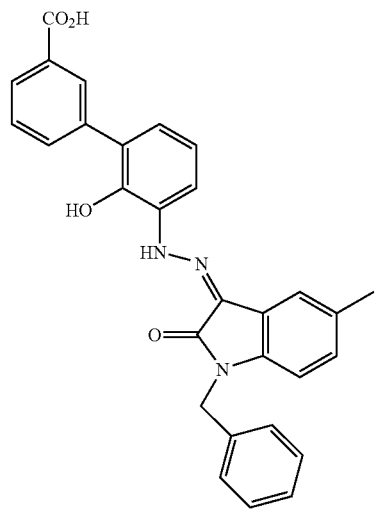

This compound was prepared as described in Scheme III.
¹H NMR (500 MHz, DMSO-d₆) δ 13.04 (s, 1H), 13.03 (s, 1H), 9.25 (s, 1H), 8.13 (t, J=1.5 Hz, 1H), 7.96 (dt, J=7.8, 1.5 Hz, 1H), 7.80 (m, 1H), 7.69 (dd, J=7.8, 1.6 Hz, 1H), 7.60 (t, J=7.8 Hz, 1H), 7.48 (d, J=1.8 Hz, 1H), 7.37-7.31 (m, 4H), 7.27 (m, 1H), 7.10 (t, J=7.8 Hz, 1H), 7.07 (dd, J=8.1, 1.8 Hz, 1H), 6.99 (dd, J=7.8, 1.6 Hz, 1H), 6.95 (d, J=8.1 Hz, 1H), 5.01 (s, 2H), 2.33 (s, 3H).

Example 13

3'-[N'-(1-Benzyl-2-oxo-1,2-dihydro-indol-3-ylidene)-hydrazino]-2'-hydroxy-biphenyl-3-carboxylic acid (Compound 113)

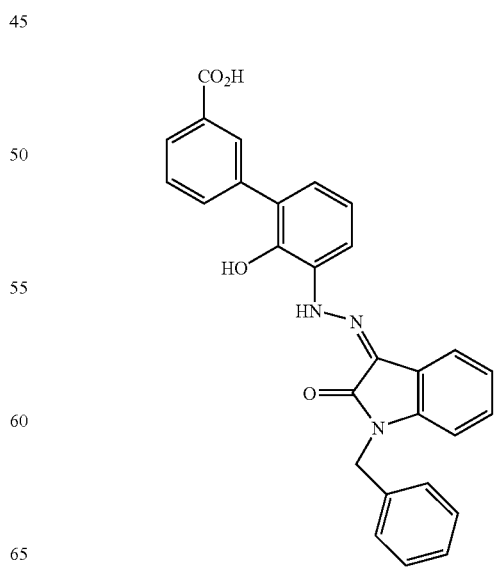

This compound was prepared as described in Scheme III.
¹H NMR (500 MHz, DMSO-d₆) δ13.07 (s, 1H), 13.04 (s, 1H), 9.28 (s, 1H), 8.13 (t, J=1.5 Hz, 1H), 7.94 (dm, J=7.7 Hz, 1H), 7.80 (dm, J=7.7 Hz, 1H), 7.70 (dd, J=7.8, 1.3 Hz, 1H), 7.65 (d, J=7.8 Hz, 1H), 7.60 (t, J=7.7 Hz, 1H), 7.39-7.32 (m, 4H), 7.29-7.24 (m, 2H), 7.14-7.09 (m, 2H), 7.07 (d, J=7.8 Hz, 1H), 7.00 (dd, J=7.8, 1.3 Hz, 1H), 5.05 (s, 2H).

Example 14

2'-Hydroxy-3'-{N'-[2-oxo-1-(4-trifluoromethyl-phenyl)-1,2-dihydro-indol-3-ylidene]-hydrazino}-biphenyl-4-carboxylic acid (Compound 114)

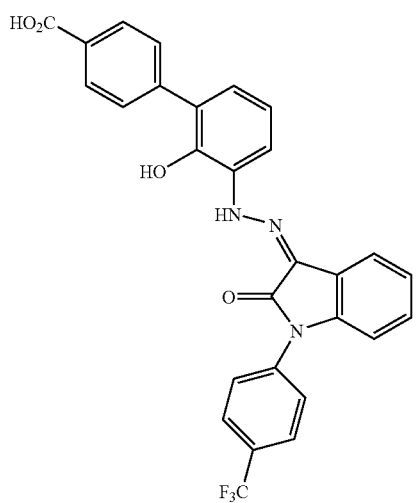

This compound was prepared as described in Scheme 11.
¹H NMR (500 MHz, DMSO-d₆) δ 13.03 (s, 1H), 12.96 (s, 1H), 9.36 (s, 1H), 8.02 (d, J=8.3 Hz, 2H), 7.98 (d, J=8.3 Hz, 2H), 7.83 (d, J=8.3 Hz, 2H), 7.77 (dd, J=7.7, 1.2 Hz, 1H), 7.75 (dd, J=7.8, 1.6 Hz, 1H), 7.68 (d, J=8.3 Hz, 2H), 7.32 (td, J=7.7, 1.2 Hz, 1H), 7.24 (td, J=7.7, 0.7 Hz, 1H), 7.13 (t, J=7.8 Hz, 1H), 7.03 (dd, J=7.8, 1.6 Hz, 1H) 7.04 (dd, J=7.7, 0.7 Hz, 1H).

Example 15

3'-{N'-[1-(3,4-Dichloro-phenyl)-2-oxo-1,2-dihydro-indol-3-ylidene]-hydrazino}-2'-hydroxy-biphenyl-3-carboxylic acid (Compound 115)

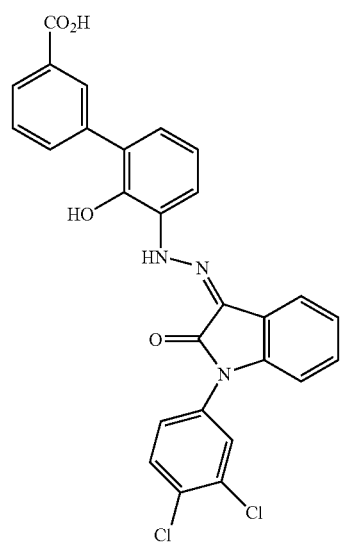

This compound was prepared as described in Scheme II.
¹H NMR (500 MHz, DMSO-d₆) δ 13.04 (s, 1H), 13.01 (s, 1H), 9.32 (s, 1H), 8.12 (t, J=1.6 Hz, 1H), 7.95 (dt, J=7.7, 1.4 Hz, 1H), 7.93 (d, J=2.4 Hz, 1H), 7.88 (d, J=8.5 Hz, 1H), 7.79 (m, 1H), 7.75 (ddd, J=7.6, 1.0, 0.5 Hz, 1H), 7.73 (dd, J=7.7, 1.6 Hz, 1H), 7.61 (dd, J=8.5, 2.4 Hz, 1H), 7.60 (t, J=7.7 Hz, 1H), 7.31 (td, J=7.6, 1.0 Hz, 1H), 7.22 (td, J=7.6, 0.8 Hz, 1H), 7.12 (t, J=7.7 Hz, 1H), 6.98 (ddd, J=7.6, 0.8, 0.5 Hz, 1H), 7.01 (dd, J=7.7, 1.6 Hz, 1H).

Example 16

2'-Hydroxy-3'-{N'-[1-(4-methyl-3-trifluoromethyl-phenyl)-2-oxo-1,2-dihydro-indol-3-ylidene]-hydrazino}-biphenyl-3-carboxylic acid (Compound 116)

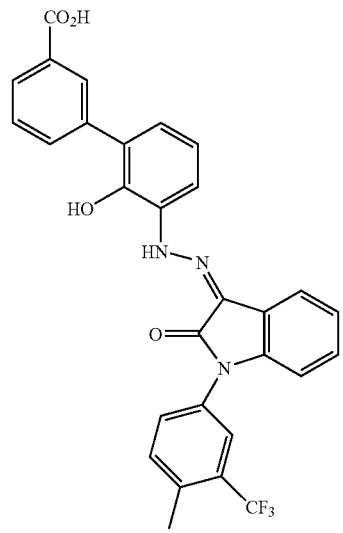

This compound was prepared as described in Scheme II.
¹H NMR (500 MHz, DMSO-d₆) δ 13.04 (s, 1H), 13.02 (s, 1H), 9.30 (s, 1H), 8.12 (t, J=1.6 Hz, 1H), 7.94 (ddd, J=7.8, 1.6, 1.2 Hz, 1H), 7.88 (d, J=2.0 Hz, 1H), 7.79 (ddd, J=7.8, 1.6, 1.2 Hz, 1H), 7.77 (dd, J=8.3, 2.0 Hz, 1H), 7.76-7.72 (m, 2H), 7.68 (d, J=8.3 Hz, 1H), 7.60 (t, J=7.8 Hz, 1H), 7.30 (td, J=7.7, 1.2 Hz, 1H), 7.21 (td, J=7.7, 0.9 Hz, 1H), 7.12 (t, J=7.7 Hz, 1H), 7.01 (dd, J=7.7, 1.6 Hz, 1H), 6.92 (dm, J=7.7 Hz, 1H), 2.54 (q, J=1.4 Hz, 3H).

Example 17

3'-{N'-[1-(3-Fluoro-4-trifluoromethyl-phenyl)-2-oxo-1,2-dihydro-indol-3-ylidene]-hydrazino}-2'-hydroxy-biphenyl-3-carboxylic acid (Compound 117)

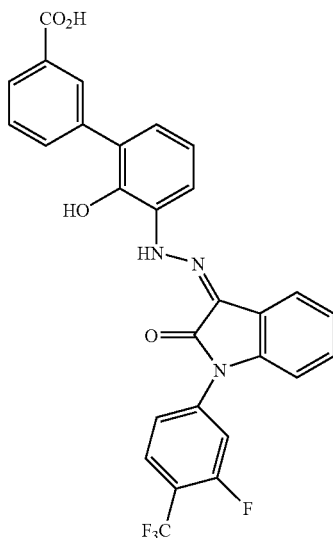

This compound was prepared as described in Scheme II.
¹H NMR (500 MHz, DMSO-d₆) δ 13.04 (s, 1H), 13.01 (s, 1H), 9.35 (s, 1H), 8.12 (t, J=1.7 Hz, 1H), 8.03 (t, J=8.4 Hz, 1H), 7.94 (ddd, J=7.7, 1.7, 1.2 Hz, 1H), 7.86 (dd, J=11.8, 1.5 Hz, 1H), 7.80 (ddd, J=7.7, 1.7, 1.2 Hz, 1H), 7.77 (dd, J=7.7, 1.0 Hz, 1H), 7.74 (dd, J=7.7, 1.6 Hz, 1H), 7.68 (dd, J=8.4, 1.5 Hz, 1H), 7.60 (t, J=7.7 Hz, 1H), 7.34 (td, J=7.7, 1.0 Hz, 1H), 7.25 (td, J=7.7, 1.0 Hz, 1H), 7.14 (dd, J=7.7, 1.0 Hz, 1H), 7.12 (t, J=7.7 Hz, 1H), 7.02 (dd, J=7.7, 1.6 Hz, 1H).

Example 18

3'-{N'-[1-(3,5-Bis-trifluoromethyl-phenyl)-2-oxo-1,2-dihydro-indol-3-ylidene]-hydrazino}-2'-hydroxy-biphenyl-3-carboxylic acid (Compound 118)

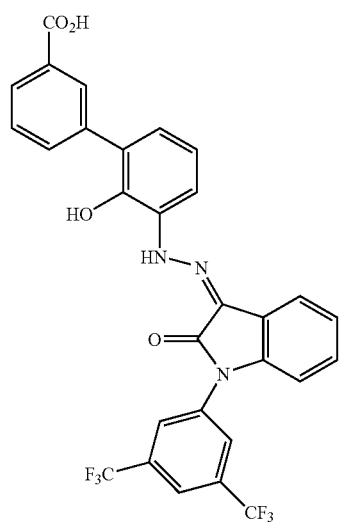

This compound was prepared as described in Scheme II.
¹H NMR (500 MHz, DMSO-d₆) δ 13.04 (s, 1H), 12.99 (s, 1H), 9.34 (s, 1H), 8.38-8.37 (m, 2H), 8.27 (m, 1H), 8.12 (t, J=1.6 Hz, 1H), 7.94 (ddd, J=7.7, 1.6, 1.2 Hz, 1H), 7.79 (ddd, J=7.7, 1.6, 1.2 Hz, 1H), 7.78 (ddd, J=7.7, 1.3, 0.6 Hz, 1H), 7.75 (dd, J=7.8, 1.7 Hz, 1H), 7.60 (t, J=7.7 Hz, 1H), 7.34 (td, J=7.7, 1.3 Hz, 1H), 7.25 (td, J=7.7, 1.0 Hz, 1H), 7.13 (t, J=7.8 Hz, 1H), 7.02 (dd, J=7.8, 1.7 Hz, 1H), 7.02 (ddd, J=7.7, 1.0, 0.6 Hz, 1H).

Example 19

3'-{N'-[3-(3,4-Dimethyl-phenyl)-4-oxo-2-thioxo-thiazolidin-5-ylidene]-hydrazino}-2'-hydroxy-biphenyl-3-carboxylic acid (Compound 119)

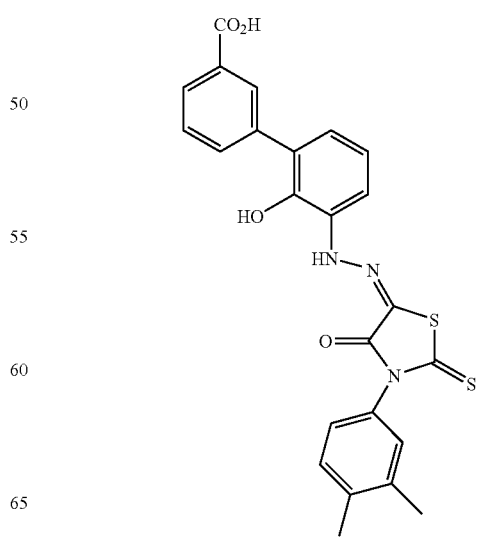

This compound was prepared as described in Scheme IV. ¹H NMR (500 MHz, DMSO-$d_6$) δ 12.83 (s, 1H), 10.76 (s, 1H), 9.35 (s, 1H), 8.15 (t, J=1.5 Hz, 1H), 7.91 (m, 1H), 7.79 (dt, J=7.7, 1.5 Hz, 1H), 7.56 (t, J=7.7 Hz, 1H), 7.34 (m, 1H), 7.29 (d, J=7.9 Hz, 1H), 7.14-6.96 (m, 4H), 2.28 (s, 3H), 2.26 (s, 3H).

Example 20

2'-Hydroxy-3'-{N'-[1-(4-isopropyl-phenyl)-2-oxo-1,2-dihydro-indol-3-ylidene]-hydrazino}-biphenyl-3-carboxylic acid (Compound 120)

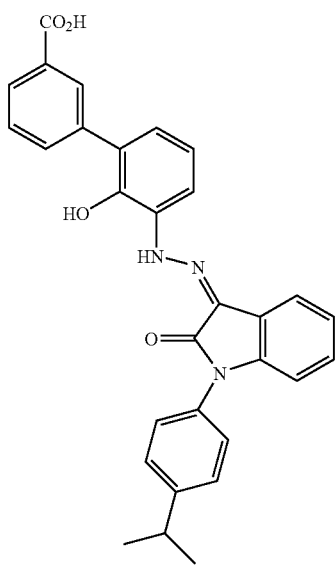

This compound was prepared as described in Scheme II. ¹H NMR (500 MHz, DMSO-$d_6$) δ 13.06 (s, 1H), 9.27 (s, 1H), 8.11 (t, J=1.7 Hz, 1H), 7.94 (ddd, J=7.7, 1.7, 1.2 Hz, 1H), 7.79 (ddd, J=7.7, 1.7, 1.2 Hz, 1H), 7.73 (dd, J=7.7, 1.3 Hz, 1H), 7.73 (dd, J=7.7, 1.6 Hz, 1H), 7.60 (t, J=7.7 Hz, 1H), 7.47 (d, J=8.8 Hz, 2H), 7.45 (d, J=8.8 Hz, 2H), 7.29 (td, J=7.7, 1.3 Hz, 1H), 7.19 (td, J=7.7, 0.8 Hz, 1H), 7.11 (t, J=7.7 Hz, 1H), 7.00 (dd, J=7.7, 1.6 Hz, 1H), 6.88 (dd, J=7.7, 0.8 Hz, 1H), 3.00 (sept, J=6.9 Hz, 1H), 1.27 (d, J=6.9 Hz, 6H).

Example 21

3'-{N'-[1-(2-Fluoro-4-trifluoromethyl-phenyl)-2-oxo-1,2-dihydro-indol-3-ylidene]-hydrazino}-2'-hydroxy-biphenyl-3-carboxylic acid (Compound 121)

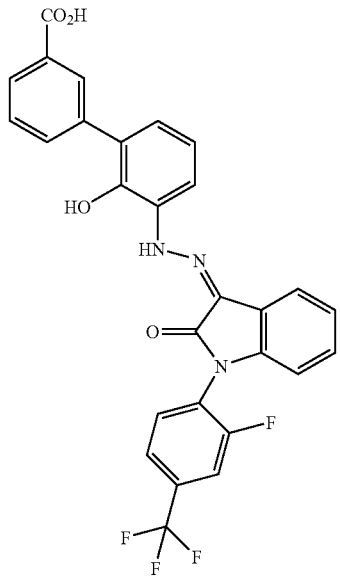

This compound was prepared as described in Scheme II. ¹H NMR (500 MHz, DMSO-$d_6$) δ 12.95 (s, 1H), 9.34 (s, 1H), 8.11 (t, J=1.7 Hz, 1H), 8.09 (m, 1H), 7.96 (t, J=8.0 Hz, 1H), 7.94 (ddd, J=7.7, 1.7, 1.2 Hz, 1H), 7.86 (m, 1H), 7.79 (ddd, J=7.7, 1.7, 1.2 Hz, 1H), 7.77 (m, 1H), 7.75 (dd, J=8.0, 1.5 Hz, 1H), 7.60 (t, J=7.7 Hz, 1H), 7.32 (td, J=7.6, 1.4 Hz, 1H), 7.24 (td, J=7.6, 0.9 Hz, 1H), 7.13 (t, J=7.7 Hz, 1H), 7.03 (dd, J=7.7, 1.6 Hz, 1H), 6.86 (dm, J=7.6 Hz, 1H).

Example 22

3'-{N'-[1-(2-Fluoro-4-methyl-phenyl)-2-oxo-1,2-dihydro-indol-3-ylidene]-hydrazino}-2'-hydroxy-biphenyl-3-carboxylic acid (Compound 122)

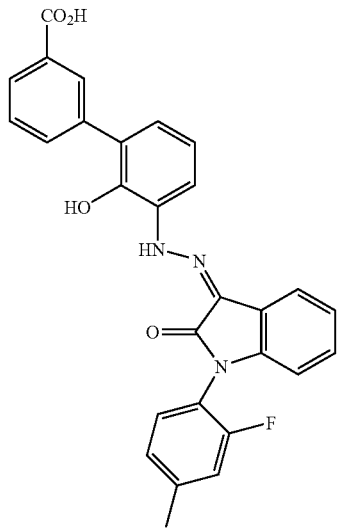

This compound was prepared as described in Scheme II. ¹H NMR (500 MHz, DMSO-$d_6$) δ 12.99 (s, 1H), 9.29 (s, 1H), 8.11 (t, J=1.7 Hz, 1H), 7.94 (ddd, J=7.7, 1.7, 1.2 Hz, 1H), 7.79 (ddd, J=7.7, 1.7, 1.2 Hz, 1H), 7.75-7.72 (m, 2H), 7.59 (t, J=7.7 Hz, 1H), 7.52 (t, J=8.0 Hz, 1H), 7.37 (dd, J=11.3, 1.4 Hz, 1H), 7.29 (td, J=7.7, 1.2 Hz, 1H), 7.25 (dm, J=8.0 Hz, 1H), 7.21 (td, J=7.7, 1.0 Hz, 1H) 7.12 (t, J=7.7 Hz, 1H), 7.01 (dd, J=7.7, 1.6 Hz, 1H), 6.71 (dm, J=7.7 Hz, 1H), 2.43 (s, 3H).

Example 23

3'-{N'-[1-(4-Chloro-3-trifluoromethyl-phenyl)-2-oxo-1,2-dihydro-indol-3-ylidene]-hydrazino}-2'-hydroxy-biphenyl-3-carboxylic acid (Compound 123)

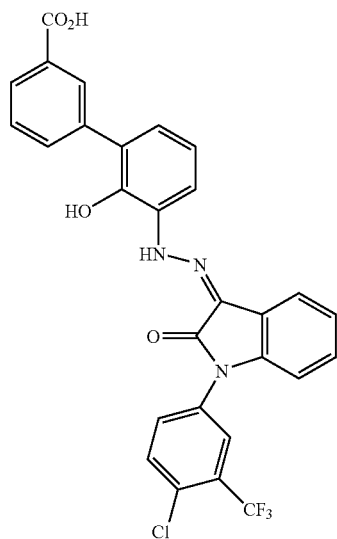

This compound was prepared as described in Scheme II. ¹H NMR (500 MHz, DMSO-$d_6$) δ12.99 (s, 1H), 9.32 (s, 1H), 8.12 (m, 2H), 7.98 (d, J=8.7 Hz, 1H), 7.94 (dd, J=8.7, 2.2 Hz, 1H), 7.94 (m, 1H), 7.79 (ddd, J=7.7, 1.7, 1.2 Hz, 1H), 7.76 (dd, J=7.6, 1.0 Hz, 1H), 7.74 (dd, J=7.9, 1.6 Hz, 1H), 7.60 (t, J=7.7 Hz, 1H), 7.32 (td, J=7.6, 1.4 Hz, 1H), 7.23 (td, J=7.6, 1.0 Hz, 1H), 7.12 (t, J=7.9 Hz, 1H), 7.03-7.00 (m, 2H).

Example 24

3'-{N'-[1-(4-Butyl-phenyl)-2-oxo-1,2-dihydro-indol-3-ylidene]-hydrazino}-2'-hydroxy-biphenyl-3-carboxylic acid (Compound 124)

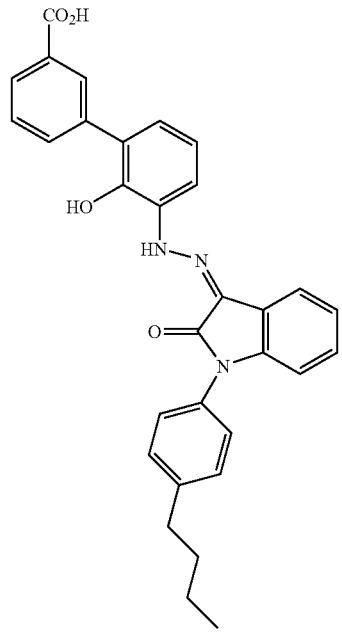

This compound was prepared as described in Scheme II. ¹H NMR (500 MHz, DMSO-$d_6$) δ13.22 (s, 1H), 8.19 (t, J=1.6 Hz, 1H), 8.03 (dt, J=7.8, 1.6 Hz, 1H), 7.79 (dt, J=7.8, 1.6 Hz, 1H), 7.78 (dd, J=7.8, 1.6 Hz, 1H), 7.76 (dd, J=7.7, 1.0 Hz, 1H), 7.60 (t, J=7.8 Hz, 1H), 7.46 (d, J=8.4 Hz, 2H), 7.44 (d, J=8.4 Hz, 2H), 7.29 (td, J=7.7, 1.0 Hz, 1H), 7.19 (td, J=7.7, 1.0 Hz, 1H), 7.12 (t, J=7.8 Hz, 1H), 7.01 (dd, J=7.8, 1.6 Hz, 1H), 6.92 (d, J=7.7, 1.0 Hz, 1H), 2.72 (t, J=7.5 Hz, 2H), 1.67 (m, 2H), 1.40 (m, 2H), 0.95 (t, J=7.5 Hz, 3H).

Example 25

3'-{N'-[1-(3-Fluoro-phenyl)-2-oxo-1,2-dihydro-indol-3-ylidene]-hydrazino}-2'-hydroxy-biphenyl-3-carboxylic acid (Compound 125)

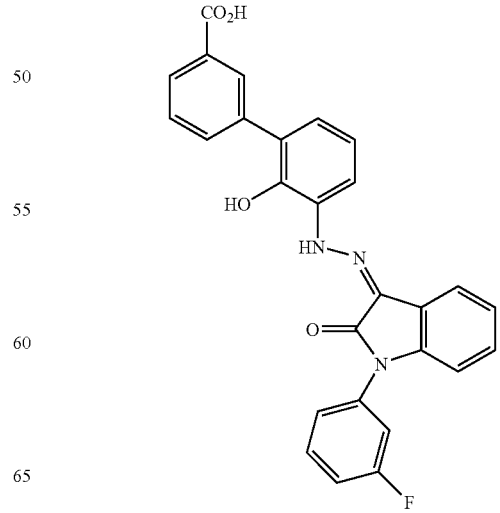

This compound was prepared as described in Scheme II. ¹H NMR (500 MHz, DMSO-d₆) δ13.03 (s, 1H), 9.31 (s, 1H), 8.12 (t, J=1.6 Hz, 1H), 7.94 (ddd, J=7.7, 1.6, 1.2 Hz, 1H), 7.79 (ddd, J=7.7, 1.6, 1.2 Hz, 1H), 7.74 (ddd, J=7.6, 1.2, 0.6 Hz, 1H), 7.73 (dd, J=7.7, 1.6 Hz, 1H), 7.65 (ddd, J=8.5, 8.0, 6.6 Hz, 1H), 7.60 (t, J=7.7 Hz, 1H), 7.49 (ddd, J=9.9, 2.6, 2.0 Hz, 1H) 7.42 (ddd, J=8.0, 2.0, 0.8 Hz, 1H), 7.36 (tdd, J=8.5, 2.6, 0.8 Hz, 1H), 7.31 (td, J=7.6, 1.2 Hz, 1H), 7.21 (td, J=7.6, 0.8 Hz, 1H), 7.11 (t, J=7.7 Hz, 1H), 7.01 (dd, J=7.7, 1.6 Hz, 1H), 6.96 (ddd, J=7.6, 0.8, 0.6 Hz, 1H).

Example 26

2'-Hydroxy-3'-[N'-(2-oxo-1-m-tolyl-1,2-dihydro-indol-3-ylidene)-hydrazino]-biphenyl-3-carboxylic acid (Compound 126)

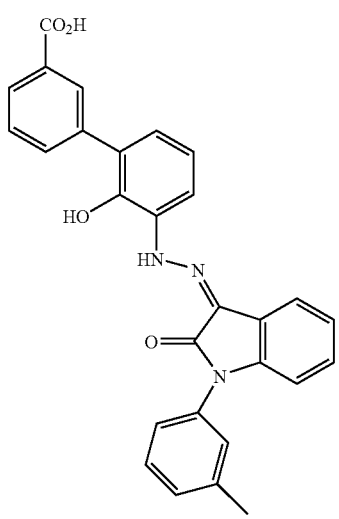

This compound was prepared as described in Scheme II. ¹H NMR (500 MHz, DMSO-d₆) δ13.22 (s, 1H), 8.20 (t, J=1.6 Hz, 1H), 8.03 (dt, J=7.8, 1.6 Hz, 1H), 7.80-7.77 (m, 2H), 7.76 (dd, J=7.7, 1.0 Hz, 1H), 7.60 (t, J=7.8 Hz, 1H), 7.48 (t, J=7.8 Hz, 1H), 7.38 (t, J=1.6 Hz, 1H), 7.35 (m, 1H), 7.30 (m, 1H), 7.29 (td, J=7.7, 1.0 Hz, 1H), 7.19 (td, J=7.7, 1.0 Hz, 1H), 7.12 (t, J=7.8 Hz, 1H), 7.01 (dd, J=7.8, 1.7 Hz, 1H), 6.93 (dd, J=7.7, 1.0 Hz, 1H), 2.44 (s, 3H).

Example 27

3'-{N'-[1-(4-Fluoro-phenyl)-2-oxo-1,2-dihydro-indol-3-ylidene]-hydrazino}-2'-hydroxy-biphenyl-3-carboxylic acid (Compound 127)

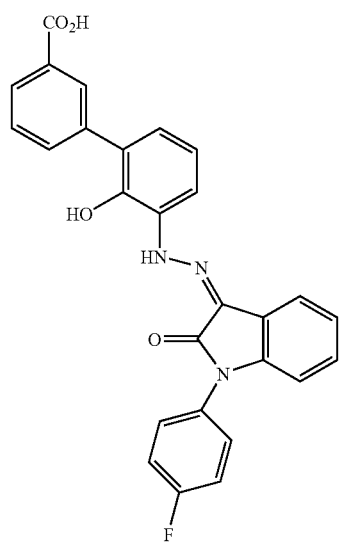

This compound was prepared as described in Scheme II. ¹H NMR (500 MHz, DMSO-d₆) δ13.04 (s, 1H), 9.28 (s, 1H), 8.11 (t, J=1.6 Hz, 1H), 7.94 (dt, J=7.9, 1.6 Hz, 1H), 7.78 (dt, J=7.9, 1.6 Hz, 1H), 7.74 (dd, J=7.8, 1.0 Hz, 1H), 7.73 (dd, J=7.9, 1.6 Hz, 1H), 7.63-7.57 (m, 3H), 7.44 (t, J=8.6 Hz, 2H), 7.29 (td, J=7.8, 1.0 Hz, 1H), 7.20 (td, J=7.8, 1.0 Hz, 1H), 7.11 (t, J=7.9 Hz, 1H), 7.00 (dd, J=7.9, 1.6 Hz, 1H), 6.86 (d, J=7.8 Hz, 1H).

Example 28

3'-[N'-(1-Benzyl-5-methoxy-2-oxo-1,2-dihydro-indol-3-ylidene)-hydrazino]-2'-hydroxy-biphenyl-3-carboxylic acid (Compound 128)

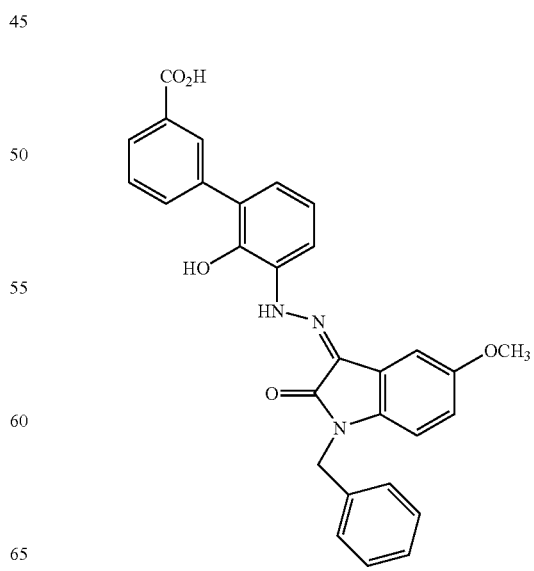

This compound was prepared as described in Scheme III. ¹H NMR (500 MHz, DMSO-$d_6$) δ 13.10 (s, 1H), 9.27 (s, 1H), 8.13 (s, 1H), 7.95 (d, J=7.5 Hz, 1H), 7.80 (d, J=8.0 Hz, 1H), 7.74 (d, J=6.5 Hz, 1H), 7.60 (t, J=7.5 Hz, 1H), 7.36-7.32 (m, 4H), 7.28-7.25 (m, 1H), 7.24 (d, J=2.5 Hz, 1H), 7.11 (t, J=7.5 Hz, 1H), 7.00 (d, J=8.0 Hz, 1H), 6.97 (d, J=8.5 Hz, 1H), 6.84 (dd, J=2.5, 9.0 Hz, 1H), 5.01 (s, 2H), 3.79 (s, 3H).

Example 29

2'-Hydroxy-3'-{N'-[2-oxo-1-(3-trifluoromethyl-phenyl)-1,2-dihydro-indol-3-ylidene]-hydrazino}-biphenyl-3-carboxylic acid (Compound 129)

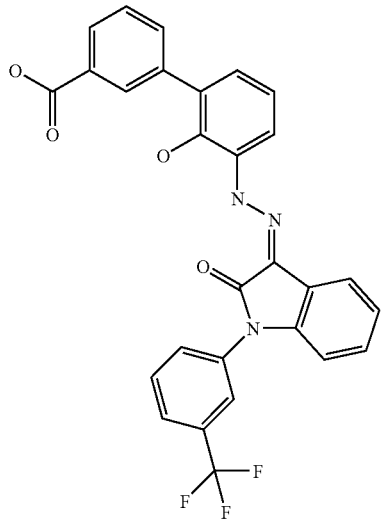

This compound was prepared as described in Scheme II. ¹H NMR (500 MHz, DMSO-$d_6$) δ 13.03 (s, 1H), 9.32 (s, 1H), 8.12 (s, 1H), 7.99 (s, 1H), 7.95-7.91 (m, 4H), 7.81-7.73 (m, 3H), 7.60 (t, J=7.5 Hz, 1H), 7.32 (t, J=7.5 Hz, 1H), 7.23 (t, J=7.5 Hz, 1H), 7.12 (t, J=7.5 Hz, 1H), 7.02 (dd, J=1.5, 7.5 Hz, 1H), 6.95 (d, J=7.5 Hz, 1H).

Example 30

3'-{N'-[5-Chloro-1-(4-isopropyl-phenyl)-2-oxo-1,2-dihydro-indol-3-ylidene]-hydrazino}-2'-hydroxy-biphenyl-3-carboxylic acid (Compound 130)

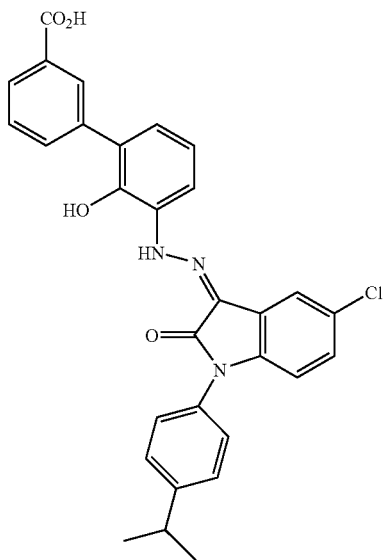

This compound was prepared as described in Scheme II. ¹H NMR (500 MHz, DMSO-$d_6$) δ13.09 (s, 2H), 9.35 (s, 1H), 8.11 (d, J=1.5 Hz, 1H), 7.94 (d, J=7.8 Hz, 1H), 7.79 (d, J=8.3 Hz, 2H), 7.76 (d, J=2.0 Hz, 1H), 7.60 (t, 1H), 7.46 (q, J=6.0 Hz, 4H), 7.30 (dd, J=8.3, 2.4 Hz, 1H), 7.12 (t, J=7.8 Hz, 1H), 7.03 (dd, J=7.8, 1.5 Hz, 1H), 6.88 (d, J=8.8 Hz, 1H), 3.00 (sept, J=7.0 Hz, 1H), 1.27 (d, J=6.8 Hz, 8H).

Example 31

3'-{N'-[6-Chloro-1-(4-isopropyl-phenyl)-2-oxo-1,2-dihydro-indol-3-ylidene]-hydrazino}-2'-hydroxy-biphenyl-3-carboxylic acid (Compound 131)

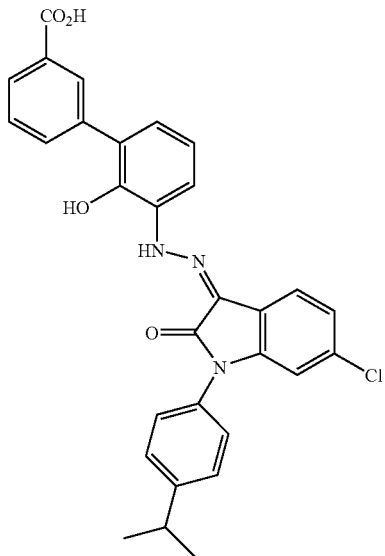

This compound was prepared as described in Scheme II. ¹H NMR (500 MHz, DMSO-$d_6$) δ13.05 (s, 1H), 9.30 (s, 1H), 8.11 (t, J=1.5 Hz, 1H), 7.94 (qn, J=2.3 Hz, 1H), 7.79 (dt, J=7.8, 1.5 Hz, 1H), 7.73 (dd, J=7.8, 1.5 Hz, 2H), 7.59 (t, J=7.8 Hz, 1H), 7.48 (m, 4H), 7.24 (dd, J=8.1, 1.7 Hz, 1H), 7.11 (t, 1H), 7.02 (dd, J=7.6, 1.7 Hz, 1H), 6.82 (d, J=1.5 Hz, 1H), 3.00 (sept, J=6.8 Hz, 1H), 1.27 (d, J=6.8 Hz, 6H).

Example 32

3'-{N'-[5-Fluoro-1-(4-isopropyl-phenyl)-2-oxo-1,2-dihydro-indol-3-ylidene]-hydrazino}-2'-hydroxy-biphenyl-3-carboxylic acid (Compound 132)

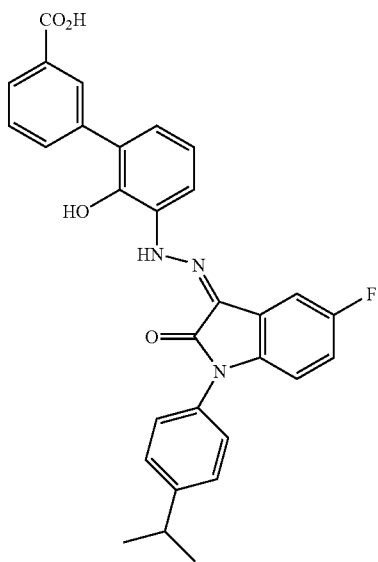

This compound was prepared as described in Scheme II. ¹H NMR (500 MHz, DMSO-$d_6$) δ13.12 (s, 1H), 13.04 (s, 1H), 9.34 (s, 1H), 8.11 (t, 1H), 7.94 (t, 1H), 7.78 (dt, J=9.1, 5.2 Hz, 2H), 7.58 (m, 2H), 7.46 (m, 4H), 7.09-7.09 (m, 2H), 7.03 (dd, J=7.8, 2.0 Hz, 1H), 6.87 (dd, J=8.8, 3.9 Hz, 1H), 3.00 (sept, J=7.0 Hz, 1H), 1.27 (d, J=6.8 Hz, 6H).

Example 33

3'-{N'-[5-Methoxy-1-(4-isopropyl-phenyl)-2-oxo-1,2-dihydro-indol-3-ylidene]-hydrazino}-2'-hydroxy-biphenyl-3-carboxylic acid (Compound 133)

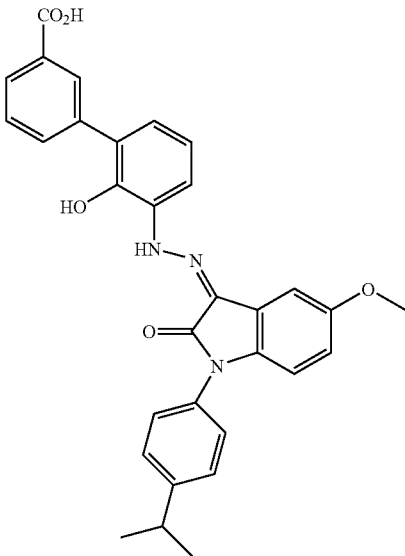

This compound was prepared as described in Scheme II. ¹H NMR (500 MHz, DMSO-$d_6$) δ13.09 (s, 1H), 13.03 (s, 1H), 9.26 (s, 1H), 8.11 (t, J=1.5 Hz, 1H), 7.94 (d, J=7.8 Hz, 1H), 7.78 (dt, J=9.9, 5.5 Hz, 2H), 7.60 (t, J=7.8 Hz, 1H), 7.45 (q, J=5.4 Hz, 4H), 7.32 (d, J=2.4 Hz, 1H), 7.11 (t, 1H), 7.00 (dd, J=7.6, 1.7 Hz, 1H), 6.86 (dd, J=8.5, 2.7 Hz, 1H), 6.82 (d, J=8.8 Hz, 1H), 3.83 (s,3H), 3.00 (sept, J=6.8 Hz, 1H), 1.27 (d, J=6.8 Hz, 6H).

Example 34

3'-{N'-[1-(3,4-Dimethyl-phenyl)-5-fluoro-2-oxo-1,2-dihydro-indol-3-ylidene]-hydrazino}-2'-hydroxy-biphenyl-3-carboxylic acid (Compound 134)

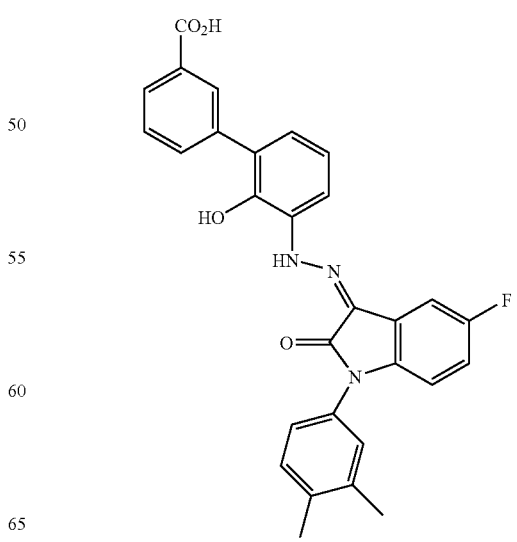

This compound was prepared as described in Scheme II. ¹H NMR (500 MHz, DMSO-d₆) δ13.13 (s, 1H), 13.03 (s, 1H), 9.33 (s, 1H), 8.12 (t, 1H), 7.94 (d, J=7.8 Hz, 1H), 7.79 (dt, J=4.8, 3.8 Hz, 2H), 7.60 (t, J=7.8 Hz, 1H), 7.56 (dd, J=8.1, 2.7 Hz, 1H), 7.35 (d, J=8.3 Hz, 1H), 7.30 (d, J=2.0 Hz, 1H), 7.23 (dd, J=8.1, 2.2 Hz, 1H), 7.14-7.08 (m, 2H), 7.03 (dd, J=7.8, 1.5 Hz, 1H), 6.85 (q, J=4.2 Hz, 1H), 2.31 (s, 3H), 2.30 (s, 3H).

Example 35

3'-{N'-[1-(4-Fluoro-3-trifluoromethyl-phenyl)-5-fluoro-2-oxo-1,2-dihydro-indol-3-ylidene]-hydrazino}-2'-hydroxy-biphenyl-3-carboxylic acid (Compound 135)

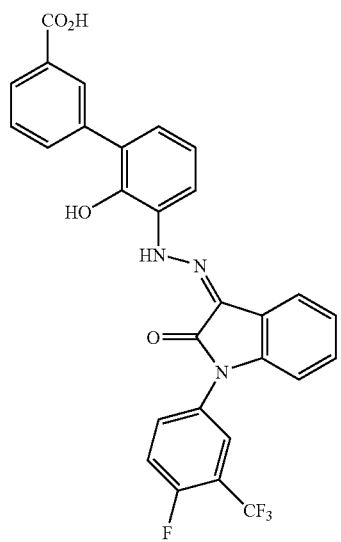

This compound was prepared as described in Scheme II. ¹H NMR (500 MHz, DMSO-d₆) δ13.03 (s, 1H), 13.00 (s, 1H), 9.31 (s, 1H), 8.12 (t, J=1.6 Hz, 1H), 8.06 (dd, J=6.6, 2.7 Hz, 1H), 7.99 (dd, J=8.8, 4.4, 2.7 Hz, 1H), 7.94 (ddd, J=7.8, 1.6, 1.3 Hz, 1H), 7.80-7.72 (m, 4H), 7.60 (t, J=7.8 Hz, 1H), 7.31 (td, J=7.7, 1.3 Hz, 1H), 7.22 (td, J=7.7, 1.0 Hz, 1H), 7.12 (t, J=7.8 Hz, 1H), 7.01 (dd, J=7.8, 1.6 Hz, 1H), 6.94 (ddd, J=7.7, 1.0, 0.6 Hz, 1H).

Example 36

3'-{N'-[1-(3,5-Dichloro-phenyl)-5-fluoro-2-oxo-1,2-dihydro-indol-3-ylidene]-hydrazino}-2'-hydroxy-biphenyl-3-carboxylic acid (Compound 136)

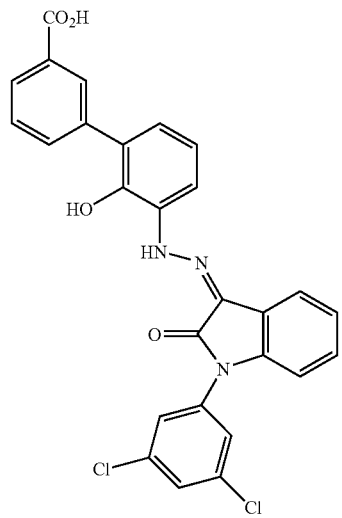

This compound was prepared as described in Scheme II. ¹H NMR (500 MHz, DMSO-d₆) δ 13.02 (s, 1H), 12.99 (s, 1H), 9.33 (s, 1H), 8.12 (t, J=1.6 Hz, 1H), 7.94 (ddd, J=7.7, 1.6, 1.1 Hz, 1H), 7.80 (ddd, J=7.7, 1.6, 1.1 Hz, 1H), 7.78 (t, J=1.9 Hz, 1H), 7.76-7.72 (m, 4H), 7.60 (t, J=7.7 Hz, 1H), 7.32 (td, J=7.6, 1.2 Hz, 1H), 7.23 (td, J=7.6, 0.7 Hz, 1H), 7.12 (t, J=7.8 Hz, 1H), 7.01 (dd, J=7.8, 1.7 Hz, 1H), 7.00 (d, J=7.6 Hz, 1H).

Example 37

3'-{N'-[1-(4-Propyl-phenyl)-6-chloro-2-oxo-1,2-dihydro-indol-3-ylidene]-hydrazino}-2'-hydroxy-biphenyl-3-carboxylic acid (Compound 137)

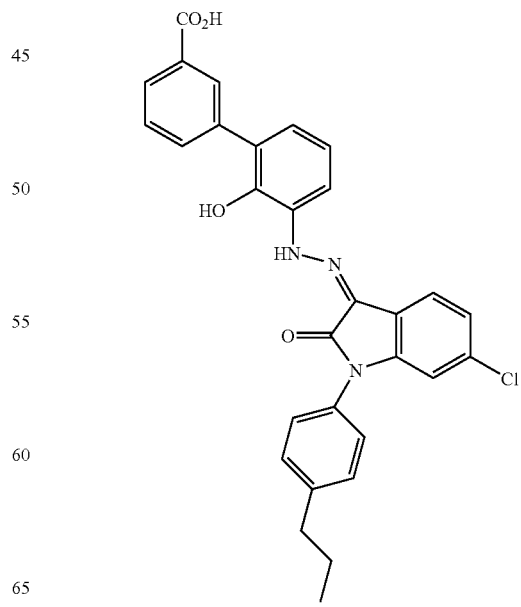

This compound was prepared as described in Scheme II. ¹H NMR (500 MHz, DMSO-$d_6$) δ13.05 (s, 1H), 13.02 (s, 1H), 9.32 (s, 1H), 8.11 (t, J=1.7 Hz, 1H), 7.94 (ddd, J=7.7, 1.7, 1.2 Hz, 1H), 7.79 (ddd, J=7.7, 1.7, 1.2 Hz, 1H), 7.73 (dd, J=8.0, 1.8 Hz, 1H), 7.73 (d, J=8.0 Hz, 1H), 7.59 (t, J=7.7 Hz, 1H), 7.45 (d, J=8.6 Hz, 2H), 7.42 (d, J=8.6 Hz, 2H), 7.23 (dd, J=8.0, 1.9 Hz, 1H), 7.11 (dd, J=7.7, 8.0 Hz, 1H), 7.02 (dd, J=7.7, 1.8 Hz, 1H), 6.81 (d, J=1.9 Hz, 1H), 2.66 (t, J=7.4 Hz, 2H), 1.66 (sext, J=7.4 Hz, 2H), 0.95 (t, J=7.4 Hz, 3H).

Example 38

(±)-2'-Hydroxy-3'-(N'-{2-oxo-1-[4-(2,2,2-trifluoro-1-hydroxy-ethyl)-phenyl]-1,2-dihydro-indol-3-ylidene}-hydrazino)-biphenyl-3-carboxylic acid (Compound 138)

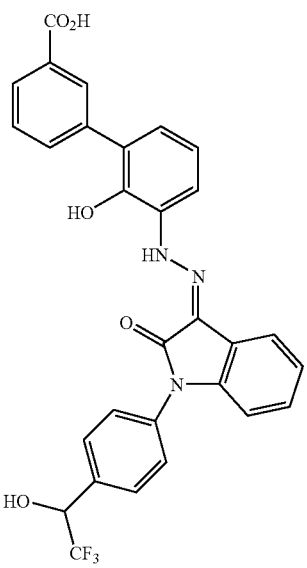

This compound was prepared as described in Scheme II. ¹H NMR (500 MHz, DMSO-$d_6$) δ 13.05 (s, 1H), 13.03 (s, 1H), 9.29 (s, 1H), 8.12 (s, 1H), 7.94 (d, J=7.8 Hz, 1H), 7.79 (d, J=7.8 Hz, 1H), 7.76-7.70 (m, 4H), 7.62-7.59 (m, 3H), 7.30 (t, J=7.6 Hz, 1H), 7.21 (t, J=7.6 Hz, 1H), 7.12 (t, J=7.9 Hz, 1H), 7.02-6.99 (m, 2H), 6.93 (d, J=7.8 Hz, 1H), 5.32 (m, 1H), 3.17 (d, J=5.3 Hz, 1H).

Example 39

(±)-2'-Hydroxy-3'-(N'-{2-oxo-1-[4-(2,2,2-trifluoro-1-methoxy-ethyl)-phenyl]-1,2-dihydro-indol-3-ylidene}-hydrazino)-biphenyl-3-carboxylic acid (Compound 139)

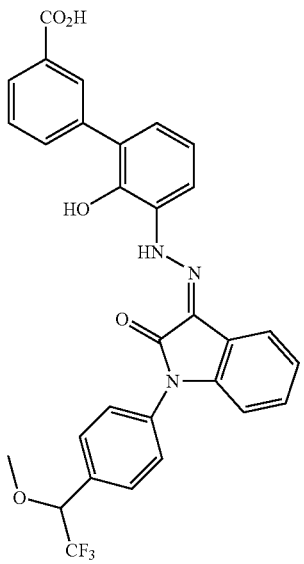

This compound was prepared as described in Scheme II. ¹H NMR (500 MHz, DMSO-$d_6$) δ13.06 (s, 1H), 13.03 (s, 1H), 9.30 (s, 1H), 8.12 (s, 1H), 7.94 (d, J=7.0 Hz, 1H), 7.79 (d, J=7.0 Hz, 1H), 7.75 (m, 2H), 7.68 (m, 4H), 7.60 (t, J=7.0 Hz, 1H), 7.31 (t, J=7.4 Hz, 1H), 7.22 (t, J=7.4 Hz, 1H), 7.12 (t, J=7.6 Hz, 1H), 7.01 (d, J=7.6 Hz, 1H), 6.97 (m, 1H), 5.22 (q, J=6.7 Hz, 1H), 3.42 (s, 3H).

Example 40

2'-Hydroxy-3'-(N'-{2-oxo-1-[4-(2,2,2-trifluoro-ethyl)-phenyl]-1,2-dihydro-indol-3-ylidene}-hydrazino)-biphenyl-3-carboxylic acid (Compound 140)

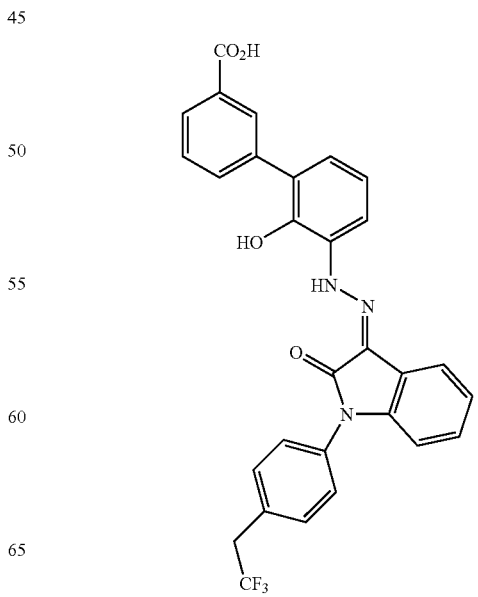

This compound was prepared as described in Scheme II. ¹H NMR (500 MHz, DMSO-d₆) δ 13.05 (s, 1H), 13.02 (s, 1H), 9.28 (s, 1H), 8.12 (t, J=1.7 Hz, 1H), 7.94 (ddd, J=7.7, 1.7, 1.2 Hz, 1H), 7.79 (ddd, J=7.7, 1.7, 1.2 Hz, 1H), 7.74 (m, 2H), 7.62-7.56 (m, 5H), 7.30 (td, J=7.6, 1.2 Hz, 1H), 7.21 (td, J=7.6, 0.8 Hz, 1H), 7.12 (t, J=7.8 Hz, 1H), 7.01 (dd, J=7.8, 1.6 Hz, 1H), 6.92 (d, J=7.8 Hz, 1H), 3.79 (q, J=11.5 Hz, 2H).

Example 41

3'-{N'-[1-(3,4-Dimethyl-phenyl)-4,5-dimethyl-2-oxo-1,2-dihydro-indol-3-ylidene]-hydrazino}-2'-hydroxy-biphenyl-3-carboxylic acid (Compound 141)

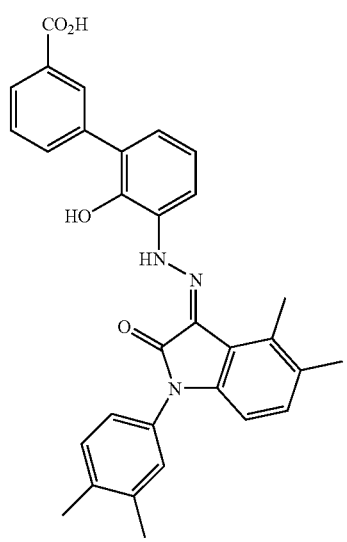

This compound was prepared as described in Scheme II. ¹H NMR (500 MHz, CD3OD) δ 8.17 (s, 1H), 8.00 (d, J=7.7 Hz, 1H), 7.74 (d, J=7.7 Hz, 1H), 7.65 (d, J=7.7 Hz, 1H), 7.54 (t, J=7.7 Hz, 1H), 7.32 (d, J=7.7 Hz, 1H), 7.21 (s, 1H), 7.15 (d, J=7.7 Hz, 1H), 7.08 (t, J=7.7 Hz, 1H), 7.02 (m, 1H), 6.95 (d, J=7.7 Hz, 1H), 6.57 (m, 1H), 2.72 (s, 3H), 2.35 (s, 3H), 2.34 (s, 3H), 2.33 (s, 3H).

Example 42

3'-{N'-[1-(3,4-Dimethyl-phenyl)-5-fluoro-4-methyl-2-oxo-1,2-dihydro-indol-3-ylidene]-hydrazino}-2'-hydroxy-biphenyl-3-carboxylic acid (Compound 142)

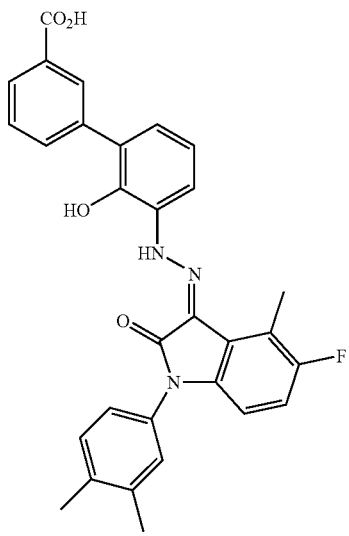

This compound was prepared as described in Scheme II. ¹H NMR (500 MHz, DMSO-d₆) δ13.29 (s, 1H), 8.11 (s, 1H), 7.91 (d, J=7.3 Hz, 1H), 7.74 (d, J=7.3 Hz, 1H), 7.61 (d, J=7.8 Hz, 1H), 7.54 (t, J=7.3 Hz, 1H), 7.35 (d, J=8.0 Hz, 1H), 7.28 (s, 1H), 7.21 (dd, J=8.0, 1.7 Hz, 1H), 7.10 (m, 1H), 7.06 (t, J=9.3 Hz, 1H), 7.01 (d, J=7.8 Hz, 1H), 6.65 (dd, J=8.6, 3.8 Hz, 1H), 2.63 (br s, 3H), 2.31 (s, 3H), 2.30 (s, 3H).

Example 43

3'-{N'-[1-(3,4-Dimethyl-phenyl)-5-fluoro-6-methyl-2-oxo-1,2-dihydro-indol-3-ylidene]-hydrazino}-2'-hydroxy-biphenyl-3-carboxylic acid (Compound 143)

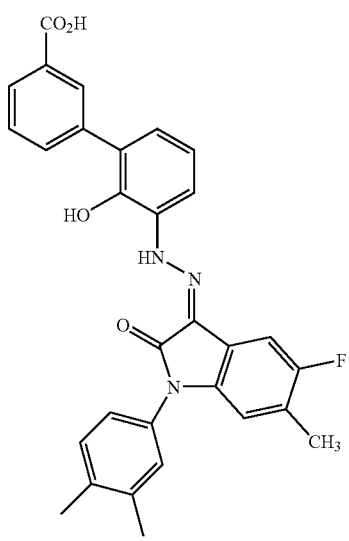

This compound was prepared as described in Scheme II. ¹H NMR (300 MHz, DMSO-$d_6$) δ 9.28 (s, 1H), 8.11 (t, J=1.6 Hz, 1H), 7.94 (ddd, J=7.7, 1.6, 1.2 Hz, 1H), 7.79 (ddd, J=7.6, 1.6, 1.2 Hz, 1H), 7.74 (dd, J=7.9, 1.6 Hz, 1H), 7.59 (t, J=7.7 Hz, 1H), 7.49 (d, J=9.0 Hz, 1H), 7.35 (d, J=8.0 Hz, 1H), 7.28 (d, J=2.1 Hz, 1H), 7.22 (dd, J=8.0, 2.1 Hz, 1H), 7.11 (t, J=7.9 Hz, 1H), 7.01 (dd, J=7.9, 1.6 Hz, 1H), 6.74 (d, J=5.8 Hz, 1H), 2.31 (s, 3H), 2.30 (s, 3H), 2.24 (d, J=1.8 Hz, 3H).

Example 44

5-(4-{N'-[1-(3,4-Dimethyl-phenyl)-2-oxo-6-trifluoromethyl-1,2-dihydro-indol-3-ylidene]-hydrazino}-3-hydroxy-benzylidene)-thiazolidine-2,4-dione (Compound 144)

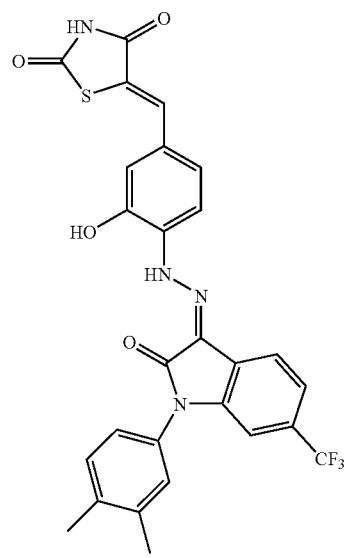

This compound was prepared as described in Scheme V. ¹H NMR (500 MHz, DMSO-$d_6$) δ 13.13 (s, 1H), 12.57 (s, 1H), 10.88 (s, 1H), 7.92 (d, J=7.9 Hz, 1H), 7.82 (d, J=8.4 Hz, 1H), 7.70 (s, 1H), 7.55 (d, J=8.1 Hz, 1H), 7.39 (d, J=7.9 Hz, 1H), 7.33 (br s, 1H), 7.28-7.24 (m, 2H), 7.16 (br s, 1H), 6.96 (s, 1H), 2.33 (s, 3H), 2.31 (s, 3H).

Example 45

5-(4-{N'-[1-(3,4-Dimethyl-phenyl)-2-oxo-1,2-dihydro-indol-3-ylidene]-hydrazino}-3-hydroxy-benzylidene)-thiazolidine-2,4-dione (Compound 145)

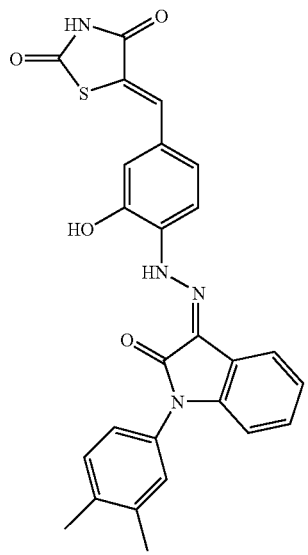

This compound was prepared as described in Scheme V. ¹H NMR (500 MHz, DMSO-$d_6$) δ 13.00 (s, 1H), 12.54 (s, 1H), 10.74 (s, 1H), 7.76 (d, J=8.3 Hz, 1H), 7.72 (d, J=7.5 Hz, 1H), 7.68 (s, 1H), 7.36 (d, J=8.3 Hz, 1H), 7.32-7.29 (m, 2H), 7.25-7.22 (m, 2H), 7.19 (t, J=7.5, 1H), 7.15 (d, J=1.8 Hz, 1H), 6.86 (d, J=7.5 Hz, 1H), 2.32 (s, 3H), 2.31 (s, 3H).

Example 46

3'-{N'-[1-(3,4-Dimethyl-phenyl)-4-fluoro-2-oxo-6-trifluoromethyl-1,2-dihydro-indol-3-ylidene]-hydrazino}-2'-hydroxy-biphenyl-3-carboxylic acid (Compound 146)

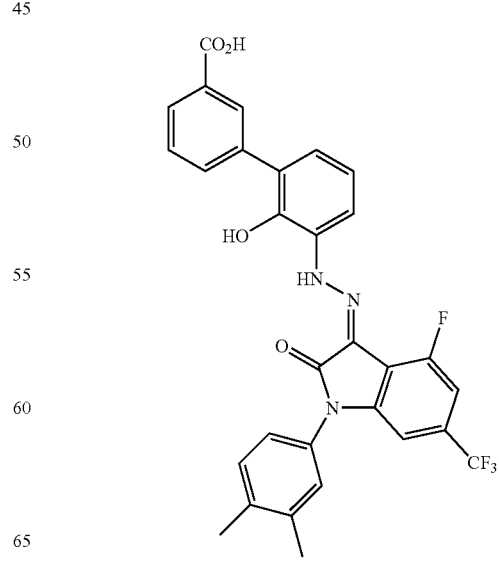

This compound was prepared as described in Scheme II. ¹H NMR (500 MHz, DMSO-d₆) δ13.37 (s, 1H), 13.05 (s, 1H), 9.49 (s, 1H), 8.12 (t, J=1.6 Hz, 1H), 7.95 (ddd, J=7.7, 1.6, 1.2 Hz, 1H), 7.80 (ddd, J=7.7, 1.6, 1.3 Hz, 1H), 7.67 (dd, J=7.9, 1.6 Hz, 1H), 7.60 (t, J=7.7 Hz, 1H), 7.50 (d, J=9.5 Hz, 1H), 7.39 (d, J=8.0 Hz, 1H), 7.32 (d, J=2.1 Hz, 1H), 7.26 (dd, J=8.0, 2.1 Hz, 1H), 7.15 (t, J=7.9 Hz, 1H), 7.08 (dd, J=7.9, 1.6 Hz, 1H), 6.81 (s, 1H), 2.32 (s, 3H), 2.31 (s, 3H).

Example 47

3'-{N'-[4-Chloro-1-(3,4-dimethyl-phenyl)-2-oxo-6-trifluoromethyl-1,2-dihydro-indol-3-ylidene]-hydrazino}-2'-hydroxy-biphenyl-3-carboxylic acid (Compound 147)

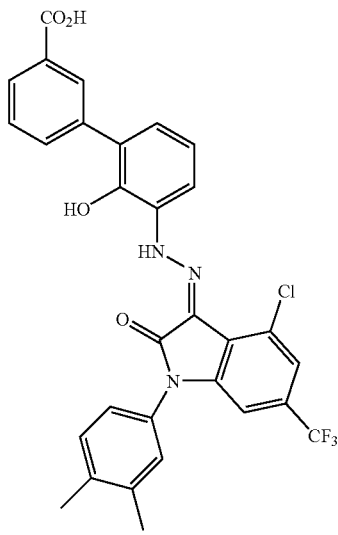

This compound was prepared as described in Scheme II. ¹H NMR (500 MHz, DMSO-d₆) δ13.45 (s, 1H), 13.06 (s, 1H), 9.51 (s, 1H), 8.12 (t, J=1.6 Hz, 1H), 7.95 (ddd, J=7.7, 1.6, 1.2 Hz, 1H), 7.80 (ddd, J=7.7, 1.6, 1.2 Hz, 1H), 7.74 (dd, J=7.8, 1.5 Hz, 1H), 7.62 (m, 1H), 7.60 (t, J=7.7 Hz, 1H), 7.39 (d, J=8.2 Hz, 1H), 7.32 (d, J=2.1 Hz, 1H), 7.26 (dd, J=8.2, 2.1 Hz, 1H), 7.16 (t, J=7.8 Hz, 1H), 7.09 (dd, J=7.8, 1.5 Hz, 1H), 6.89 (m, 1H), 2.32 (s, 3H), 2.31 (s, 3H).

Example 48

5-(4-{N'-[1-(3,4-Dimethyl-phenyl)-4-fluoro-2-oxo-6-trifluoromethyl-1,2-dihydro-indol-3-ylidene]-hydrazino}-3-hydroxy-benzylidene)-thiazolidine-2,4-dione (Compound 148)

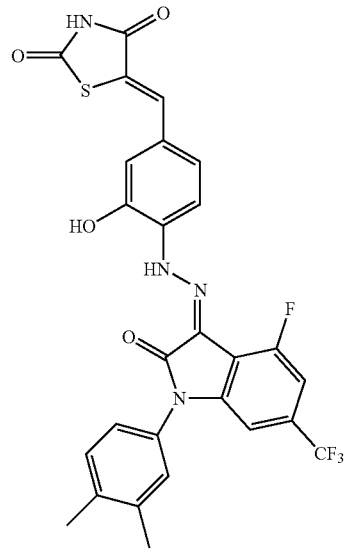

This compound was prepared as described in Scheme V. ¹H NMR (500 MHz, DMSO-d₆) δ13.26 (s, 1H), 12.57 (s, 1H), 10.91 (s, 1H), 7.69 (d, J=8.3 Hz, 1H), 7.66 (s, 1H), 7.51 (d, J=9.4 Hz, 1H), 7.39 (d, J=8.3 Hz, 1H), 7.32 (d, J=1.9 Hz, 1H), 7.27 (s, 1H), 7.25 (d, J=1.9 Hz, 1H), 7.17 (d, J=1.9 Hz, 1H), 6.80 (s, 1H), 2.33 (s, 3H), 2.31 (s, 3H).

Example 49

5-(4-{N'-[4-Chloro-1-(3,4-dimethyl-phenyl)-2-oxo-6-trifluoromethyl-1,2-dihydro-indol-3-ylidene]-hydrazino}-3-hydroxy-benzylidene)-thiazolidine-2,4-dione (Compound 149)

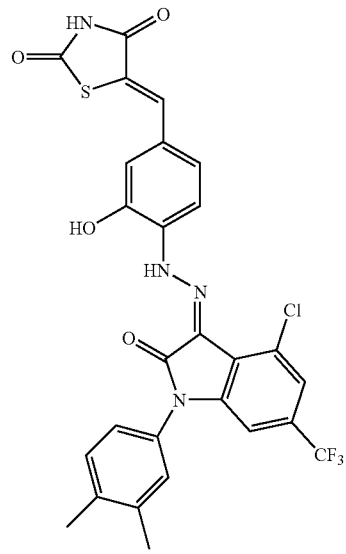

This compound was prepared as described in Scheme V. ¹H NMR (500 MHz, DMSO-d₆) δ13.33 (s, 1H), 12.58 (s, 1H), 10.94 (s, 1H), 7.76 (d, J=8.3 Hz, 1H), 7.70 (s, 1H), 7.63 (s, 1H), 7.39 (d, J=8.0 Hz, 1H), 7.32 (d, J=1.9 Hz, 1H), 7.27 (dt, J=8.3, 1.9 Hz, 1H), 7.26 (d, J=8.0 Hz, 1H), 7.17 (d, J=1.9 Hz, 1H), 6.88 (s, 1H), 2.33 (s, 3H), 2.31 (s, 3H).

Example 50

3-(4-{N'-[1-(3,4-Dimethyl-phenyl)-2-oxo-6-trifluoromethyl-1,2-dihydro-indol-3-ylidene]-hydrazino}-3-hydroxy-phenyl)-acrylic acid (Compound 150)

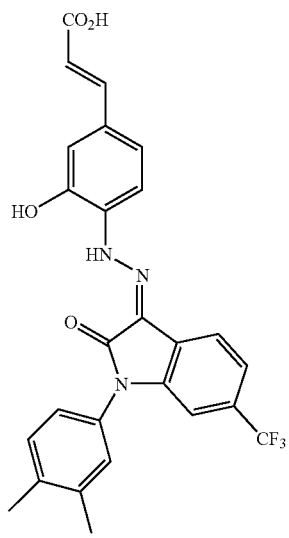

This compound was prepared as described in Scheme V. ¹H NMR (500 MHz, DMSO-d₆) δ13.12 (s, 1H), 12.33 (s, 1H), 10.68 (s, 1H), 7.92 (d, J=7.8 Hz, 1H), 7.73 (d, J=8.3 Hz, 1H), 7.53-7.52 (m, 2H), 7.39 (d, J=8.4 Hz, 1H), 7.33-7.31 (m, 2H), 7.26 (dd, J=8.3, 2.1 Hz, 1H), 7.15 (d, J=1.8 Hz, 1H), 6.95 (s, 1H), 6.33 (d, J=15.9 Hz, 1H), 2.33 (s, 3H), 2.31 (s, 3H).

Example 51

1-(3,4-Dimethyl-phenyl)-3-{[2-hydroxy-4-(4-oxo-2-thioxo-thiazolidin-5-ylidenemethyl)-phenyl]-hydrazono}-6-trifluoromethyl-1,3-dihydro-indol-2-one (Compound 151)

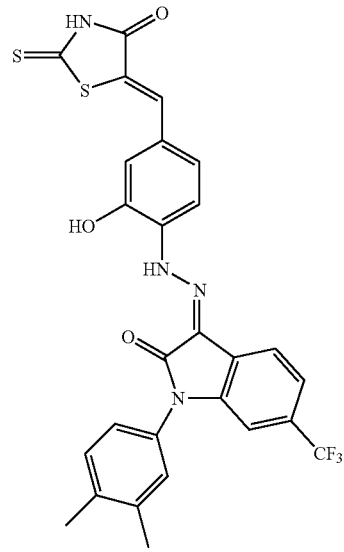

This compound was prepared as described in Scheme V. ¹H NMR (500 MHz, DMSO-d₆) δ13.81 (s, 1H), 13.14 (s, 1H), 10.90 (s, 1H), 7.92 (d, J=7.8 Hz, 1H), 7.82 (d, J=8.3 Hz, 1H), 7.56-7.55 (m, 2H), 7.39 (d, J=8.0 Hz, 1H), 7.33 (d, J=2.1 Hz, 1H), 7.29-7.27 (m, 2H), 7.15 (d, J=1.8 Hz, 1H), 6.96 (m, 1H), 2.33 (s, 3H), 2.31 (s, 3H).

Example 52

1-(3,4-Dimethyl-phenyl)-4-fluoro-3-{[2-hydroxy-4-(4-oxo-2-thioxo-thiazolidin-5-ylidenemethyl)-phenyl]-hydrazono}-6-trifluoromethyl-1,3-dihydro-indol-2-one (Compound 152)

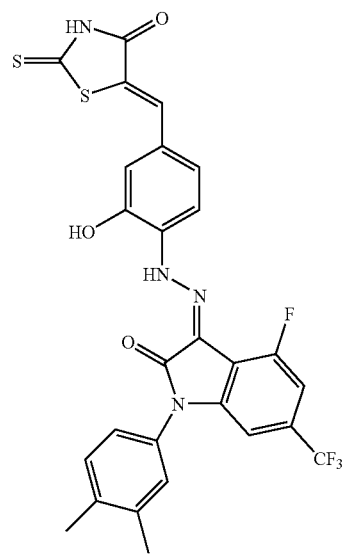

This compound was prepared as described in Scheme V. ¹H NMR (500 MHz, DMSO-d₆) δ13.81 (s, 1H), 13.27 (s, 1H), 10.94 (s, 1H), 7.70 (d, J=8.4 Hz, 1H), 7.55 (s, 1H), 7.52 (d, J=9.9 Hz, 1H), 7.39 (d, J=8.0 Hz, 1H), 7.32-7.30 (m, 2H), 7.26 (dd, J=8.0, 1.6 Hz, 1H), 7.16 (s, 1H), 6.81 (s, 1H), 2.33 (s, 3H), 2.31 (s, 3H).

Example 53

5-(3-{N'-[1-(3,4-Dimethyl-phenyl)-2-oxo-6-trifluoromethyl-1,2-dihydro-indol-3-ylidene]-hydrazino}-2-hydroxy-benzylidene)-thiazolidine-2,4-dione (Compound 153)

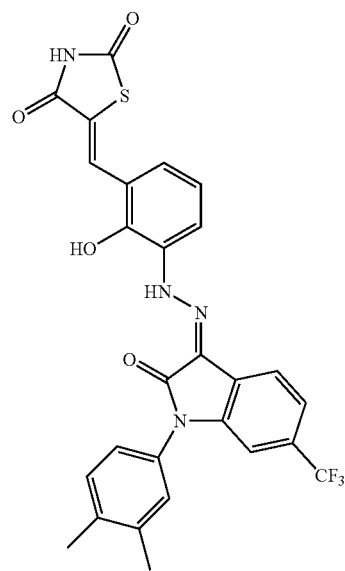

This compound was prepared as described in Scheme V. ¹H NMR (500 MHz, DMSO-d₆) δ 13.16 (s, 1H), 8.05 (s, 1H), 7.91 (d, J=7.7 Hz, 1H), 7.81 (m, 1H), 7.53 (d, J=7.7, 1H), 7.39 (d, J=8.2 Hz, 1H), 7.33 (d, J=2.0 Hz, 1H), 7.27 (dd, J=8.2, 2.0 Hz, 1H), 7.17-7.12 (m, 2H), 6.95 (s, 1H), 2.33 (s, 3H), 2.31 (s, 3H).

Example 54

3'-{N'-[5-Chloro-2-oxo-1-(4-propyl-phenyl)-1,2-dihydro-indol-3-ylidene]-hydrazino}-2'-hydroxy-biphenyl-3-carboxylic acid (Compound 154)

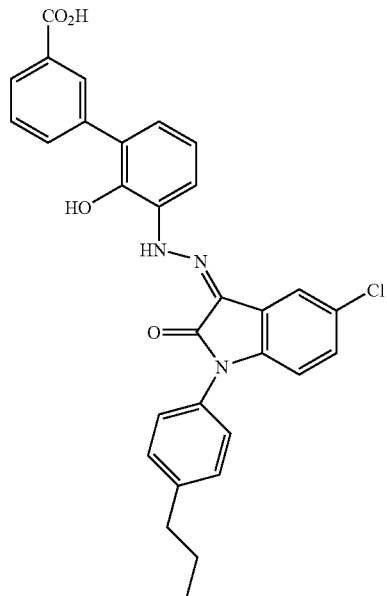

This compound was prepared as described in Scheme II. ¹H NMR (500 MHz, DMSO-d₆) 13.09 (s, 1H), 13.02 (s, 1H), 9.35 (s, 1H), 8.12 (t, J=1.6 Hz, 1H), 7.94 (ddd, J=7.8, 1.6, 1.2 Hz, 1H), 7.81-7.78 (m, 2H), 7.76 (d, J=2.2 Hz, 1H), 7.60 (t, J=7.8 Hz, 1H), 7.43 (d, J=8.8 Hz, 2H), 7.41 (d, J=8.8 Hz, 2H), 7.30 (dd, J=8.4, 2.2 Hz, 1H), 7.12 (t, J=7.8 Hz, 1H), 7.03 (dd, J=7.8, 1.6 Hz, 1H), 6.87 (d, J=8.4 Hz, 1H), 2.65 (t, J=7.4 Hz, 2H), 1.66 (sext, J=7.4 Hz, 2H), 0.94 (t, J=7.4 Hz, 3H).

Example 55

2'-Hydroxy-3'-{N'-[1-(4-methylsulfanyl-phenyl)-2-oxo-1,2-dihydro-indol-3-ylidene]-hydrazino}-biphenyl-3-carboxylic acid (Compound 155)

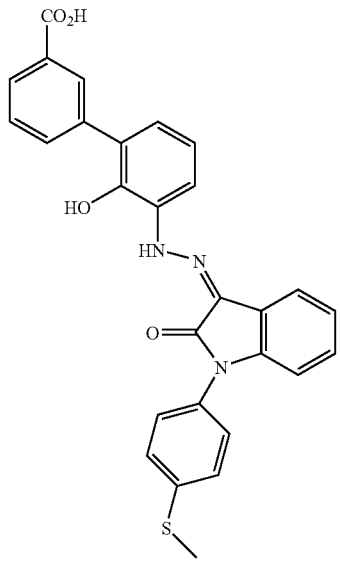

Example 56

2'-Hydroxy-3'-{N'-[1-(4-methoxymethyl-phenyl)-2-oxo-1,2-dihydro-indol-3-ylidene]-hydrazino}-biphenyl-3carboxylic acid (Compound 156)

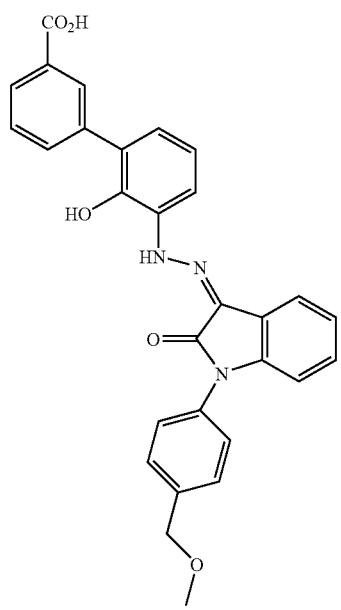

This compound was prepared as described in Scheme II.
¹H NMR (500 MHz, DMSO-d₆) 13.07 (s, 1H), 13.03 (s, 1H), 9.28 (s, 1H), 8.12 (t, J=1.7 Hz, 1H), 7.94 (ddd, J=7.7, 1.7, 1.2 Hz, 1H), 7.79 (ddd, J=7.7, 1.7, 1.2 Hz, 1H), 7.74 (m, 1H), 7.73 (dd, J=7.9, 1.6 Hz, 1H), 7.60 (t, J=7.7 Hz, 1H), 7.54 (d, J=9.0 Hz, 2H), 7.52 (d, J=9.0 Hz, 2H), 7.29 (td, J=7.8, 1.2 Hz, 1H), 7.20 (td, J=7.8, 0.8 Hz, 1H), 7.12 (t, J=7.9 Hz, 1H), 7.01 (dd, J=7.9, 1.6 Hz, 1H), 6.90 (dd, J=7.8, 0.8 Hz, 1H), 4.52 (s, 2H), 3.36 (s, 3H).

Example 57

(±)-2'-Hydroxy-3'-(N'-{2-oxo-1-[4-(2,2,2-trifluoro-1-hydroxy-1-methyl-ethyl)-phenyl]-1,2-dihydro-indol-3-ylidene}-hydrazino)-biphenyl-3-carboxylic acid (Compound 157)

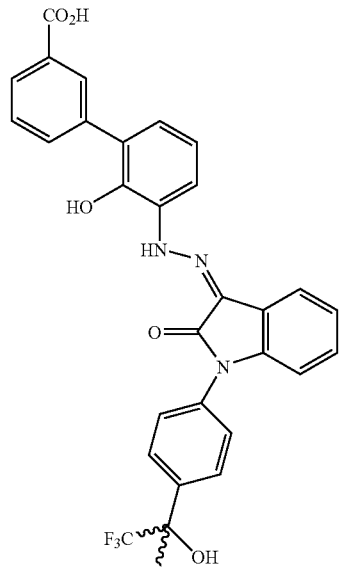

This compound was prepared as described in Scheme II.
¹H NMR (500 MHz, DMSO-d₆) 13.06 (s, 1H), 13.03 (s, 1H), 9.29 (s, 1H), 8.12 (s, 1H), 7.94 (d, J=7.6 Hz, 1H), 7.83-7.72 (m, 5H), 7.62-7.58 (m, 3H), 7.30 (t, J=7.9 Hz, 1H), 7.21 (t, J=7.9 Hz, 1H), 7.12 (t, J=7.8 Hz, 1H), 7.01 (d, J=7.8 Hz, 1H), 6.93 (d, J=7.9 Hz, 1H), 6.77 (s, 1H), 1.76 (s, 3H).

Example 58

3'-{N'-[5-Fluoro-1-(4-methyl-3-trifluoromethyl-phenyl)-2-oxo-1,2-dihydro-indol-3-ylidene]-hydrazino}-2'-hydroxy-biphenyl-3-carboxylic acid (Compound 158)

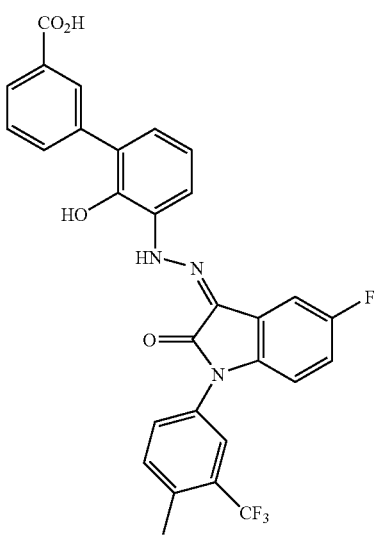

This compound was prepared as described in Scheme II. ¹H NMR (500 MHz, DMSO-d₆) 13.07 (s, 1H), 13.03 (s, 1H), 9.37 (s, 1H), 8.12 (s, 1H), 7.94 (d, J=7.6 Hz, 1H), 7.88 (s, 1H), 7.81-7.75 (m, 3H), 7.68 (d, J=8.1 Hz, 1H), 7.63-7.57 (m, 2H), 7.15-7.09 (m, 2H), 7.04 (d, J=7.6 Hz, 1H), 6.93 (m, 1H), 2.54 (s, 3H).

Example 59

2'-Hydroxy-3'-(N'-{2-oxo-1-[4-(2,2,2-trifluoro-1-methoxy-1-methyl-ethyl)-phenyl]-1,2-dihydro-indol-3-ylidene}-hydrazino)-biphenyl-3-carboxylic acid (Compound 159)

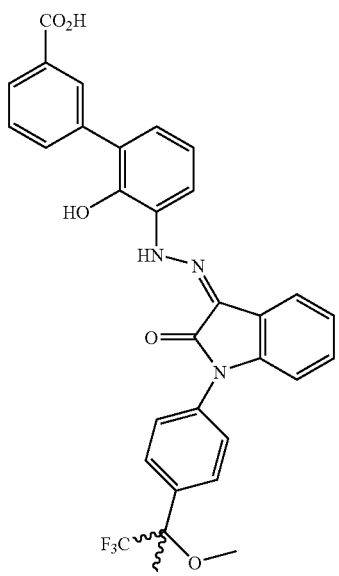

This compound was prepared as described in Scheme II. ¹H NMR (500 MHz, DMSO-d₆) 13.05 (s, 1H), 13.02 (s, 1H), 9.29 (s, 1H), 8.12 (s, 1H), 7.94 (d, J=7.8 Hz, 1H), 7.81-7.72 (m, 5H), 7.68-7.65 (m, 2H), 7.60 (t, J=7.8 Hz, 1H), 7.31 (t, J=7.6 Hz, 1H), 7.22 (t, J=7.6 Hz, 1H), 7.12 (t, J=7.9 Hz, 1H), 7.03 (d, J=7.8 Hz, 1H), 6.99 (d, J=7.8 Hz, 1H), 3.24 (s, 3H), 1.85 (s, 3H).

Example 60

3'-{N'-[1-(3,4-Dimethyl-phenyl)-6-fluoro-2-oxo-1,2-dihydro-indol-3-ylidene]-hydrazino}-2'-hydroxy-biphenyl-3-carboxylic acid (Compound 160)

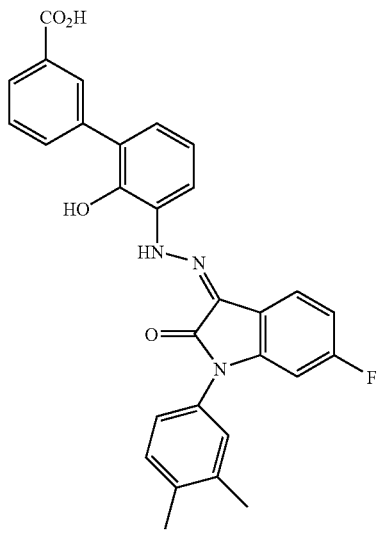

This compound was prepared as described in Scheme II. ¹H NMR (500 MHz, DMSO-d₆) 13.03 (s, 1H), 12.99 (s, 1H), 9.27 (s, 1H), 8.12 (t, J=1.5 Hz, 1H), 7.94 (ddd, J=7.7, 1.5, 1.2 Hz, 1H), 7.79 (ddd, J=7.7, 1.5, 1.2 Hz, 1H), 7.74 (dd, J=8.4, 5.3 Hz, 1H), 7.72 (dd, J=7.8, 1.4 Hz, 1H), 7.60 (t, J=7.7 Hz, 1H), 7.36 (d, J=8.0 Hz, 1H), 7.31 (d, J=1.8 Hz, 1H), 7.25 (dd, J=7.8, 1.8 Hz, 1H), 7.11 (t, J=7.8 Hz, 1H), 7.03-6.98 (m, 2H), 6.66 (dd, J=9.3, 2.2 Hz, 1H), 2.31 (s, 3H), 2.30 (s, 3H).

Example 61

3'-{N'-[6-Fluoro-1-(4-isopropyl-phenyl)-2-oxo-1,2-dihydro-indol-3-ylidene]-hydrazino}-2'-hydroxy-biphenyl-3-carboxylic acid (Compound 161)

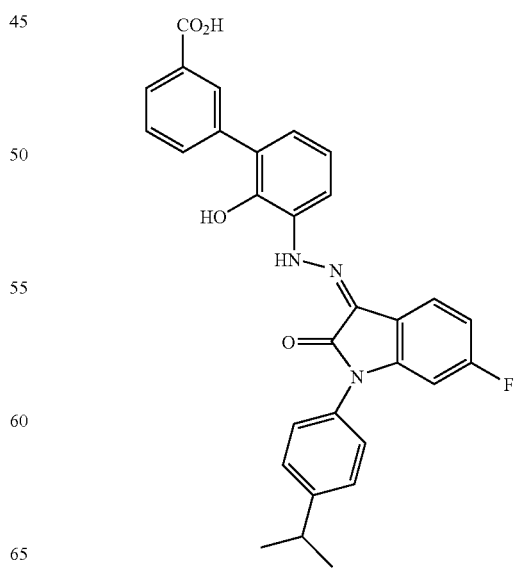

93

This compound was prepared as described in Scheme II.
¹H NMR (500 MHz, DMSO-d₆) 13.02 (s, 1H), 12.98 (s, 1H), 9.28 (s, 1H), 8.11 (t, J=1.6 Hz, 1H), 7.94 (ddd, J=7.8, 1.6, 1.1 Hz, 1H), 7.79 (m, 1H), 7.75 (dd, J=7.7, 4.9 Hz, 1H), 7.73 (dd, J=7.8, 1.5 Hz, 1H), 7.59 (t, J=7.8 Hz, 1H), 7.48 (d, J=9.2 Hz, 2H), 7.46 (d, J=9.2 Hz, 2H), 7.11 (t, J=7.8 Hz, 1H), 7.02 (m, 1H), 7.00 (dd, J=7.8, 1.5 Hz, 1H), 6.69 (dd, J=9.3, 2.2 Hz, 1H), 3.01 (sept, J=6.9 Hz, 1H), 1.27 (d, J=6.9 Hz, 6H).

Example 62

3'-{N'-[1-(3,4-Dimethyl-phenyl)-2-oxo-5-trifluoromethyl-1,2-dihydro-indol-3-ylidene]-hydrazino}-2'-hydroxy-biphenyl-3-carboxylic acid (Compound 162)

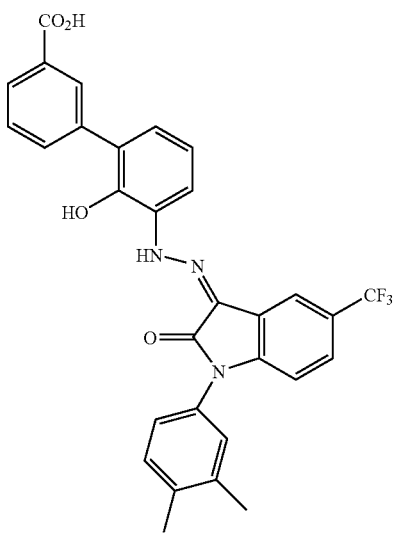

This compound was prepared as described in Scheme II.
¹H NMR (500 MHz, DMSO-d₆) 13.12 (s, 1H), 12.99 (s, 1H), 9.38 (s, 1H), 8.12 (t, J=1.6 Hz, 1H), 8.03 (m, 1H), 7.94 (ddd, J=7.8, 1.6, 1.1 Hz, 1H), 7.85 (dd, J=7.8, 1.5 Hz, 1H), 7.80 (ddd, J=7.8, 1.6, 1.1 Hz, 1H), 7.62 (m, 1H), 7.60 (t, J=7.8 Hz, 1H), 7.37 (d, J=8.0 Hz, 1H), 7.33 (d, J=1.9 Hz, 1H), 7.26 (dd, J=8.0, 1.9 Hz, 1H), 7.13 (t, J=7.8 Hz, 1H), 7.05 (dd, J=7.8, 1.5 Hz, 1H), 7.01 (d, J=8.3 Hz, 1H), 2.32 (s, 3H), 2.31 (s, 3H).

Example 63

3'-{N'-[6-Fluoro-2-oxo-1-(4-propyl-phenyl)-1,2-dihydro-indol-3-ylidene]-hydrazino}-2'-hydroxy-biphenyl-3-carboxylic acid (Compound 163)

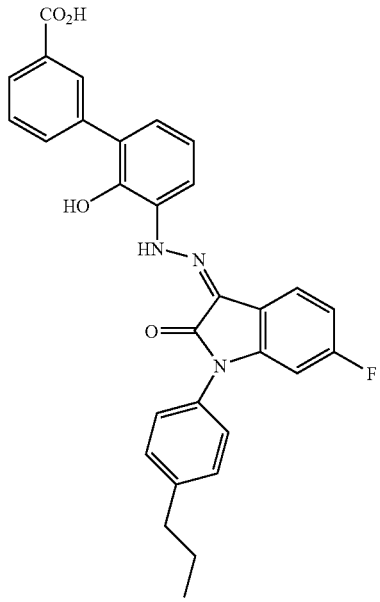

This compound was prepared as described in Scheme II.
¹H NMR (500 MHz, DMSO-d₆) 12.98 (s, 1H), 9.28 (s, 1H), 8.11 (t, J=1.7 Hz, 1H), 7.94 (ddd, J=7.7, 1.7, 1.2 Hz, 1H), 7.79 (ddd, J=7.7, 1.7, 1.2 Hz, 1H), 7.75 (dd, J=7.5, 4.7 Hz, 1H), 7.72 (dd, J=7.8, 1.6 Hz, 1H), 7.59 (t, J=7.7 Hz, 1H), 7.45 (d, J=8.5 Hz, 2H), 7.42 (d, J=8.5 Hz, 2H), 7.11 (t, J=7.8 Hz, 1H), 7.02 (m, 1H), 7.00 (dd, J=7.8, 1.6 Hz, 1H), 6.68 (dd, J=9.4, 2.3 Hz, 1H), 2.66 (t, J=7.4 Hz, 2H), 1.66 (sext, J=7.4 Hz, 2H), 0.95 (t, J=7.4 Hz, 3H).

Example 64

2'-Hydroxy-3'-{N'-[2-oxo-1-(4-propyl-phenyl)-5-trifluoromethyl-1,2-dihydro-indol-3-ylidene]-hydrazino}-biphenyl-3-carboxylic acid (Compound 164)

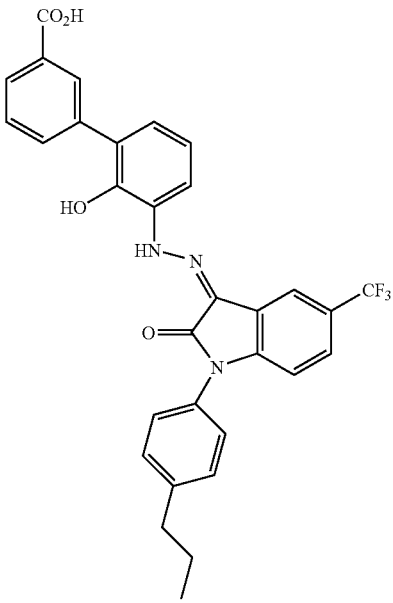

This compound was prepared as described in Scheme II. ¹H NMR (500 MHz, DMSO-d₆) 13.11 (s, 1H), 12.99 (s, 1H), 9.38 (s, 1H), 8.12 (t, J=1.7 Hz, 1H), 8.03 (d, J=1.5 Hz, 1H), 7.95 (ddd, J=7.7, 1.7, 1.2 Hz, 1H), 7.85 (dd, J=8.2, 1.5 Hz, 1H), 7.80 (ddd, J=7.7, 1.7, 1.2 Hz, 1H), 7.62 (m, 1H), 7.60 (t, J=7.7 Hz, 1H), 7.46 (d, J=8.6 Hz, 2H), 7.43 (d, J=8.6 Hz, 2H), 7.13 (t, J=7.8 Hz, 1H), 7.05 (dd, J=7.8, 1.6 Hz, 1H), 7.02 (d, J=8.2 Hz, 1H), 2.66 (t, J=7.4 Hz, 2H), 1.67 (sext, J=7.4 Hz, 2H), 0.95 (t, J=7.4 Hz, 3H).

Example 65

3'-{N'-[4,5-Difluoro-1-(4-isopropyl-phenyl)-2-oxo-1,2-dihydro-indol-3-ylidene]-hydrazino}-2'-hydroxy-biphenyl-3-carboxylic acid (Compound 165)

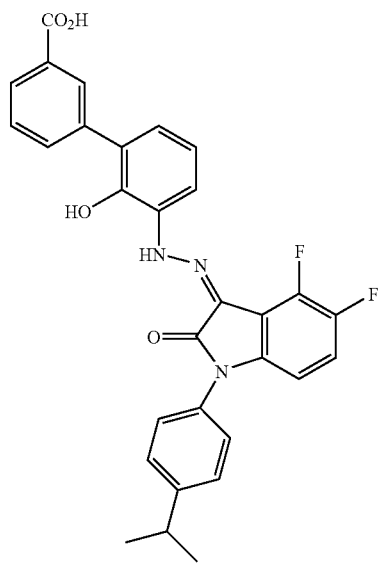

This compound was prepared as described in Scheme II. ¹H NMR (500 MHz, DMSO-d₆) 13.25 (s, 1H), 13.01 (s, 1H), 9.39 (s, 1H), 8.12 (t, J=1.6 Hz, 1H), 7.94 (ddd, J=7.7, 1.6, 1.2 Hz, 1H), 7.79 (ddd, J=7.7, 1.6, 1.2 Hz, 1H), 7.64 (dd, J=7.8, 1.6 Hz, 1H), 7.60 (t, J=7.7 Hz, 1H), 7.47 (d, J=8.7 Hz, 2H), 7.43 (d, J=8.7 Hz, 2H), 7.29 (dt, J=11.2, 8.5 Hz, 1H), 7.14 (t, J=7.8 Hz, 1H), 7.05 (dd, J=7.8, 1.6 Hz, 1H), 6.65 (dd, J=8.5, 3.1 Hz, 1H), 3.00 (sept, J=7.0 Hz, 1H), 1.27 (d, J=7.0 Hz, 6H).

Example 66

2'-Hydroxy-3'-[N'-(2-oxo-1-piperidin-4-yl-1,2-dihydro-indol-3-ylidene)-hydrazino]-biphenyl-3-carboxylic acid (Compound 166)

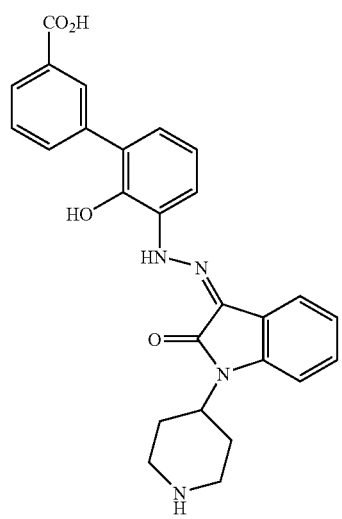

This compound was prepared as described in Scheme II. ¹H NMR (500 MHz, DMSO-d₆) 13.15 (s, 1H), 8.13 (t, J=1.4 Hz, 1H), 7.91 (d, J=7.8 Hz, 1H), 7.68 (d, J=7.8 Hz, 1H), 7.66-7.63 (m, 2H), 7.51 (t, J=7.8 Hz, 1H), 7.38 (d, J=7.6 Hz, 1H), 7.28 (td, J=7.6, 1.0 Hz, 1H), 7.11 (t, J=7.6 Hz, 1H), 7.03 (t, J=7.6 Hz, 1H), 6.96 (dd, J=7.6, 1.5 Hz, 1H), 4.42 (m, 1H), 3.26 (m, 2H), 2.84 (m, 2H), 2.45 (m, 2H), 1.76 (m, 2H).

Example 67

3'-{N'-[5-Fluoro-1-(2-fluoro-4-methyl-phenyl)-2-oxo-1,2-dihydro-indol-3-ylidene]-hydrazino}-2'-hydroxy-biphenyl-3-carboxylic acid (Compound 167)

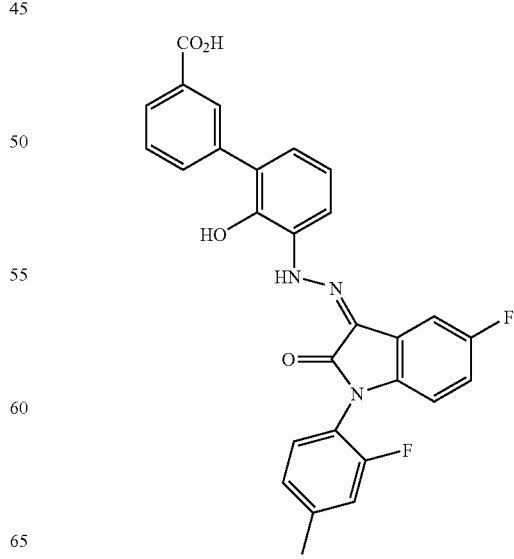

This compound was prepared as described in Scheme II. ¹H NMR (500 MHz, DMSO-$d_6$) 13.05 (s, 1H), 13.02 (s, 1H), 9.37 (s, 1H), 8.12 (t, J=1.7 Hz, 1H), 7.94 (ddd, J=7.8, 1.7, 1.3 Hz, 1H), 7.79 (m, 1H), 7.78 (dd, J=7.8, 1.5 Hz, 1H), 7.60 (t, J=7.8 Hz, 1H), 7.58 (dd, J=8.2, 2.7 Hz, 1H), 7.52 (t, J=8.1 Hz, 1H), 7.37 (dd, J=11.3, 1.2 Hz, 1H), 7.25 (dd, J=8.1, 1.2 Hz, 1H), 7.13 (t, J=7.8 Hz, 1H), 7.11 (ddd, J=9.2, 8.7, 2.7 Hz, 1H), 7.04 (dd, J=7.8, 1.5 Hz, 1H), 6.72 (ddd, J=8.7, 4.1, 1.0 Hz, 1H), 2.43 (s, 3H).

Example 68

2'-Hydroxy-3'-[N'-(1-methyl-2-oxo-1,2-dihydro-indol-3-ylidene)-hydrazino]-biphenyl-3-carboxylic acid (Compound 168)

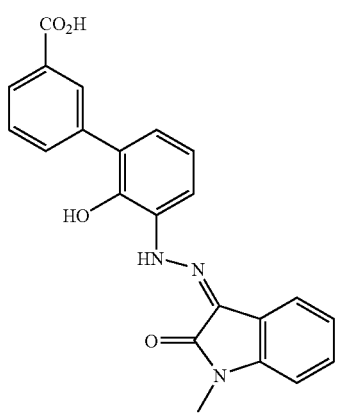

This compound was prepared as described in Scheme II. ¹H NMR (500 MHz, DMSO-$d_6$) 13.05 (s, 1H), 13.03 (s, 1H), 9.24 (s, 1H), 8.12 (t, J=1.7 Hz, 1H), 7.94 (ddd, J=7.7, 1.7, 1.1 Hz, 1H), 7.79 (ddd, J=7.7, 1.7, 1.1 Hz, 1H), 7.68 (dd, J=7.9, 1.6 Hz, 1H), 7.63 (dd, J=7.7, 1.0 Hz, 1H), 7.60 (t, J=7.7 Hz, 1H), 7.35 (td, J=7.7, 1.0 Hz, 1H), 7.16-7.12 (m, 2H), 7.09 (t, J=7.9 Hz, 1H), 6.98 (dd, J=7.9, 1.6 Hz, 1H), 3.28 (s, 3H).

Example 69

3'-[N'-(1-Cyclopentyl-2-oxo-1,2-dihydro-indol-3-ylidene)-hydrazino]-2'-hydroxy-biphenyl-3-carboxylic acid (Compound 169)

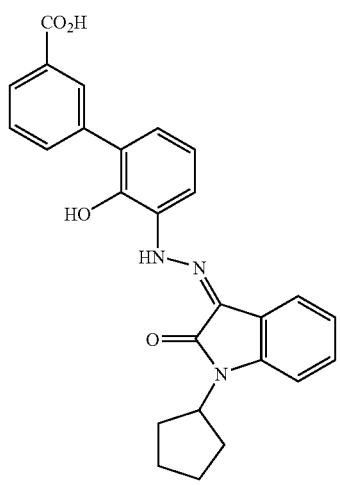

This compound was prepared as described in Scheme II. ¹H NMR (500 MHz, DMSO-$d_6$) 13.12 (s, 1H), 13.00 (s, 1H), 9.23 (s, 1H), 8.13 (t, J=1.7 Hz, 1H), 7.94 (ddd, J=7.8, 1.7, 1.1 Hz, 1H), 7.79 (ddd, J=7.6, 1.7, 1.1 Hz, 1H), 7.68 (dd, J=7.8, 1.6 Hz, 1H), 7.65 (dd, J=7.6, 1.1 Hz, 1H), 7.60 (t, J=7.7 Hz, 1H), 7.32 (td, J=7.6, 1.1 Hz, 1H), 7.21 (dd, J=7.6, 0.8 Hz, 1H), 7.13 (td, J=7.6, 0.8 Hz, 1H), 7.09 (t, J=7.8 Hz, 1H), 6.98 (dd, J=7.8, 1.6 Hz, 1H), 4.76 (qn, J=8.5 Hz, 1H), 2.10 (m, 2H), 1.97-1.89 (m, 4H), 1.68 (m, 2H).

Example 70

3'-{N'-[1-(3,4-Dimethyl-phenyl)-6-methyl-2-oxo-1,2-dihydro-indol-3-ylidene]-hydrazino}-2'-hydroxy-biphenyl-3-carboxylic acid (Compound 170)

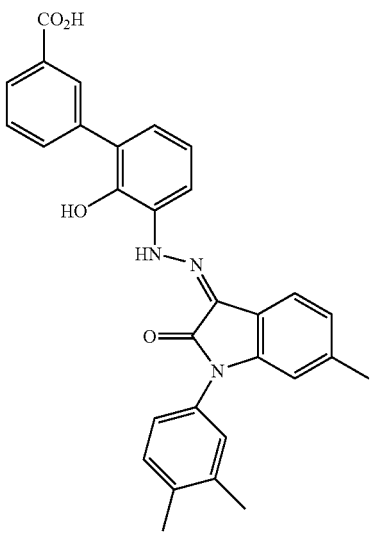

This compound was prepared as described in Scheme II. $^1$H NMR (300 MHz, DMSO-d$_6$) 12.98 (s, 2H), 9.22 (s, 1H), 8.12 (t, J=1.6 Hz, 1H), 7.94 (ddd, J=7.7, 1.6, 1.2 Hz, 1H), 7.79 (ddd, J=7.7, 1.6, 1.2 Hz, 1H), 7.70 (dd, J=8.0, 1.5 Hz, 1H), 7.60 (dd, J=7.7, 1.6 Hz, 1H), 7.59 (t, J=7.7 Hz, 1H), 7.35 (d, J=8.0 Hz, 1H), 7.28 (d, J=1.9 Hz, 1H), 7.21 (dd, J=8.0, 1.9 Hz, 1H), 7.10 (t, J=7.7 Hz, 1H), 7.00 (m, 1H), 6.98 (dd, J=7.7, 1.6 Hz, 1H), 6.65 (m, 1H), 2.31 (s, 6H), 2.30 (s, 3H).

Example 71

2'-Hydroxy-3'-[N'-(2-oxo-1-phenyl-1,2-dihydro-indol-3-ylidene)-hydrazino]-biphenyl-3-carboxylic acid (Compound 171)

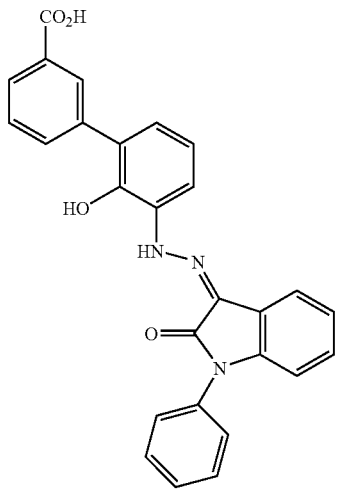

This compound was prepared as described in Scheme II. $^1$H NMR (500 MHz, DMSO-d$_6$) 13.07 (s, 1H), 13.04 (s, 1H), 9.28 (s, 1H), 8.12 (t, J=1.5 Hz, 1H), 7.94 (ddd, J=7.6, 1.5, 1.1 Hz, 1H), 7.79 (ddd, J=7.6, 1.5, 1.1 Hz, 1H), 7.76-7.72 (m, 2H), 7.61 (td, J=7.4, 1.0 Hz, 2H), 7.60 (t, J=7.6 Hz, 1H), 7.55 (dd, J=7.4, 1.0 Hz, 2H), 7.50 (tt, J=7.4, 1.0 Hz, 1H), 7.30 (td, J=7.6, 1.1 Hz, 1H), 7.20 (td, J=7.6, 0.6 Hz, 1H), 7.12 (t, J=7.8 Hz, 1H), 7.01 (dd, J=7.8, 1.5 Hz, 1H), 6.89 (d, J=7.6 Hz, 1H)

Example 72

3'-[N'-(6-Fluoro-2-oxo-1-phenyl-2,3-dihydro-1H-indol-3-yl)-hydrazino]-2'-hydroxy-biphenyl-3-carboxylic acid (Compound 172)

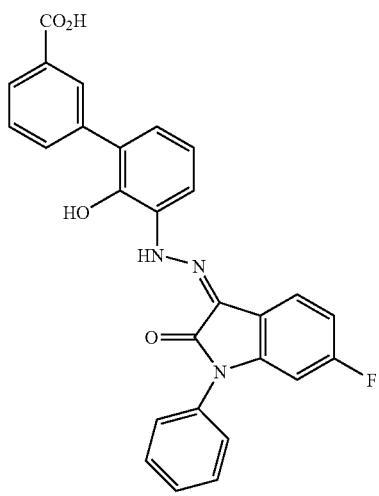

This compound was prepared as described in Scheme II. $^1$H NMR (500 MHz, DMSO-d$_6$) 13.04 (s, 1H), 12.98 (s, 1H), 9.30 (s, 1H), 8.12 (t, J=1.5 Hz, 1H), 7.94 (ddd, J=7.7, 1.5, 0.9 Hz, 1H), 7.79 (ddd, J=7.7, 1.5, 0.9 Hz, 1H), 7.76 (dd, J=8.5, 5.7 Hz, 1H), 7.73 (dd, J=7.8, 1.2 Hz, 1H), 7.64-7.55 (m, 5H), 7.51 (t, J=7.3 Hz, 1H), 7.11 (t, J=7.8 Hz, 1H), 7.05-6.99 (m, 2H), 6.71 (dd, J=9.4, 2.2 Hz, 1H).

Example 73

3'-{N'-[1-(3,4-Dimethyl-phenyl)-6-isopropyl-2-oxo-1,2-dihydro-indol-3-ylidene]-hydrazino}-2'-hydroxy-biphenyl-3-carboxylic acid (Compound 173)

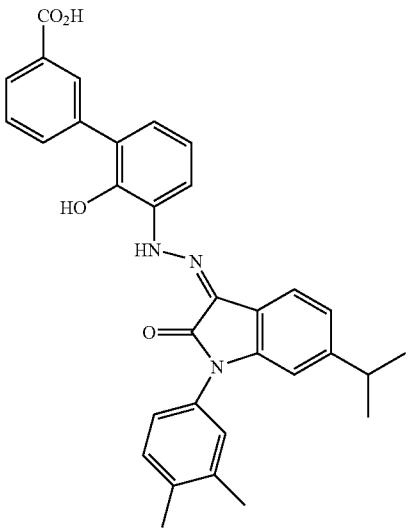

This compound was prepared as described in Scheme II. ¹H NMR (300 MHz, DMSO-d₆) 13.03 (s, 1H), 13.00 (s, 1H), 9.23 (s, 1H), 8.12 (t, J=1.6 Hz, 1H), 7.94 (ddd, J=7.8, 1.6, 1.2 Hz, 1H), 7.79 (ddd, J=7.8, 1.6, 1.2 Hz, 1H), 7.70 (dd, J=7.8, 1.6 Hz, 1H), 7.64 (d, J=7.9 Hz, 1H), 7.59 (t, J=7.8 Hz, 1H), 7.36 (d, J=8.0 Hz, 1H), 7.29 (d, J=2.0 Hz, 1H), 7.23 (dd, J=8.0, 2.0 Hz, 1H), 7.10 (t, J=7.8 Hz, 1H), 7.08 (dd, J=7.9, 1.2 Hz, 1H), 6.98 (dd, J=7.8, 1.6 Hz, 1H), 6.68 (d, J=1.2 Hz, 1H), 2.89 (sept, J=6.8 Hz, 1H), 2.31 (s, 3H), 2.31 (s, 3H), 1.17 (d, J=6.8 Hz, 6H).

Example 74

3'-{N'-[1-(3,4-Dimethyl-phenyl)-4-isopropyl-2-oxo-1,2-dihydro-indol-3-ylidene]-hydrazino}-2'-hydroxy-biphenyl-3-carboxylic acid (Compound 74)

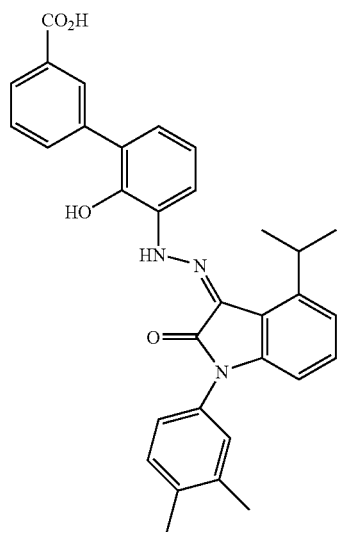

This compound was prepared as described in Scheme II. ¹H NMR (300 MHz, DMSO-d₆) 13.29 (s, 1H), 8.13 (s, 1H), 7.94 (d, J=7.6 Hz, 1H), 7.76 (d, J=7.6 Hz, 1H), 7.61-7.54 (m, 2H), 7.35 (d, J=8.3 Hz, 1H), 7.28 (m, 1H), 7.22 (m, 2H), 7.16-7.10 (m, 2H), 6.98 (dd, J=7.6, 1.1 Hz, 1H), 6.65 (d, J=7.6 Hz, 1H), 3.99 (m, 1H), 2.31 (s, 3H), 2.30 (s, 3H), 1.38 (d, J=6.9 Hz, 6H).

Example 75

3'-{N'-[1-(3,4-Dimethyl-phenyl)-2-oxo-6-trifluoromethyl-1,2-dihydro-indol-3-ylidene]-hydrazino}-4-fluoro-2'-hydroxy-biphenyl-3-carboxylic acid (Compound 175)

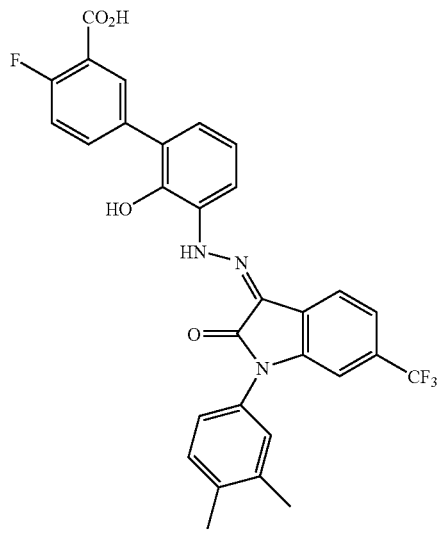

This compound was prepared as described in Scheme II. ¹H NMR (500 MHz, DMSO-d₆) 13.22 (s, 1H), 9.44 (s, 1H), 8.01 (dd, J=7.0, 2.4 Hz, 1H), 7.92 (d, J=7.8 Hz, 1H), 7.78 (dd, J=7.8, 1.5 Hz, 1H), 7.78 (m, 1H), 7.54 (d, J=7.8 Hz, 1H), 7.41 (dd, J=10.4, 8.4 Hz, 1H), 7.39 (d, J=7.9 Hz, 1H), 7.33 (d, J=1.9 Hz, 1H), 7.27 (dd, J=7.9, 1.9 Hz, 1H), 7.13 (t, J=7.8 Hz, 1H), 7.05 (dd, J=7.8, 1.5 Hz, 1H), 6.96 (s, 1H), 2.32 (s, 3H), 2.31 (s, 3H).

Example 76

5'-Chloro-3'-{N'-[1-(3,4-dimethyl-phenyl)-2-oxo-6-trifluoromethyl-1,2-dihydro-indol-3-ylidene]-hydrazino}-4-fluoro-2'-hydroxy-biphenyl-3-carboxylic acid (Compound 176)

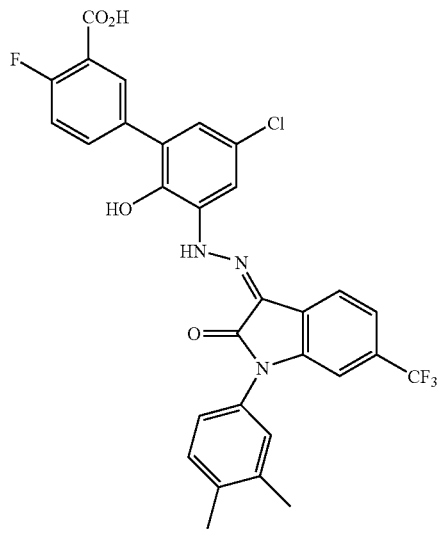

This compound was prepared as described in Scheme II. ¹H NMR (300 MHz, DMSO-$d_6$) 13.38 (s, 1H), 13.11 (s, 1H), 9.70 (s, 1H), 8.02 (d, J=8.0 Hz, 1 H), 8.02 (dd, J=6.9, 2.4 Hz, 1H), 7.80 (ddd, J=8.5, 4.6, 2.4 Hz, 1H), 7.76 (d, J=2.6 Hz, 1H), 7.54 (d, J=8.0 Hz, 1H), 7.42 (dd, J=10.7, 8.5 Hz, 1H), 7.39 (d, J=7.9 Hz, 1H), 7.33 (d, J=2.0 Hz, 1H), 7.27 (dd, J=7.9, 2.0 Hz, 1H), 7.08 (d, J=2.6 Hz, 1H), 6.95 (s, 1H), 2.32 (s, 3H), 2.31 (s, 3H).

Example 77

3'-{N'-[1-(3,4-Dimethyl-phenyl)-2-oxo-6-trifluoromethyl-1,2-dihydro-indol-3-ylidene]-hydrazino}-6-fluoro-2'-hydroxy-biphenyl-3-carboxylic acid (Compound 177)

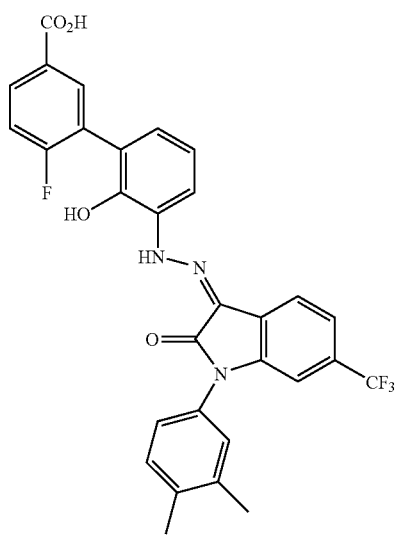

This compound was prepared as described in Scheme II. ¹H NMR (300 MHz, DMSO-$d_6$) 13.19 (s, 1H), 13.13 (s, 1H), 9.56 (s, 1H), 7.98 (m, 1H), 7.92 (d, J=7.8 Hz, 1H), 7.82 (dd, J=7.7, 1.1 Hz, 1H), 7.54 (d, J=7.8 Hz, 1H), 7.44 (m, 1H), 7.38 (d, J=8.0 Hz, 1H), 7.33 (d, J=1.7 Hz, 1H), 7.26 (dd, J=8.0, 1.7 Hz, 1H), 7.11 (t, J=7.7 Hz, 1H), 7.00 (dd, J=7.7, 1.1 Hz, 1H), 6.95 (s, 1H), 2.32 (s, 3H), 2.31 (s, 3H).

Example 78

3'-{N'-[1-(3,4-Dimethyl-phenyl)-4,5-difluoro-2-oxo-1,2-dihydro-indol-3-ylidene]-hydrazino}-2'-hydroxy-biphenyl-3-carboxylic acid (Compound 178)

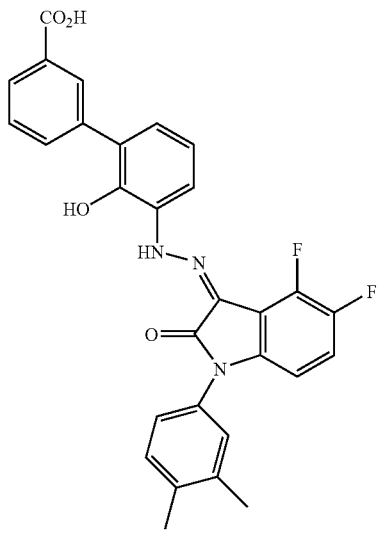

This compound was prepared as described in Scheme II. ¹H NMR (500 MHz, DMSO-$d_6$) 13.27 (s, 1H), 13.05 (s, 1H), 9.40 (s, 1H), 8.12 (t, J=1.7 Hz, 1H), 7.94 (ddd, J=7.7, 1.7, 1.2 Hz, 1H), 7.79 (ddd, J=7.7, 1.7, 1.2 Hz, 1H), 7.64 (dd, J=7.9, 1.6 Hz, 1H), 7.60 (t, J=7.7 Hz, 1H), 7.36 (d, J=8.2 Hz, 1H), 7.29 (dt, J=11.1, 8.5 Hz, 1H), 7.29 (d, J=2.1 Hz, 1H), 7.22 (dd, J=8.2, 2.1 Hz, 1H), 7.14 (t, J=7.9 Hz, 1H), 7.05 (dd, J=7.9, 1.6 Hz, 1H), 6.63 (dd, J=8.5, 3.2 Hz, 1H), 2.31 (s, 3H), 2.29 (s, 3H).

Example 79

3'-{N'-[1-(3,4-Dimethyl-phenyl)-2-oxo-6-trifluoromethyl-1,2-dihydro-indol-3-ylidene]-hydrazino}-2'-hydroxy-3-methyl-biphenyl-4-carboxylic acid (Compound 179)

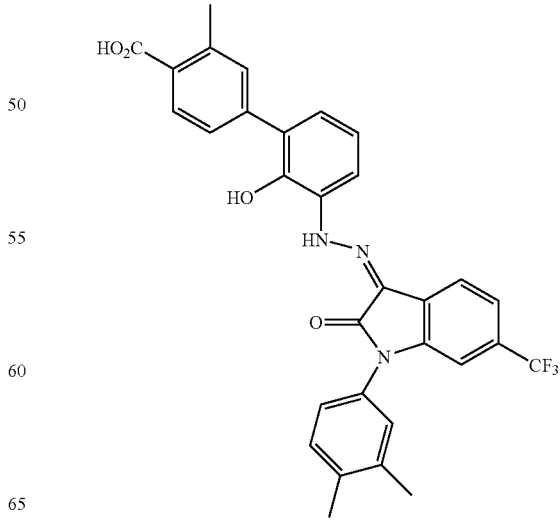

This compound was prepared as described in Scheme II.
$^1$H NMR (500 MHz, DMSO-$d_6$) 13.23 (s, 1H), 12.83 (s, 1H), 9.43 (s, 1H), 7.92 (d, J=7.9 Hz, 1H), 7.91 (d, J=7.9 Hz, 1H), 7.78 (dd, J=7.8, 1.5 Hz, 1H), 7.54 (d, J=7.9 Hz, 1H), 7.49 (s, 1H), 7.46 (d, J=7.9 Hz, 1H), 7.39 (d, J=7.9 Hz, 1H), 7.33 (d, J=1.8 Hz, 1H), 7.27 (dd, J=7.9, 1.8 Hz, 1H), 7.13 (t, J=7.8 Hz, 1H), 7.05 (dd, J=7.8, 1.6 Hz, 1H), 6.96 (s, 1H), 2.59 (s, 3H), 2.32 (s, 3H), 2.31 (s, 3H).

Example 80

3'-{N'-[1-(3,4-Dimethyl-phenyl)-2-oxo-6-trifluoromethyl-2,3-dihydro-1H-indol-3-yl]-hydrazino}-2-fluoro-2'-hydroxy-biphenyl-4-carboxylic acid (Compound 180)

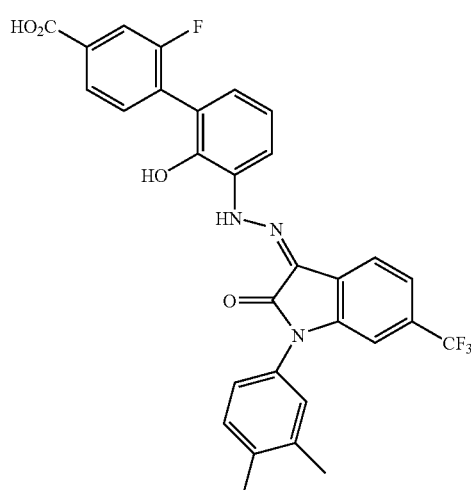

This compound was prepared as described in Scheme II.
$^1$H NMR (500 MHz, DMSO-$d_6$) 13.31 (s, 1H), 13.19 (s, 1H), 9.58 (s, 1H), 7.93 (d, J=7.9 Hz, 1H), 7.85 (dd, J=7.8, 1.5 Hz, 1H), 7.82 (dd, J=7.8, 1.5 Hz, 1H), 7.75 (dd, J=10.4, 1.5 Hz, 1H), 7.58 (t, J=7.8 Hz, 1H), 7.54 (d, J=7.9 Hz, 1H), 7.38 (d, J=8.0 Hz, 1H), 7.33 (d, J=1.9 Hz, 1H), 7.27 (dd, J=8.0, 1.9 Hz, 1H, 7.12 (t, J=7.8 Hz, 1H), 6.99 (dd, J=7.8, 1.5 Hz, 1H), 6.95 (s, 1H), 2.32 (s, 3H), 2.31 (s, 3H).

Example 81

3'-{N'-[1-(3,4-Dimethyl-phenyl)-4-fluoro-2-oxo-6-trifluoromethyl-2,3-dihydro-1H-indol-3-yl]-hydrazino}-4-fluoro-2'-hydroxy-biphenyl-3-carboxylic acid (Compound 181)

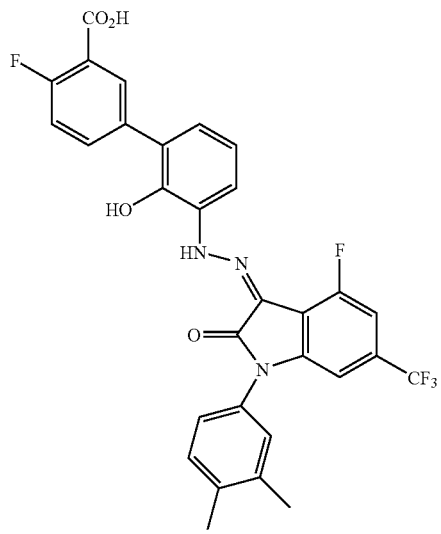

This compound was prepared as described in Scheme II.
$^1$H NMR (500 MHz, DMSO-$d_6$) 13.36 (s, 1H), 8.00 (dd, J=6.9, 2.1 Hz, 1H), 7.78 (m, 1H), 7.66 (dd, J=7.7, 1.4 Hz, 1H), 7.50 (d, J=9.5 Hz, 1H), 7.41 (m, 1H), 7.39 (d, J=8.1 Hz, 1H), 7.32 (d, J=1.6 Hz, 1H), 7.26 (dd, J=8.1, 1.6 Hz, 1H), 7.14 (t, J=7.7 Hz, 1H), 7.07 (dd, J=7.7, 1.4 Hz, 1H), 6.80 (s, 1H), 2.32 (s, 3H), 2.31 (s, 3H).

Example 82

5'-Chloro-3'-{N'-[1-(3,4-dimethyl-phenyl)-4-fluoro-2-oxo-6-trifluoromethyl-1,2-dihydro-indol-3-ylidene]-hydrazino}-4-fluoro-2'-hydroxy-biphenyl-3-carboxylic acid (Compound 182)

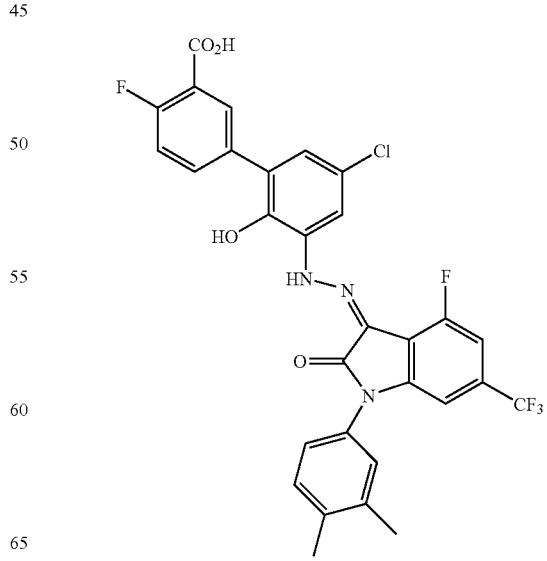

This compound was prepared as described in Scheme II. ¹H NMR (500 MHz, DMSO-d₆) 13.38 (s, 1H), 13.22 (s, 1H), 9.78 (s, 1H), 8.01 (dd, J=7.0, 2.3 Hz, 1H), 7.80 (ddd, J=8.6, 4.2, 2.3 Hz, 1H), 7.55 (d, J=2.5 Hz, 1H), 7.51 (d, J=9.5 Hz, 1H), 7.42 (dd, J=10.5, 8.6 Hz, 1H), 7.38 (d, J=8.0 Hz, 1H), 7.31 (d, J=1.6 Hz, 1H), 7.25 (dd, J=8.0, 1.6 Hz, 1H), 7.10 (d, J=2.5 Hz, 1H), 6.80 (s, 1H), 2.32 (s, 3H), 2.30 (s, 3H).

Example 83

3-[(3'-Carboxy-2-hydroxy-biphenyl-3-yl)-hydrazono]-1-(3,5-dimethyl-phenyl)-2-oxo-2,3-dihydro-1H-indole-6-carboxylic acid methyl ester (Compound183)

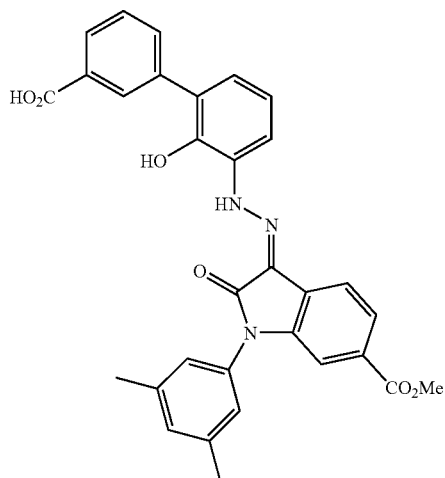

This compound was prepared as described in Scheme II. ¹H NMR (500 MHz, DMSO-d₆) δ 13.26 (s, 1H), 13.05 (s, 1H), 9.42 (s, 1H), 8.12 (t, J=1.6 Hz, 1H), 7.95 (ddd, J=7.7, 1.6, 1.2 Hz, 1H), 7.86 (d, J=7.9 Hz, 1H), 7.81 (dd, J=7.9, 1.4 Hz, 1H), 7.80 (ddd, J=7.7, 1.6, 1.2 Hz, 1H), 7.77 (dd, J=7.8, 1.6 Hz, 1H), 7.61 (t, J=7.7 Hz, 1H), 7.29 (d, J=1.4 Hz, 1H), 7.18 (s, 1H), 7.16 (s, 2H), 7.14 (t, J=7.8 Hz, 1H), 7.8, 1.6 Hz, 1H), 3.83 (s, 3H), 2.38 (s, 6H).

Example 84

3-[(3'-Carboxy-4'-fluoro-2-hydroxy-biphenyl-3-yl)-hydrazono]-1-(3,5-dimethyl-phenyl)-2-oxo-2,3-dihydro-1H-indole-6-carboxylic acid methyl ester (Compound 184)

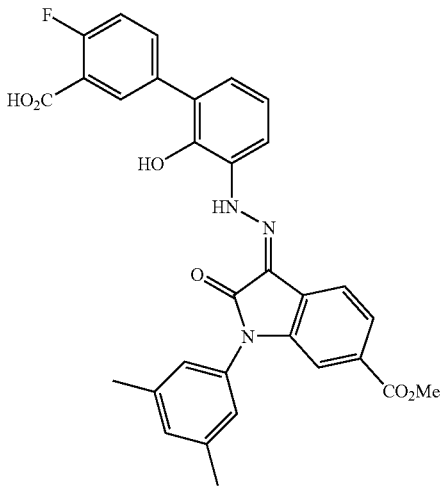

This compound was prepared as described in Scheme II. ¹H NMR (500 MHz, DMSO-d₆) δ13.35 (s, 1H), 13.24 (s, 1H), 9.43 (s, 1H), 8.01 (dd, J=7.2, 2.6 Hz, 1H), 7.85 (d, J=7.9 Hz, 1H), 7.81 (dd, J=7.9, 1.3 Hz, 1H), 7.79 (m, 1H), 7.77 (dd, J=7.8, 1.6 Hz, 1H), 7.42 (dd, J=10.7, 8.5 Hz, 1H), 7.28 (d, J=1.3 Hz, 1H), 7.18 (s, 1H), 7.16 (s, 2H), 7.13 (t, J=7.8 Hz, 1H), 7.05 (dd, J=7.8, 1.6 Hz, 1H), 3.83 (s, 3H), 2.37 (s, 6H).

Example 85

3-[(3'-Carboxy-4'-fluoro-2-hydroxy-biphenyl-3-yl)-hydrazono]-1-(3,4-dimethyl-phenyl)-2-oxo-2,3-dihydro-1H-indole-6-carboxylic acid methyl ester (Compound 185)

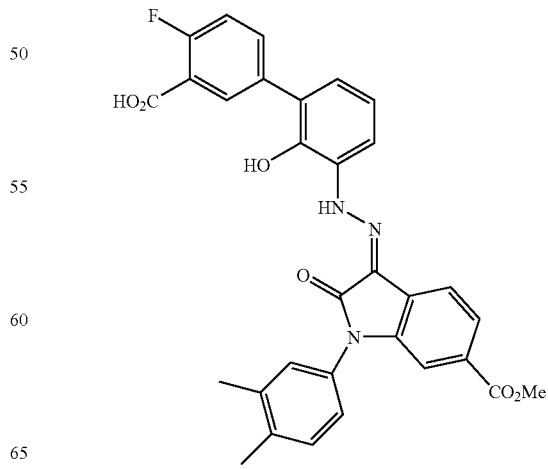

This compound was prepared as described in Scheme II. $^1$H NMR (500 MHz, DMSO-d$_6$) δ 13.34 (s, 1H), 13.24 (s, 1H), 9.43 (s, 1H), 8.01 (dd, J=7.1, 2.1 Hz, 1H), 7.85 (d, J=7.9 Hz, 1H), 7.81 (m, 1H), 7.79 (m, 1H), 7.77 (m, 1H), 7.41 (dd, J=10.5, 8.8 Hz, 1H), 7.39 (d, J=8.0 Hz, 1H), 7.32 (d, J=1.8 Hz, 1H), 7.27 (d, J=1.0 Hz, 1H), 7.26 (m, 1H), 7.13 (t, J=7.8 Hz, 1H), 7.05 (dd, J=7.8, 1.6 Hz, 1H), 3.82 (s, 3H), 2.33 (s, 3H), 2.31 (s, 3H).

Example 86

3-[(3'-Carboxy-5-chloro-4'-fluoro-2-hydroxy-biphenyl-3-yl)-hydrazono]-1-(3,5-dimethyl-phenyl)-2-oxo-2,3-dihydro-1H-indole-6-carboxylic acid methyl ester (Compound 186)

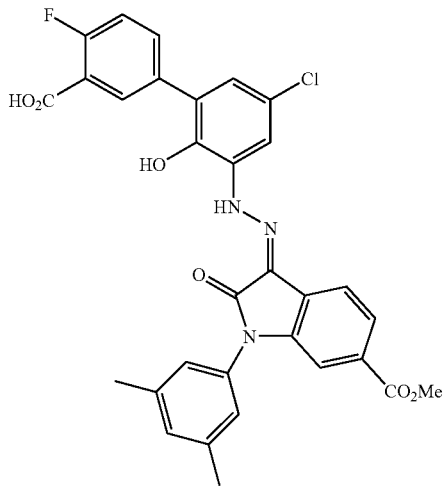

This compound was prepared as described in Scheme II. $^1$H NMR (500 MHz, CD$_3$OD-d$_4$) δ 8.05 (dd, J=6.7, 1.2 Hz, 1H), 7.89–7.81 (m, 2H), 7.75–7.70 (m, 2H), 7.40 (s, 1H), 7.29 (dd, J=10.3, 8.7 Hz, 1H), 7.18 (s, 1H), 7.09 (s, 2H), 6.97 (d, J=1.7 Hz, 1H), 3.86 (s, 3H), 2.41 (s, 6H).

Example 87

3'-{N'-[1-(2-Cyano-thiophen-3-yl)-2-oxo-1,2-dihydro-indol-3-ylidene]-hydrazino}-2'-hydroxy-biphenyl-3-carboxylic acid (Compound 187)

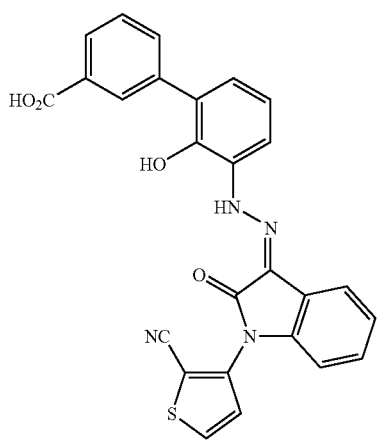

This compound was prepared as described in Scheme II. $^1$H NMR (500 MHz, CD$_3$OD-d$_4$) δ 8.05 (t, J=1.5 Hz, 1H), 8.03 (d, J=5.3 Hz, 1H), 7.89 (ddd, J=7.7, 1.5, 1.0 Hz, 1H), 7.74 (ddd, J=7.6, 1.1, 0.6 Hz, 1H), 7.73 (dd, J=7.8, 1.6 Hz, 1H), 7.56 (ddd, J=7.7, 1.5, 1.0 Hz, 1H), 7.41 (t, J=7.7 Hz, 1H), 7.37 (d, J=5.3 Hz, 1H), 7.28 (td, J=7.6, 1.1 Hz, 1H), 7.20 (td, J=7.6, 0.8 Hz, 1H), 7.03 (t, J=7.8 Hz, 1H), 6.97 (dd, J=7.8, 1.6 Hz, 1H), 6.93 (ddd, J=7.8, 0.8, 0.6 Hz, 1H).

Example 88

2'-Hydroxy-3'-[N'-(2-oxo-1-thiophen-3-yl-1,2-dihydro-indol-3-ylidene)-hydrazino]-biphenyl-3-carboxylic acid (Compound 188)

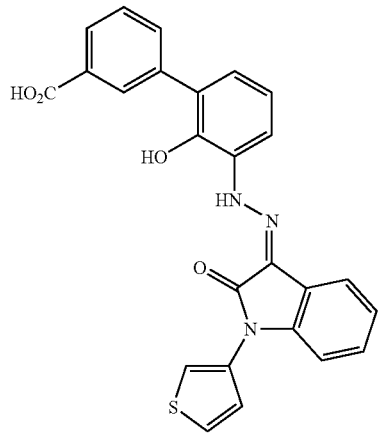

This compound was prepared as described in Scheme II. $^1$H NMR (500 MHz, CD$_3$OD-d$_4$) δ 8.15 (t, J=1.6 Hz, 1H), 7.99 (ddd, J=7.7, 1.6, 1.2 Hz, 1H), 7.74 (dd, J=7.8, 1.6 Hz, 1H), 7.73 (m, 1H), 7.71 (ddd, J=7.7, 1.6, 1.2 Hz, 1H), 7.65–7.62 (m, 2H), 7.52 (t, J=7.7 Hz, 1H), 7.33 (dd, J=3.9, 2.7 Hz, 1H), 7.28 (td, J=7.6, 1.2 Hz, 1H), 7.18 (td, J=7.6, 0.8 Hz, 1H), 7.07 (t, J=7.8 Hz, 1H), 7.04 (d, J=7.6 Hz, 1H), 6.98 (dd, J=7.8, 1.6 Hz, 1H).

Example 89

3-[(3'-Carboxy-2-hydroxy-biphenyl-3-yl)-hydrazono]-1-(3,4-dimethyl-phenyl)-2-oxo-2,3-dihydro-1H-indole-6-carboxylic acid methyl ester (Compound 189)

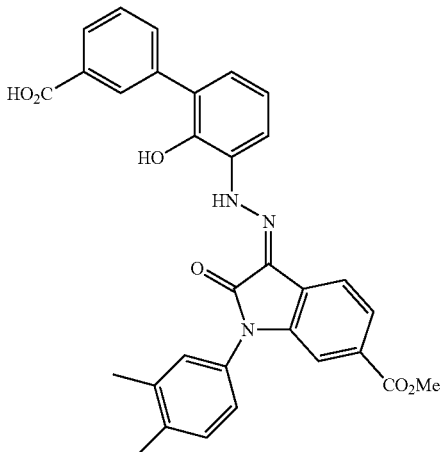

This compound was prepared as described in Scheme II. ¹H NMR (500 MHz, DMSO-d₆) δ 13.25 (s, 1H), 13.05 (s, 1H), 9.42 (s, 1H), 8.12 (t, J=1.6 Hz, 1H), 7.95 (ddd, J=7.8, 1.6, 1.2 Hz, 1H), 7.85 (d, J=8.0 Hz, 1H), 7.81 (dd, J=8.0, 1.4 Hz, 1H), 7.79 (ddd, J=7.8, 1.6, 1.2 Hz, 1H), 7.77 (dd, J=7.9, 1.6 Hz, 1H), 7.60 (t, J=7.8 Hz, 1H), 7.39 (d, J=8.0 Hz, 1H), 7.32 (d, J=2.0 Hz, 1H), 7.28 (d, J=1.4 Hz, 1H), 7.26 (dd, J=8.0, 2.0 Hz, 1H), 7.14 (t, J=7.9 Hz, 1H), 7.06 (dd, J=7.9, 1.6 Hz, 1H), 3.82 (s, 3H), 2.33 (s, 3H), 2.31 (s, 3H).

Example 90

3'-{N'-[1-(4-Chloro-3-trifluoromethyl-phenyl)-6-cyano-2-oxo-1,2-dihydro-indol-3-ylidene]-hydrazino}-2'-hydroxy-biphenyl-3-carboxylic acid (Compound 190)

Example 91

5'-Chloro-3'-{N'-[6-cyano-1-(4-isopropyl-phenyl)-2-oxo-1,2-dihydro-indol-3-ylidene]-hydrazino}-4-fluoro-2'-hydroxy-biphenyl-3-carboxylic acid (Compound 191)

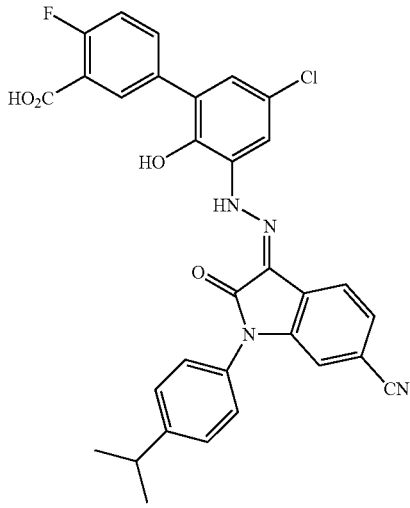

This compound was prepared as described in Scheme II. ¹H NMR (500 MHz, DMSO-d₆) δ 13.37 (s, 1H), 13.14 (s, 1H), 9.74 (s, 1H), 8.01 (dd, J=7.0, 2.4 Hz, 1H), 7.99 (d, J=7.8 Hz, 1H), 7.80 (ddd, J=8.5, 4.6, 2.4 Hz, 1H), 7.77 (d, J=2.6 Hz, 1H), 7.64 (dd, J=7.8, 1.3 Hz, 1H), 7.49 (d, J=9.1 Hz, 2H), 7.47 (d, J=9.1 Hz, 2H), 7.42 (dd, J=10.7, 8.5 Hz, 1H), 7.24 (d, J=1.3 Hz, 1H), 7.09 (d, J=2.6 Hz, 1H), 3.01 (sept, J=6.9 Hz, 1H), 1.28 (d, J=6.9 Hz, 6H).

Example 92

3'-{N'-[6-Cyano-1-(4-isopropyl-phenyl)-2-oxo-1,2-dihydro-indol-3-ylidene]-hydrazino}-4-fluoro-2'-hydroxy-biphenyl-3-carboxylic acid (Compound 192)

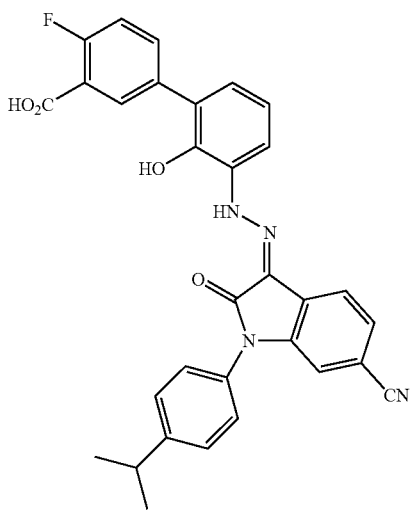

This compound was prepared as described in Scheme II. ¹H NMR (500 MHz, DMSO-d₆) δ 13.20 (s, 1H), 13.02 (s, 1H), 9.49 (s, 1H), 8.12 (t, J=1.7 Hz, 1H), 8.11 (d, J=2.4 Hz, 1H), 7.98 (d, J=8.5 Hz, 1H), 7.95 (ddd, J=7.7, 1.7, 1.3 Hz, 1H), 7.94 (dd, J=8.5, 2.4 Hz, 1H), 7.90 (d, J=7.8 Hz, 1H), 7.79 (dd, J=7.8, 1.6 Hz, 1H), 7.79 (m, 1H), 7.66 (dd, J=7.8, 1.3 Hz, 1H), 7.60 (t, J=7.7 Hz, 1H), 7.51 (d, J=1.3 Hz, 1H), 7.15 (t, J=7.8 Hz, 1H), 7.09 (dd, J=7.8, 1.6 Hz, 1H).

This compound was prepared as described in Scheme II. ¹H NMR (500 MHz, CD₃OD-d₄) δ 7.91 (dd, J=6.8, 2.4 Hz, 1H), 7.81 (d, J=7.8 Hz, 1H), 7.73 (dd, J=7.7, 1.6 Hz, 1H), 7.62 (ddd, J=8.5, 4.6, 2.4 Hz, 1H), 7.48 (d, J=8.4 Hz, 2H), 7.47 (m, 1H), 7.40 (d, J=8.4 Hz, 2H), 7.21 (dd, J=10.3, 8.5 Hz, 1H), 7.09 (d, J=1.0 Hz, 1H), 7.05 (t, J=7.7 Hz, 1H), 7.00 (dd, J=7.7, 1.6 Hz, 1H), 3.02 (sept, J=6.9 Hz, 1H), 1.32 (d, J=6.9 Hz, 6H).

Example 93

(±)-1-(3,4-Dimethyl-phenyl)-3-{[2-hydroxy-3'-(2,2,2-trifluoro-1-hydroxy-ethyl)-biphenyl-3-yl]-hydrazono}-6-methanesulfonyl-1,3-dihydro-indol-2-one (Compound 193)

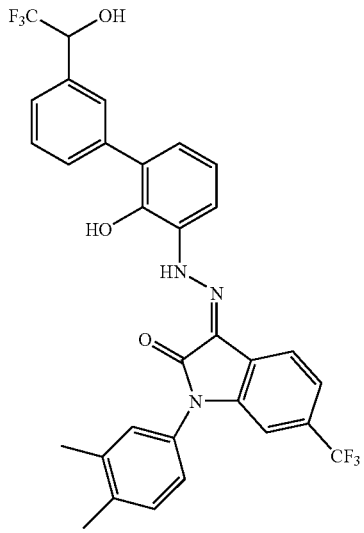

This compound was prepared as described in Scheme II. ¹H NMR (500 MHz, CD₃OD-d₄) δ 7.88 (d, J=7.7 Hz, 1H), 7.78 (d, J=7.7 Hz, 1H), 7.65 (s, 1H), 7.58 (m, 1H), 7.53-7.44 (m, 3H), 7.37 (d, J=8.0 Hz, 1H), 7.25 (s, 1H), 7.19 (d, J=8.0 Hz, 1H), 7.09 (t, J=7.5 Hz, 1H), 7.01 (d, J=7.5 Hz, 1H), 6.99 (s, 1H), 5.10 (q, J=7.0 Hz, 1H), 2.37 (s, 3H), 2.37 (s, 3H).

Example 94

3'-{N'-[6-Cyano-1-(4-isopropyl-phenyl)-2-oxo-1,2-dihydro-indol-3-ylidene]-hydrazino}-2'-hydroxy-biphenyl-3-carboxylic acid (Compound 194)

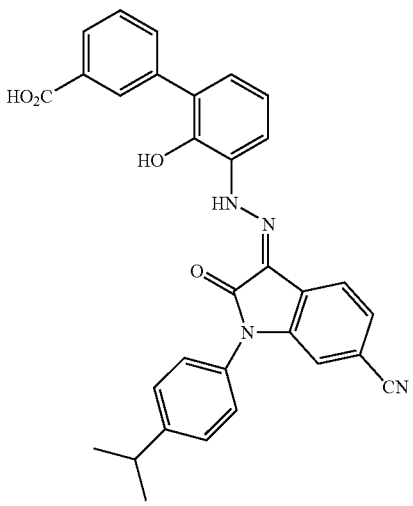

This compound was prepared as described in Scheme II. ¹H NMR (500 MHz, CD₃OD-d₄) δ 8.06 (s, 1H), 7.90 (d, J=7.8 Hz, 1H), 7.78 (m, 1H), 7.71 (d, J=7.8 Hz, 1H), 7.62 (m, 1H), 7.44 (m, 2H), 7.40 (d, J=8.2 Hz, 2H), 7.32 (d, J=8.2 Hz, 2H), 7.04 (s, 1H), 7.00 (t, J=7.6 Hz, 1H), 6.95 (d, J=7.6 Hz, 1H), 2.94 (sept, J=7.0 Hz, 1H), 1.23 (d, J=7.0 Hz, 6H).

Example 95

3'-{N'-[1-(3,4-Dimethyl-phenyl)-5-nitro-2-oxo-1,2-dihydro-indol-3-ylidene]-hydrazino}-2'-hydroxy-biphenyl-3-carboxylic acid (Compound 195)

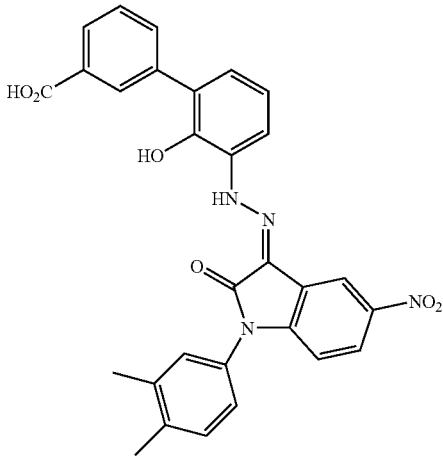

This compound was prepared as described in Scheme II. ¹H NMR (500 MHz, DMSO-d₆) δ 13.10 (s, 1H), 12.93 (s, 1H), 8.47 (d, J=2.3 Hz, 1H), 8.16 (dd, J=8.7, 2.3 Hz, 1H), 8.10 (t, J=1.6 Hz, 1H), 7.93 (ddd, J=7.7, 1.6, 1.2 Hz, 1H), 7.85 (dd, J=7.8, 1.7 Hz, 1H), 7.78 (ddd, J=7.7, 1.6, 1.2 Hz, 1H), 7.58 (t, J=7.7 Hz, 1H), 7.36 (d, J=8.0 Hz, 1H), 7.32-7.21 (m, 2H), 7.12 (t, J=7.8 Hz, 1H), 7.05 (dd, J=7.8, 1.7 Hz, 1H), 6.99 (d, J=8.7 Hz, 1H), 2.30 (s, 3H), 2.28 (s, 3H).

Example 96

3'-{N'-[1-(3,4-Dimethyl-phenyl)-6-methanesulfonyl-2-oxo-1,2-dihydro-indol-3-ylidene]-hydrazino}-2'-hydroxy-biphenyl-3-carboxylic acid (Compound 196)

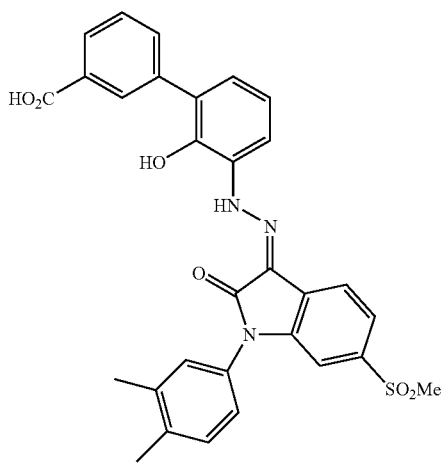

This compound was prepared as described in Scheme II. ¹H NMR (500MHz, CD₃OD-d₄) δ 8.43 (s, 2H), 8.11 (t, J=1.2 Hz, 1H), 7.94 (dt, J=7.6, 1.2 Hz, 1H), 7.71 (dd, J=7.8, 1.6 Hz, 1H), 7.69 (dd, J=7.4, 0.9 Hz, 1H), 7.66 (dt, J=7.6, 1.2 Hz, 1H), 7.47 (t, J=7.6 Hz, 1H), 7.30 (d, J=8.1 Hz, 1H), 7.22-7.18 (m, 2H), 7.14 (dd, J=7.9, 2.0 Hz, 1H), 7.12 (m, 1H), 7.03 (t, J=7.8 Hz, 1H), 6.94 (dd, J=7.8, 1.6 Hz, 1H), 6.81 (d, J=7.8 Hz, 1H), 3.30 (s, 3H), 2.31 (s, 6H).

Example 97

3'-{N'-[6-Cyano-1-(3,4-dimethyl-phenyl)-2-oxo-1,2-dihydro-indol-3-ylidene]-hydrazino}-2'-hydroxy-biphenyl-3-carboxylic acid (Compound 17)

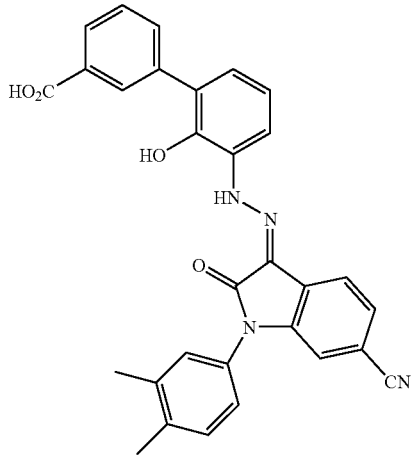

This compound was prepared as described in Scheme II. ¹H NMR (500 MHz, DMSO-d₆) δ8.25 (d, J=7.8 Hz, 1H), 8.22 (t, J=1.5 Hz, 1H), 7.87-7.82 (m, 2H), 7.51 (t, J=7.8 Hz, 1H), 7.41 (dd, J=7.7, 1.3 Hz, 1H), 7.31-7.26 (m, 2H), 7.22 (d, J=1.9 Hz, 1H), 7.15 (dd, J=7.9, 1.9 Hz, 1H), 6.99 (dd, J=7.6, 1.5 Hz, 1H), 6.92-6.88 (m, 2H), 2.27 (s, 6H).

Example 98

3'-{N'-[1-(5-Cyano-pyridin-3-yl)-2-oxo-1,2-dihydro-indol-3-ylidene]-hydrazino}-2'-hydroxy-biphenyl-3-carboxylic acid (Compound 198)

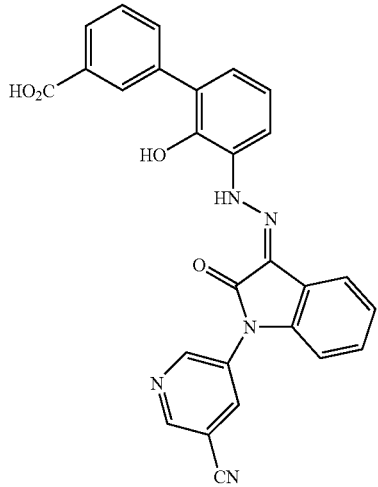

This compound was prepared as described in Scheme II. ¹H NMR (300 MHz, DMSO-d₆) δ 8.91 (m, 1H), 8.85 (m, 0.5H), 8.72 (m, 0.5H), 8.43 (t, J=2.0 Hz, 0.5H), 8.30 (t, J=2.1 Hz, 0.5H), 8.06 (m, 0.5H), 8.02 (t, J=1.5 Hz, 0.5H), 7.90 (t, J=1.6 Hz, 0.5H), 7.73 (m, 0.5H), 7.72-7.53 (m, 3H), 7.37 (t, J=7.6 Hz, 0.5H), 7.30 (t, J=7.7 Hz, 0.5H), 7.12 (m, 1H), 7.03 (m, 0.5H), 6.95-6.61 (m, 3.5H).

Example 99

3'-[N'-(1-Furan-3-yl-2-oxo-1,2-dihydro-indol-3-ylidene)-hydrazino]-2'-hydroxy-biphenyl-3-carboxylic acid (Compound 199)

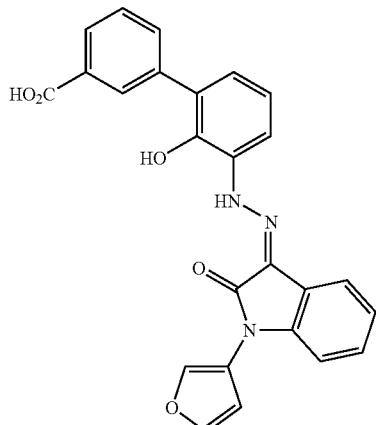

This compound was prepared as described in Scheme II. ¹H NMR (500 MHz, CD₃OD-d₄) δ 8.07 (s, 1H), 7.90 (m, 2H), 7.66-7.59 (m, 4H), 7.42 (t, J=7.7 Hz, 1H), 7.21 (t, J=7.6 Hz, 1H), 7.09 (t, J=7.6 Hz, 1H), 7.01 (d, J=7.6 Hz, 1H), 6.97 (t, J=7.6 Hz, 1H), 6.88 (dd, J=7.6, 1.3 Hz, 1H), 6.74 (dd, J=2.0, 0.7 Hz, 1H).

Example 100

3'-[N'-(1-Benzo[1,3]dioxol-5-yl-2-oxo-1,2-dihydro-indol-3-ylidene)-hydrazino]-2'-hydroxy-biphenyl-3-carboxylic acid (Compound 200)

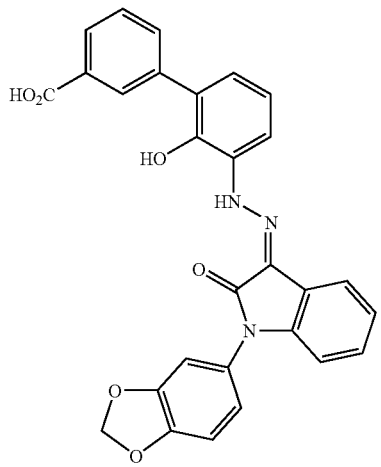

This compound was prepared as described in Scheme II. ¹H NMR (500 MHz, DMSO-d₆) δ13.02 (s, 1H), 8.09 (t, J=1.6 Hz, 1H), 7.92 (ddd, J=7.7, 1.6, 1.2 Hz, 1H), 7.76 (ddd, J=7.7, 1.6, 1.2 Hz, 1H), 7.70 (dd, J=7.8, 1.6 Hz, 1H), 7.70 (m, 1H), 7.57 (t, J=7.7 Hz, 1H), 7.27 (td, J=7.7, 1.1 Hz, 1H), 7.16 (t, J=7.8 Hz, 1H), 7.13-7.07 (m, 3H), 6.99-6.96 (m, 2H), 6.82 (d, J=8.1 Hz, 1H), 6.13 (s, 2H). Mixture~90:10

Example 101

2'-Hydroxy-3'-{N'-[1-(3-methyl-thiophen-2-yl)-2-oxo-1,2-dihydro-indol-3-ylidene]-hydrazino}-biphenyl-3-carboxylic acid (Compound 201)

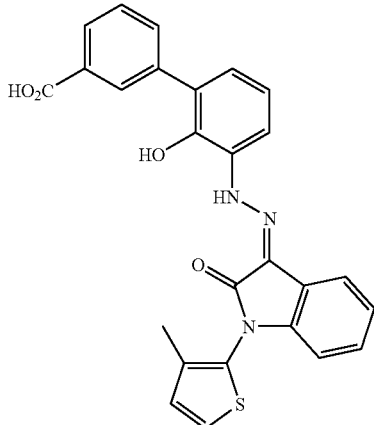

This compound was prepared as described in Scheme II. ¹H NMR (500 MHz, DMSO-d₆) δ 12.94 (s, 1H), 8.10 (s, 1H), 7.92 (d, J=7.6 Hz, 1H), 7.79-7.69 (m, 3H), 7.63-7.54 (m, 2H), 7.30 (t, J=7.6 Hz, 1H), 7.20 (t, J=7.6 Hz, 1H), 7.14-7.06 (m, 2H), 6.99 (d, J=7.4 Hz, 1H), 6.73 (d, J=7.6 Hz, 1H), 2.01 (s, 3H).

Example 102

2'-Hydroxy-3'-[N'-(2-oxo-1-thiophen-2-yl-1,2-dihydro-indol-3-ylidene)-hydrazino]-biphenyl-3-carboxylic acid (Compound 202)

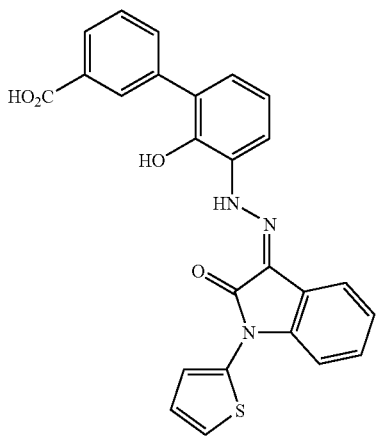

This compound was prepared as described in Scheme II. ¹H NMR (300 MHz, DMSO-d₆) δ 12.96 (s, 1H), 9.33 (s, 1H), 8.11 (s, 1H), 7.93 (d, J=7.6 Hz, 1H), 7.78 (d, J=7.6 Hz, 1H), 7.74-7.69 (m, 2H), 7.63 (dd, J=5.5, 1.4 Hz, 1H), 7.58 (t, J=7.6 Hz, 1H), 7.36-7.28 (m, 2H), 7.25-7.15 (m, 2H), 7.10 (t, J 7.8 Hz, 1H), 7.08 (d, J=7.8 Hz, 1H), 7.00 (dd, J=7.6, 1.2 Hz, 1H),

Example 103

2'-Hydroxy-3'-{N'-[1-(4-isopropyl-phenyl)-2-oxo-6-trifluoromethyl-1,2-dihydro-indol-3-ylidene]-hydrazino}-biphenyl-3-carboxylic acid (Compound 203)

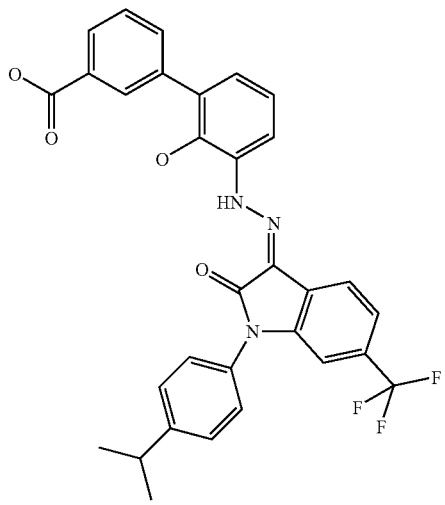

This compound was prepared as described in Scheme II. ¹H NMR (500 MHz, DMSO) δ 13.23 (s, 1H), 13.04 (s, 1H), 9.43 (s, 1H), 8.12 (t, J=1.6 Hz, 1H), 7.95 (ddd, J=7.7, 1.6, 1.2 Hz, 1H), 7.93 (d, J=8.0 Hz, 1H), 7.80 (dd, J=7.7, 1.6, 1.2 Hz, 1H), 7.79 (d, J=7.6 Hz, 1H), 7.78 (dd, J=7.9, 1.6 Hz, 1H), 7.60 (t, J=7.7 Hz, 1H), 7.55 (d, J=8.0, 1.1 Hz, 1H), 7.51 (d, J=8.8 Hz, 2H), 7.48 (d, J=8.8 Hz, 2H), 7.14 (t, J=7.9 Hz, 1H), 7.06 (dd, J=7.9, 1.6 Hz, 1H), 7.00 (d, J=1.1 Hz, 1H), 3.01 (sept, J=6.8 Hz, 1H), 1.28 (d, J=6.8 Hz, 6H).

Example 104

2'-Hydroxy-3'-{N'-[2-oxo-1-(4-propyl-phenyl)-6-trifluoromethyl-1,2-dihydro-indol-3-ylidene]-hydrazino}-biphenyl-3-carboxylic acid (Compound 204)

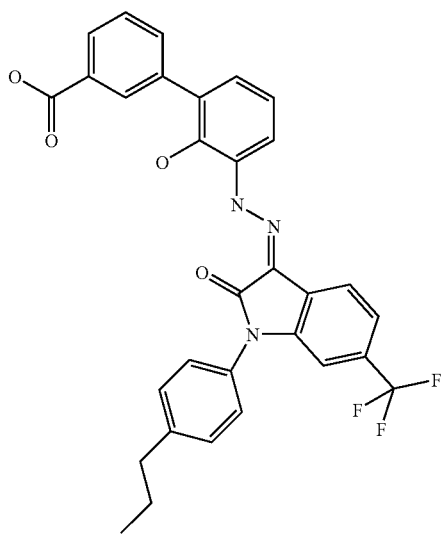

This compound was prepared as described in Scheme II.
¹H NMR (500 MHz, DMSO) δ 13.23 (s, 1H), 13.04 (s, 1H), 9.43 (s, 1H), 8.12 (t, J=1.6 Hz, 1H), 7.95 (d, J=7.7, 1.6, 1.2 Hz, 1H), 7.93 (d, J=8.0 Hz, 1H), 7.80 (dd, J=7.7, 1.6, 1.2 Hz, 1H), 7.78 (dd, J=7.7, 1.5 Hz, 1H), 7.60 (t, J=7.7 Hz, 1H), 7.55 (m, 1H), 7.47 (d, J=8.5 Hz, 2H), 7.44 (d, J=8.5 Hz, 2H), 7.14 (t, J=7.7 Hz, 1H), 7.06 (dd, J=7.7, 1.5 Hz, 1H), 6.98 (m, 1H), 2.67 (t, J=7.4 Hz, 2H), 1.67 (sext, J=7.4 Hz, 2H), 0.95 (t, J=7.4 Hz, 3H).

Example 105

3'-{N'-[1-(4-Ethyl-phenyl)-5,7-difluoro-2-oxo-1,2-dihydro-indol-3-ylidene]-hydrazino}-2'-hydroxy-biphenyl-3-carboxylic acid (Compound 205)

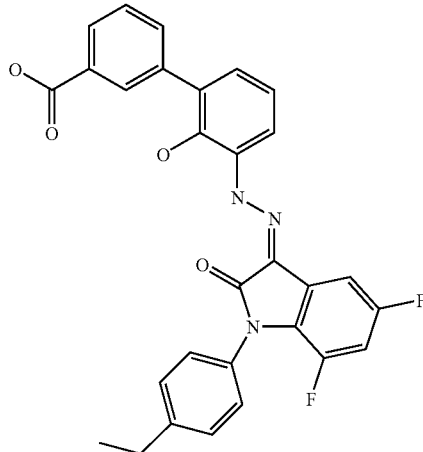

This compound was prepared as described in Scheme II.
¹H NMR (500 MHz, DMSO) δ 13.15 (s, 1H), 13.03 (s, 1H), 9.40 (s, 1H), 8.11 (t, J=1.6 Hz, 1H), 7.94 (d, J=7.7, 1.6, 1.1 Hz, 1H), 7.79 (m, 2H), 7.60 (t, J=7.7 Hz, 1H), 7.48 (dd, J=7.8, 2.3 Hz, 1H), 7.41 (dd, J=8.3, 1.4 Hz, 2H), 7.36 (d, J=8.3 Hz, 2H), 7.21 (ddd, J=11.6, 9.7, 2.3 Hz, 1H) 7.13 (t, J=7.8 Hz, 1H), 7.05 (dd, J=7.8, 1.3 Hz, 1H), 2.69 (q, J=7.5 Hz, 2H), 1.24 (t, J=7.5 Hz, 3H).

Example 106

3'-{N'-[1-(3,4-Dimethyl-phenyl)-5,7-difluoro-2-oxo-1,2-dihydro-indol-3-ylidene]-hydrazino}-2'-hydroxy-biphenyl-3-carboxylic acid (Compound 206)

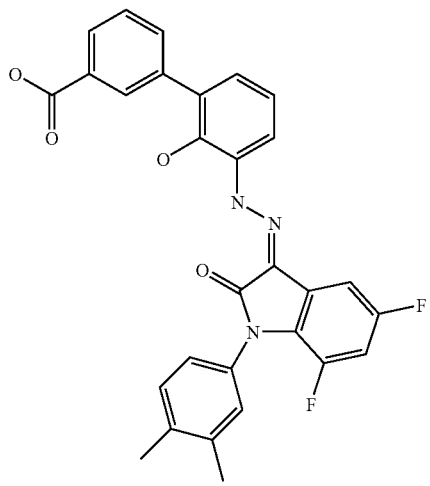

This compound was prepared as described in Scheme II.
¹H NMR (500 MHz, DMSO) δ 13.16 (s, 1H), 12.99 (s, 1H), 9.40 (s, 1H), 8.11 (t, J=1.6 Hz, 1H), 7.94 (ddd, J=7.7, 1.6, 1.2 Hz, 1H), 7.79 (m, 1H), 7.78 (dd, J=7.8, 1.5 Hz, 1H), 7.60 (t, J=7.7 Hz, 1H), 7.47 (dd, J=7.7, 2.3 Hz, 1H), 7.28 (m, 2H), 7.23-7.17 (m, 1H), 7.13 (t, J=7.8 Hz, 1H), 7.05 (dd, J=7.8, 1.5 Hz, 1H), 2.29 (s, 3H), 2.27 (s, 3H).

Example 107

3'-{N'-[5,7-Difluoro-2-oxo-1-(4-propyl-phenyl)-1,2-dihydro-indol-3-ylidene]-hydrazino}-2'-hydroxy-biphenyl-3-carboxylic acid (Compound 207)

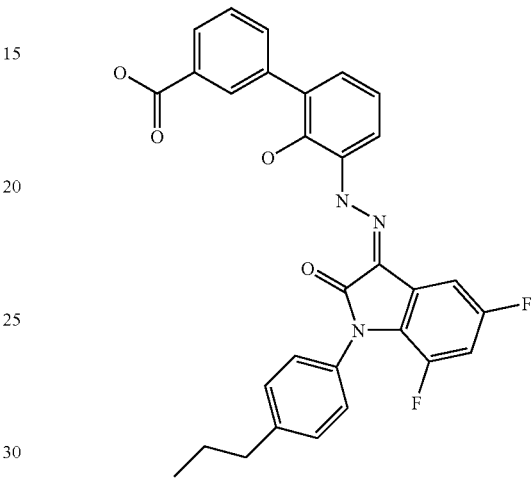

This compound was prepared as described in Scheme II.
¹H NMR (500 MHz, DMSO) δ 13.15 (s, 1H), 13.03 (s, 1H), 9.40 (s, 1H), 8.11 (t, J=1.6 Hz, 1H), 7.94 (ddd, J=7.7, 1.6, 1.2 Hz, 1H), 7.79 (m, 2H), 7.60 (t, J=7.7 Hz, 1H), 7.48 (dd, J=7.8, 2.4 Hz, 1H), 7.40 (dd, J=8.3, 1.7 Hz, 2H), 7.34 (d, J=8.3 Hz, 2H), 7.21 (ddd, J=11.6, 9.7, 2.4 Hz, 1H), 7.13 (t, J=7.8 Hz, 1H), 7.05 (dd, J=7.8, 1.6 Hz, 1H), 2.64 (t, J=7.4 Hz, 2H), 1.65 (sext, J=7.4 Hz, 2H), 0.93 (t, J=7.4 Hz, 3H).

Example 108

3'-{N'-[5,7-Difluoro-1-(4-isopropyl-phenyl)-2-oxo-1,2-dihydro-indol-3-ylidene]-hydrazino}-2'-hydroxy-biphenyl-3-carboxylic acid (Compound 208)

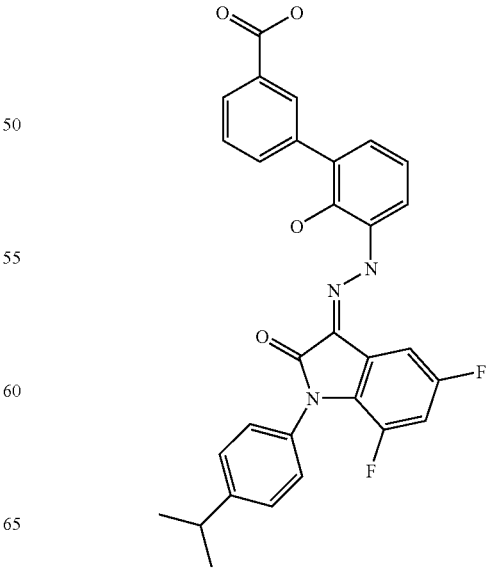

This compound was prepared as described in Scheme II.
¹H NMR (500 MHz, DMSO) δ 13.15 (s, 1H), 13.04 (s, 1H), 9.41 (s, 1H), 8.11 (t, J=1.6 Hz, 1H), 7.94 (ddd, J=7.7, 1.6, 1.1 Hz, 1H), 7.79 (m, 1H), 7.78 (dd, J=7.8, 1.7 Hz, 1H), 7.60 (t, J=7.7 Hz, 1H), 7.48 (dd, J=7.8, 2.2 Hz, 1H), 7.42 (dd, J=8.8, 1.4 Hz, 2H), 7.39 (d, J=8.8 Hz, 2H), 7.21 (ddd, J=11.8, 9.5, 2.2 Hz, 1H), 7.13 (t, J=7.8 Hz, 1H), 7.05 (dd, J=7.8, 1.7 Hz, 1H), 2.98 (sept, J=6.9 Hz, 1H), 1.26 (d, J=6.9 Hz, 6H).

Example 109

3'-{N'-[1-(3,4-Dimethyl-phenyl)-2-oxo-6-trifluoromethyl-1,2-dihydro-indol-3-ylidene]-hydrazino}-2'-hydroxy-biphenyl-3-carboxylic acid (Compound 209)

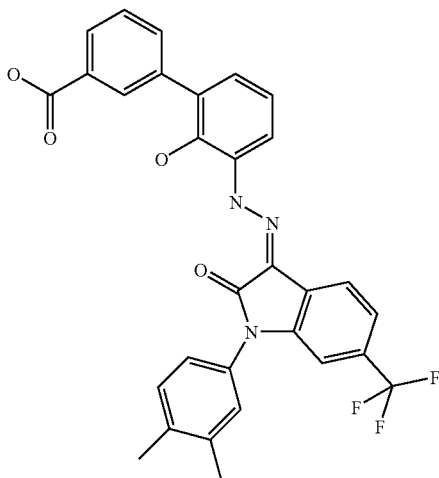

This compound was prepared as described in Scheme II.
¹H NMR (500 MHz, DMSO) δ 13.22 (s, 1H), 13.02 (s, 1H), 9.41 (s, 1H), 8.10 (t, J=1.6 Hz, 1H), 7.94 (ddd, J=7.7, 1.6, 1.2 Hz, 1H), 7.91 (d, J=7.9 Hz, 1H), 7.79 (dd, J=7.7, 1.6, 1.2 Hz, 1H), 7.76 (dd, J=7.8, 1.5 Hz, 1H), 7.59 (t, J=7.7 Hz, 1H), 7.52 (m, 1H), 7.37 (d, J=8.0 Hz, 1H), 7.31 (m, 1H), 7.25 (dd, J=8.0, 1.9 Hz, 1H), 7.12 (t, J=7.8 Hz, 1H), 7.04 (dd, J=7.8, 1.5 Hz, 1H), 6.94 (m, 1H), 2.30 (s, 3H), 2.29 (s, 3H).

Example 110

3'-{N'-[1-(3,4-Dimethyl-phenyl)-6-ethyl-2-oxo-1,2-dihydro-indol-3-ylidene]-hydrazino}-2'-hydroxy-biphenyl-3-carboxylic acid (Compound 210)

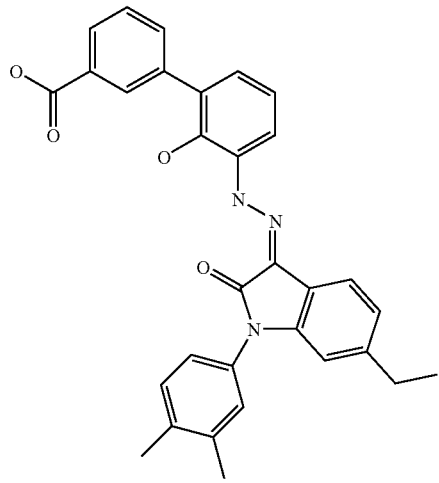

This compound was prepared as described in Scheme II.
¹H NMR (300 MHz, DMSO) δ 13.04 (s, 1H), 12.99 (s, 1H), 9.23 (s, 1H), 8.12 (t, J=1.6 Hz, 1H), 7.94 (ddd, J=7.6, 1.6, 1.2 Hz, 1H), 7.79 (ddd, J=7.6, 1.6, 1.2 Hz, 1H), 7.70 (dd, J=7.8, 1.6 Hz, 1H), 7.63 (d, J=7.5 Hz, 1H), 7.59 (t, J=7.6 Hz, 1H), 7.36 (d, J=8.0 Hz, 1H), 7.29 (d, J=2.0 Hz, 1H), 7.22 (dd, J=8.0, 2.0 Hz, 1H), 7.10 (t, J=7.8 Hz, 1H), 7.04 (m, 1H), 6.98 (dd, J=7.8, 1.6 Hz, 1H), 6.67 (m, 1H), 2.61 (q, J=7.6 Hz, 2H), 2.31 (s, 3H), 2.30 (s, 3H), 1.14 (t, J=7.6 Hz, 3H).

Example 111

3'-{N'-[1-(3,4-Dimethyl-phenyl)-6-methoxy-2-oxo-1,2-dihydro-indol-3-ylidene]-hydrazino}-2'-hydroxy-biphenyl-3-carboxylic acid (Compound 211)

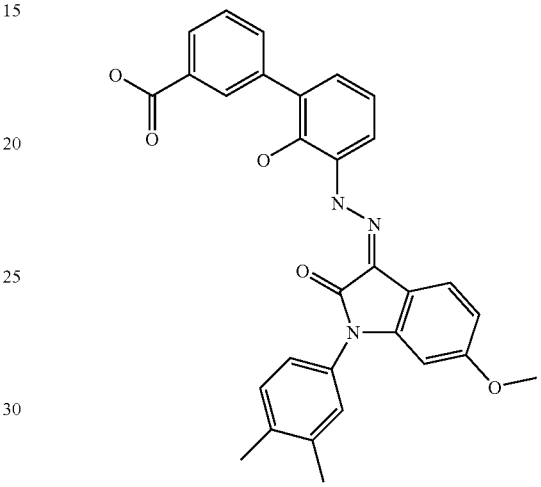

This compound was prepared as described in Scheme II.
¹H NMR (300 MHz, DMSO) δ 12.85 (s, 1H), 9.16 (s, 1H), 8.09 (t, J=1.7 Hz, 1H), 7.91 (ddd, J=7.6, 1.7, 1.2 Hz, 1H), 7.76 (ddd, J=7.6, 1.7, 1.2 Hz, 1H), 7.66 (dd, J=7.9, 1.6 Hz, 1H), 7.62 (d, J=8.4 Hz, 1H), 7.57 (t, J=7.6 Hz, 1H), 7.33 (d, J=8.0 Hz, 1H), 7.28 (d, J=2.1 Hz, 1H), 7.21 (dd, J=8.0, 2.1 Hz, 1H), 7.07 (t, J=7.9 Hz, 1H), 6.93 (dd, J=7.9, 1.6 Hz, 1H), 6.74 (dd, J=8.4, 2.2 Hz, 1H), 6.33 (d, J=2.2 Hz, 1H), 3.73 (s, 3H), 2.29 (s, 3H), 2.28 (s, 3H).

Example 112

3'-{N'-[5-Chloro-1-(3,4-dimethyl-phenyl)-2-oxo-6-trifluoromethyl-1,2-dihydro-indol-3-ylidene]-hydrazino}-2'-hydroxy-biphenyl-3-carboxylic acid (Compound 212)

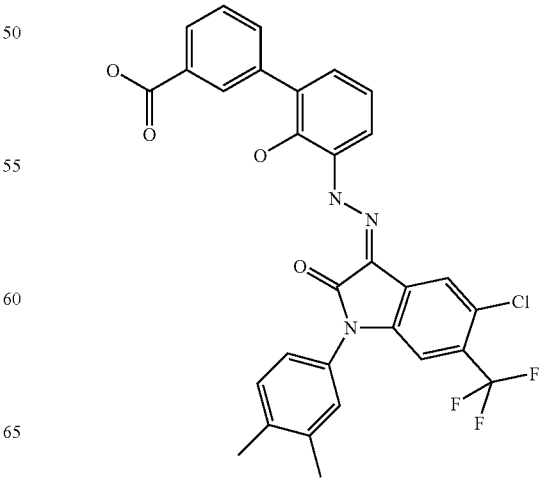

This compound was prepared as described in Scheme II. ¹H NMR (300 MHz, DMSO) δ 13.25 (s, 1H), 13.01 (s, 1H), 9.49 (s, 1H), 8.10 (t, J=1.7 Hz, 1H), 8.01 (s, 1H), 7.93 (ddd, J=7.7, 1.7, 1.1 Hz, 1H), 7.83 (dd, J=7.8, 1.9 Hz, 1H), 7.77 (ddd, J=7.7, 1.7, 1.1 Hz, 1H), 7.58 (t, J=7.7 Hz, 1H), 7.36 (d, 8.0 Hz, 1H), 7.31 (d, 2.0 Hz, 1H), 7.25 (dd, J=8.0, 2.0 Hz, 1H), 7.12 (t, J=7.8 Hz, 1H), 7.07 (dd, J=7.8, 1.9 Hz, 1H), 7.02 (s, 1H).

Example 113

3'-{N'-[1-(3,4-Dimethyl-phenyl)-6,7-dimethyl-2-oxo-1,2-dihydro-indol-3-ylidene]-hydrazino}-2'-hydroxy-biphenyl-3-carboxylic acid (Compound 213)

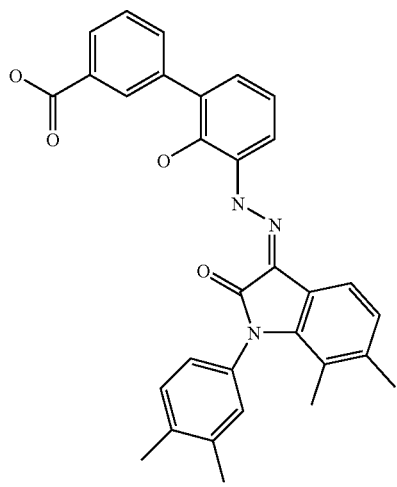

This compound was prepared as described in Scheme II. ¹H NMR (300 MHz, DMSO) δ 13.03 (s, 1H), 12.94 (s, 1H), 9.17 (s, 1H), 8.10 (t, J=1.5 Hz, 1H), 7.93 (d, J=7.7 Hz, 1H), 7.77 (d, J=7.7 Hz, 1H), 7.69 (dd, J=7.8, 1.2 Hz, 1H), 7.58 (t, J=7.7 Hz, 1H), 7.48 (d, J=7.5 Hz, 1H), 7.30 (d, J=7.9 Hz, 1H), 7.20 (d, J=1.8 Hz, 1H), 7.14 (dd, J=7.9, 1.8 Hz, 1H), 7.09 (t, J=7.8 Hz, 1H), 7.02 (d, J=7.8 Hz, 1H), 6.96 (d, J=7.5 Hz, 1H), 2.31 (s, 3H), 2.28 (s, 3H), 2.23 (s, 3H), 1.62 (s, 3H).

Example 114

2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-2-methyl-propionic acid (Compound 214)

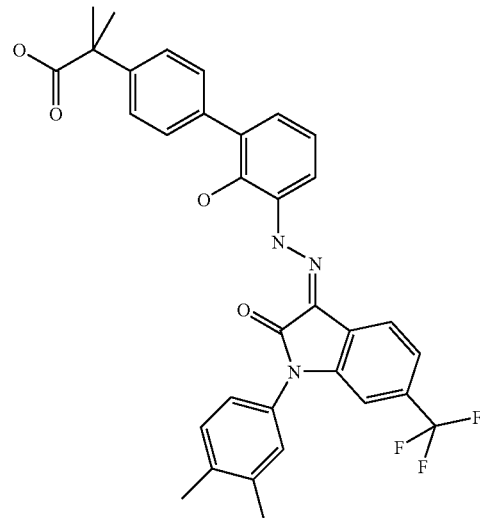

This compound was prepared as in Scheme II. ¹H NMR (300 MHz, DMSO) δ 13.23 (s, 1H), 12.39 (s, 1H), 9.35 (s, 1H), 7.92 (d, J=7.9 Hz, 1H), 7.74 (dd, J=7.8, 1.7 Hz, 1H), 7.55 (d, J=8.5 Hz, 2H), 7.53 (m, 1H), 7.45 (d, J=8.5 Hz, 2H), 7.39 (d, J=8.0 Hz, 1H), 7.33 (d, J=2.2 Hz, 1H), 7.27 (dd, J=8.0, 2.2 Hz, 1H), 7.11 (t, J=7.8 Hz, 1H), 7.03 (dd, J=7.8, 1.7 Hz, 1H), 6.96 (m, 1H), 2.32 (s, 3H), 2.31 (s, 3H), 1.52 (s, 6H).

Example 115

(−)-2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-propionic acid (Compound 215) and (+)-2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-propionic acid (Compound 215a)

Chiral

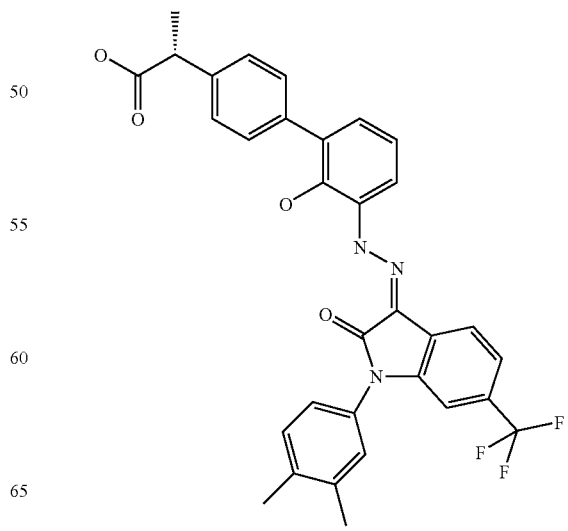

These compounds were prepared as described in Scheme II. ¹H NMR (300 MHz, DMSO) δ 13.23 (s, 1H), 12.36 (s, 1H), 9.34 (s, 1H), 7.92 (d, J=7.9 Hz, 1H), 7.74 (dd, J=7.8, 1.6 Hz, 1H), 7.53 (d, J=8.4 Hz, 2H), 7.53 (m, 1H), 7.39 (d, J=8.4 Hz, 2H), 7.38 (d, J=8.2 Hz, 1H), 7.33 (d, J=2.0 Hz, 1H), 7.27 (dd, J=8.2, 2.0 Hz, 1H), 7.11 (t, J=7.8 Hz, 1H), 7.02 (dd, J=7.8, 1.6 Hz, 1H), 6.96 (m, 1H), 3.73 (q, J=7.0 Hz, 1H), 2.32 (s, 3H), 2.31 (s, 3H), 1.40 (d, J=7.0 Hz, 3H).

Example 116

(±)-(3'-{N'-[1-(3,4-Dimethyl-phenyl)-2-oxo-6-trifluoromethyl-1,2-dihydro-indol-3-ylidene]-hydrazino}-2'-hydroxy-5'-methyl-biphenyl-4-yl)-propionic acid (Compoud 216)

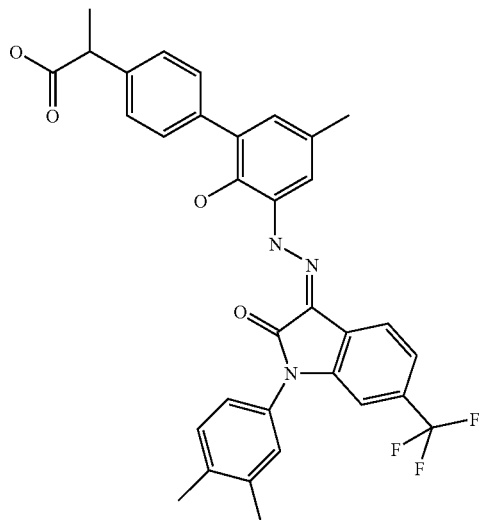

This compound was prepared as in Scheme II. ¹H NMR (300 MHz, DMSO) δ 13.21 (s, 1H), 12.34 (s, 1H), 9.07 (s, 1H), 7.94 (d, J=8.0 Hz, 1H), 7.57 (d, J=1.6 Hz, 1H), 7.53 (d, J=8.0 Hz, 1H), 7.52 (d, J=8.3 Hz, 2H), 7.38 (d, J=8.0 Hz, 1H), 7.37 (d, J=8.3 Hz, 2H), 7.33 (d, J=2.0 Hz, 1H), 7.27 (dd, J=8.0, 2.0 Hz, 1H), 6.96 (m, 1H), 6.85 (d, J=1.6 Hz, 1H), 3.73 (q, J=7.0 Hz, 1H), 2.35 (s, 3H), 2.32 (s, 3H), 2.31 (s, 3H), 1.40 (d, J=7.0 Hz, 3H).

Example 117

(±)-2-(3'-{N'-[1-(3,4-Dimethyl-phenyl)-2-oxo-6-trifluoromethyl-1,2-dihydro-indol-3-ylidene]-hydrazino}-5'-fluoro-2'-hydroxy-biphenyl-4-yl)-propionic acid (Compound 217)

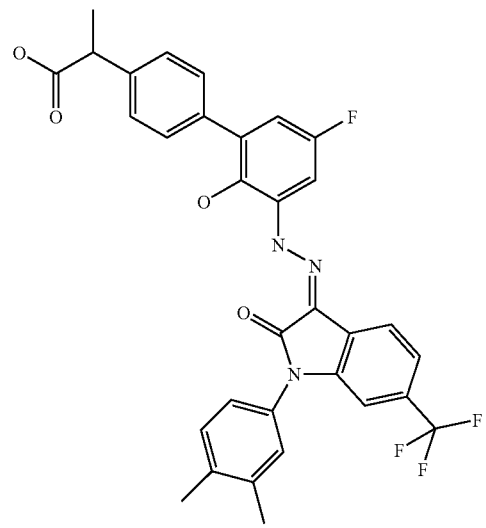

This compound was prepared as in Scheme II. ¹H NMR (300 MHz, DMSO) δ 13.13 (s, 1H), 12.37 (s, 1H), 9.26 (s, 1H), 7.99 (d, J=7.8 Hz, 1H), 7.57 (d, J=8.4 Hz, 2H), 7.55 (m, 1H), 7.53 (dd, J=9.7, 3.1 Hz, 1H), 7.40 (d, J=8.4 Hz, 2H), 7.39 (m, 1H), 7.33 (d, J=2.0 Hz, 1H), 7.27 (dd, J=7.9, 2.0 Hz, 1H), 6.96 (m, 1H), 6.86 (dd, J=9.4, 3.1 Hz, 1H), 3.74 (q, J=7.1 Hz, 1H), 2.32 (s, 3H), 2.31 (s, 3H) 1.40 (d, J=7.1 Hz, 3H).

Example 118

5-(4-{N'-[1-(3,4-Dimethyl-phenyl)-5,7-difluoro-2-oxo-1,2-dihydro-indol-3-ylidene]-hydrazino}-3-hydroxy-benzylidene)-thiazolidine-2,4-dione (Compound 218)

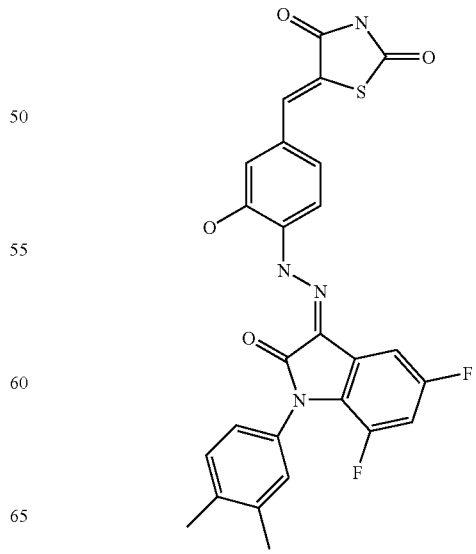

This compound was prepared as in Scheme V. ¹H NMR (300 MHz, DMSO) δ 13.03 (s, 1H), 12.56 (s, 1H), 10.86 (s, 1H), 7.80 (d, J=8.4 Hz, 1H), 7.68 (s, 1H), 7.46 (dd, J=7.6, 2.3 Hz, 1H), 7.30-7.18 (m, 5H), 7.14 (d, J=1.6 Hz, 1H), 2.30 (s, 3H), 2.28 (s, 3H).

Example 119

5-(4-{N'-[1-(4-Ethyl-phenyl)-5,7-difluoro-2-oxo-1,2-dihydro-indol-3-ylidene]-hydrazino}-3-hydroxy-benzylidene)-thiazolidine-2,4-dione (Compound 29)

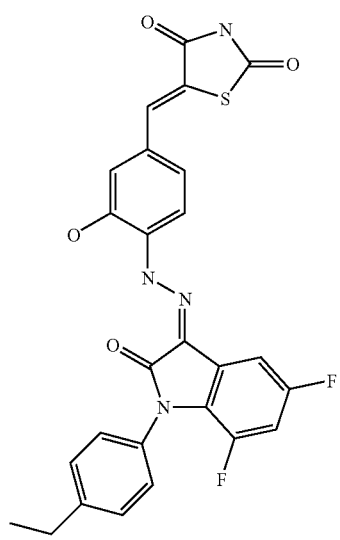

This compound was prepared as in Scheme V. ¹H NMR (500 MHz, DMSO) δ 13.03 (s, 1H), 12.56 (s, 1H), 10.87 (s, 1H), 7.80 (d, J=8.3 Hz, 1H), 7.68 (s, 1H), 7.47 (dd, J=7.5, 1.8 Hz, 1H), 7.41 (d, J=8.2 Hz, 2H), 7.36 (d, J=8.2 Hz, 2H), 7.27-7.21 (m, 2H), 7.14 (s, 1H), 2.70 (q, J=7.6 Hz, 2H), 1.24 (t, J=7.6 Hz, 3H).

Example 120

5-(4-{N'-[5,7-Difluoro-2-oxo-1-(4-propyl-phenyl)-1,2-dihydro-indol-3-ylidene]-hydrazino}-3-hydroxy-benzylidene)-thiazolidine-2,4-dione (Compound 220)

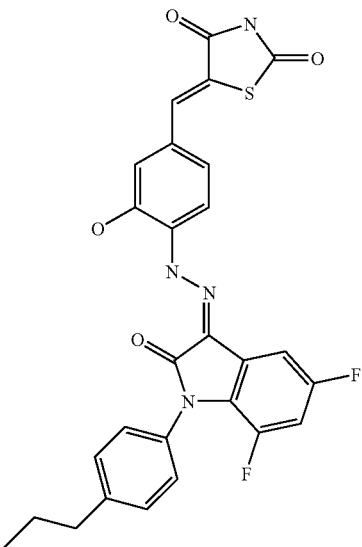

This compound was prepared as in Scheme V. ¹H NMR (500 MHz, DMSO) δ 13.03 (s, 1H), 12.56 (s, 1H), 10.87 (s, 1H), 7.80 (d, J=8.3 Hz, 1H), 7.69 (s, 1H), 7.46 (dd, J=7.7, 2.3 Hz, 1H), 7.40 (d, J=8.2 Hz, 2H), 7.34 (d, J=8.2 Hz, 2H), 7.26-7.20 (m, 2H), 7.14 (d, J=1.6 Hz, 1H), 2.64 (t, J=7.4 Hz, 2H), 1.65 (q, J=7.4 Hz, 2H), 0.93 (t, J=7.4 Hz, 3H).

Example 121

5-(3-Hydroxy-4-{N'-[1-(4-isopropyl-phenyl)-2-oxo-6-trifluoromethyl-1,2-dihydro-indol-3-ylidene]-hydrazino}-benzylidene)-thiazolidine-2,4-dione (Compound 221)

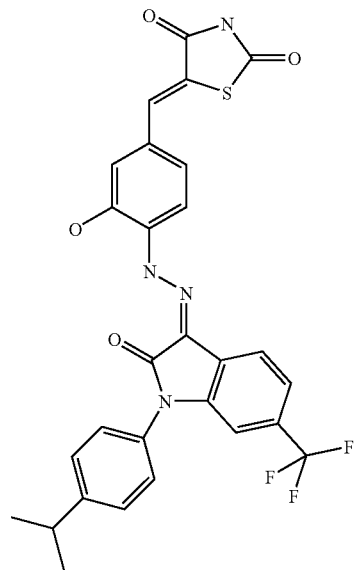

This compound was prepared as in Scheme V. $^1$H NMR (500 MHz, DMSO) δ 13.13 (s, 1H), 12.57 (s, 1H), 10.89 (s, 1H), 7.92 (d, J=7.8 Hz, 1H), 7.81 (d, J=8.4 Hz, 1H), 7.69 (s, 1H), 7.55 (d, J=7.8 Hz, 1H), 7.51 (d, J=8.6 Hz, 2H), 7.48 (d, J=8.6 Hz, 2H), 7.25 (dd, J=8.4, 1.6 Hz, 1H), 7.16 (d, J=1.6 Hz, 1H), 6.99 (s, 1H), 3.02 (sept, J=6.9 Hz, 1H), 1.28 (d, J=6.9 Hz, 6H).

Example 122

5-(3-Hydroxy-4-{N'-[1-(4-isopropyl-phenyl)-2-oxo-5,7-difluoro-1,2-dihydro-indol-3-ylidene]-hydrazino}-benzylidene)-thiazolidine-2,4-dione (Compound 222)

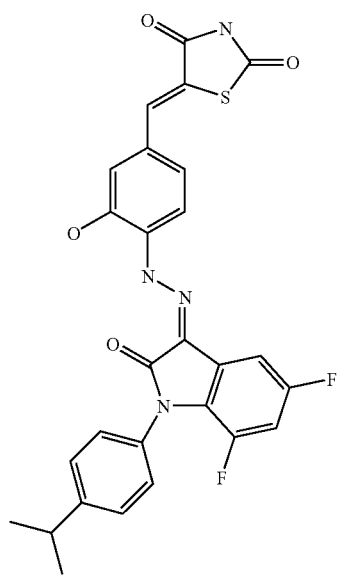

This compound was prepared as in Scheme V. $^1$H NMR (500 MHz, DMSO) δ 13.05 (s, 1H), 12.56 (s, 1H), 10.87 (s, 1H), 7.81 (d, J=8.4 Hz, 1H), 7.69 (s, 1H), 7.48 (dd, J=7.7, 2.1 Hz, 1H), 7.42 (d, J=8.4 Hz, 2H), 7.39 (d, J=8.4 Hz, 2H), 7.27-7.21 (m, 2H), 7.15 (d, J=1.6 Hz, 1H), 2.99 (sept, J=7.0 Hz, 1H), 1.26 (d, J=7.0 Hz, 6H).

Example 123

3'-{N'-[1-(3,4-Dimethyl-phenyl)-2-oxo-6-trifluoromethyl-1,2-dihydro-indol-3-ylidene]-hydrazino}-5'-fluoro-2'-hydroxy-biphenyl-3-carboxylic acid (Compound 22)

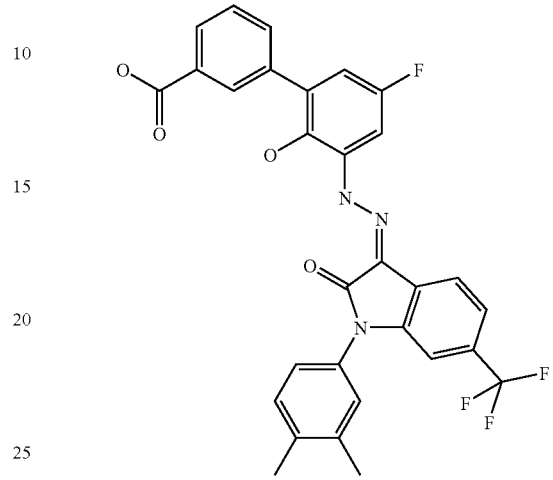

This compound was prepared as described in Scheme II. $^1$H NMR (500 MHz, DMSO) δ 13.14 (s, 1H), 13.08 (s, 1H), 9.35 (s, 1H), 8.15 (m, 1H), 8.00 (d, J=7.8 Hz, 1H), 7.96 (dd, J=7.7, 1.2 Hz, 1H), 7.82 (m, 1H), 7.61 (t, J=7.7 Hz, 1H), 7.57 (dd, J=9.2, 3.0 Hz, 1H), 7.55 (d, J=7.7 Hz, 1H), 7.39 (d, J=8.1 Hz, 1H), 7.33 (d, J=1.5 Hz, 1H), 7.27 (dd, J=8.1, 1.5 Hz, 1H), 6.95 (s, 1H), 6.92 (dd, J=9.2, 3.0 Hz, 1H), 2.32 (s, 3H), 2.31 (s, 3H).

Example 124

5'-Chloro-3'-{N'-[1-(3,4-dimethyl-phenyl)-2-oxo-6-trifluoromethyl-1,2-dihydro-indol-3-ylidene]-hydrazino}-2'-hydroxy-biphenyl-3-carboxylic acid (Compound 224)

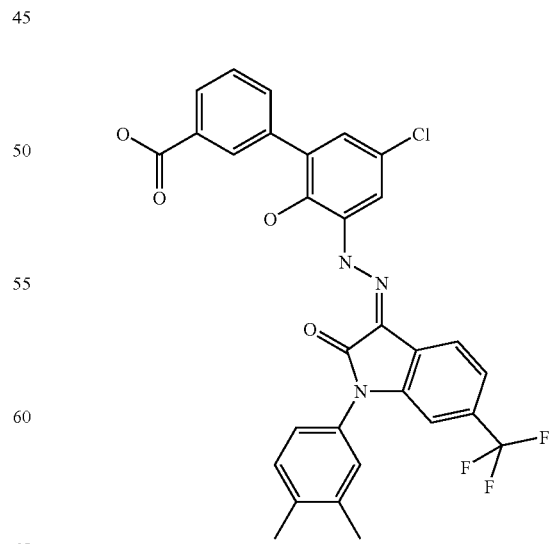

This compound was prepared as described in Scheme II.
¹H NMR (500 MHz, DMSO) δ 13.12 (s, 1H), 13.09 (s, 1H), 9.68 (s, 1H), 8.12 (t, J=1.7 Hz, 1H), 8.02 (d, J=7.8 Hz, 1H), 7.97 (ddd, J=7.7, 1.7, 1.1 Hz, 1H), 7.81 (ddd, J=7.7, 1.7, 1.1 Hz, 1H), 7.76 (d, J=2.6 Hz, 1H), 7.61 (t, J=7.7 Hz, 1H), 7.54 (d, J=7.8 Hz, 1H), 7.39 (d, J=8.0 Hz, 1H), 7.33 (d, J=2.0 Hz, 1H), 7.27 (dd, J=8.0, 2.0 Hz, 1H), 7.08 (d, J=2.6 Hz, 1H), 6.95 (s, 1H), 2.32 (s, 3H), 2.31 (s, 3H).

Example 125

3'-{N'-[1-(3,4-Dimethyl-phenyl)-2-oxo-6-trifluoromethyl-1,2-dihydro-indol-3-ylidene]-hydrazino}-2'-hydroxy-5'-methyl-biphenyl-3-carboxylic acid (Compound 225)

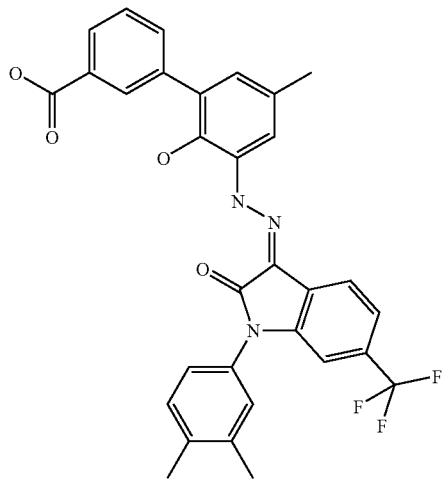

This compound was prepared as described in Scheme II.
¹H NMR (500 MHz, DMSO) δ 13.22 (s, 1H), 13.04 (s, 1H), 9.16 (s, 1H), 8.11 (t, J=1.6 Hz, 1H), 7.94 (ddd, J=7.7, 1.6, 1.2 Hz, 1H), 7.94 (d, J=7.8 Hz, 1H), 7.79 (ddd, J=7.7, 1.6, 1.2 Hz, 1H), 7.61 (d, J=1.9 Hz, 1H), 7.59 (t, J=7.7 Hz, 1H), 7.53 (d, J=7.8 Hz, 1H), 7.38 (d, J=8.0 Hz, 1H), 7.33 (d, J=1.9 Hz, 1H), 7.27 (dd, J=8.0, 1.9 Hz, 1H), 6.96 (s, 1H), 6.89 (d, J=1.9 Hz, 1H), 2.37 (s, 3H), 2.32 (s, 3H), 2.31 (s, 3H).

Example 126

2'-Hydroxy-3'-{N'-[2-oxo-6-trifluoromethyl-1-(4-trifluoromethyl-phenyl)-1,2-dihydro-indol-3-ylidene]-hydrazino}-biphenyl-3-carboxylic acid (Compound 226)

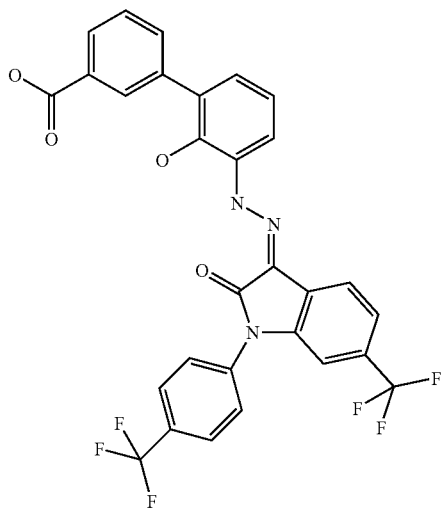

This compound was prepared as described in Scheme II.
¹H NMR (500 MHz, DMSO) δ 13.20 (s, 1H), 13.06 (s, 1H), 9.48 (s, 1H), 8.12 (m, 1H), 8.01 (d, J=8.4 Hz, 2H), 7.98-7.94 (m, 2H), 7.86 (d, J=8.4 Hz, 2H), 7.81-7.78 (m, 2H), 7.61 (t, J=7.7 Hz, 1H), 7.59 (d, J=7.5 Hz, 1H), 7.20 (s, 1H), 7.15 (t, J=7.8 Hz, 1H), 7.08 (dd, J=7.8, 1.2 Hz, 1H).

Example 127

3'-{N'-[1-(4-Ethyl-3-methyl-phenyl)-2-oxo-6-trifluoromethyl-1,2-dihydro-indol-3-ylidene]-hydrazino}-2'-hydroxy-biphenyl-3-carboxylic acid (Compound 227)

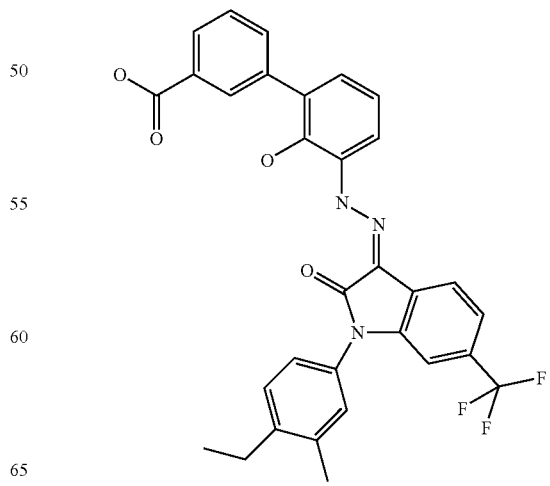

This compound was prepared as described in Scheme II. ¹H NMR (500 MHz, DMSO) δ 13.24 (s, 1H), 13.05 (s, 1H), 9.43 (s, 1H), 8.12 (m, 1H), 7.96-7.91 (m, 2H), 7.81-7.77 (m, 2H), 7.61 (t, J=7.7 Hz, 1H), 7.54 (d, J=8.0 Hz, 1H), 7.40 (d, J=7.9 Hz, 1H), 7.34-7.30 (m, 2H), 7.14 (t, J=7.8 Hz, 1H), 7.06 (d, J=7.8 Hz, 1H), 6.97 (s, 1H), 2.69 (q, J=7.5 Hz, 2H), 2.35 (s, 3H), 1.23 (t, J=7.5 Hz, 3H).

Example 128

3'-{N'-[1-(4-Chloro-3-trifluoromethyl-phenyl)-2-oxo-6-trifluoromethyl-1,2-dihydro-indol-3-ylidene]-hydrazino}-2'-hydroxy-biphenyl-3-carboxylic acid (Compound 228)

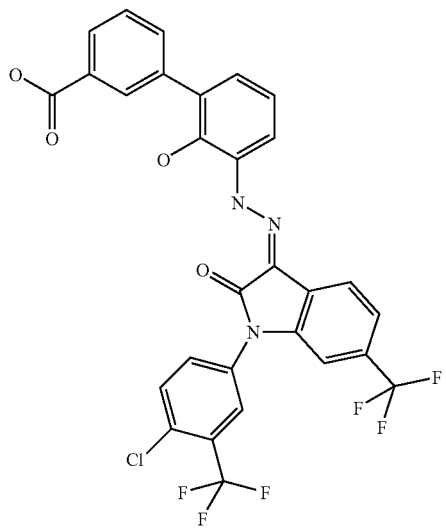

This compound was prepared as described in Scheme II. ¹H NMR (500 MHz, DMSO) δ 13.16 (s, 1H), 13.05 (s, 1H), 9.48 (s, 1H), 8.14 (d, J=2.1 Hz, 1H), 8.12 (t, J=1.5 Hz, 1H), 8.01-7.93 (m, 4H), 7.81-7.78 (m, 2H), 7.61 (t, J=7.7 Hz, 1H), 7.58 (d, J=8.0 Hz, 1H), 7.23 (s, 1H), 7.15 (t, J=7.7 Hz, 1H), 7.08 (dd, J=7.7, 1.3 Hz, 1H).

Example 129

3'-{N'-[1-(3,5-Dimethyl-phenyl)-2-oxo-6-trifluoromethyl-1,2-dihydro-indol-3-ylidene]-hydrazino}-5'-fluoro-2'-hydroxy-biphenyl-3-carboxylic acid (Compound 229)

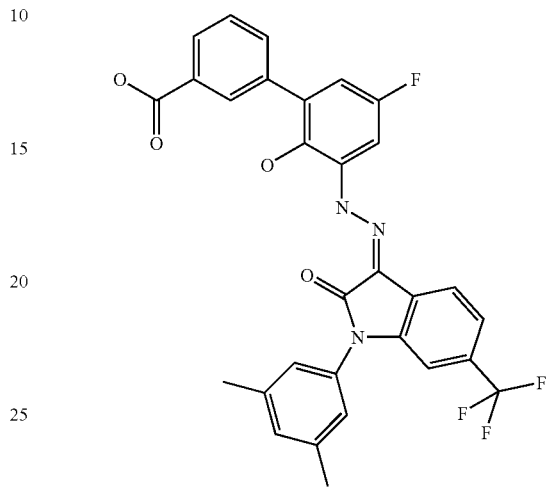

This compound was prepared as described in Scheme II. ¹H NMR (500 MHz, DMSO) δ 13.14 (s, 1H), 13.09 (s, 1H), 9.35 (s, 1H), 8.16 (t, J=1.6 Hz, 1H), 8.00 (d, J=7.9 Hz, 1H), 7.97 (ddd, J=7.8, 1.6, 1.0 Hz, 1H), 7.82 (ddd, J=7.8, 1.6, 1.0 Hz, 1H), 7.62 (t, J=7.8 Hz, 1H), 7.57 (dd, J=9.5, 3.1 Hz, 1H), 7.56 (m, 1H), 7.17 (s, 1H), 7.16 (s, 2H), 6.98 (s, 1H), 6.92 (dd, J=9.3, 3.1 Hz, 1H), 2.37 (s, 6H).

Example 130

3'-{N'-[1-(3,4-Dimethyl-phenyl)-2-oxo-6-trifluoromethyl-1,2-dihydro-indol-3-ylidene]-hydrazino}-4,5'-difluoro-2'-hydroxy-biphenyl-3-carboxylic acid (Compound 230)

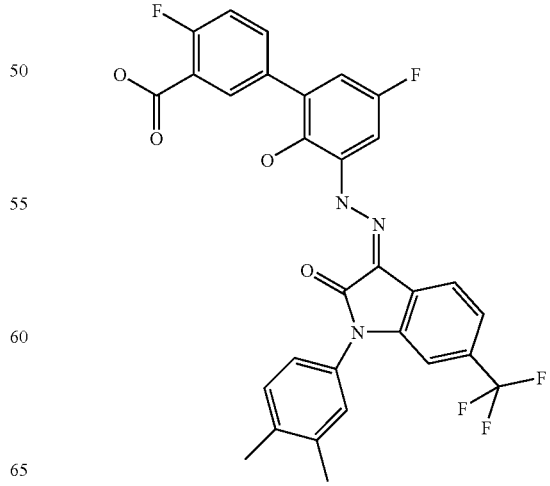

This compound was prepared as described in Scheme II. ¹H NMR (500 MHz, DMSO) δ 13.37 (s, 1H), 13.11 (s, 1H), 9.35 (s, 1H), 8.04 (dd, J=1.5, 7.0 Hz, 1H), 7.98 (d, J=7.5 Hz, 1H), 7.82-7.79 (m, 1H), 7.56-7.53 (m, 2H), 7.41 (t, J=10.5 Hz, 1H), 7.37 (d, J=8.5 Hz, 1H), 7.31 (s, 1H), 7.26 (d, J=8 Hz, 1H), 6.94 (s, 1H), 6.91 (dd, J=2.5, 9.5 Hz, 1H), 2.29 (s, 6H).

Example 131

3'-{N'-[1-(3,5-Dimethyl-phenyl)-2-oxo-6-trifluoromethyl-1,2-dihydro-indol-3-ylidene]-hydrazino}-4,5'-difluoro-2'-hydroxy-biphenyl-3-carboxylic acid (Compound 231)

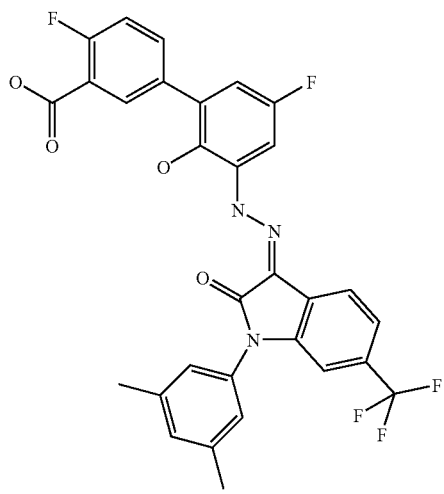

This compound was prepared as described in Scheme II. ¹H NMR (500 MHz, DMSO) δ 13.37 (s, 1H), 13.11 (s, 1H), 9.35 (s, 1H), 8.04 (dd, J=1.5, 7.0 Hz, 1H), 7.98 (d, J=7.5 Hz, 1H), 7.82-7.79 (m, 1H), 7.56-7.53 (m, 2H), 7.41 (t, J=10.5 Hz, 1H), 7.16 (s, 1H), 7.15 (s, 1H), 6.96 (s, 1H), 6.91 (dd, J=2.5, 9.5 Hz, 1H), 2.35 (s, 6H).

Example 132

4,5'-Difluoro-2'-hydroxy-3'-{N'-[2-oxo-6-trifluoromethyl-1-(4-trifluoromethyl-phenyl)-1,2-dihydro-indol-3-ylidene]-hydrazino}-biphenyl-3-carboxylic acid (Compound 232)

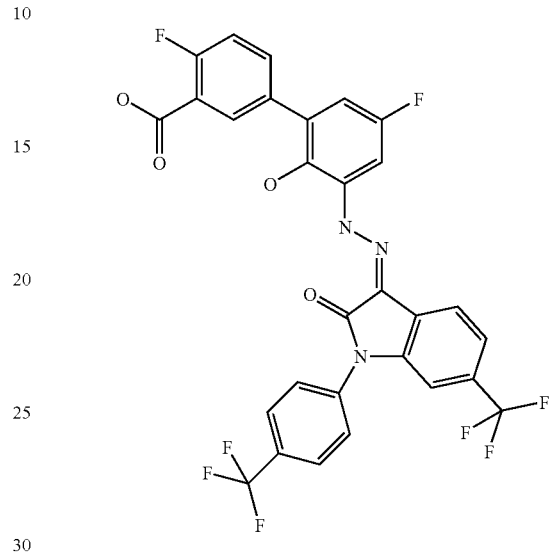

This compound was prepared as described in Scheme II. ¹H NMR¹H NMR (500 MHz, DMSO) δ 13.37 (s, 1H), 13.07 (s, 1H), 9.39 (s, 1H), 8.04 (dd, J=1.5, 7.0 Hz, 1H), 7.97 (d, J=9.0 Hz, 1H), 7.82-7.79 (m, 1H), 7.59-7.56 (m, 2H), 7.42 (t, J=9.5 Hz, 1H), 7.18 (s, 1H), 6.92 (dd, J=3.0, 9.5 Hz, 1H).

Example 133

3'-{N'-[1-(4-Fluoro-3,5-dimethyl-phenyl)-2-oxo-6-trifluoromethyl-1,2-dihydro-indol-3-ylidene]-hydrazino}-2'-hydroxy-biphenyl-3-carboxylic acid (Compound 233)

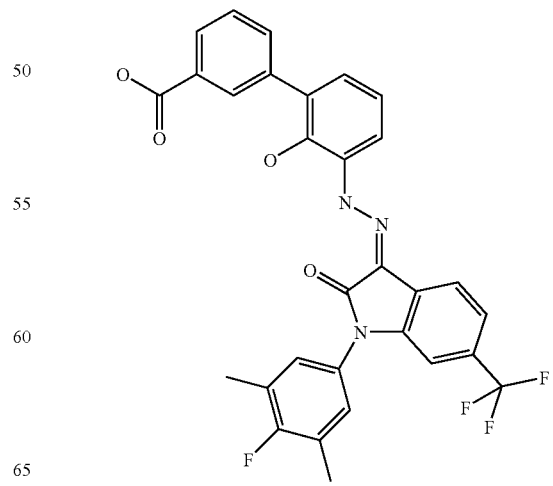

This compound was prepared as described in Scheme II. ¹H NMR (500 MHz, DMSO) δ 13.20 (s, 1H), 13.04 (s, 1H), 9.42 (s, 1H), 8.10 (s, 1H), 7.94-7.89 (m, 2H), 7.79-7.75 (m, 2H), 7.59 (t, J=13 Hz, 1H), 7.52 (d, J=13.5 Hz, 1H), 7.30 (d, J=10.5 Hz, 1H), 7.12 (t, J=13 Hz, 1H), 7.04 (dd, J=2.0, 12.5 Hz, 1H), 6.98 (s, 1H), 2.29 (s, 6H).

Example 134

2'-Hydroxy-3'-{N'-[1-(4-methoxy-phenyl)-2-oxo-6-trifluoromethyl-1,2-dihydro-indol-3-ylidene]-hydrazino}-biphenyl-3-carboxylic acid (Compound 234)

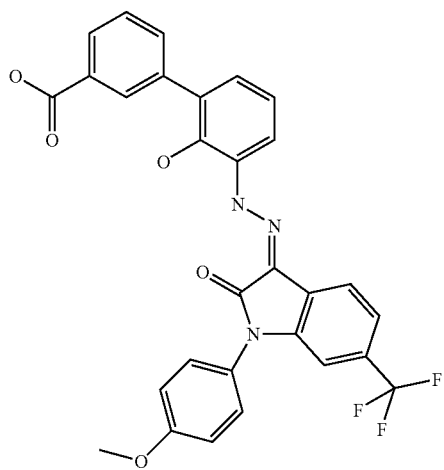

This compound was prepared as described in Scheme II. ¹H NMR (500 MHz, DMSO) δ 13.21 (s, 1H), 13.04 (s, 1H), 9.41 (s, 1H), 8.10 (s, 1H), 7.92 (dd, J=7.5, 12 Hz, 2H), 7.77 (t, J=7.5 Hz, 2H), 7.59 (t, J=7.5 Hz, 1H), 7.52 (d, J=7.5 Hz, 1H), 7.47 (d, J=8.5 Hz, 2H), 7.16 (d, J=8.5 Hz, 2H), 7.12 (d, J=8.0 Hz, 1H), 7.05 (dd, J=1.0, 8.0 Hz, 1H), 6.92 (s, 1H), 3.84 (s, 3H).

Example 135

3'-{N'-[1-(4-Fluoro-phenyl)-2-oxo-6-trifluoromethyl-1,2-dihydro-indol-3-ylidene]-hydrazino}-2'-hydroxy-biphenyl-3-carboxylic acid (Compound 235)

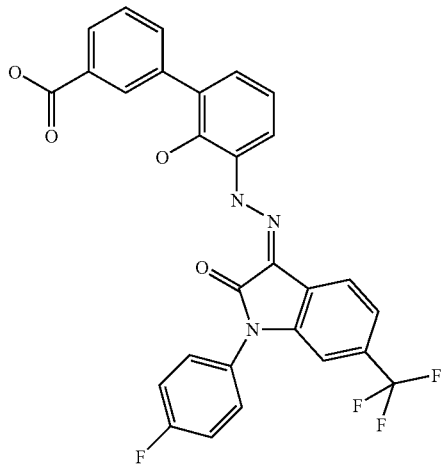

This compound was prepared as described in Scheme II. ¹H NMR (500 MHz, DMSO) δ 13.19 (s, 1H), 13.04 (s, 1H), 9.43 (s, 1H), 8.10 (s, 1H), 7.93 (t, J=6.0 Hz, 2H), 7.78 (t, J=6.0 Hz, 2H), 7.65-7.62 (m, 2H), 7.59 (t, J=7.0 Hz, 1H), 7.54 (d, J=8.5 Hz, 1H), 7.46 (d, J=8.5 Hz, 2H), 7.13 (t, J=8.0 Hz, 1H), 7.05 (dd, J=1.5, 8.0 Hz, 1H), 6.99 (s, 1H).

Example 136

3'-{N'-[1-(3,5-Dimethoxy-phenyl)-2-oxo-6-trifluoromethyl-1,2-dihydro-indol-3-ylidene]-hydrazino}-2'-hydroxy-biphenyl-3-carboxylic acid (Compound 236)

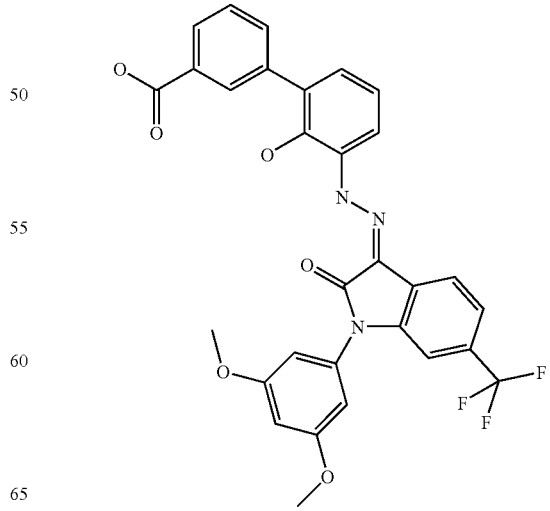

This compound was prepared as described in Scheme II. ¹H NMR (500 MHz, DMSO) δ 13.21 (s, 1H), 13.04 (s, 1H), 9.44 (s, 1H), 8.11 (s, 1H), 7.92 (dd, J=8.0, 10.5 Hz, 2H), 7.78 (t, J=7.5 Hz, 2H), 7.59 (t, J=7.5 Hz, 1H), 7.53 (d, J=8.0 Hz, 1H), 7.13 (t, J=8.0 Hz, 1H), 7.06-7.04 (m, 2H), 6.73 (s, 2H), 6.66 (s, 1H), 3.79 (s, 6H).

Example 137

3'-{N'-[1-(3,4-Dimethoxy-phenyl)-2-oxo-6-trifluoromethyl-1,2-dihydro-indol-3-ylidene]-hydrazino}-2'-hydroxy-biphenyl-3-carboxylic acid (Compound 237)

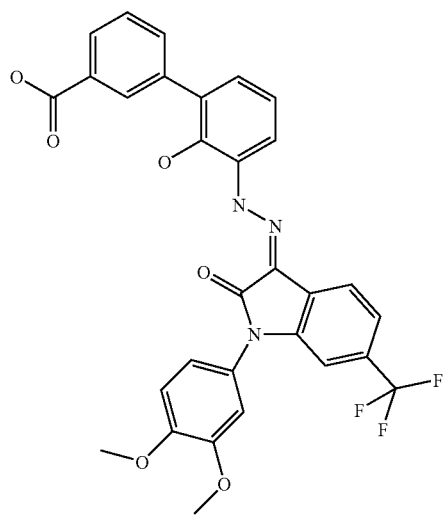

This compound was prepared as described in Scheme II. ¹H NMR (500 MHz, DMSO) δ 13.23 (s, 1H), 13.04 (s, 1H), 9.42 (s, 1H), 8.11 (s, 1H), 7.92 (dd, J=7.5, 14.0 Hz, 2H), 7.78 (t, J=7.5 Hz, 2H), 7.59 (t, J=7.5 Hz, 1H), 7.52 (d, J=8.0 Hz, 1H), 7.17-7.04 (m, 5H), 6.96 (s, 1H), 3.84 (s, 3H), 3.76 (s, 3H).

Example 138

3'-{N'-[1-(3,5-Difluoro-phenyl)-2-oxo-6-trifluoromethyl-1,2-dihydro-indol-3-ylidene]-hydrazino}-2'-hydroxy-biphenyl-3-carboxylic acid (Compound 238)

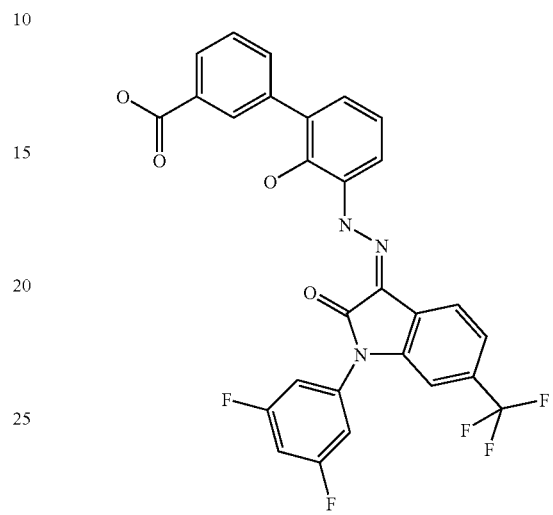

This compound was prepared as described in Scheme II. ¹H NMR (500 MHz, DMSO) δ 13.16 (s, 1H), 13.04 (s, 1H), 9.48 (s, 1H), 8.11 (s, 1H), 7.94 (d, J=7.5Hz, 2H), 7.80-7.77 (m, 2H), 7.60 (t, J=7.5, Hz, 1H), 7.57 (d, J=8.0 Hz, 1H), 7.46-7.44 (m, 3H), 7.22 (s, 1H), 7.13 (t, J=7.5 Hz, 1H), 7.06 (d, J=7.5 Hz, 1H).

Example 139

5'-Fluoro-3'-{N'-[1-(4-fluoro-3,5-dimethyl-phenyl)-2-oxo-6-trifluoromethyl-1,2-dihydro-indol-3-ylidene]-hydrazino}-2'-hydroxy-biphenyl-3-carboxylic acid (Compound (239)

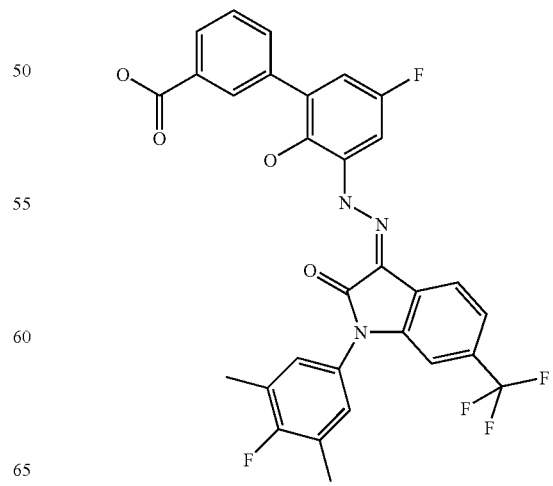

This compound was prepared as described in Scheme II. ¹H NMR (500 MHz, DMSO) δ 13.11 (s, 1H), 13.07 (s, 1H), 9.34 (s, 1H), 8.14 (s, 1H), 7.97 (dd, J=7.5, 16.0 Hz, 2H), 7.81 (d, J=7.5 Hz, 1H), 7.60 (t, J=7.5, Hz, 1H), 7.57-7.54 (m, 2H), 7.31 (d, J=6.0 Hz, 2H), 6.98 (s, 1H), 6.91 (dd, J=2.5, 9.5 Hz, 1H), 2.29 (s, 6H).

Example 140

4,5'-Difluoro-3'-{N'-[1-(4-fluoro-3,5-dimethyl-phenyl)-2-oxo-6-trifluoromethyl-1,2-dihydro-indol-3-ylidene]-hydrazino}-2'-hydroxy-biphenyl-3-carboxylic acid (Compound 240)

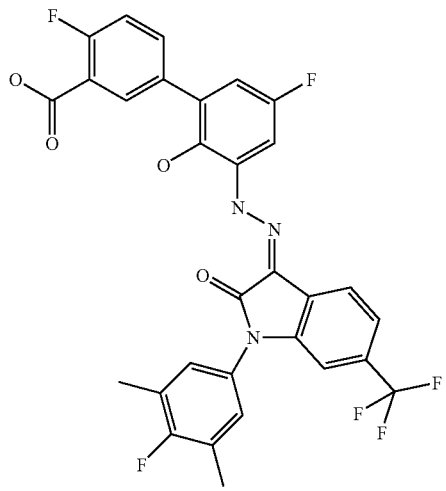

This compound was prepared as described in Scheme II. ¹H NMR (500 MHz, DMSO) δ 13.37 (s, 1H), 13.10 (s, 1H), 9.35 (s, 1H), 8.04 (dd, J=2.0, 7.0 Hz, 1H), 7.98 (d, J=7.5 Hz, 1H), 7.82-7.79 (m, 1H), 7.57-7.54 (m, 2H), 7.42 (t, J=9.0 Hz, 1H), 7.30 (d, J=6.5 Hz, 2H), 6.98 (s, 1H), 6.91 (dd, J=2.5, 9.5 Hz, 1H), 2.29 (s, 6H).

Example 141

2'-Hydroxy-3'-{N'-[1-(4-methoxy-3,5-dimethyl-phenyl)-2-oxo-6-trifluoromethyl-1,2-dihydro-indol-3-ylidene]-hydrazino}-biphenyl-3-carboxylic acid (Compound 241)

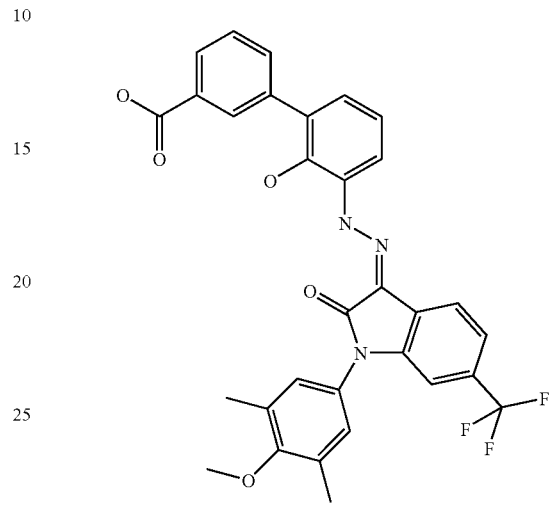

This compound was prepared as described in Scheme II. ¹H NMR (500 MHz, DMSO) δ 13.21 (s, 1H), 13.03 (s, 1H), 9.40 (s, 1H), 8.10 (s, 1H), 7.91 (dd, J=8.0, 15.0 Hz, 2H), 7.77 (t, J=7.5 Hz, 2H), 7.59 (t, J=8.0 Hz, 1H), 7.52 (d, J=7.5 Hz, 1H), 7.21 (s, 2H), 7.12 (t, J=8.0 Hz, 1H), 7.04 (dd, J=1.5, 7.5 Hz, 1H), 6.96 (s, 1H), 3.73 (s, 3H), 2.29 (s, 6H).

Example 142

2'-Hydroxy-3'-{N'-[1-(4-hydroxy-3,5-dimethyl-phenyl)-2-oxo-6-trifluoromethyl-1,2-dihydro-indol-3-ylidene]-hydrazino}-biphenyl-3-carboxylic acid (Compound 242)

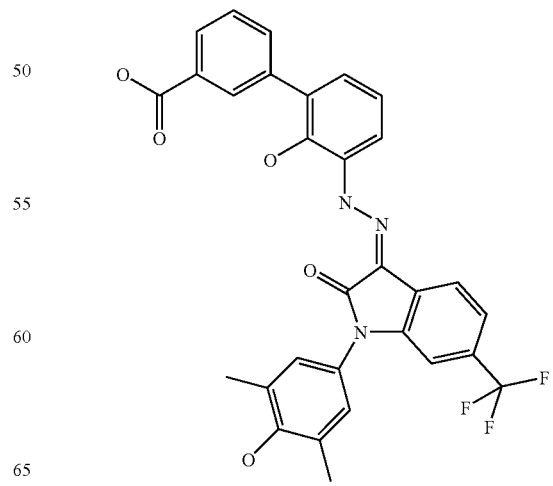

This compound was prepared as described in Scheme II. ¹H NMR (500 MHz, DMSO) δ 13.22 (s, 1H), 13.03 (s, 1H), 9.39 (s, 1H), 8.69 (s, 1H), 8.10 (s, 1H), 7.93 (d, J=8.0 Hz, 1H), 7.88 (d, J=8.0Hz, 1H), 7.78-7.75 (m, 2H), 7.58 (t, J=8.0 Hz, 1H), 7.50 (d, J=8.5 Hz, 1H), 7.11 (t, J=8.0 Hz, 1H), 7.06 (s, 2H), 7.03 (dd, J=1.5, 7.5 Hz, 1H), 6.89 (s, 1H), 2.21 (s, 6H).

Example 143

3'-{N'-[1-(4-Cyclohexyl-phenyl)-2-oxo-1,2-dihydro-indol-3-ylidene]-hydrazino}-2'-hydroxy-biphenyl-3-carboxylic acid (Compound 243)

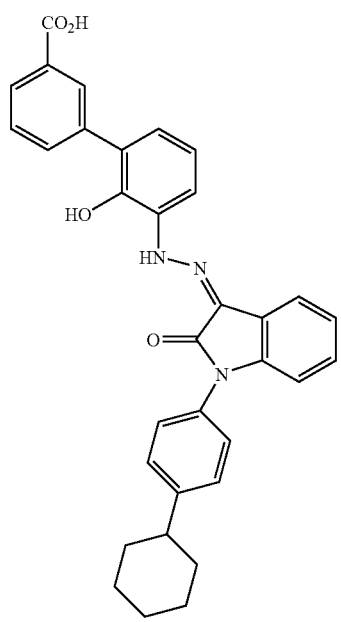

This compound was prepared as described in Scheme II. ¹H NMR (500 MHz, DMSO-d₆) δ 13.06 (s, 1H), 9.27 (s, 1H), 8.11 (s, 1H), 7.94 (d, J=7.8 Hz, 1H), 7.79 (d, J=7.8 Hz, 1H), 7.73 (m, 2H), 7.60 (t, J=7.8 Hz, 1H), 7.44 (s, 4H), 7.29 (t, J=7.6 Hz, 1H), 7.19 (t, J=7.6 Hz, 1H), 7.11 (t, J=7.8 Hz, 1H), 7.00 (d, J=7.6 Hz, 1H), 6.88 (d, J=7.6 Hz, 1H), 2.61 (m, 1H), 1.85 (m, 4H), 1.72 (m, 1H), 1.44 (m, 4H), 1.26 (m, 1H).

Example 144

2'-Hydroxy-3'-[N'-(2-oxo-1-pyridin-2-yl-1,2-dihydro-indol-3-ylidene)-hydrazino]-biphenyl-3-carboxylic acid (Compound 244)

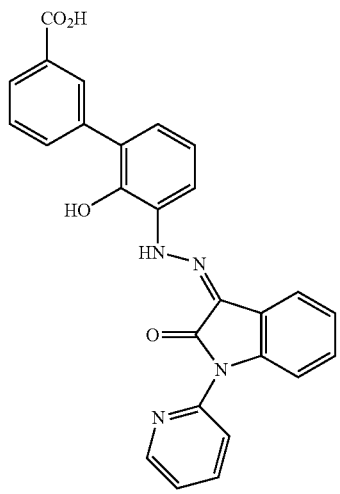

This compound was prepared as described in Scheme II. ¹H NMR (500 MHz, DMSO-d₆) δ 13.08 (s, 1H), 9.34 (s, 1H), 8.66 (ddd, J=4.9, 1.9, 0.9 Hz, 1H), 8.13 (t, J=1.6 Hz, 1H), 8.07 (ddd, J=7.6, 8.0, 1.9 Hz, 1H), 7.95 (ddd, J=7.7, 1.6, 1.2 Hz, 1H), 7.89 (dt, J=8.0, 1.0 Hz, 1H), 7.81 (ddd, J=7.7, 1.6, 1.2 Hz, 1H), 7.77-7.74 (m, 2H), 7.67 (d, J=7.8 Hz, 1H), 7.61 (t, J=7.7 Hz, 1H), 7.47 (ddd, J=7.6, 4.9, 1.0 Hz, 1H), 7.34 (td, J=7.8, 1.3 Hz, 1H), 7.25 (td, J=7.8, 0.9 Hz, 1H), 7.13 (t, J=7.8 Hz, 1H), 7.02 (dd, J=7.8, 1.6 Hz, 1H).

Example 145

2'-Hydroxy-3'-[N'-(2-oxo-1-pyridin-3-yl-1,2-dihydro-indol-3-ylidene)-hydrazino]-biphenyl-3-carboxylic acid (Compound 245)

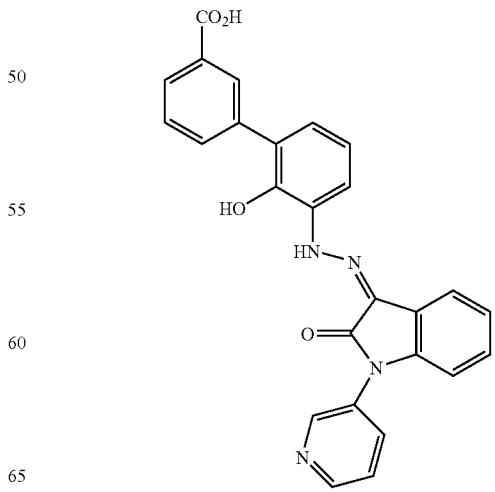

This compound was prepared as described in Scheme II. ¹H NMR (300 MHz, DMSO-d$_6$) δ 13.02 (s, 1H), 9.33 (s, 1H), 8.81 (s, 1H), 8.69 (s, 1H), 8.12 (t, J=1.6 Hz, 1H), 8.05 (ddd, J=8.2, 2.0, 1.6 Hz, 1H), 7.94 (ddd, J=7.7, 1.6, 1.2 Hz, 1H), 7.82-7.73 (m, 3H), 7.67 (m, 1H), 7.60 (t, J=7.7 Hz, 1H), 7.32 (td, J=7.6, 1.4 Hz, 1H), 7.23 (td, J=7.6, 1.0 Hz, 1H), 7.12 (t, J=7.8 Hz, 1H), 7.02 (dd, J=7.8, 1.7 Hz, 1H), 6.94 (d, J=7.8 Hz, 1H).

Example 146

3'-{N'-[1-(4-Ethyl-phenyl)-2-oxo-6-trifluoromethyl-1,2-dihydro-indol-3-ylidene]-hydrazino}-2'-hydroxy-biphenyl-3-carboxylic acid (Compound 246)

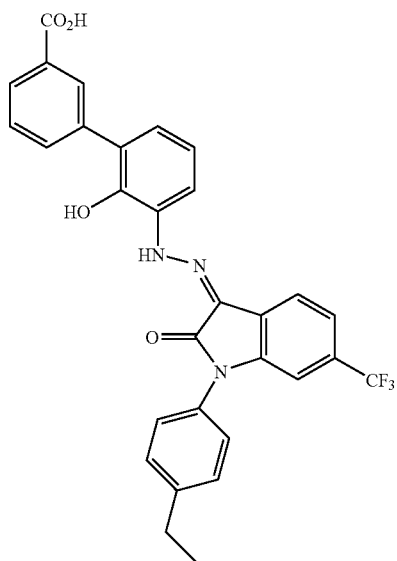

This compound was prepared as described in Scheme II. ¹H NMR (300 MHz, DMSO-d$_6$) δ 13.21 (s, 1H), 13.04 (s, 1H), 9.42 (s, 1H), 8.10 (s, 1H), 7.96-7.88 (m, 2H), 7.80-7.74 (m, 2H), 7.58 (t, J=7.7 Hz, 1H), 7.52 (d, J=7.9 Hz, 1H), 7.46 (s, 4H), 7.12 (t, J=7.8 Hz, 1H), 7.04 (d, J=7.8 Hz, 1H), 6.96 (s, 1H), 2.70 (q, J=7.6 Hz, 2H), 1.24 (t, J=7.6 Hz, 3H).

Example 147

3'-{N'-[1-(4-Ethyl-phenyl)-4-fluoro-2-oxo-6-trifluoromethyl-1,2-dihydro-indol-3-ylidene]-hydrazino}-2'-hydroxy-biphenyl-3-carboxylic acid (Compound 247)

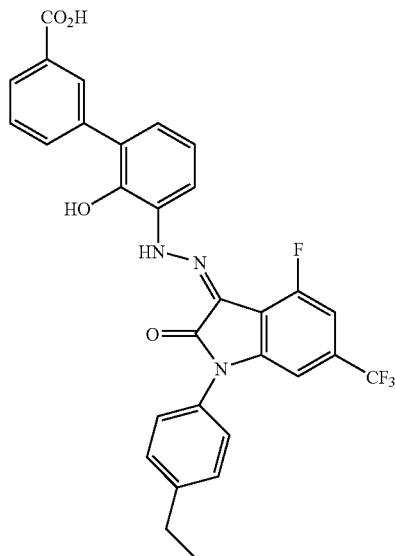

This compound was prepared as described in Scheme II. ¹H NMR (500 MHz, DMSO-d$_6$) δ 13.36 (s, 1H), 13.05 (s, 1H), 9.50 (s, 1H), 8.12 (t, J=1.6 Hz, 1H), 7.95 (ddd, J=7.7, 1.6, 1.2 Hz, 1H), 7.80 (ddd, J=7.7, 1.6, 1.2 Hz, 1H), 7.67 (dd, J=7.8, 1.6 Hz, 1H), 7.60 (t, J=7.7 Hz, 1H), 7.51 (d, J=9.5 Hz, 1H), 7.47 (s, 4H), 7.15 (t, J=7.8 Hz, 1H), 7.08 (dd, J=7.8, 1.6 Hz, 1H), 6.83 (s, 1H), 2.72 (q, J=7.6 Hz, 2H), 1.26 (t, J=7.6 Hz, 3H).

Example 148

3-[(3'-Carboxy-2-hydroxy-biphenyl-3-yl)-hydrazono]-1-(3,5-dimethyl-phenyl)-2-oxo-2,3-dihydro-1-H-indole-5-carboxylic acid methyl ester (Compound 248)

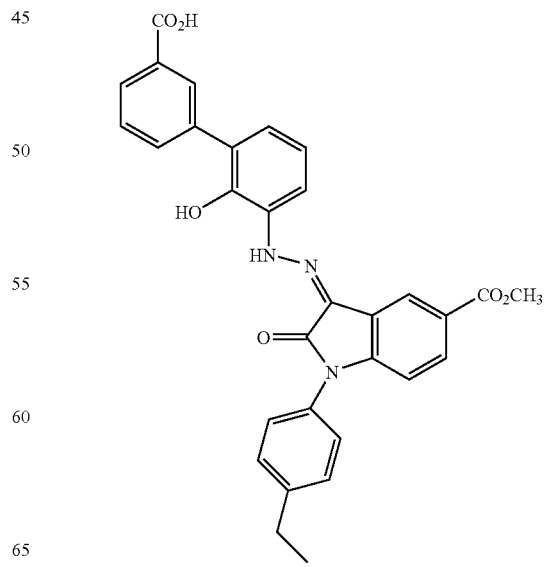

This compound was prepared as described in Scheme II. ¹H NMR (300 MHz, DMSO-d$_6$) δ 13.07 (s, 1H), 13.05 (s, 1H), 9.37 (s, 1H), 8.25 (s, 1H), 8.12 (s, 1H), 7.97-7.89 (m, 2H), 7.83-7.77 (m, 2H), 7.60 (t, J=7.8 Hz, 1H), 7.46 (s, 4H), 7.13 (t, J=7.8 Hz, 1H), 7.04 (d, J=7.8 Hz, 1H), 6.97 (d, J=8.6 Hz, 1H), 3.89 (s, 3H), 2.72 (q, J=7.5 Hz, 2H), 1.25 (t, J=7.5 Hz, 3H).

Example 149

3'-{N'-[1-(3-Chloro-4-methyl-phenyl)-2-oxo-6-trifluoromethyl-1,2-dihydro-indol-3-ylidene]-hydrazino}-2'-hydroxy-biphenyl-3-carboxylic acid (Compound 249)

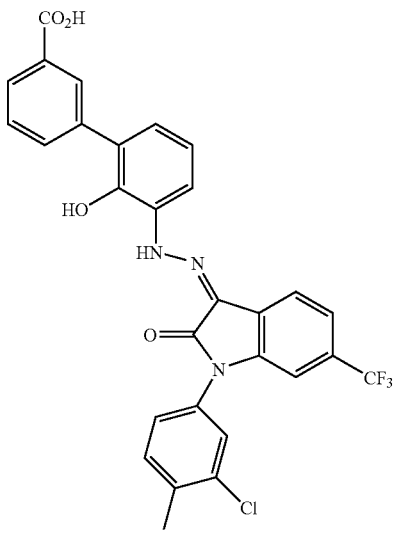

This compound was prepared as described in Scheme II. ¹H NMR (500 MHz, DMSO-d$_6$) δ 13.19 (s, 1H), 13.05 (s, 1H), 9.46 (s, 1H), 8.12 (t, J=1.7 Hz, 1H), 7.95 (ddd, J=7.6, 1.7, 1.2 Hz, 1H), 7.93 (d, J=7.9 Hz, 1H), 7.80 (ddd, J=7.6, 1.7, 1.2 Hz, 1H), 7.78 (dd, J=7.8, 1.6 Hz, 1H), 7.70 (d, J=2.1 Hz, 1H), 7.61 (t, J=7.6 Hz, 1H), 7.61 (d, J=8.2 Hz, 1H), 7.56 (dq, J=7.9, 0.7 Hz, 1H), 7.49 (dd, J=8.2, 2.1 Hz, 1H), 7.14 (t, J=7.8 Hz, 1H), 7.07 (dd, J=7.8, 1.6 Hz, 1H), 7.04 (m, 1H), 2.44 (s, 3H).

Example 150

5-(4-{N'-[1-(3,5-Dimethyl-phenyl)-2-oxo-6-trifluoromethyl-1,2-dihydro-indol-3-ylidene]-hydrazino}-3-hydroxy-benzylidene)-thiazolidine-2,4-dione (Compound 250)

This compound was prepared as described in Scheme V. ¹H NMR (500 MHz, DMSO-d$_6$) δ 13.12 (s, 1H), 12.57 (s, 1H), 10.88 (s, 1H), 7.91 (d, J=7.9 Hz, 1H), 7.80 (d, J=8.4 Hz, 1H), 7.68 (s, 1H), 7.54 (dq, J=7.9, 0.8 Hz, 1H), 7.24 (dd, J=8.4, 1.8 Hz, 1H), 7.18 (s, 1H), 7.17-7.15 (m, 3 H), 6.97 (m, 1H), 2.37 (s, 6H).

Example 151

2'-Hydroxy-3'-(N'-{2-oxo-1-[4-(4,4,4-trifluoro-butyl)-phenyl]-1,2-dihydro-indol-3-ylidene}-hydrazino)-biphenyl-3-carboxylic acid (Compound 251)

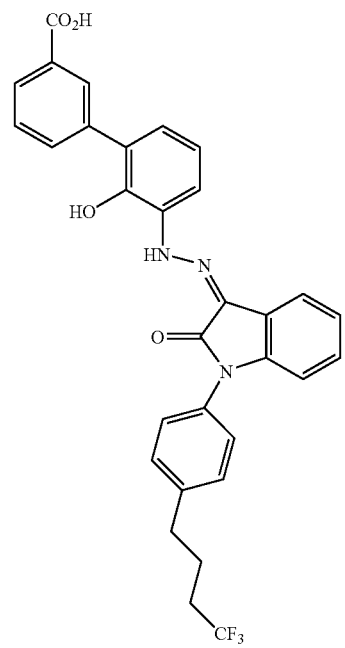

This compound was prepared as described in Scheme II.
¹H NMR (500 MHz, DMSO-d₆) δ 13.02 (s, 1H), 9.26 (s, 1H), 8.12 (t, J=1.7 Hz, 1H), 7.95 (ddd, J=7.7, 1.7, 1.2 Hz, 1H), 7.79 (ddd, J=7.7, 1.7, 1.2 Hz, 1H), 7.69 (dd, J=7.8, 1.6 Hz, 1H), 7.65 (dd, J=7.6, 1.2 Hz, 1H), 7.60 (t, J=7.7 Hz, 1H), 7.35 (td, J=7.6, 1.2 Hz, 1H), 7.24 (d, J=7.6 Hz, 1H), 7.14 (td, J=7.6, 0.8 Hz, 1H), 7.10 (t, J=7.8 Hz, 1H), 6.98 (dd, J=7.8, 1.6 Hz, 1H), 3.90 (t, J=7.0 Hz, 2H), 2.39 (m, 2H), 1.88 (m, 2H).

Example 152

3'-{N'-[1-(3,5-Dimethyl-phenyl)-4-fluoro-2-oxo-6-trifluoromethyl-1,2-dihydro-indol-3-ylidene]-hydrazino}-2'-hydroxy-biphenyl-3-carboxylic acid (Compound 252)

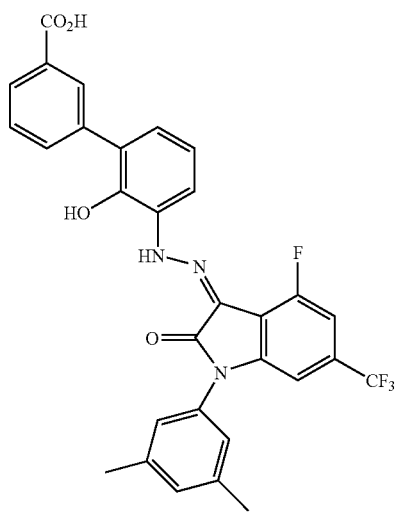

This compound was prepared as described in Scheme II.
¹H NMR (500 MHz, DMSO-d₆) δ 13.37 (s, 1H), 13.06 (s, 1H), 9.49 (s, 1H), 8.12 (t, J=1.7 Hz, 1H), 7.95 (ddd, J=7.7, 1.7, 1.2 Hz, 1H), 7.80 (ddd, J=7.7, 1.7, 1.2 Hz, 1H), 7.67 (dd, J=7.8, 1.6 Hz, 1H), 7.61 (t, J=7.7 Hz, 1H), 7.50 (d, J=9.5 Hz, 1H), 7.18 (m, 1H), 7.16 (m, 2H), 7.15 (t, J=7.8 Hz, 1H), 7.08 (dd, J=7.8, 1.6 Hz, 1H), 6.83 (s, 1H), 2.37 (s, 6H).

Example 153

3'-{N'-[1-(4-tert-Butyl-phenyl)-2-oxo-6-trifluoromethyl-1,2-dihydro-indol-3-ylidene]-hydrazino}-2'-hydroxy-biphenyl-3-carboxylic acid (Compound 253)

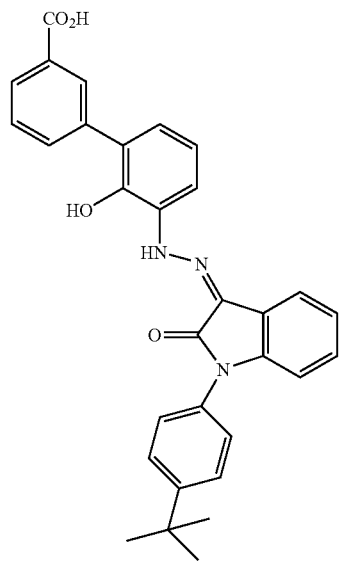

This compound was prepared as described in Scheme II.
¹H NMR (500 MHz, DMSO-d₆) δ 13.23 (s, 1H), 13.05 (s, 1H), 9.44 (s, 1H), 8.12 (t, J=1.7 Hz, 1H), 7.95 (ddd, J=7.7, 1.7, 1.1 Hz, 1H), 7.93 (d, J=7.8 Hz, 1H), 7.80 (ddd, J=7.7, 1.7, 1.1 Hz, 1H), 7.78 (dd, J=7.8, 1.6 Hz, 1H), 7.65 (d, J=8.7 Hz, 2H), 7.61 (t, J=7.7 Hz, 1H), 7.55 (dq, J=7.8, 0.7 Hz, 1H), 7.50 (d, J=8.7 Hz, 2H), 7.14 (t, J=7.8 Hz, 1H), 7.06 (dd, J=7.8, 1.6 Hz, 1H), 7.01 (q, J=0.8 Hz, 1H), 1.36 (s, 9H).

Example 154

3'-{N'-[1-(3,4-Dimethyl-phenyl)-2-oxo-6-trifluoromethyl-1,2-dihydro-indol-3-ylidene]-hydrazino}-2'-hydroxy-biphenyl-4-carboxylic acid (Compound 254)

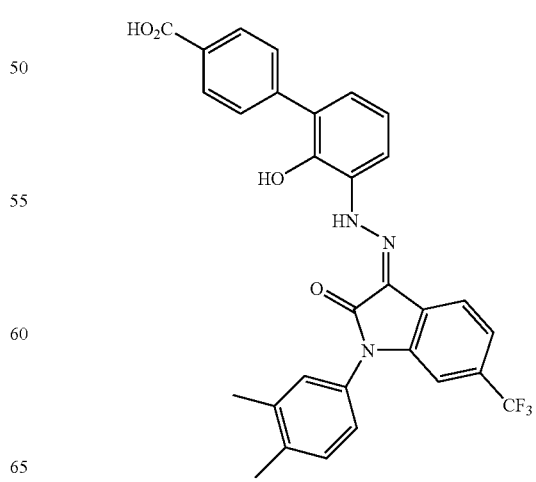

This compound was prepared as described in Scheme II.
$^1$H NMR (500 MHz, CD$_3$OD) δ 8.09 (d, J=8.2 Hz, 2H), 7.89 (d, J=7.9 Hz, 1H), 7.81 (dd, J=7.9, 1.6 Hz, 1H), 7.63 (d, J=8.2 Hz, 2H), 7.47 (d, J=7.9 Hz, 1H), 7.38 (d, J=8.0 Hz, 1H), 7.26 (d, J=1.8 Hz, 1H), 7.19 (dd, J=8.0, 1.8 Hz, 1H), 7.10 (t, J=7.9 Hz, 1H), 7.04 (dd, J=7.9, 1.6 Hz, 1H), 6.99 (s, 1H), 2.38 (s, 3H), 2.37 (s, 3H).

Example 155

3'-{N'-[1-(3,4-Dimethyl-phenyl)-2-oxo-6-bromo-1,2-dihydro-indol-3-ylidene]-hydrazino}-2'-hydroxy-biphenyl-3-carboxylic acid (Compound 255)

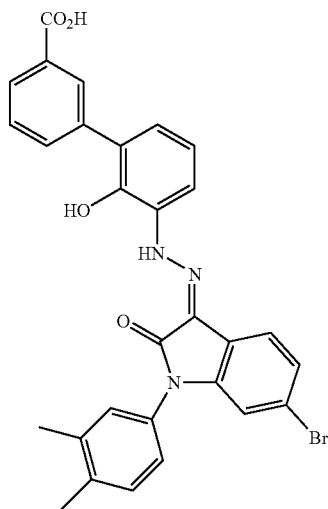

This compound was prepared as described in Scheme II.
$^1$H NMR (500 MHz, DMSO-d$_6$) δ 13.08 (s, 1H), 13.04 (s, 1H), 9.33 (s, 1H), 8.12 (m, 1H), 7.94 (d, J=7.7 Hz, 1H), 7.79 (m, 1H), 7.74 (d, J=7.7 Hz, 1H), 7.67 (d, J=8.0 Hz, 1H), 7.60 (t, J=7.7 Hz, 1H), 7.37 (d, J=8.0 Hz, 1H), 7.37 (d, J=8.0 Hz, 1H), 7.31 (d, J=1.8 Hz, 1H), 7.24 (dd, J=8.0, 1.8 Hz, 1H), 7.12 (t, J=7.9 Hz, 1H), 7.03 (m, 1H), 6.91 (m, 1H), 2.32 (s, 3H), 2.31 (s, 3H).

Example 156

3'-{N'-[1-(3,4-Dimethyl-phenyl)-2-oxo-6-trifluoromethyl-1,2-dihydro-indol-3-ylidene]-hydrazino}-3-fluoro-2'-hydroxy-biphenyl-4-carboxylic acid (Compound 256)

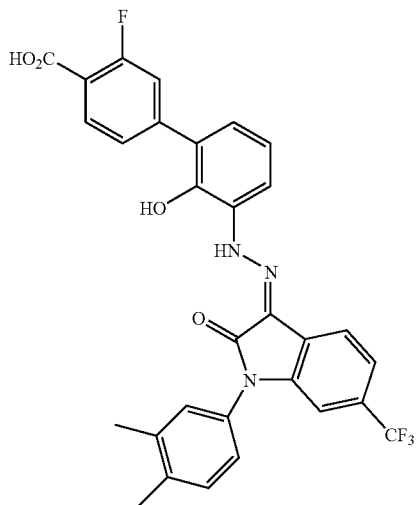

This compound was prepared as described in Scheme II.
$^1$H NMR (500 MHz, DMSO-d$_6$) δ 13.27 (s, 1H), 13.22 (s, 1H), 9.59 (s, 1H), 7.97-7.91 (m, 2H), 7.81 (dd, J=7.7, 1.5 Hz, 1H), 7.54 (d, J=7.6 Hz, 1H), 7.51-7.47 (m, 2H), 7.39 (d, J=8.0 Hz, 1H), 7.33 (d, J=1.8 Hz, 1H), 7.27 (dd, J=8.0, 1.8 Hz, 1H), 7.15 (t, J=7.7 Hz, 1H), 7.10 (dd, J=7.7, 1.5 Hz, 1H), 6.96 (s, 1H), 2.32 (s, 3H), 2.31 (s, 3H).

Example 157

3'-{N'-[1-(3,5-Bis-trifluoromethyl-phenyl)-2-oxo-6-trifluoromethyl-1,2-dihydro-indol-3-ylidene]-hydrazino}-2'-hydroxy-biphenyl-3-carboxylic acid (Compound 257)

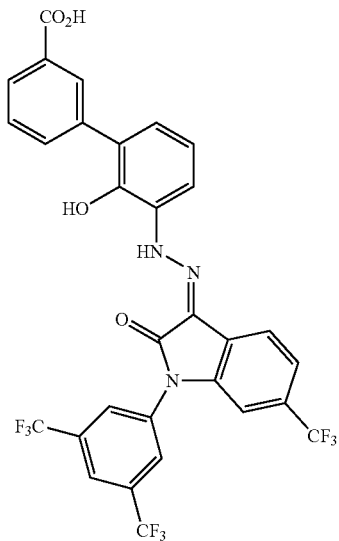

This compound was prepared as described in Scheme II.
¹H NMR (300 MHz, CD₃OD) δ 8.24 (s, 2H), 8.11 (s, 2H), 7.99-7.92 (m, 2H), 7.81 (m, 1H), 7.65 (m, 1H), 7.56-7.45 (m, 2H), 7.18 (s, 1H), 7.11-7.02 (m, 2H).

Example 158

3'-{N'-[1-(3,4-Dichloro-phenyl)-2-oxo-6-trifluoromethyl-1,2-dihydro-indol-3-ylidene]-hydrazino}-2'-hydroxy-biphenyl-3-carboxylic acid (Compound 258)

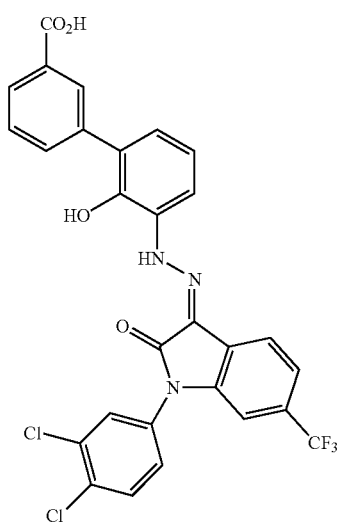

This compound was prepared as described in Scheme II.
¹H NMR (500 MHz, DMSO-d₆) δ 13.17 (s, 1H), 13.05 (s, 1H), 9.47 (s, 1H), 8.12 (t, J=1.7, Hz, 1H), 7.97-7.93 (m, 3H), 7.91 (d, J=8.5 Hz, 1H), 7.81-7.77 (m, 2H), 7.64 (dd, J=8.5, 2.4 Hz, 1H), 7.61 (t, J=7.7 Hz, 1H), 7.57 (d, J=8.5 Hz, 1H), 7.18 (s, 1H), 7.14 (t, J=7.7 Hz, 1H), 7.07 (dd, J=7.7, 1.6 Hz, 1H).

Example 159

3'-{N'-[1-(3,5-Dichloro-phenyl)-2-oxo-6-trifluoromethyl-1,2-dihydro-indol-3-ylidene]-hydrazino}-2'-hydroxy-biphenyl-3-carboxylic acid (Compound 259)

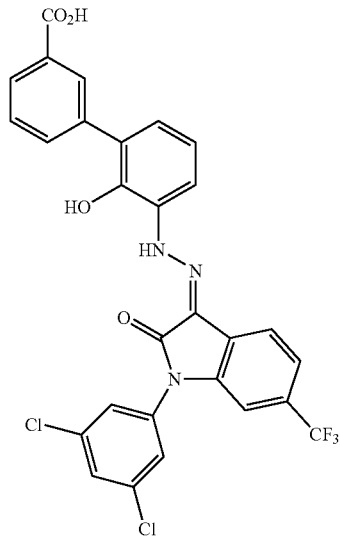

This compound was prepared as described in Scheme II.
1H NMR (300 MHz, CD₃OD) δ 8.13 (s, 1H), 7.97 (d, J=7.7 Hz, 1H), 7.91 (d, J=7.7 Hz, 1H), 7.79 (m, 1H), 7.66 (d, J=7.7 Hz, 1H), 7.62-7.59 (m, 3H), 7.54-7.47 (m, 2H), 7.16-7.02 (m, 3H).

Example 160

3-(4-{N'-[1-(3,5-Dimethyl-phenyl)-2-oxo-6-trifluoromethyl-1,2-dihydro-indol-3-ylidene]-hydrazino}-3-hydroxy-phenyl)-2-methyl-acrylic acid (Compound 260)

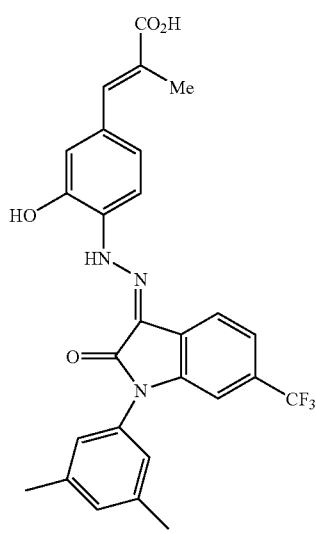

This compound was prepared as described in Scheme V. ¹H NMR (500 MHz, DMSO-$d_6$) δ 13.14 (s, 1H), 12.45 (s, 1H), 10.61 (s, 1H), 7.90 (d, J=8.0 Hz, 1H), 7.75 (d, J=8.1 Hz, 1H), 7.55-7.51 (m, 2H), 7.18 (s, 1H), 7.16 (s, 2H), 7.12-7.09 (m, 2H), 6.98 (s, 1H), 2.37 (s, 6H), 2.08 (d, J=1.0 Hz, 3H).

Example 161

3-(4-{N'-[1-(3,4-Dimethyl-phenyl)-2-oxo-6-trifluoromethyl-1,2-dihydro-indol-3-ylidene]-hydrazino}-3-hydroxy-phenyl)-2-methyl-acrylic acid (Compound 261)

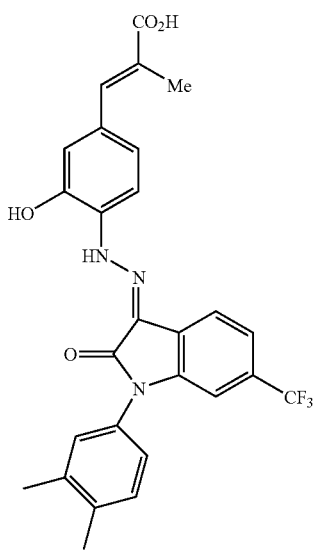

This compound was prepared as described in Scheme V. ¹H NMR (300 MHz, DMSO-$d_6$) δ 13.13 (s, 1H), 12.45 (s, 1H), 10.61 (s, 1H), 7.90 (m, 1H), 7.75 (m, 1H), 7.56-7.50 (m, 2H), 7.39 (m, 1H), 7.33 (s, 1H), 7.26 (m, 1H), 7.13-7.08 (m, ,2H), 6.96 (s, 1H), 2.32 (s, 3H), 2.31 (s, 3H), 2.08 (s, 3H).

Example 162

2'-Hydroxy-3'-[N'-(2-oxo-7-phenyl-1,2-dihydro-indol-3-ylidene)-hydrazino]-biphenyl-3-carboxylic acid (Compound 262)

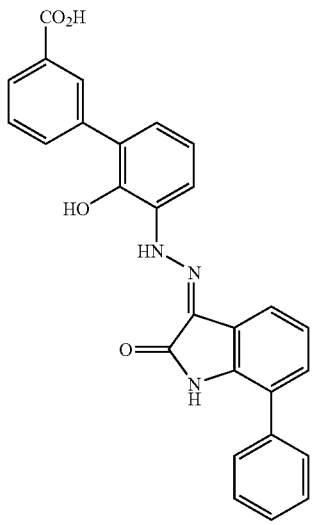

This compound was prepared as described in Scheme II. ¹H NMR (500 MHz, DMSO-$d_6$) δ 13.16 (s, 1H), 10.91 (s, 1H), 8.15 (t, J=1.4 Hz, 1H), 7.95 (ddd, J=7.8, 1.4, 1.2 Hz, 1H), 7.79 (ddd, J=7.8, 1.4, 1.2 Hz, 1H), 7.72 (dd, J=7.9, 1.5 Hz, 1H), 7.63 (dd, J=7.6, 1.2 Hz, 1H), 7.58 (t, J=7.8 Hz, 1H), 7.56-7.46 (m, 4H), 7.41 (m, 1H), 7.26 (dd, J=7.6, 1.2 Hz, 1H), 7.18 (t, J =7.6 Hz, 1H), 7.11 (t, J =7.9 Hz, 1H), 6.99 (dd, J =7.9, 1.5 Hz, 1H).

Example 163

3'-{N'-[1-(3,4-Dimethyl-phenyl)-2-oxo-6-trifluoromethoxy-1,2-dihydro-indol-3-ylidene]-hydrazino}-2'-hydroxy-biphenyl-3-carboxylic acid (Compound 263)

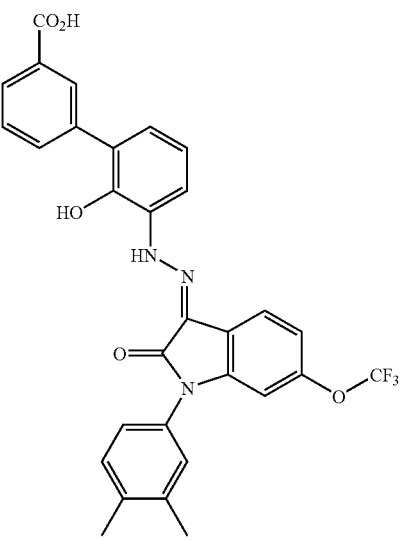

This compound was prepared as described in Scheme II. ¹H NMR (500 MHz, DMSO-d$_6$) δ 13.27 (s, 1H), 13.02 (s, 1H), 9.39 (s, 1H), 8.12 (s, 1H), 7.95 (m, 1H), 7.80 (m, 1H), 7.65-7.58 (m, 2H), 7.42-7.24 (m, 4H), 7.22-7.11 (m, 2H), 7.04 (m, 1H), 6.89 (m, 1H), 2.32 (s, 3H), 2.30 (s, 3H).

Example 164

3'-{N'-[1-(3,4-Dimethyl-phenyl)-2-oxo-6-(1,1,2,2-tetrafluoro-ethoxy)-1,2-dihydro-indol-3-ylidene]-hydrazino}-2'-hydroxy-biphenyl-3-carboxylic acid (Compound 24)

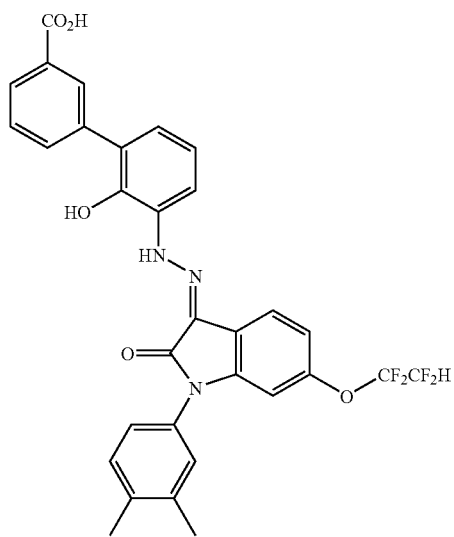

This compound was prepared as described in Scheme II. ¹H NMR (500 MHz, DMSO) δ 13.07 (s, 1H), 13.04 (s, 1H), 9.33 (s, 1H), 8.12 (t, J=1.6 Hz, 1H), 7.94 (ddd, J=7.7, 1.6, 1.2 Hz, 1H), 7.80 (d, J=8.2 Hz, 1H), 7.79 (ddd, J=7.7, 1.6, 1.2 Hz, 1H), 7.74 (dd, J=7.8, 1.6 Hz, 1H), 7.60 (t, J=7.7 Hz, 1H), 7.37 (d, J=8.1 Hz, 1H), 7.32 (d, J=2.0 Hz, 1H), 7.25 (dd, J=8.1, 2.0 Hz, 1H), 7.12 (t, J=7.8 Hz, 1H), 7.09 (dd, J=8.2, 2.1 Hz, 1H), 7.02 (dd, J=7.8, 1.6 Hz, 1H), 6.78 (tt, J=52.1, 3.1 Hz, 1H), 6.63 (d, J=2.1 Hz, 1H), 2.32 (s, 3H), 2.30 (s, 3H).

Example 165

3'-{N'-[1-(3,4-Dimethyl-phenyl)-5-methyl-2-oxo-1,2-dihydro-indol-3-ylidene]-hydrazino}-2'-hydroxy-biphenyl-3-carboxylic acid (Compound 265)

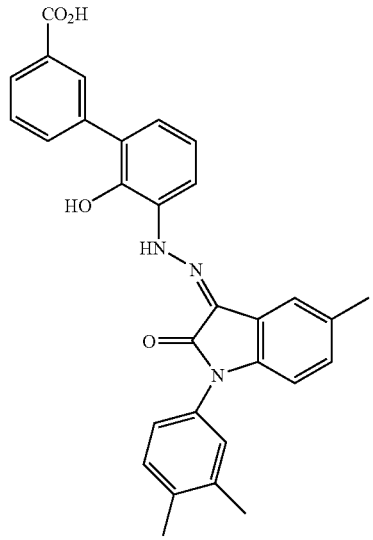

This compound was prepared as described in Scheme II. ¹H NMR (500 MHz, DMSO-d$_6$) δ13.04 (s, 2H), 9.26 (s, 1H), 8.12 (t, J=1.6 Hz, 1H), 7.94 (ddd, J=7.7, 1.6, 1.2 Hz, 1H), 7.78 (ddd, J=7.7, 1.6, 1.2 Hz, 1H), 7.72 (dd, J=7.9, 1.6 Hz, 1H), 7.59 (t, J=7.7 Hz, 1H), 7.55 (s, 1H), 7.34 (d, J=8.1 Hz, 1H), 7.28 (d, J=2.0 Hz, 1H), 7.22 (dd, J=8.1, 2.0 Hz, 1H), 7.11 (t, J=7.9, Hz, 1H), 7.09 (m, 1H), 6.99 (dd, J=7.9, 1.6 Hz, 1H), 6.76 (d, J=8.0 Hz, 1H), 2.37 (s, 3H), 2.31 (s, 3H), 2.30 (s, 3H).

Example 166

3'-{N'-[1-(4-Isopropyl-phenyl)-5-methyl-2-oxo-1,2-dihydro-indol-3-ylidene]-hydrazino}-2'-hydroxy-biphenyl-3-carboxylic acid (Compound 266)

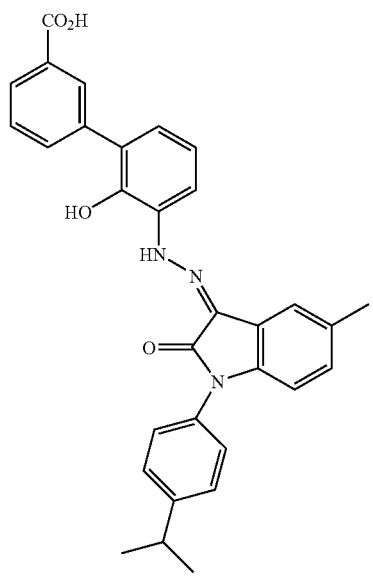

This compound was prepared as described in Scheme II. ¹H NMR (500 MHz, DMSO-$d_6$) δ13.03 (s, 2H), 9.26 (s, 1H), 8.11 (t, J=1.6 Hz, 1H), 7.94 (ddd, J=7.7, 1.6, 1.2 Hz, 1H), 7.79 (ddd, J=7.7, 1.6, 1.2 Hz, 1H), 7.72 (dd, J=7.9, 1.6 Hz, 1H), 7.59 (t, J=7.7 Hz, 1H), 7.56 (s, 1H), 7.46 (d, J=8.6 Hz, 2H), 7.43 (d, J=8.6 Hz, 2H), 7.11(t, J=7.9 Hz, 1H), 7.10 (m, 1H), 6.99 (dd, J=7.9, 1.6 Hz, 1H), 6.79 (d, J=8.2 Hz, 1H), 3.00 (sept, J=6.9 Hz, 1H), 2.37 (s, 3H), 1.26 (d, J=6.9 Hz, 6H).

Example 167

3'-{N'-[1-(3,4-Dimethyl-phenyl)-6-phenyl-2-oxo-1,2-dihydro-indol-3-ylidene]-hydrazino}-2'-hydroxy-biphenyl-3-carboxylic acid (Compound 267)

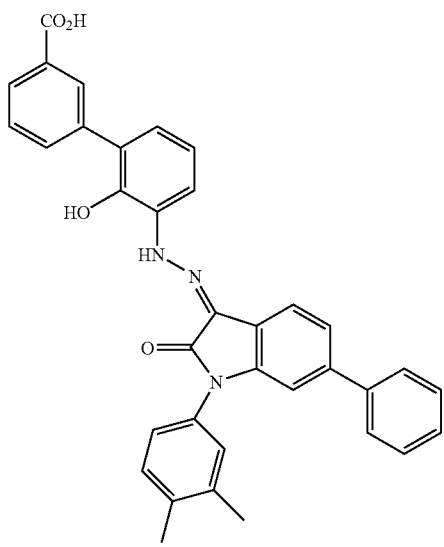

This compound was prepared as described in Scheme II. ¹H NMR (500 MHz, DMSO-$d_6$) δ13.10 (s, 1H), 13.05 (s, 1H), 9.30 (s, 1H), 8.13 (t, J=1.6 Hz, 1H), 7.95 (ddd, J=7.7, 1.6, 1.2 Hz, 1H), 7.81 (d, J=7.8 Hz, 1H), 7.80 (ddd, J=7.7, 1.6, 1.2 Hz, 1H), 7.75 (dd, J=7.9, 1.5 Hz, 1H), 7.62-7.57 (m, 3H), 7.48 (dd, J=7.8, 1.8 Hz, 1H), 7.47-7.42 (m, 2H), 7.39-7.34 (m, 3H), 7.30 (dd, J=7.8, 2.2 Hz, 1H), 7.13 (t, J=7.9 Hz, 1H), 7.02-7.00 (m, 2H), 2.32 (s, 3H), 2.31 (s, 3H).

Example 168

3'-{N'-[1-(3-Trifluoromethyl-phenyl)-6-trifluoromethyl-2-oxo-1,2-dihydro-indol-3-ylidene]-hydrazino}-2'-hydroxy-biphenyl-3-carboxylic acid (Compound 26)

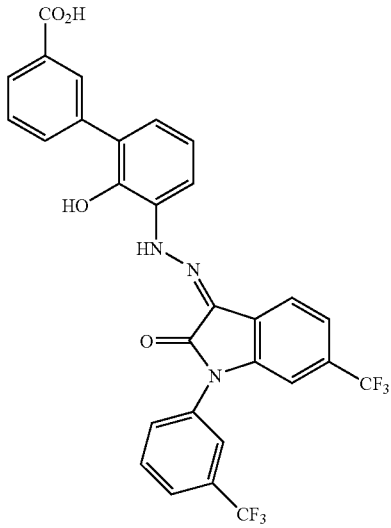

This compound was prepared as described in Scheme II. 1H NMR (500 MHz, DMSO-$d_6$) δ13.19 (s, 1H), 13.05 (s, 1H), 9.47 (s, 1H), 8.12 (t, J=1.7 Hz, 1H), 8.03 (s, 1H), 7.97-7.93 (m, 3H), 7.93-7.86 (m, 2H), 7.80 (dd, J=7.8, 1.6 Hz, 1H), 7.80 (ddd, J=7.8, 1.7, 1.2 Hz, 1H), 7.61 (t, J=7.8 Hz, 1H), 7.58 (dq, J=7.8, 0.8 Hz, 1H), 7.15 (t, J=7.8 Hz, 1H), 7.10 (d, J=0.7 Hz, 1H), 7.08 (dd, J=7.8, 1.6 Hz, 1H).

Example 169

3'-{N'-[1-(4-Trifluoromethoxy-phenyl)-5-trifluoromethoxy-2-oxo-1,2-dihydro-indol-3-ylidene]-hydrazino}-2'-hydroxy-biphenyl-3-carboxylic acid (Compound 269)

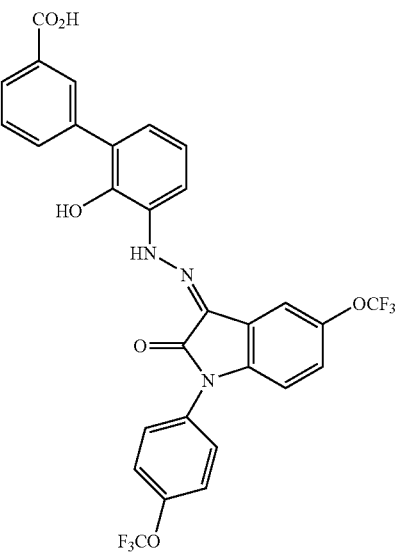

This compound was prepared as described in Scheme II. ¹H NMR (500 MHz, DMSO-d$_6$) δ13.10 (s, 1H), 13.05 (s, 1H), 9.40 (s, 1H), 8.12 (t, J=1.6 Hz, 1H), 7.95 (ddd, J=7.7, 1.6, 1.2 Hz, 1H), 7.82 (dd, J=7.8, 1.6 Hz, 1H), 7.80 (ddd, J=7.7, 1.6, 1.2 Hz, 1H), 7.74 (m, 1H), 7.73 (d, J=9.0 Hz, 2H), 7.62 (dq, J=9.0, 0.9 Hz, 2H), 7.60 (t, J=7.7 Hz, 1H), 7.28 (ddq, J=8.6, 2.1, 0.9 Hz, 1H), 7.13 (t, J=7.8 Hz, 1H), 7.05 (dd, J=7.8, 1.6 Hz, 1H), 7.02 (d, J=8.6 Hz, 1 H).

Example 170

3'-{N'-[1-(3,5-Dimethyl-phenyl)-6-trifluoromethyl-2-oxo-1,2-dihydro-indol-3-ylidene]-hydrazino}-2'-hydroxy-biphenyl-3-carboxylic acid (Compound 270)

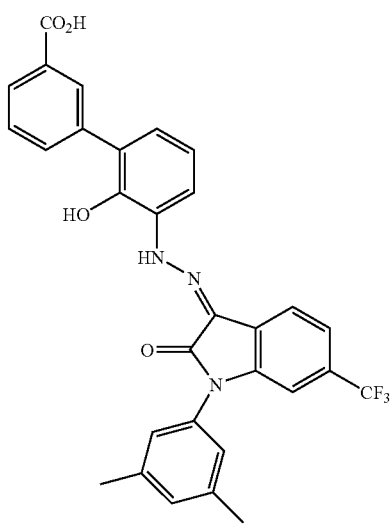

This compound was prepared as described in Scheme II. ¹H NMR (500 MHz, DMSO-d$_6$) δ13.24 (s, 1H), 13.05 (s, 1H), 9.43 (s, 1H), 8.12 (t, J=1.7 Hz, 1H), 7.95 (ddd, J=7.7, 1.7, 1.2 Hz, 1H), 7.93 (d, J=7.8 Hz, 1H), 7.80 (ddd, J=7.7, 1.7, 1.2 Hz, 1H), 7.78 (dd, J=7.7, 1.7 Hz, 1H), 7.61 (t, J=7.7 Hz, 1H), 7.54 (dq, J=7.8, 0.8 Hz, 1H), 7.18-7.16 (m, 3H), 7.14 (t, J=7.7 Hz, 1H), 7.07 (dd, J=7.7, 1.7 Hz, 1H), 6.98 (m, 1H), 2.37(s, 3H), 2.37 (s, 3H).

Example 171

3'-{N'-[1-(3-Trifluoromethyl-phenyl)-4,6-dimethyl-2-oxo-1,2-dihydro-indol-3-ylidene]-hydrazino}-2'-hydroxy-biphenyl-3-carboxylic acid (Compound 271)

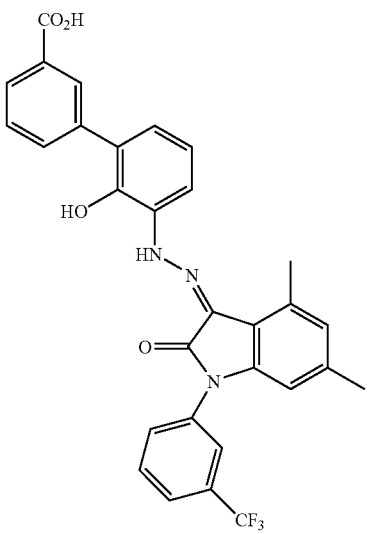

This compound was prepared as described in Scheme II. 1H NMR (500 MHz, DMSO-d$_6$) δ13.04 (s, 1H), 13.03 (s, 1H), 9.23 (s, 1H), 8.12 (t, J=1.7 Hz, 1H), 7.95 (m, 1H), 7.94 (ddd, J=7.7, 1.7, 1.2 Hz, 1H), 7.89-7.83 (m, 3H), 7.79 (ddd, J=7.7, 1.7, 1.2 Hz, 1H), 7.61 (dd, J=8.1, 1.4 Hz, 1H), 7.60 (t, J=7.7 Hz, 1H), 7.12 (t, J=7.8 Hz, 1H), 6.98 (dd, J=7.8, 1.6 Hz, 1H), 6.87 (s, 1H), 6.57 (s, 1H), 2.65 (s, 3H), 2.29 (s, 3H).

Example 172

3'-{N'-[1-(3-Trifluoromethyl-phenyl)-5,6-dimethyl-2-oxo-1,2-dihydro-indol-3-ylidene]-hydrazino}-2'-hydroxy-biphenyl-3-carboxylic acid (Compound 272)

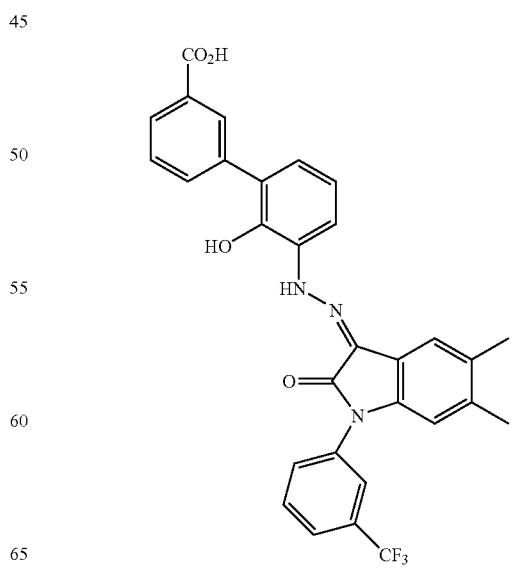

This compound was prepared as described in Scheme II. 1H NMR (500 MHz, DMSO-$d_6$) δ13.04 (s, 1H), 12.91 (s, 1H), 9.25 (s, 1H), 8.12 (t, J=1.7 Hz, 1H), 7.95 (m, 1H), 7.94 (ddd, J=7.7, 1.7, 1.2 Hz, 1H), 7.90-7.84 (m, 3H), 7.79 (ddd, J=7.7, 1.7, 1.2 Hz, 1H), 7.71 (dd, J=8.0, 1.4 Hz, 1H), 7.60 (t, J=7.7 Hz, 1H), 7.55 (s, 1H), 7.11 (t, J=7.8 Hz, 1H), 6.99 (dd, J=7.8, 1.6 Hz, 1H), 6.76 (s, 1H), 2.29 (s, 3H), 2.25 (s, 3H).

Example 173

3'-{N'-[1-(3,5-Dimethyl-phenyl)-6-trifluoromethyl-2-oxo-1,2-dihydro-indol-3-ylidene]-hydrazino}-2'-hydroxy-5'-chloro-4-fluoro-biphenyl-3-carboxylic acid (Compound 273)

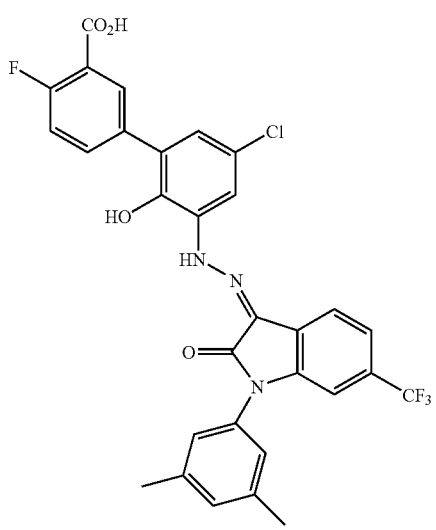

This compound was prepared as described in Scheme II. $^1$H NMR (500 MHz, DMSO-$d_6$) δ13.39 (s, 1H), 13.11 (s, 1H), 9.69 (s, 1H), 8.02 (d, J=8.0 Hz, 1H), 8.02 (dd, J=7.0, 2.5 Hz, 1H), 7.81 (ddd, J=8.5, 4.6, 2.5 Hz, 1H), 7.76 (d, J=2.6 Hz, 1H), 7.54 (dq, J=8.0, 0.7 Hz, 1H), 7.43 (dd, J=10.7, 8.5 Hz, 1H), 7.17 (s, 1H), 7.16 (s, 2H), 7.08 (d, J=2.6 Hz, 1H), 6.97 (s, 1H), 2.37 (s, 6H).

Example 174

3'-{N'-[1-(3,5-Dimethyl-phenyl)-6-trifluoromethyl-2-oxo-1,2-dihydro-indol-3-ylidene]-hydrazino}-2'-hydroxy-4-fluoro-biphenyl-3-carboxylic acid (Compound 274)

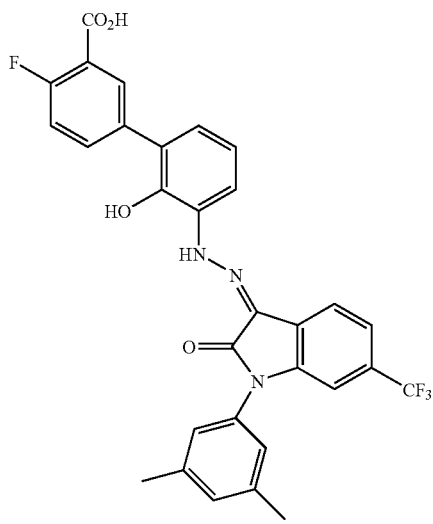

This compound was prepared as described in Scheme II. $^1$H NMR (500 MHz, DMSO-$d_6$) δ13.35 (s, 1H), 13.23 (s, 1H), 9.44 (s, 1H), 8.01 (dd, J=7.2, 2.4 Hz, 1H), 7.92 (d, J=8.0 Hz, 1H), 7.79 (ddd, J=8.6, 4.6, 2.4 Hz, 1H), 7.79 (dd, J=7.8, 1.5 Hz, 1H), 7.54 (dq, J=8.0, 0.8 Hz, 1H), 7.42 (dd, J=10.7, 8.6 Hz, 1H), 7.17 (s, 1H), 7.16 (s, 2H), 7.13 (t, J=7.8 Hz, 1H), 7.05 (dd, J=7.8, 1.5 Hz, 1H), 6.98 (s, 1H), 2.37 (s, 6H).

Example 175

3'-{N'-[6-Chloro-1-(3,4-dimethyl-phenyl)-2-oxo-12-dihydro-indol-3-ylidene]-hydrazino}-2'-hydroxy-biphenyl-3-carboxylic acid (Compound 275)

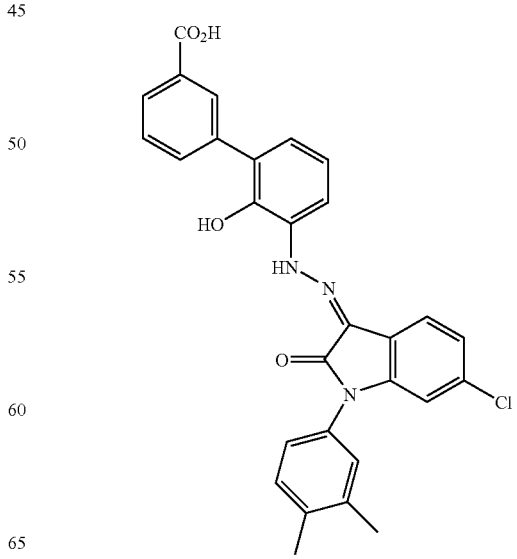

This compound was prepared as described in Scheme II. ¹H NMR (500 MHz, DMSO-$d_6$) δ13.06 (s, 1H), 13.00 (s, 1H), 9.33 (s, 1H), 8.12 (s, 1H), 7.94 (m, 1H), 7.81-7.70 (m, 3H), 7.60 (t, J=7.9 Hz, 1H), 7.37 (d, J=8.4 Hz, 1H), 7.31 (m, 1H), 7.27-7.21 (m, 2H), 7.12 (t, J=7.8 Hz, 1H), 7.02 (d, J=7.8, 1H), 6.79 (m, 1H), 2.31 (s, 3H), 2.31 (s, 3H).

Example 176

3'-{N-[5-Fluoro-2-oxo-1-(4-propyl-phenyl)-1,2-dihydro-indol-3-ylidene]-hydrazino}-2'-hydroxy-biphenyl-3-carboxylic acid (Compoun 276)

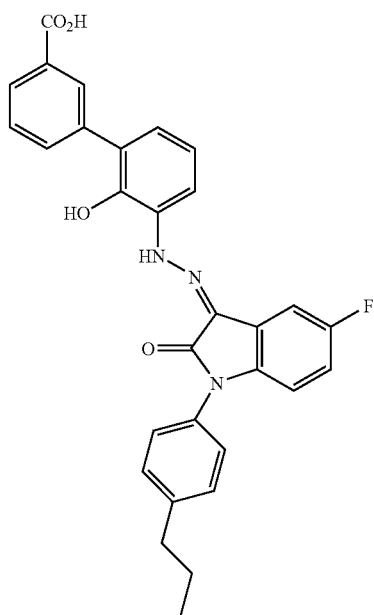

This compound was prepared as described in Scheme II. ¹H NMR (300 MHz, acetone-$d_6$) δ8.19 (t, J=1.5 Hz, 1H), 8.03 (m, 1H), 7.83 (dd, J=7.8, 1.6 Hz, 1H), 7.77 (m, 1H), 7.59 (t, J=7.6 Hz, 1H), 7.53 (dd, J=8.3, 2.6 Hz, 1H), 7.47 (d, J=8.8 Hz, 2H), 7.43 (d, J=8.8 Hz, 2H), 7.13 (t, J=7.8 Hz, 1H), 7.06-7.02 (m, 2H), 6.92 (dd, J=8.8, 4.3 Hz, 1H), 2.69 (dd, J=7.9, 7.3 Hz, 2H), 1.71 (m, 2H), 0.98 (t, J=7.3 Hz, 3H).

Example 177

3'-{N'-[5-Cyano-1-(3,4-dimethyl-phenyl)-2-oxo-1,2-dihydro-indol-3-ylidene]-hydrazino}-2'-hydroxy-biphenyl-3-carboxylic acid (Compound 277)

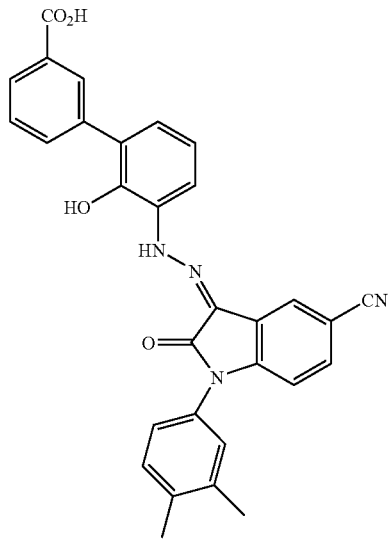

This compound was prepared as described in Scheme II. ¹H NMR (300 MHz, methanol-$d_4$) δ8.46 (s, 1H), 8.14 (m, 1H), 8.05 (s, 1H), 7.99 (d, J=7.6 Hz, 1H), 7.82 (dd, J=7.7, 1.4 Hz, 1H), 7.70 (d, J=7.6 Hz, 1H), 7.58 (m, 1H), 7.52 (t, J=7.6 Hz, 1H), 7.36 (m, 1H), 7.25 (s, 1H), 7.19 (m, 1H), 7.10 (t, J=7.7 Hz, 1H), 7.03 (dd, J=7.7, 1.4 Hz, 1H), 6.99 (m, 1H), 2.36 (s, 6H).

Example 178

3'-{N'-[6-Chloro-1-(3,5-dimethyl-phenyl)-2-oxo-1,2-dihydro-indol-3-ylidene]-hydrazino}-2'-hydroxy-biphenyl-3-carboxylic acid (Compound 278)

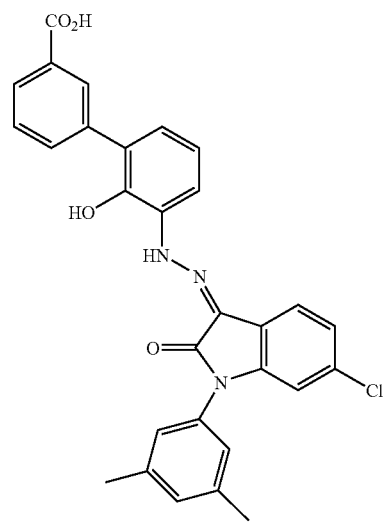

was prepared as described in Scheme II. ¹H NMR (300 MHz, acetone-d₆) δ13.22 (s, 1H), 8.49 (s, 1H), 8.19 (t, J=1.6 Hz, 1H), 8.04 (ddd, J=7.7, 1.6, 1.2 Hz, 1H), 7.82-7.77 (m, 2H), 7.76 (d, J=8.0 Hz, 1H), 7.61 (t, J=7.7 Hz, 1H), 7.21 (dd, J=8.0, 1.8 Hz, 1H), 7.19-7.15 (m, 3H), 7.13 (t, J=7.7 Hz, 1H), 7.04 (dd, J=7.7, 1.6 Hz, 1H), 6.90 (d, J=1.8 Hz, 1H), 2.40 (s, 6H).

Example 179

4-Fluoro-3'-{N'-[1-(3-fluoro-4-methyl-phenyl)-2-oxo-6-trifluoromethyl-1,2-dihydro-indol-3-ylidene]-hydrazino}-2'-hydroxy-biphenyl-3-carboxylic acid (Compound 279)

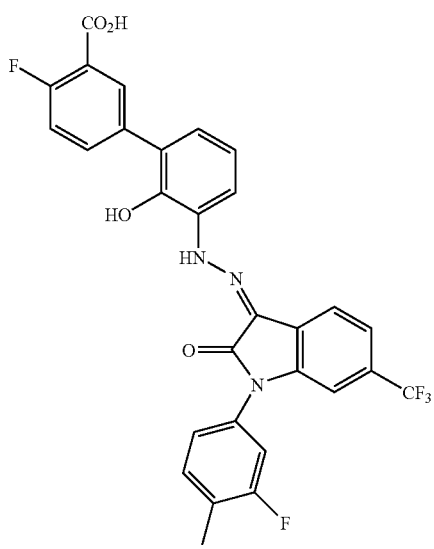

This compound was prepared as described in Scheme II. ¹H NMR (300 MHz, acetone-d₆) δ8.09 (dd, J=7.0, 2.4 Hz, 1H), 7.96 (d, J=7.9 Hz, 1H), 7.85 (dd, J=7.8, 1.6 Hz, 1H), 7.80 (ddd, J=8.5, 4.5, 2.4 Hz, 1H), 7.57-7.50 (m, 2H), 7.44-7.32 (m, 3H), 7.20 (m, 1H), 7.15 (t, J=7.8, 1H), 7.07 (dd, J=7.8, 1.6 Hz, 1H), 2.37 (d, J=1.9 Hz, 3H).

Example 180

3'-{N'-[1-(4-Chloro-3,5-dimethylphenyl)-2-oxo-6-trifluoromethyl-1,2-dihydroindol-3-ylidene]hydrazino}-2'-hydroxy-biphenyl-3-carboxylic acid (Compound 280)

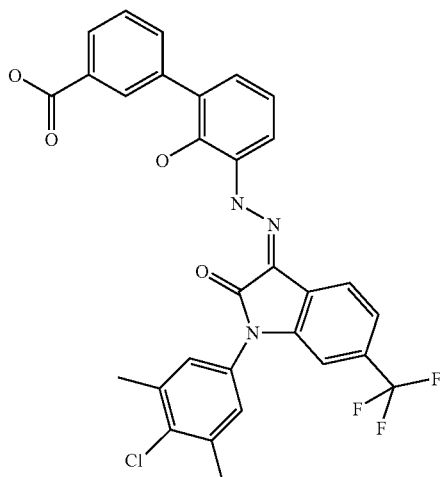

This compound was prepared as described in Scheme II. ¹H NMR (500 MHz, CDCl₃) 7.75 (s, 1H), 7.45-7.41 (m, 2H), 7.39 (m, 1H), 7.09 (m, 1H), 3.25 (t, J=7.3, 2H), 3.03 (t, J=7.3, 2H), 1.81 (sext, J=7.3, 2H), 1.63 (sext, J=7.3, 2H), 1.12 (t, J=7.3, 3H), 1.01 (t, J=7.3, 3H).

Example 181

3'-{N'-[1-(3,5-Dimethylphenyl)-4-fluoro-2-oxo-6-trifluoromethyl-1,2-dihydroindol-3-ylidene]hydrazino}-2'-hydroxybiphenyl-4-fluoro-3-carboxylic acid (Compound 281)

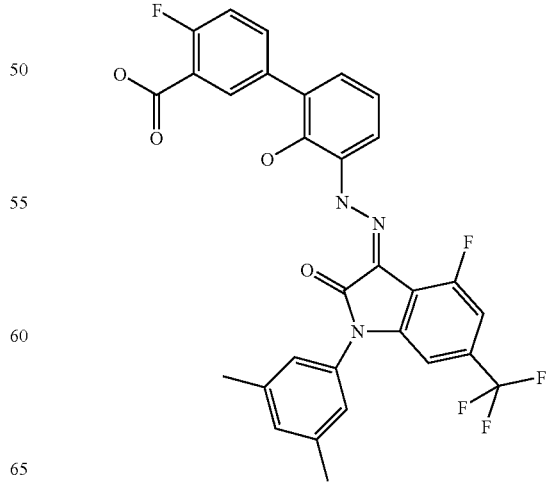

This compound was prepared as described in Scheme II. $^1$H NMR (500 MHz, DMSO-d$_6$) 13.35 (s, 1H), 8.01 (dd, J=7.1, 2.4, 1H), 7.78 (ddd, J=8.5, 4.5, 2.4, 1H), 7.66 (dd, J=7.9, 1.6, 1H), 7.50 (d, J=9.4, 1H), 7.41 (dd, J=10.7, 8.5, 1H), 7.18 (s, 1H), 7.15 (s, 2H), 7.14 (t, J=7.9, 1H), 7.07 (dd, J=7.9, 1.6, 1H), 6.83 (q, J=0.7, 1H), 2.37 (s, 6H).

Example 182

3'-{N'-[1-Benzo[1,3]dioxo-5-yl-2-oxo-6-trifluoromethyl-1,2-dihydroindol-3-ylidene]hydrazino}-2'-hydroxybiphenyl-3-carboxylic acid (Compound 282)

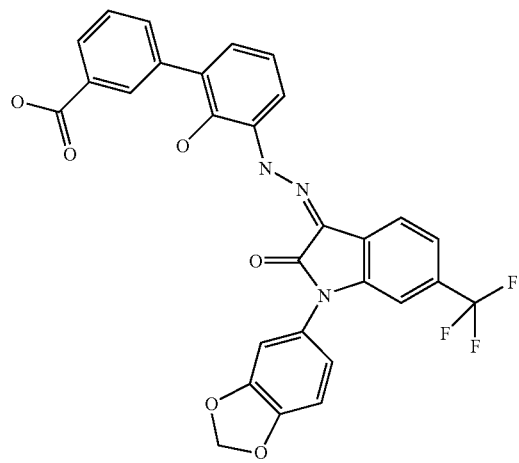

This compound was prepared as described in Scheme II. $^1$H NMR (500 MHz, DMSO-d$_6$) 13.21 (s, 1H), 13.05 (s, 1H), 9.43 (s, 1H), 8.12 (t, J=1.6, 1H), 7.95 (ddd, J=7.7, 1.6, 1.2, 1H), 7.92 (d, J=7.8, 1H), 7.80 (dd, J=7.7, 1.6, 1.2, 1H), 7.78 (dd, J=7.9, 1.6, 1H), 7.60 (t, J=7.7, 1H), 7.54 (dq, J=7.8, 0.8, 1H), 7.18 (d, J=2.1, 1H), 7.14 (d, J=8.2, 1H), 7.14 (t, J=7.9, 1H), 7.06 (dd, J=7.9, 1.6, 1H), 7.03 (dd, J=8.2, 2.1, 1H), 6.98 (q, J=0.6, 1H), 6.16 (s, 2H).

Example 183

3'-{N'-[1-Benzo[1,3]dioxo-5-yl-2-oxo-6-trifluoromethyl-1,2-dihydroindol-3-ylidene]hydrazino}-2'-hydroxybiphenyl-2-fluoro-3-carboxylic acid (Compound 283)

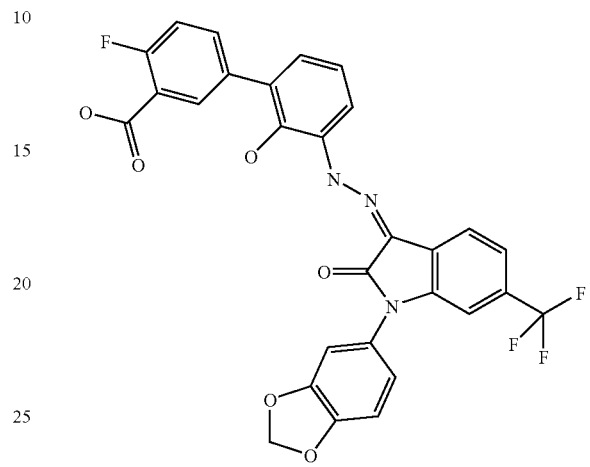

This compound was prepared as described in Scheme II. $^1$H NMR (500 MHz, DMSO-d$_6$) 13.35 (s, 1H), 13.19 (s, 1H), 9.45 (s, 1H), 8.01 (dd, J=7.2, 2.5, 1H), 7.91 (d, J=7.9, 1H), 7.79 (ddd, J=8.5, 4.6, 2.5, 1H), 7.77 (dd, J=7.8, 1.6, 1H), 7.54 (dq, J=7.9, 0.7 Hz, 1H), 7.42 (dd, J=10.7, 8.5, 1H), 7.18 (d, J=2.1, 1H), 7.14 (d, J=8.2, 1H), 7.13 (t, J=7.8, 1H), 7.05 (dd, J=7.8, 1.6, 1H), 7.03 (dd, J=8.2, 2.1, 1H), 6.98 (q, J=0.9, 1H), 6.16 (s, 2H).

Example 184

3'-{N'-[1-(3,5-Dimethylphenyl)-2-oxo-6-trifluoromethyl-1,2-dihydroindol-3-ylidene]hydrazino}-2'-hydroxybiphenyl-2-hydroxy-3-carboxylic acid (Compound 284)

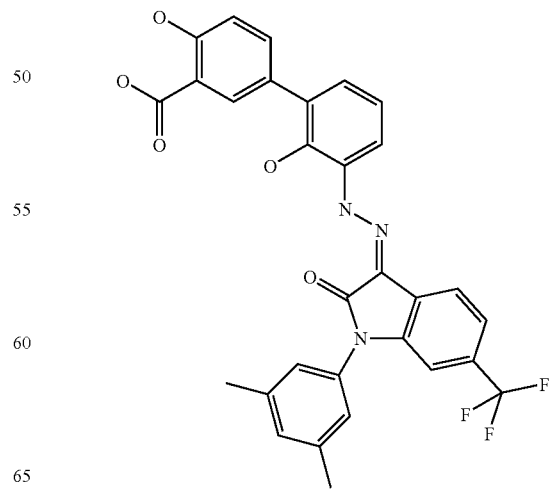

This compound was prepared as described in Scheme II.
¹H NMR (500 MHz, DMSO-d₆) 13.23 (s, 1H), 9.31 (s, 1H), 7.97 (d, J =2.3, 1H), 7.92 (d, J=7.9, 1H), 7.73 (dd, J=7.8, 1.5, 1H), 7.69 (dd, J=8.6, 2.3, 1H), 7.54 (dq, J=7.9, 0.7, 1H), 7.17 (s, 1H), 7.16 (s, 2H), 7.10 (t, J=7.8, 1H), 7.06 (d, J=8.6, 1H), 7.02 (dd, J=7.8, 1.5, 1H), 6.98 (d, J=0.9, 1H), 2.37 (s, 6H).

Example 185

3'-{N'-[1-(3-Methoxycarbonylphenyl)-2-oxo-6-trifluoromethyl-1,2-dihydroindol-3-ylidene]hydrazino}-2'-hydroxybiphenyl-3-carboxylic acid (Compound 285)

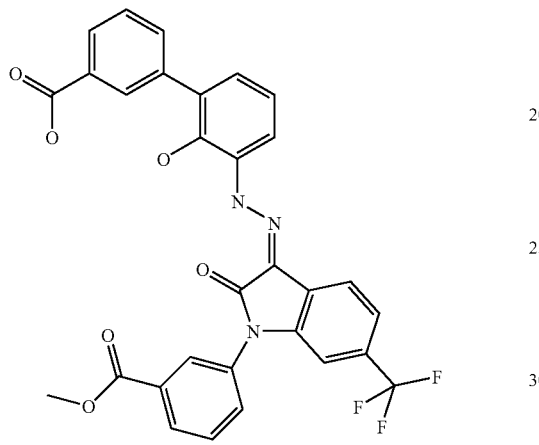

This compound was prepared as described in Scheme II.
¹H NMR (500 MHz, DMSO-d₆) 13.20 (s, 1H), 13.05 (s, 1H), 9.45 (s, 1H), 8.15 (t, J=1.7, 1H), 8.12 (t, J=1.7, 1H), 8.10 (ddd, J=7.8, 1.7, 1.2, 1H), 7.95 (m, 2H), 7.90 (m, 1H), 7.80 (t, J=7.8, 1H), 7.82-7.78 (m, 2H), 7.61 (t, J=7.8, 1H), 7.57 (dq, J=7.9, 0.8, 1H), 7.15 (t, J=7.8, 1H), 7.08 (m, 1H), 7.07 (dd, J=7.8, 1.6, 1H), and 3.90 (s, 3H).

Example 186

3'-{N'-[1-(3-Methoxycarbonylphenyl)-2-oxo-1,2-dihydroindol-3-ylidene]hydrazino}-2'-hydroxybiphenyl-3-carboxylic acid (Compound 286)

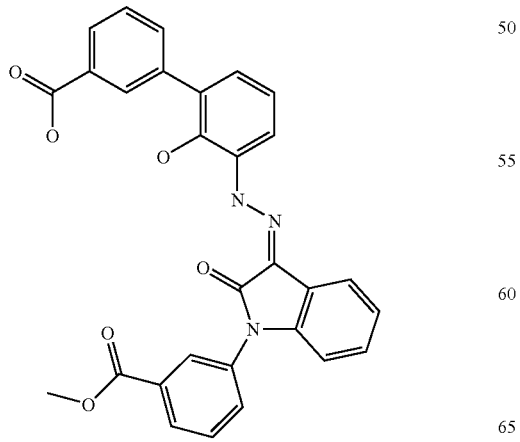

This compound was prepared as described in Scheme II.
¹H NMR (500 MHz, DMSO-d₆) 13.04 (s, 1H), 9.30 (s, 1H), 8.12 (t, J=1.7, 1H), 8.12 (t, J=1.7, 1H), 8.06 (ddd, J=7.8, 1.7, 1.2, 1H), 7.94 (ddd, J=7.8, 1.7, 1.2, 1H), 7.88 (m, 1H), 7.80 (ddd, J=7.8, 1.7, 1.2, 1H), 7.77 (t, J=7.8, 1H), 7.76 (dd, J=7.6, 0.8, 1H), 7.74 (dd, J=7.8, 1.6, 1H), 7.60 (t, J=7.8 Hz, 1H), 7.31 (td, J=7.6, 1.3, 1H), 7.22 (td, J=7.6, 0.8, 1H), 7.12 (t, J=7.8, 1H), 7.01 (dd, J=7.8, 1.6, 1H), 6.95 (d, J=7.6, 1H), 4.11 (s, 1H) and 3.90 (s, 3H).

Example 187

3'-{N'-[7-Aza-1-(3 4-dimethylphenyl)-2-oxo-1,2-dihydroindol-3-ylidene]hydrazino}-2'-hydroxybiphenyl-3-carboxylic acid (Compound 287)

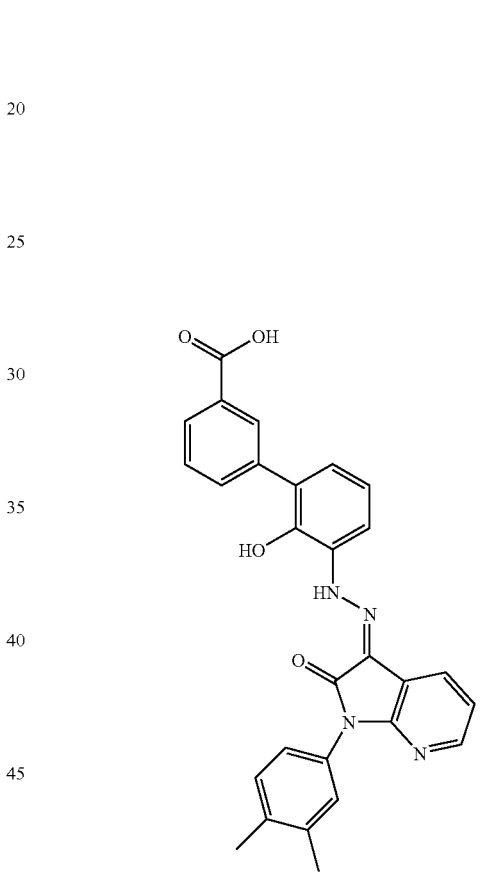

This compound was prepared as described in Scheme I.
¹H NMR (500 MHz, DMSO-d₆) 13.10 (s, 1H), 13.04 (s, 1H), 9.36 (s, 1H), 8.16 (dd, J=5.1, 1.6 Hz, 1H), 8.12 (t, J=1.6 Hz, 1H), 8.04 (dd, J=7.4, 1.6 Hz, 1H), 7.94 (ddd, J=7.7, 1.6, 1.2 Hz, 1H), 7.80 (ddd, J=7.7, 1.6, 1.2 Hz, 1H), 7.74 (dd, J=7.8, 1.6 Hz, 1H), 7.60 (t, J=7.7 Hz, 1H), 7.34 (d, J=1.8 Hz, 1H), 7.30 (d, J=8.1 Hz, 1H), 7.28 (dd, J=8.1, 1.8 Hz, 1H), 7.21 (dd, J=7.4, 5.1 Hz, 1H), 7.13 (t, J=7.8 Hz, 1H), 7.03 (dd, J=7.8, 1.6 Hz, 1H), 2.30 (s, 3H), 2.29 (s, 3H).

Example 188

3'-{N'-[1-(3,5-Dimethylphenyl)-2-oxo-1,2-dihydroindol-6-trifluoromethyl-3-ylidene]hydrazino}-2'-hydroxybiphenyl-3-(2-methyl-2-propionic acid) (Compound 288)

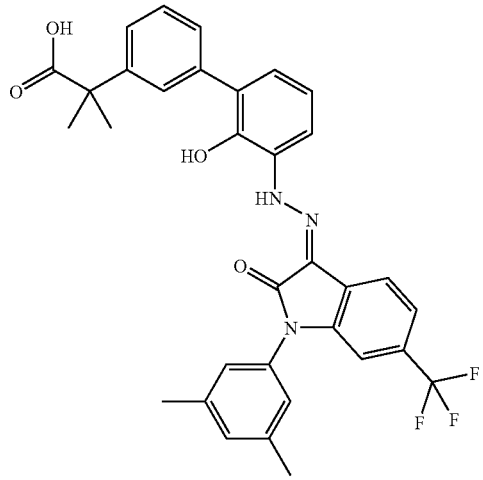

This compound was prepared as described in Scheme I. $^1$H NMR (500 MHz, DMSO-$d_6$) 13.25 (s, 1H), 12.39 (s, 1H), 9.35 (s, 1H), 7.92 (d, J =7.8 Hz, 1H), 7.75 (dd, J=8.0, 1.5 Hz, 1H), 7.56-7.53 (m, 2H), 7.46-7.42 (m, 2H), 7.35 (m, 1H), 7.17 (s, 3H), 7.12 (t, J=7.8 Hz, 1H), 7.02 (dd, J=7.8, 1.6 Hz, 1H), 6.99 (q, J=0.7 Hz, 1H), 2.37 (s, 6H), 1.52 (s, 6H).

Example 189

3'-{N'-[1,3-N,N-Dimethylbarbitur-5-ylidene]hydrazino}-2'-hydroxybiphenyl-3-carboxylic acid (Compound 289)

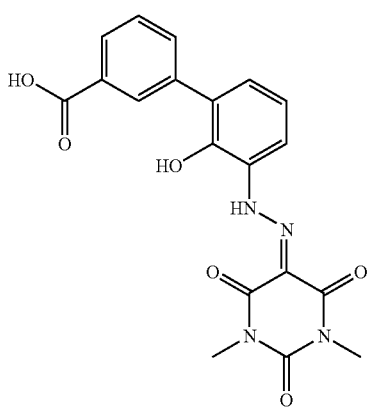

This compound was prepared as described in Scheme I. $^1$H NMR (500 MHz, DMSO-$d_6$) 8.14 (t, J=1.3 Hz, 1H), 7.95 (d, J=7.7 Hz, 1H), 7.81 (dt, J=7.7, 1.3 Hz, 1H), 7.65 (d, J=7.7 Hz, 1H), 7.61 (t, J =7.7 Hz, 1H), 7.18 (dd, J=7.7, 1.2 Hz, 1H), 7.13 (m, 1H), 3.22 (s, 6H).

Example 190

3'-{N'-[1-N-(4-Trifluoromethylbenzyl)-2,8-dioxo-1,2,7,8-tetrahydroisoquinolin-7-ylidene]hydrazino}-2'-hydroxybiphenyl-3-carboxylic acid (Compound 290)

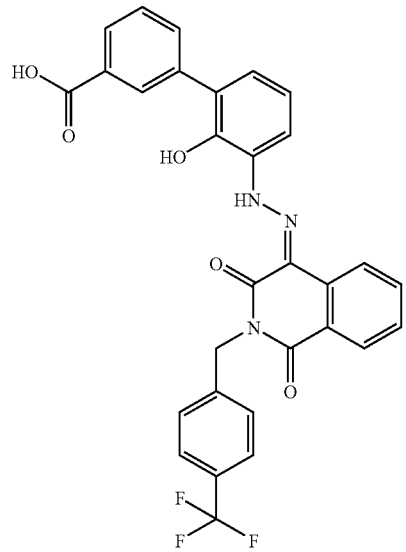

This compound was prepared as described in Scheme I. $^1$H NMR (500 MHz, DMSO-$d_6$) 14.24 (s, 1H), 13.06 (s, 1H), 9.49 (s, 1H), 8.36 (d, J=7.9 Hz, 1H), 8.16-8.12 (m, 2H), 7.95 (d, J=7.7 Hz, 1H), 7.88 (dd, J=7.8, 1.0 Hz, 1H), 7.84-7.79 (m, 2H), 7.68 (d, J=8.2 Hz, 2H), 7.61 (t, J=7.7 Hz, 1H), 7.58 (d, J=8.2 Hz, 2H), 7.55 (td, J=7.7, 0.9 Hz, 1H), 7.15 (t, J=7.8 Hz, 1H), 7.10 (dd, J=7.8, 1.0 Hz, 1H), 5.28 (s, 2H).

Example 191

3'-{N'-[1-N-(4-Methylbenzyl)-2,8-dioxo-1,2,7,8-tetrahydroisoquinolin-7-ylidene]hydrazino}-2'-hydroxybiphenyl-3-carboxylic acid (Compound 291)

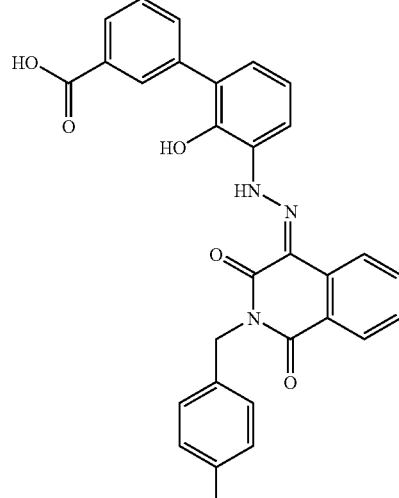

This compound was prepared as described in Scheme I.
¹H NMR (500 MHz, DMSO-d₆) 14.28 (s, 1H), 13.06 (s, 1H), 9.49 (s, 1H), 8.34 (d, J=8.0 Hz, 1H), 8.15-8.12 (m, 2H), 7.96 (dm, J=7.8 Hz, 1H), 7.87 (dm, J=7.8 Hz, 1H), 7.82-7.78 (m, 2H), 7.61 (t, J=7.8 Hz, 1H), 7.54 (td, J=7.7, 0.9 Hz, 1H), 7.25 (d, J=8.2 Hz, 2H), 7.15 (t, J=7.8 Hz, 1H), 7.10 (m, 1H), 7.12 (d, J=8.2 Hz, 2H), 5.16 (s, 2H), 2.25 (s, 3H).

Example 192

3'-{N'-[1-N-Benzyl-2,8-dioxo-1,2,7,8-tetrahydroisoquinolin-7-ylidene]hydrazino}-2'-hydroxybiphenyl-3-carboxylic acid (Compound 292)

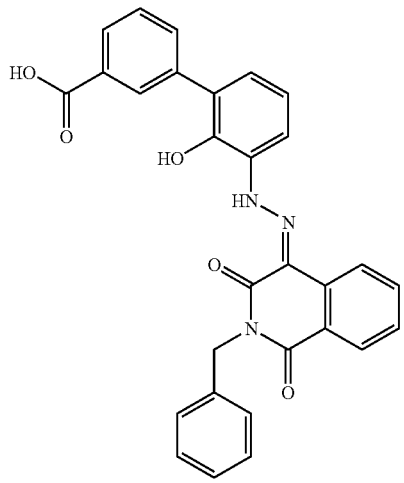

This compound was prepared as described in Scheme I.
¹H NMR (500 MHz, DMSO-d₆) 14.28 (s, 1H), 13.06 (s, 1H), 9.49 (s, 1H), 8.35 (d, J=7.9 Hz, 1H), 8.16-8.12 (m, 2H), 7.95 (dd, J=7.7, 1.2 Hz, 1H), 7.88 (d, J=7.8 Hz, 1H), 7.82-7.78 (m, 2H), 7.61 (t, J=7.7 Hz, 1H), 7.55 (td, J=7.6, 0.8 Hz, 1H), 7.36 (d, J=7.4 Hz, 2H), 7.32 (t, J=7.4 Hz, 2H), 7.25 (t, J=7.4 Hz, 1H), 7.15 (t, J=7.8 Hz, 1H), 7.10 (dd, J=7.8, 1.2 Hz, 1H), 5.21 (s, 2H).

Example 193

3'-{N'-[1-N-(4-Trifluoromethylphenyl)-2,8-dioxo-1,2,7,8-tetrahydroisoquinolin-7-ylidene]hydrazino}-2'-hydroxybiphenyl-3-carboxylic acid (Compound 293)

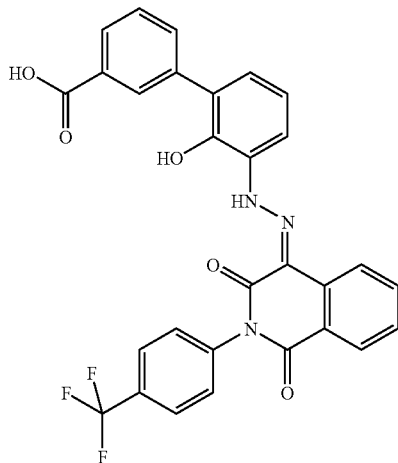

This compound was prepared as described in Scheme I.
¹H NMR (500 MHz, DMSO-d₆) 14.11 (s, 1H), 13.05 (s, 1H), 9.41 (s, 1H), 8.42 (d, J=8.0 Hz, 1H), 8.15-8.11 (m, 2H), 7.95 (dd, J=7.7, 1.3 Hz, 1H), 7.93 (d, J=8.2 Hz, 2H), 7.90 (dd, J=7.8, 1.3 Hz, 1H), 7.85 (ddd, J=8.0, 7.6, 1.3 Hz, 1H), 7.79 (dd, J=7.7, 1.3 Hz, 1H), 7.67 (d, J=8.2 Hz, 2H), 7.61 (t, J=7.7 Hz, 1H), 7.58 (td, J=7.6, 1.3 Hz, 1H), 7.16 (t, J=7.8 Hz, 1H), 7.09 (dd, J=7.8, 1.3 Hz, 1H).

Example 194

3'-{N-[1-N-(3-Trifluoromethylphenyl)-2,8-dioxo-1,2,7,8-tetrahydroisoquinolin-7-ylidene]hydrazino}-2'-hydroxybiphenyl-3-carboxylic acid (Compound 294)

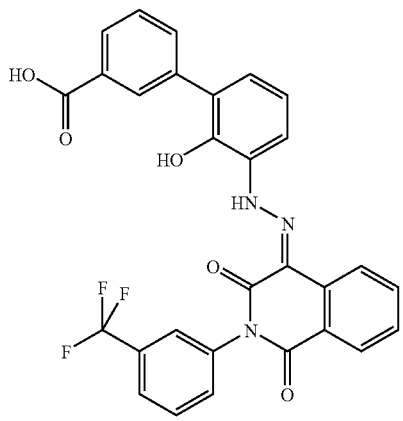

Example 195

3'-{N'-[1-N-(3,5-Dimethylphenyl)-2,8-dioxo-1,2,7,8-tetrahydroisoquinolin-7-ylidene]hydrazino}-2'-hydroxybiphenyl-3-carboxylic acid (Compound 295)

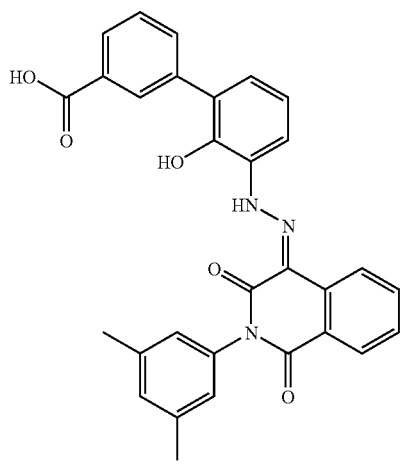

This compound was prepared as described in Scheme I.
$^1$H NMR (500 MHz, DMSO-d$_6$) 14.18 (s, 1H), 13.06 (s, 1H), 9.38 (s, 1H), 8.38 (dd, J=7.6, 0.9 Hz, 1H), 8.12-8.09 (m, 2H), 7.94 (dt, J=7.7, 1.4 Hz, 1H), 7.88 (dd, J=7.9, 1.3 Hz, 1H), 7.82 (td, J=7.6, 0.9 Hz, 1H), 7.78 (dt, J=7.7, 1.4 Hz, 1H), 7.60 (t, J=7.7 Hz, 1H), 7.56 (td, J=7.6, 0.9 Hz, 1H), 7.15 (t, J=7.9 Hz, 1H), 7.10 (s, 1H), 7.08 (dd, J=7.9, 1.3 Hz, 1H), 6.96 (s, 2H), 2.32 (s, 6H).

Example 196

3'-{N'-[1-N-Phenyl-2,8-dioxo-1,2,7,8-tetrahydroisoquinolin-7-ylidene]hydrazino}-2'-hydroxybiphenyl-3-carboxylic acid (Compound 296)

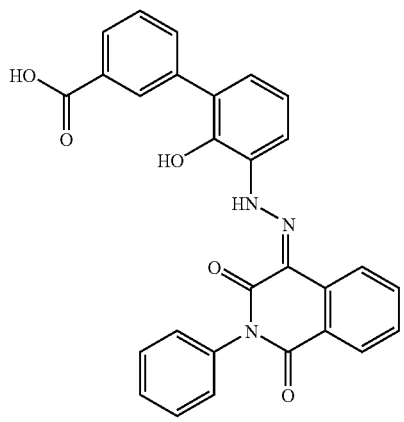

This compound was prepared as described in Scheme I.
$^1$H NMR (500 MHz, DMSO-d$_6$) 14.16 (s, 1H), 13.04 (s, 1H), 9.38 (s, 1H), 8.40 (dd, J=7.7, 0.9 Hz, 1H), 8.14-8.10 (m, 2H), 7.94 (dt, J=7.7, 1.4 Hz, 1H), 7.89 (dd, J=7.8, 1.3 Hz, 1H), 7.83 (td, J=7.7, 0.9 Hz, 1H), 7.78 (dt, J=7.7, 1.4 Hz, 1H), 7.60 (t, J=7.7 Hz, 1H), 7.57 (td, J=7.7, 0.9 Hz, 1H), 7.53 (t, J=7.5 Hz, 2H), 7.47 (t, J=7.5 Hz, 1H), 7.38 (m, 2H), 7.15 (t, J=7.8 Hz, 1H), 7.08 (dd, J=7.8, 1.3 Hz, 1H).

Example 197

3'-{N'-[1-N-(3,4-Dimethylphenyl)-2,8-dioxo-1,2,7,8-tetrahydroisoquinolin-7-ylidene]hydrazino}-2'-hydroxybiphenyl-3-carboxylic acid (Compound 297)

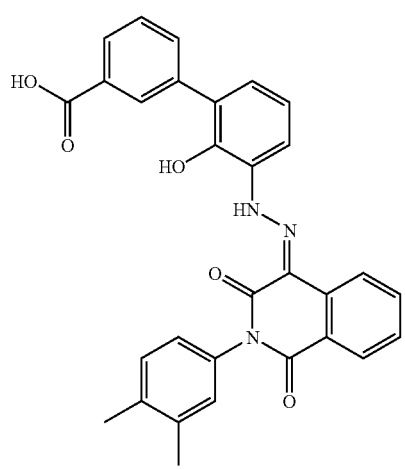

This compound was prepared as described in Scheme I.
$^1$H NMR (500 MHz, DMSO-d$_6$) 14.19 (s, 1H), 13.04 (s, 1H), 9.39 (s, 1H), 8.41 (dd, J=7.6, 0.9 Hz, 1H), 8.14-8.10 (m, 2H), 7.94 (dt, J=7.6, 1.4 Hz, 1H), 7.90 (dd, J=7.8, 1.2 Hz, 1H), 7.85 (td, J=7.6, 0.9 Hz, 1H), 7.78 (dt, J=7.6, 1.4 Hz, 1H), 7.60 (t, J=7.6 Hz, 1H), 7.57 (td, J=7.6, 0.9 Hz, 1H), 7.27 (d, J=7.4 Hz, 1H), 7.22 (t, J=7.8 Hz, 1H), 7.18-7.12 (m, 2H), 7.08 (dd, J=7.8, 1.2 Hz, 1H), 2.33 (s, 3H), 1.95 (s, 3H).

Example 198

3'-{N'-[1-N-(3,4-Dimethylphenyl)-2-oxo-6-trifluoromethyl-1,2-dihydroindol-3-ylidene]hydrazino}-2'-fluorobiphenyl-3-carboxylic acid (Compound 298)

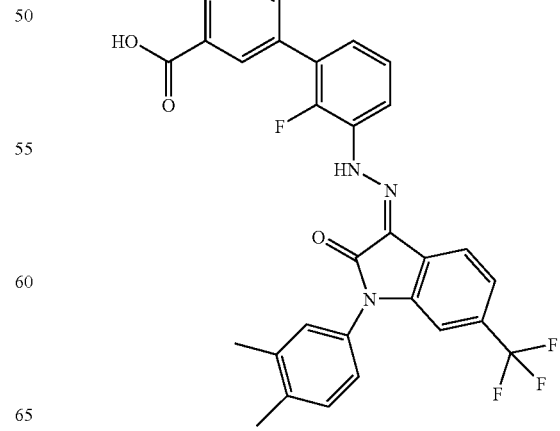

This compound was prepared as described in Scheme I. ¹H NMR (500 MHz, DMSO-$d_6$) 13.06 (s, 1H), 8.13 (m, 1H), 8.00 (dt, J=7.8, 1.3 Hz, 1H), 7.94 (d, J=7.9 Hz, 1H), 7.90 (m, 1H), 7.85 (m, 1H), 7.64 (t, J=7.7 Hz, 1H), 7.56 (dq, J=7.9, 0.7 Hz, 1H), 7.42 (t, J =7.9 Hz, 1H), 7.38 (d, J =8.0 Hz, 1H), 7.32 (d, J=2.0 Hz, 1H), 7.30 (m, 1H), 7.26 (dd, J=8.0, 2.0 Hz, 1H), 6.95 (q, J=0.6 Hz, 1H), 2.31 (s, 3H), 2.29 (s, 3H).

Example 199

3-(3-{N'-[1-N-(3,4-Dimethylphenyl)-2-oxo-6-trifluoromethyl-1,2-dihydroindol-3-ylidene]hydrazino}-2-hydroxyphenyl)-2(Z)-propenoic acid (Compound 299)

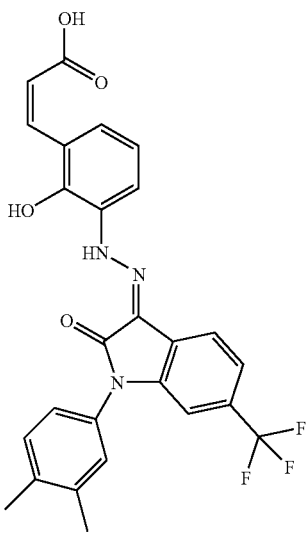

This compound was prepared as described in Scheme V. ¹H NMR (500 MHz, DMSO-$d_6$) 13.26 (s, 1H), 8.13 (d, J=9.6 Hz, 1H), 8.03 (m, 1H), 7.96 (d, J=7.9 Hz, 1H), 7.57 (dq, J=7.9, 0.7 Hz, 1H), 7.48-7.44 (m, 2H), 7.40 (d, J=8.1 Hz, 1H), 7.36 (d, J=2.2 Hz, 1H), 7.29 (dd, J=8.1, 2.2 Hz, 1H), 6.99 (m, 1H), 6.59 (d, J=9.6 Hz, 1H), 2.33 (s, 3H), 2.32 (s, 3H).

Example 200

3-(3-{N'-[1-N-(3,4-Dimethylphenyl)-2-oxo-4-fluoro-6-trifluoromethyl-1,2-dihydroindol-3-ylidene]hydrazino}-2-hydroxyphenyl)-2(Z)-propenoic acid (Compound 300)

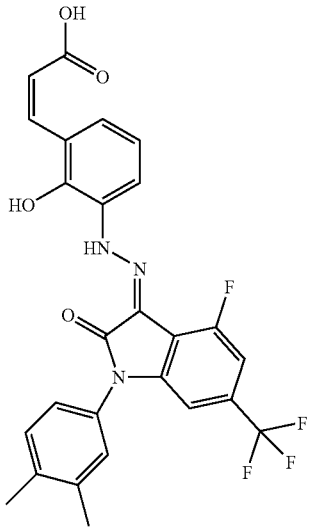

This compound was prepared as described in Scheme V. ¹H NMR (500 MHz, DMSO-$d_6$) 13.39 (s, 1H), 8.13 (d, J=9.6 Hz, 1H), 7.90 (m, 1H), 7.55 (d, J=9.5 Hz, 1H), 7.49-7.47 (m, 2H), 7.40 (d, J=8.0 Hz, 1H), 7.35 (d, J=1.9 Hz, 1H), 7.29 (dd, J=8.0, 1.9 Hz, 1H), 6.84 (s, 1H), 6.59 (d, J=9.6 Hz, 1H), 2.33 (s, 3H), 2.32 (s, 3H).

Example 201

5-(3-{N'-[1-(3,4-Dimethylphenyl)-2-oxo-4-fluoro-6-trifluoromethyl-1,2-dihydroindol-3-ylidene]hydrazino}-2-hydroxybenzylidene)thiazolidine-2,4-dione (Compound 301)

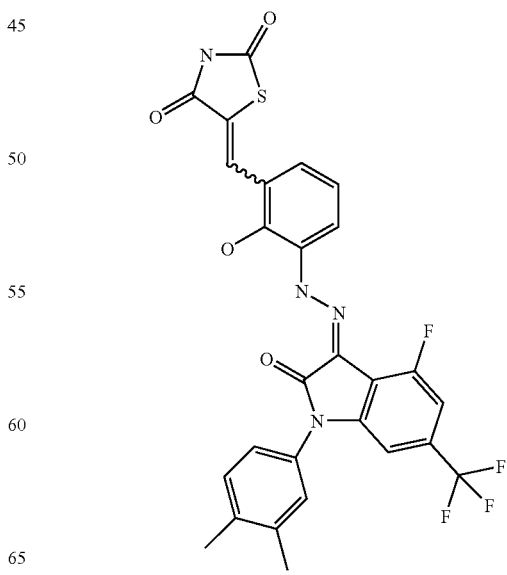

This compound was prepared as described in Scheme V. ¹H NMR (500 MHz, DMSO-d₆) 13.29 (s, 1H), 8.06 (s, 1H), 7.70 (m, 1H), 7.50 (d, J=9.6 Hz, 1H), 7.39 (d, J=8.1 Hz, 1H), 7.32 (d, J=2.1 Hz, 1H), 7.26 (dd, J=8.1, 2.1 Hz, 1H), 7.17-7.14 (m, 2H), 6.80 (q, J=0.7 Hz, 1H), 2.33 (s, 3H), 2.31 (s, 3H).

Example 202

2-Chloro-3-(4-{N'-[1-(3,4-dimethylphenyl)-2-oxo-6-trifluoromethyl-1,2-dihydroindol-3-ylidene]hydrazino}-3-hydroxyphenyl)-2-propenoic acid (Compound 302)

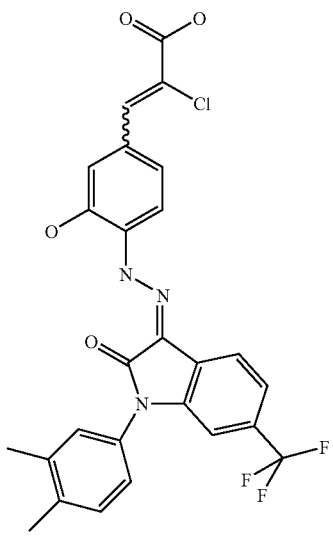

This compound was prepared as described in Scheme V. ¹H NMR (500 MHz, DMSO-d₆) 13.13 (s, 1H), 10.74 (s, 1H), 7.92 (d, J=8.2 Hz, 1H), 7.85 (s, 1H), 7.77 (d, J=8.6 Hz, 1H), 7.72 (d, J =1.4 Hz, 1H), 7.54 (d, J=8.2 Hz, 1H), 7.45 (dd, J=8.6, 1.4 Hz, 1H), 7.39 (d, J=8.0 Hz, 1H), 7.33 (d, J=1.6 Hz, 1H), 7.27 (dd, J=8.0, 1.6 Hz, 1H), 6.96 (m, 1H), 2.33 (s, 3H), 2.31 (s, 3H).

Example 203

2-Ethyl-3-(4-{N'-[1-(3 4-dimethylphenyl)-2-oxo-6-trifluoromethyl-1,2-dihydroindol-3-ylidene]hydrazino}-3-hydroxyphenyl)-2-propenoic acid (Compound 303)

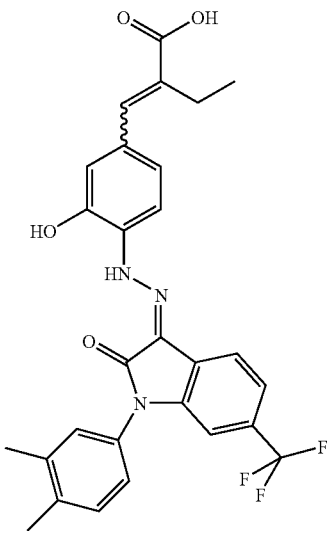

This compound was prepared as described in Scheme V. ¹H NMR (500 MHz, Acetone-d₆) 13.32 (s, 1H), 10.78 (s, 1H), 9.52 (s, 1H), 7.95 (d, J=7.9 Hz, 1H), 7.87 (d, J=8.6 Hz, 1H), 7.61 (s, 1H), 7.52 (d, J=7.9 Hz, 1H), 7.40 (d, J=8.1 Hz, 1H), 7.37 (br s, 1H), 7.31 (br d, J=8.1 Hz, 1H), 7.21 (s, 1H), 7.16 (d, J=8.6 Hz, 1H), 7.10 (s, 1H), 2.61 (q, J=7.3 Hz, 2H), 2.37 (s, 6H), 1.20 (t, J=7.3 Hz, 3H).

Example 204

1-N-Methyl-5-(4-{N'-[1-(3,5-dimethylphenyl)-2-oxo-6-trifluoromethyl-1,2-dihydroindol-3-ylidene]hydrazino}-3-hydroxybenzylidene)-1,3-diazolidine-2,4-dione (Compound 304)

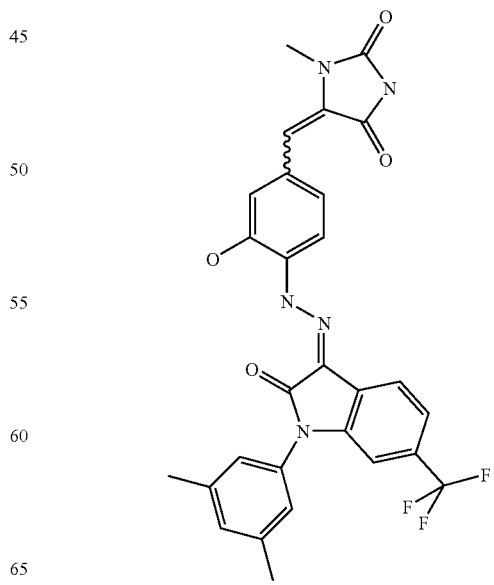

This compound was prepared as described in Scheme V. ¹H NMR (500 MHz, DMSO-d₆) 13.17 (s, 1H), 13.13 (s, 1H), 11.43 (s, 1H), 11.35 (s, 1H), 10.64 (s, 1H), 10.58 (s, 1H), 7.92-7.88 (m, 3H), 7.72 (d, J=8.3 Hz, 1H), 7.70 (d, J=8.3 Hz, 1H), 7.53 (m, 2H), 7.50 (d, J=8.3 Hz, 1H), 7.18 (s, 2H), 7.16 (s, 4H), 7.01 (d, J=8.3 Hz, 1H), 6.98 (m, 2H), 6.95 (s, 1H), 6.59 (s, 1H), 6.35 (s, 1H), 3.10 (s, 3H), 2.93 (s, 3H), 2.37 (s, 12H).

Example 205

5-(4-{N'-[1-(3,5-Dimethylphenyl)-2-oxo-6-trifluoromethyl-1,2-dihydroindol-3-ylidene]hydrazino}-3-hydroxybenzylidene)-1,3-diazolidine-2,4-dione (Compound 305)

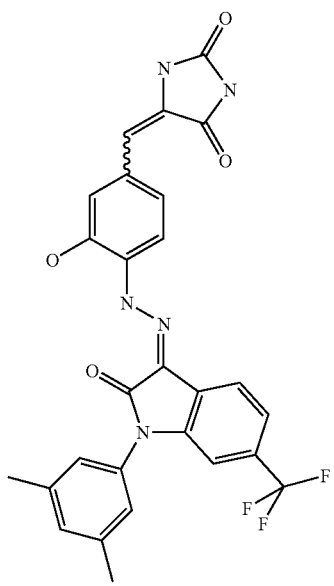

This compound was prepared as described in Scheme V. ¹H NMR (500 MHz, DMSO-d₆) 13.14 (s, 1H), 11.21 (s, 1H), 10.57 (s, 1H), 10.48 (s, 1H), 7.91 (d, J=7.9 Hz, 1H), 7.68 (d, J=8.4 Hz, 1H), 7.51 (d, J=7.9 Hz, 1H), 7.27 (d, J=8.4 Hz, 1H), 7.15 (s, 1H), 7.14 (s, 2H), 7.05 (s, 1H), 6.96 (s, 1H), 6.32 (s, 1H), 2.35 (s, 6H).

Example 206

2-Fluoro-3-(4-{N'-[1-(3,4-dimethylphenyl)-2-oxo-6-trifluoromethyl-1,2-dihydroindol-3-ylidene]hydrazino}-3-hydroxyphenyl)-2-propenoic acid (Compound 306)

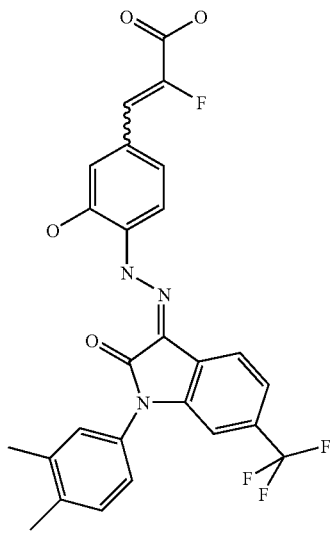

This compound was prepared as described in Scheme V. ¹H NMR (500 MHz, DMSO-d₆) 13.56 (s, 1H), 13.12 (s, 1H), 10.69 (s, 1H), 7.91 (d, J=8.0 Hz, 1H), 7.75 (d, J=8.3 Hz, 1H), 7.54 (d, J=8.0 Hz, 1H), 7.39 (d, J=8.1 Hz, 1H), 7.36 (s, 1H), 7.33 (br s, 1H), 7.29-7.25 (m, 2H), 6.95 (d, J=36.7 Hz, 1H), 6.95 (m, 1H), 2.33 (s, 3H), 2.31 (s, 3H).

Example 207

(±)-2-Methoxy-3-(4-{N'-[1-(3,5-dimethylphenyl)-2-oxo-6-trifluoromethyl-1,2-dihydroindol-3-ylidene]hydrazino}-3-hydroxyphenyl)propanoic acid (Compound 307)

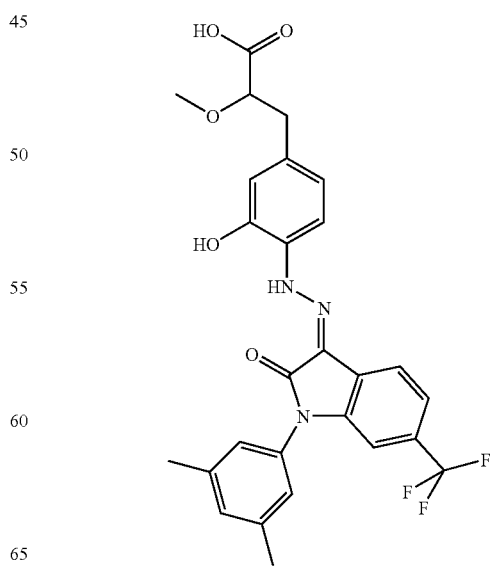

This compound was prepared as described in Scheme V. ¹H NMR (500 MHz, DMSO-d₆) 13.10 (s, 1H), 10.43 (s, 1H), 7.86 (d, J=7.9 Hz, 1H), 7.59 (d, J=8.3 Hz, 1H), 7.51 (dq, J=7.9, 0.7 Hz, 1H), 7.16 (s, 1H), 7.15 (s, 2H), 6.97 (q, J=0.6 Hz, 1H), 6.83 (d, J=1.6 Hz, 1H), 6.80 (dd, J=8.3, 1.6 Hz, 1H), 3.88 (dd, J=8.0, 4.6 Hz, 1H), 3.25 (s, 3H), 2.91 (dd, J=14.2, 4.6 Hz, 1H), 2.80 (dd, J=14.2, 8.0 Hz, 1H), 2.37 (s, 6H).

Example 208

4-(3-{N'-[1-(3,4-dimethylphenyl)-2-oxo-6-trifluoromethyl-1,2-dihydroindol-3-ylidene]hydrazino}-2-hydroxyphenyl)butanoic acid (Compound 308)

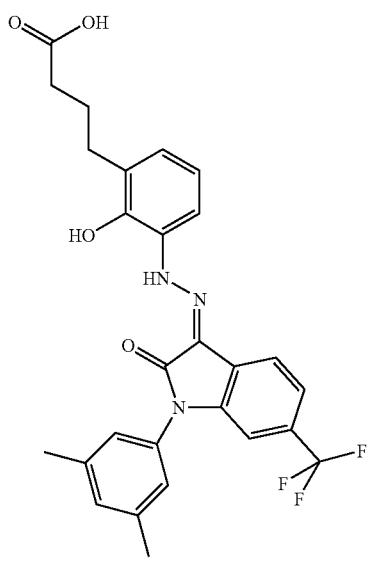

This compound was prepared as described in Scheme V. ¹H NMR (500 MHz, DMSO-d₆) 13.18 (s, 1H), 12.08 (s, 1H), 9.26 (s, 1H), 7.89 (d, J=7.9 Hz, 1H), 7.60 (dd, J=7.8, 1.6 Hz, 1H), 7.52 (dq, J=7.9, 0.7 Hz, 1H), 7.17 (s, 1H), 7.16 (s, 2H), 6.96 (m, 1H), 6.95 (t, J=7.8 Hz, 1H), 6.88 (dd, J=7.8, 1.6 Hz, 1H), 2.65 (t, J=7.6 Hz, 2H), 2.37 (s, 6H), 2.25 (t, J=7.6 Hz, 2H), 1.77 (qn, J=7.6 Hz, 2H).

Example 209

3-(2-{N'-[1-(3,5-dimethylphenyl)-2-oxo-6-trifluoromethyl-1,2-dihydroindol-3-ylidene]hydrazino}-3-hydroxyphenoxy)propanoic acid (Compound 309)

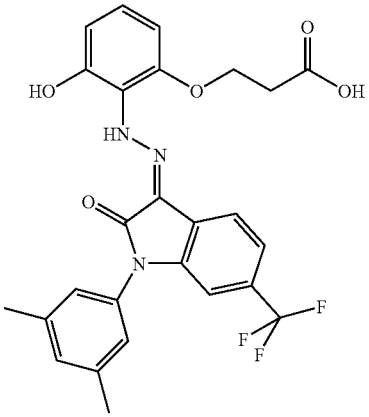

This compound was prepared as described in Scheme V. ¹H NMR (500 MHz, DMSO-d₆) 13.0 (s, 1 H), 12.4 (s, 1 H), 10.1 (s, 1 H), 7.84 (d, J=7.8 Hz, 1 H), 7.49 (d, J=7.8 Hz, 1 H), 7.18 (s, 1 H), 7.15 (s, 2 H), 6.99 (dd, J=8.8, 8.8 Hz, 1 H), 6.93 (s, 1 H), 6.68 (d, J=8.3 Hz, 1 H), 6.30 (d, J=7.8 Hz, 1 H), 4.28-4.26 (m, 2 H), 2.77-2.75 (m, 2 H), 2.37 (s, 6 H).

Example 210

4-(4-{N'-[1-(3,4-dimethylphenyl)-2-oxo-6-trifluoromethyl-1,2-dihydroindol-3-ylidene]hydrazino}-3-hydroxyphenyl)butanoic acid (Compound 310)

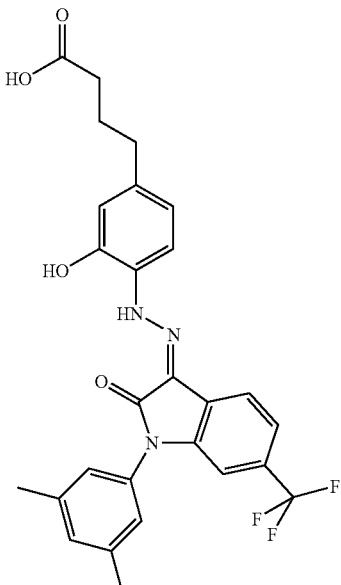

This compound was prepared as described in Scheme V.
$^1$H NMR (500 MHz, CD$_3$OD) 7.84 (d, J=7.8 Hz, 1 H), 7.65 (d, J=8.4 Hz, 1 H), 7.44 (d, J =7.8 Hz, 1 H), 7.18 (s, 1 H), 7.09 (s, 2 H), 6.99 (s, 1 H), 6.78 (d, J=7.8 Hz, 1 H), 6.74 (s, 1 H), 2.60-2.57 (m, 2 H), 2.41 (s, 6 H), 2.29-2.26 (m, 2 H), 1.92-1.88 (m, 2 H).

What is claimed is:

1. A compound of Formula III:

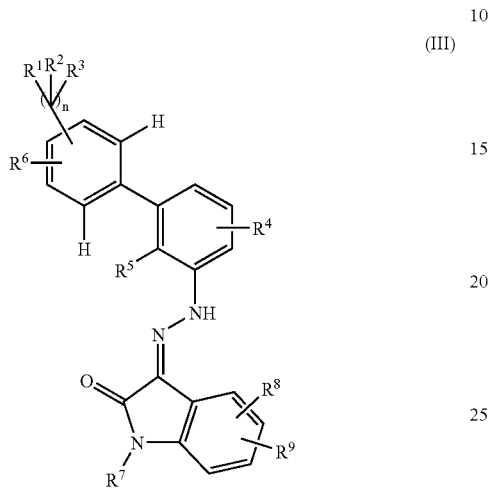

(III)

or a pharmaceutically acceptable salt, ester, or amide thereof,
wherein:
$R^1$ is selected from CO$_2$R$^{10}$, CONR$^{10}$R$^{11}$, SO$_3$R$^{10}$, and a carboxylic acid bioisostere;
$R^2$ and $R^3$ are each independently selected from null, hydrogen, OR$^{12}$, NR$^{12}$R$^{13}$, an optionally substituted C$_1$-C$_4$ aliphatic, an optionally substituted C$_1$-C$_4$ haloaliphatic, an optionally substituted C$_1$-C$_4$ heteroaliphatic, an optionally substituted ring, and (CH$_2$)$_m$R$^{14}$; or $R^2$ and $R^3$ taken together form an optionally substituted olefin; or $R^2$ and $R^3$ are linked to form an optionally substituted C$_3$-C$_8$ ring;
$R^4$ is selected from hydrogen, F, Cl, Br, C$_1$-C$_4$ aliphatic, C$_1$-C$_4$ haloaliphatic, C$_1$-C$_4$ heteroaliphatic, and a ring;
$R^5$ is selected from hydrogen, OR$^{10}$, SR$^{10}$, NHR$^{11}$, and CO$_2$H;
$R^6$ is selected from hydrogen, OR$^{12}$, NR$^{12}$R$^{13}$, F, Cl, Br, C$_1$-C$_4$ alkyl, C$_1$-C$_4$ haloalkyl, and C$_1$-C$_4$ heteroalkyl;
$R^7$ is selected from hydrogen, an optionally substituted C$_1$-C$_8$ aliphatic, an optionally substituted C$_1$-C$_8$ haloaliphatic, an optionally substituted C$_1$-C$_8$ heteroaliphatic, an optionally substituted C$_1$-C$_8$ heterohaloaliphatic, an optionally substituted ring, and (CH$_2$)$_m$R$^{14}$;
$R^8$ and $R^9$ are each independently selected from hydrogen, F, Cl, Br, CO$_2$R$^{10}$, NO$_2$, CN, SO$_2$R$^{10}$, (CH$_2$)$_m$R$^{14}$, C$_1$-C$_4$ aliphatic, C$_1$-C$_4$ haloaliphatic, C$_1$-C$_4$ heteroaliphatic, and C$_1$-C$_4$ heterohaloaliphatic;
$R^{10}$ is selected from hydrogen, an optionally substituted C$_1$-C$_4$ aliphatic, C$_1$-C$_4$ haloaliphatic, C$_1$-C$_4$ heteroaliphatic, and a ring;
$R^{11}$ is selected from hydrogen, SO$_2$R$^{15}$, C$_1$-C$_4$ aliphatic, C$_1$-C$_4$ haloaliphatic, C$_1$-C$_4$ heteroaliphatic, and a ring;
$R^{12}$ and $R^{13}$ are each independently selected from hydrogen, an optionally substituted C$_1$-C$_4$ aliphatic, an optionally substituted C$_1$-C$_4$ haloaliphatic, an optionally substituted C$_1$-C$_4$ heteroaliphatic, an optionally substituted ring, and (CH$_2$)$_m$R$^{14}$; or one of $R^{12}$ and $R^{13}$ is an optionally substituted C$_2$-C$_6$ aliphatic or an optionally substituted ring and the other of $R^{12}$ and $R^{13}$ is null; or $R^{12}$ and $R^{13}$ are linked to form an optionally substituted C$_3$-C$_8$ ring;
$R^{14}$ is selected from an optionally substituted aryl and an optionally substituted heteroaryl;
$R^{15}$ is selected from hydrogen, C$_1$-C$_3$ aliphatic, C$_1$-C$_3$ haloaliphatic, and a ring;
m is 0, 1, or 2; and
n is 0 or 1.

2. A compound of claim 1 wherein:
$R^1$ is selected from CO$_2$R$^{10}$, CONR$^{10}$R$^{11}$, SO$_3$R$^{10}$, and a carboxylic acid bioisostere selected from tetrazole, NHSO$_2$R$^{15}$, OC(S)NR$^{10}$R$^{11}$, SC(O)NR$^{10}$R$^{11}$, and

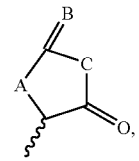

wherein A, B, and C are each independently selected from O, S, and N;
$R^2$ and $R^3$ are each independently selected from hydrogen, OR$^{12}$, NR$^{12}$R$^{13}$, an optionally substituted C$_1$-C$_4$ alkyl, an optionally substituted C$_1$-C$_4$ haloalkyl, an optionally substituted C$_1$-C$_4$ heteroalkyl, an optionally substituted ring, and (CH$_2$)$_m$R$^{14}$; or $R^2$ and $R^3$ taken together form an optionally substituted olefin; or $R^2$ and $R^3$ are linked to form an optionally substituted C$_3$-C$_8$ ring;
$R^4$ is selected from hydrogen, F, Cl, Br, C$_1$-C$_4$ alkyl, C$_1$-C$_4$ haloalkyl, C$_1$-C$_4$ heteroalkyl, and a non-aromatic ring;
$R^7$ is selected from hydrogen, an optionally substituted C$_1$-C$_8$ alkyl, an optionally substituted C$_1$-C$_8$ haloalkyl, an optionally substituted C$_1$-C$_8$ heteroalkyl, an optionally substituted C$_1$-C$_8$ heterohaloalkyl, an optionally substituted aromatic ring, and (CH$_2$)$_m$R$^{14}$;
$R^8$ and $R^9$ are each independently selected from hydrogen, F, Cl, Br, CO$_2$R$^{10}$, NO$_2$, CN, SO$_2$R$^{10}$, (CH$_2$)$_m$R$^4$, C$_1$-C$_4$ alkyl, C$_1$-C$_4$ haloalkyl, C$_1$-C$_4$ heteroalkyl, and C$_1$-C$_4$ heterohaloalkyl;
$R^{10}$ is selected from hydrogen, an optionally substituted C$_1$-C$_4$ alkyl, C$_1$-C$_4$ haloalkyl, C$_1$-C$_4$ heteroalkyl and a non-aromatic ring;
$R^{11}$ is selected from hydrogen, SO$_2$R$^{15}$, C$_1$-C$_4$ alkyl, C$_1$-C$_4$ haloalkyl, and C$_1$-C$_4$ heteroalkyl, and a non-aromatic ring;
$R^{12}$ and $R^{13}$ are each independently selected from hydrogen, an optionally substituted C$_1$-C$_4$ alkyl, an optionally substituted C$_1$-C$_4$ haloalkyl, an optionally substituted C$_1$-C$_4$ heteroalkyl, a non-aromatic ring, and (CH$_2$)$_m$R$^{14}$; or one of $R^{12}$ and $R^{13}$ is an optionally substituted C$_2$-C$_6$ alkyl or a non-aromatic ring, and the other of $R^{12}$ and $R^{13}$ is null; or $R^{12}$ and $R^{13}$ are linked to form an optionally substituted C$_3$-C$_8$ ring; and
$R^{15}$ is selected from hydrogen, C$_1$-C$_3$ alkyl, C$_1$-C$_3$ haloalkyl, and aryl.

3. The compound of claim 1 selected from:
3'-{N'-[1-(3,4-Dimethyl-phenyl)-2-oxo-1,2-dihydro-indol-3-ylidene]-hydrazino}-2'-hydroxy-biphenyl-3-carboxylic acid;

2'-Hydroxy-3'-{N'-[2-oxo-1-(4-propyl-phenyl)-1,2-dihydro-indol-3-ylidene]-hydrazino}-biphenyl-3-carboxylic acid;

2'-Hydroxy-3'-{N'-[2-oxo-1-(4-ethyl-phenyl)-1,2-dihydro-indol-3-ylidene]-hydrazino}-biphenyl-3-carboxylic acid;

2'-Hydroxy-3'-{N'-[2-oxo-1-(4-trifluoromethoxy-phenyl)-1,2-dihydro-indol-3-ylidene]-hydrazino}-biphenyl-3-carboxylic acid;

3'-{N'-[1-(3-Fluoro-4-methoxy-phenyl)-2-oxo-1,2-dihydro-indol-3-ylidene]-hydrazino}-2'-hydroxy-biphenyl-3-carboxylic acid;

3'-{N'-[1-(3,4-Dimethyl-phenyl)-2-oxo-1,2-dihydro-indol-3-ylidene]-hydrazino}-2'-hydroxy-biphenyl-4-carboxylic acid;

2'-Hydroxy-3'-{N'-[2-oxo-1-(4-propyl-phenyl)-1,2-dihydro-indol-3-ylidene]-hydrazino}-biphenyl-4-carboxylic acid;

2'-Hydroxy-3'-{N'-[2-oxo-1-(4-ethyl-phenyl)-1,2-dihydro-indol-3-ylidene]-hydrazino}-biphenyl-4-carboxylic acid;

3'-{N'-[1-(4-tert-Butyl-phenyl)-2-oxo-1,2-dihydro-indol-3-ylidene]-hydrazino}-2'-hydroxy-biphenyl-3-carboxylic acid;

2'-Hydroxy-3'-{N'-[2-oxo-1-(4-trifluoromethyl-phenyl)-1,2-dihydro-indol-3-ylidene]-hydrazino}-biphenyl-3-carboxylic acid;

3'-[N'-(1-Benzyl-5-chloro-2-oxo-1,2-dihydro-indol-3-ylidene)-hydrazino]-2'-hydroxy-biphenyl-3-carboxylic acid;

3'-[N'-(1-Benzyl-5-methyl-2-oxo-1,2-dihydro-indol-3-ylidene)-hydrazino]-2'-hydroxy-biphenyl-3-carboxylic acid;

3'-[N'-(1-Benzyl-2-oxo-1,2-dihydro-indol-3-ylidene)-hydrazino]-2'-hydroxy-biphenyl-3-carboxylic acid;

2'-Hydroxy-3'-{N'-[2-oxo-1-(4-trifluoromethyl-phenyl)-1,2-dihydro-indol-3-ylidene]-hydrazino}-biphenyl-4-carboxylic acid;

3'-{N'-[1-(3,4-Dichloro-phenyl)-2-oxo-1,2-dihydro-indol-3-ylidene]-hydrazino}-2'-hydroxy-biphenyl-3-carboxylic acid;

2'-Hydroxy-3'-{N'-[1-(4-methyl-3-trifluoromethyl-phenyl)-2-oxo-1,2-dihydro-indol-3-ylidene]-hydrazino}-biphenyl-3-carboxylic acid;

3'-{N'-[1-(3-Fluoro-4-trifluoromethyl-phenyl)-2-oxo-1,2-dihydro-indol-3-ylidene]-hydrazino}-2'-hydroxy-biphenyl-3-carboxylic acid;

3'-{N'-[1-(3,5-Bis-trifluoromethyl-phenyl)-2-oxo-1,2-dihydro-indol-3-ylidene]-hydrazino}-2'-hydroxy-biphenyl-3-carboxylic acid;

2'-Hydroxy-3'-{N'-[1-(4-isopropyl-phenyl)-2-oxo-1,2-dihydro-indol-3-ylidene]-hydrazino}-biphenyl-3-carboxylic acid;

3'-{N'-[1-(2-Fluoro-4-trifluoromethyl-phenyl)-2-oxo-1,2-dihydro-indol-3-ylidene]-hydrazino}-2'-hydroxy-biphenyl-3-carboxylic acid;

3'-{N'-[1-(2-Fluoro-4-methyl-phenyl)-2-oxo-1,2-dihydro-indol-3-ylidene]-hydrazino}-2'-hydroxy-biphenyl-3-carboxylic acid;

3'-{N'-[1-(4-Chloro-3-trifluoromethyl-phenyl)-2-oxo-1,2-dihydro-indol-3-ylidene]-hydrazino}-2'-hydroxy-biphenyl-3-carboxylic acid;

3'-{N'-[1-(4-Butyl-phenyl)-2-oxo-1,2-dihydro-indol-3-ylidene]-hydrazino}-2'-hydroxy-biphenyl-3-carboxylic acid;

3'-{N'-[1-(3-Fluoro-phenyl)-2-oxo-1,2-dihydro-indol-3-ylidene]-hydrazino}-2'-hydroxy-biphenyl-3-carboxylic acid;

2'-Hydroxy-3'-[N'-(2-oxo-1-m-tolyl-1,2-dihydro-indol-3-ylidene)-hydrazino]-biphenyl-3-carboxylic acid;

3'-{N'-[1-(4-Fluoro-phenyl)-2-oxo-1,2-dihydro-indol-3-ylidene]-hydrazino}-2'-hydroxy-biphenyl-3-carboxylic acid;

3'-[N'-(1-Benzyl-5-methoxy-2-oxo-1,2-dihydro-indol-3-ylidene)-hydrazino]-2'-hydroxy-biphenyl-3-carboxylic acid;

2'-Hydroxy-3'-{N'-[2-oxo-1-(3-trifluoromethyl-phenyl)-1,2-dihydro-indol-3-ylidene]-hydrazino}-biphenyl-3-carboxylic acid;

3'-{N'-[5-Chloro-1-(4-isopropyl-phenyl)-2-oxo-1,2-dihydro-indol-3-ylidene]-hydrazino}-2'-hydroxy-biphenyl-3-carboxylic acid;

3'-{N'-[6-Chloro-1-(4-isopropyl-phenyl)-2-oxo-1,2-dihydro-indol-3-ylidene]-hydrazino}-2'-hydroxy-biphenyl-3-carboxylic acid;

3'-{N'-[5-Fluoro-1-(4-isopropyl-phenyl)-2-oxo-1,2-dihydro-indol-3-ylidene]-hydrazino}-2'-hydroxy-biphenyl-3-carboxylic acid;

3'-{N'-[5-Methoxy-1-(4-isopropyl-phenyl)-2-oxo-1,2-dihydro-indol-3-ylidene]-hydrazino}-2'-hydroxy-biphenyl-3-carboxylic acid;

3'-{N'-[1-(3,4-Dimethyl-phenyl)-5-fluoro-2-oxo-1,2-dihydro-indol-3-ylidene]-hydrazino}-2'-hydroxy-biphenyl-3-carboxylic acid;

3'-{N'-[1-(4-Fluoro-3-trifluoromethyl-phenyl)-5-fluoro-2-oxo-1,2-dihydro-indol-3-ylidene]-hydrazino}-2'-hydroxy-biphenyl-3-carboxylic acid;

3'-{N'-[1-(3,5-Dichloro-phenyl)-5-fluoro-2-oxo-1,2-dihydro-indol-3-ylidene]-hydrazino}-2'-hydroxy-biphenyl-3-carboxylic acid;

3'-{N'-[1-(4-Propyl-phenyl)-6-chloro-2-oxo-1,2-dihydro-indol-3-ylidene]-hydrazino}-2'-hydroxy-biphenyl-3-carboxylic acid; and a pharmaceutically acceptable salt, ester, amide, thereof.

4. The compound of claim 1 selected from:

(±)-2'-Hydroxy-3'-(N'-{2-oxo-1-[4-(2,2,2-trifluoro-1-hydroxy-ethyl)-phenyl]-1,2-dihydro-indol-3-ylidene}-hydrazino)-biphenyl-3-carboxylic acid;

(±)-2'-Hydroxy-3'-(N'-{2-oxo-1-[4-(2,2,2-trifluoro-1-methoxy-ethyl)-phenyl]-1,2-dihydro-indol-3-ylidene}-hydrazino)-biphenyl-3-carboxylic acid;

2'-Hydroxy-3'-(1'-{2-oxo-1-[4-(2,2,2-trifluoro-ethyl)-phenyl]-1,2-dihydro-indol-3-ylidene}-hydrazino)-biphenyl-3-carboxylic acid;

3'-{N'-[1-(3,4-Dimethyl-phenyl)-4,5-dimethyl-2-oxo-1,2-dihydro-indol-3-ylidene]-hydrazino}-2'-hydroxy-biphenyl-3-carboxylic acid;

3'-{N'-[1-(3,4-Dimethyl-phenyl)-5-fluoro-4-methyl-2-oxo-1,2-dihydro-indol-3-ylidene]-hydrazino}-2'-hydroxy-biphenyl-3-carboxylic acid;

3'-{N'-[1-(3,4-Dimethyl-phenyl)-5-fluoro-6-methyl-2-oxo-1,2-dihydro-indol-3-ylidene]-hydrazino}-2'-hydroxy-biphenyl-3-carboxylic acid;

3'-{1-[1-(3,4-Dimethyl-phenyl)-4-fluoro-2-oxo-6-trifluoromethyl-1,2-dihydro-indol-3-ylidene]-hydrazino}-2'-hydroxy-biphenyl-3-carboxylic acid;

3'-{N'-[4-Chloro-1-(3,4-dimethyl-phenyl)-2-oxo-6-trifluoromethyl-1,2-dihydro-indol-3-ylidene]-hydrazino}-2'-hydroxy-biphenyl-3-carboxylic acid;

3'-{N'-[5-Chloro-2-oxo-1-(4-propyl-phenyl)-1,2-dihydro-indol-3-ylidene]-hydrazino}-2'-hydroxy-biphenyl-3-carboxylic acid;

2'-Hydroxy-3'-{N'-[1-(4-methylsulfanyl-phenyl)-2-oxo-1,2-dihydro-indol-3-ylidene]-hydrazino}-biphenyl-3-carboxylic acid;
2'-Hydroxy-3'-{N'-[1-(4-methoxymethyl-phenyl)-2-oxo-1,2-dihydro-indol-3-ylidene]-hydrazino}-biphenyl-3-carboxylic acid;
(±)-2'-Hydroxy-3'-(N'-{2-oxo-1-[4-(2,2,2-trifluoro-1-hydroxy-1-methyl-ethyl)-phenyl]-1,2-dihydro-indol-3-ylidene}-hydrazino)-biphenyl-3-carboxylic acid;
3'-{N'-[5-Fluoro-1-(4-methyl-3-trifluoromethyl-phenyl)-2-oxo-1,2-dihydro-indol-3-ylidene]-hydrazino}-2'-hydroxy-biphenyl-3-carboxylic acid;
2'-Hydroxy-3'-(N'-{2-oxo-1-[4-(2,2,2-trifluoro-1-methoxy-1-methyl-ethyl)-phenyl]-1,2-dihydro-indol-3-ylidene}-hydrazino)-biphenyl-3-carboxylic acid;
3'-{N'-[1-(3,4-Dimethyl-phenyl)-6-fluoro-2-oxo-1,2-dihydro-indol-3-ylidene]-hydrazino}-2'-hydroxy-biphenyl-3-carboxylic acid;
3'-{N'-[6-Fluoro-1-(4-isopropyl-phenyl)-2-oxo-1,2-dihydro-indol-3-ylidene]-hydrazino}-2'-hydroxy-biphenyl-3-carboxylic acid;
3'-{N'-[1-(3,4-Dimethyl-phenyl)-2-oxo-5-trifluoromethyl-1,2-dihydro-indol-3-ylidene]-hydrazino}-2'-hydroxy-biphenyl-3-carboxylic acid;
3'-{N'-[6-Fluoro-2-oxo-1-(4-propyl-phenyl)-1,2-dihydro-indol-3-ylidene]-hydrazino}-2'-hydroxy-biphenyl-3-carboxylic acid;
2'-Hydroxy-3'-{N'-[2-oxo-1-(4-propyl-phenyl)-5-trifluoromethyl-1,2-dihydro-indol-3-ylidene]-hydrazino}-biphenyl-3-carboxylic acid;
3'-{N'-[4,5-Difluoro-1-(4-isopropyl-phenyl)-2-oxo-1,2-dihydro-indol-3-ylidene]-hydrazino}-2'-hydroxy-biphenyl-3-carboxylic acid;
2'-Hydroxy-3'-[N'-(2-oxo-1-piperidin-4-yl-1,2-dihydro-indol-3-ylidene)-hydrazino]-biphenyl-3-carboxylic acid;
3'-{N'-[5-Fluoro-1-(2-fluoro-4-methyl-phenyl)-2-oxo-1,2-dihydro-indol-3-ylidene]-hydrazino}-2'-hydroxy-biphenyl-3-carboxylic acid;
2'-Hydroxy-3'-[N'-(1-methyl-2-oxo-1,2-dihydro-indol-3-ylidene)-hydrazino]-biphenyl-3-carboxylic acid;
3'-[N'-(1-Cyclopentyl-2-oxo-1,2-dihydro-indol-3-ylidene)-hydrazino]-2'-hydroxy-biphenyl-3-carboxylic acid;
3'-{N'-[1-(3,4-Dimethyl-phenyl)-6-methyl-2-oxo-1,2-dihydro-indol-3-ylidene]-hydrazino}-2'-hydroxy-biphenyl-3-carboxylic acid;
2'-Hydroxy-3'-[N'-(2-oxo-1-phenyl-1,2-dihydro-indol-3-ylidene)-hydrazino]-biphenyl-3-carboxylic acid;
3'-[N'-(6-Fluoro-2-oxo-1-phenyl-2,3-dihydro-1H-indol-3-yl)-hydrazino]-2'-hydroxy-biphenyl-3-carboxylic acid;
3'-{N'-[1-(3,4-Dimethyl-phenyl)-6-isopropyl-2-oxo-1,2-dihydro-indol-3-ylidene]-hydrazino}-2'-hydroxy-biphenyl-3-carboxylic acid;
3'-{N'-[1-(3,4-Dimethyl-phenyl)-4-isopropyl-2-oxo-1,2-dihydro-indol-3-ylidene]-hydrazino}-2'-hydroxy-biphenyl-3-carboxylic acid;
3'-{N'-[1-(3,4-Dimethyl-phenyl)-2-oxo-6-trifluoromethyl-1,2-dihydro-indol-3-ylidene]-hydrazino}-4-fluoro-2'-hydroxy-biphenyl-3-carboxylic acid;
5'-Chloro-3'-{N'-[1-(3,4-dimethyl-phenyl)-2-oxo-6-trifluoromethyl-1,2-dihydro-indol-3-ylidene]-hydrazino}-4-fluoro-2'-hydroxy-biphenyl-3-carboxylic acid;
3'-{N'-[1-(3,4-Dimethyl-phenyl)-2-oxo-6-trifluoromethyl-1,2-dihydro-indol-3-ylidene]-hydrazino}-6-fluoro-2'-hydroxy-biphenyl-3-carboxylic acid;
3'-{N'-[1-(3,4-Dimethyl-phenyl)-4,5-difluoro-2-oxo-1,2-dihydro-indol-3-ylidene]-hydrazino}-2'-hydroxy-biphenyl-3-carboxylic acid;
3'-{N'-[1-(3,4-Dimethyl-phenyl)-2-oxo-6-trifluoromethyl-1,2-dihydro-indol-3-ylidene]-hydrazino}-2'-hydroxy-3-methyl-biphenyl-4-carboxylic acid;
3'-{N'-[1-(3,4-Dimethyl-phenyl)-2-oxo-6-trifluoromethyl-2,3-dihydro-1H-indol-3-yl]-hydrazino}-2-fluoro-2'-hydroxy-biphenyl-4-carboxylic acid;
3'-{N'-[1-(3,4-Dimethyl-phenyl)-4-fluoro-2-oxo-6-trifluoromethyl-2,3-dihydro-1H-indol-3-yl]-hydrazino}-4-fluoro-2'-hydroxy-biphenyl-3-carboxylic acid;
5'-Chloro-3'-{N'-[1-(3,4-dimethyl-phenyl)-4-fluoro-2-oxo-6-trifluoromethyl-1,2-dihydro-indol-3-ylidene]-hydrazino}-4-fluoro-2'-hydroxy-biphenyl-3-carboxylic acid;
3-[(3'-Carboxy-2-hydroxy-biphenyl-3-yl)-hydrazono]-1-(3,5-dimethyl-phenyl)-2-oxo-2,3-dihydro-1H-indole-6-carboxylic acid methyl ester;
3-[(3'-Carboxy-4'-fluoro-2-hydroxy-biphenyl-3-yl)-hydrazono]-1-(3,5-dimethyl-phenyl)-2-oxo-2,3-dihydro-1H-indole-6-carboxylic acid methyl ester;
3-[(3'-Carboxy-4'-fluoro-2-hydroxy-biphenyl-3-yl)-hydrazono]-1-(3,4-dimethyl-phenyl)-2-oxo-2,3-dihydro-1H-indole-6-carboxylic acid methyl ester;
3-[(3'-Carboxy-5-chloro-4'-fluoro-2-hydroxy-biphenyl-3-yl)-hydrazono]-1-(3,5-dimethyl-phenyl)-2-oxo-2,3-dihydro-1H-indole-6-carboxylic acid methyl ester;
3'-{N'-[1-(2-Cyano-thiophen-3-yl)-2-oxo-1,2-dihydro-indol-3-ylidene]-hydrazino}-2'-hydroxy-biphenyl-3-carboxylic acid;
2'-Hydroxy-3'-[N'-(2-oxo-1-thiophen-3-yl-1,2-dihydro-indol-3-ylidene)-hydrazino]-biphenyl-3-carboxylic acid;
3-[(3'-Carboxy-2-hydroxy-biphenyl-3-yl)-hydrazono]-1-(3,4-dimethyl-phenyl)-2-oxo-2,3-dihydro-1H-indole-6-carboxylic acid methyl ester;
3'-{N'-[1-(4-Chloro-3-trifluoromethyl-phenyl)-6-cyano-2-oxo-1,2-dihydro-indol-3-ylidene]-hydrazino}-2'-hydroxy-biphenyl-3-carboxylic acid;
5'-Chloro-3'-{N'-[6-cyano-1-(4-isopropyl-phenyl)-2-oxo-1,2-dihydro-indol-3-ylidene]-hydrazino}-4-fluoro-2'-hydroxy-biphenyl-3-carboxylic acid;
3'-{N'-[6-Cyano-1-(4-isopropyl-phenyl)-2-oxo-1,2-dihydro-indol-3-ylidene]-hydrazino}-4-fluoro-2'-hydroxy-biphenyl-3-carboxylic acid;
(±)-1-(3,4-Dimethyl-phenyl)-3-{[2-hydroxy-3'-(2,2,2-trifluoro-1-hydroxy-ethyl)-biphenyl-3-yl]-hydrazono}-6-methanesulfonyl-1,3-dihydro-indol-2-one;
3'-{N'-[6-Cyano-1-(4-isopropyl-phenyl)-2-oxo-1,2-dihydro-indol-3-ylidene]-hydrazino}-2'-hydroxy-biphenyl-3-carboxylic acid;
3'-{N'-[1-(3,4-Dimethyl-phenyl)-5-nitro-2-oxo-1,2-dihydro-indol-3-ylidene]-hydrazino}-2'-hydroxy-biphenyl-3-carboxylic acid;
3'-{N'-[1-(3,4-Dimethyl-phenyl)-6-methanesulfonyl-2-oxo-1,2-dihydro-indol-3-ylidene]-hydrazino}-2'-hydroxy-biphenyl-3-carboxylic acid;
3'-{N'-[6-Cyano-1-(3,4-dimethyl-phenyl)-2-oxo-1,2-dihydro-indol-3-ylidene]-hydrazino}-2'-hydroxy-biphenyl-3-carboxylic acid;
3'-{N'-[1-(5-Cyano-pyridin-3-yl)-2-oxo-1,2-dihydro-indol-3-ylidene]-hydrazino}-2'-hydroxy-biphenyl-3-carboxylic acid;
3'-[N'-(1-Furan-3-yl-2-oxo-1,2-dihydro-indol-3-ylidene)-hydrazino]-2'-hydroxy-biphenyl-3-carboxylic acid;

3'-[N'-(1-Benzo[1,3]dioxol-5-yl-2-oxo-1,2-dihydro-indol-3-ylidene)-hydrazino]-2'-hydroxy-biphenyl-3-carboxylic acid;

2'-Hydroxy-3'-{N'-[1-(3-methyl-thiophen-2-yl)-2-oxo-1,2-dihydro-indol-3-ylidene]-hydrazino}-biphenyl-3-carboxylic acid;

2'-Hydroxy-3'-[N'-(2-oxo-1-thiophen-2-yl-1,2-dihydro-indol-3-ylidene)-hydrazino]-biphenyl-3-carboxylic acid;

2'-Hydroxy-3'-{N'-[1-(4-isopropyl-phenyl)-2-oxo-6-trifluoromethyl-1,2-dihydro-indol-3-ylidene]-hydrazino}-biphenyl-3-carboxylic acid;

2'-Hydroxy-3'-{N'-[2-oxo-1-(4-propyl-phenyl)-6-trifluoromethyl-1,2-dihydro-indol-3-ylidene]-hydrazino}-biphenyl-3-carboxylic acid;

3'-{N'-[1-(4-Ethyl-phenyl)-5,7-difluoro-2-oxo-1,2-dihydro-indol-3-ylidene]-hydrazino}-2'-hydroxy-biphenyl-3-carboxylic acid;

3'-{N'-[1-(3,4-Dimethyl-phenyl)-5,7-difluoro-2-oxo-1,2-dihydro-indol-3-ylidene]-hydrazino}-2'-hydroxy-biphenyl-3-carboxylic acid;

3'-{N'-[5,7-Difluoro-2-oxo-1-(4-propyl-phenyl)-1,2-dihydro-indol-3-ylidene]-hydrazino}-2'-hydroxy-biphenyl-3-carboxylic acid;

3'-{N'-[5,7-Difluoro-1-(4-isopropyl-phenyl)-2-oxo-1,2-dihydro-indol-3-ylidene]-hydrazino}-2'-hydroxy-biphenyl-3-carboxylic acid;

3'-{N'-[1-(3,4-Dimethyl-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,4-Dimethyl-phenyl)-6-ethyl-2-oxo-1,2-dihydro-indol-3-ylidene]-hydrazino}-2'-hydroxy-biphenyl-3-carboxylic acid;

3'-{N'-[1-(3,4-Dimethyl-phenyl)-6-methoxy-2-oxo-1,2-dihydro-indol-3-ylidene]-hydrazino}-2'-hydroxy-biphenyl-3-carboxylic acid;

3'-{N'-[5-Chloro-1-(3,4-dimethyl-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,4-Dimethyl-phenyl)-6,7-dimethyl-2-oxo-1,2-dihydro-indol-3-ylidene]-hydrazino}-2'-hydroxy-biphenyl-3-carboxylic acid;

2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-2-methyl-propionic acid;

(−)-2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-propionic acid;

(+)-2-(3'-{N'-[1-(3,4-Dimethyl-phenyl)-2-oxo-6-trifluoromethyl-1,2-dihydro-indol-3-ylidene]-hydrazino}-2'-hydroxy-biphenyl-4-yl)-propionic acid;

(±)-(3'-{N'-[1-(3,4-Dimethyl-phenyl)-2-oxo-6-trifluoromethyl-1,2-dihydro-indol-3-ylidene]-hydrazino}-2'-hydroxy-5'-methyl-biphenyl-4-yl)-propionic acid;

(±)-2-(3'-{N'-[1-(3,4-Dimethyl-phenyl)-2-oxo-6-trifluoromethyl-1,2-dihydro-indol-3-ylidene]-hydrazino}-5'-fluoro-2'-hydroxy-biphenyl-4-yl)-propionic acid;

3'-{N'-[1-(3,4-Dimethyl-phenyl)-2-oxo-6-trifluoromethyl-1,2-dihydro-indol-3-ylidene]-hydrazino}-5'-fluoro-2'-hydroxy-biphenyl-3-carboxylic acid;

5'-Chloro-3'-{N'-[1-(3,4-dimethyl-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,4-Dimethyl-phenyl)-2-oxo-6-trifluoromethyl-1,2-dihydro-indol-3-ylidene]-hydrazino}-2'-hydroxy-5'-methyl-biphenyl-3-carboxylic acid;

2'-Hydroxy-3'-{N'-[2-oxo-6-trifluoromethyl-1-(4-trifluoromethyl-phenyl)-1,2-dihydro-indol-3-ylidene]-hydrazino}-biphenyl-3-carboxylic acid;

3'-{N'-[1-(4-Ethyl-3-methyl-phenyl)-2-oxo-6-trifluoromethyl-1,2-dihydro-indol-3-ylidene]-hydrazino}-2'-hydroxy-biphenyl-3-carboxylic acid;

3'-{N'-[1-(4-Chloro-3-trifluoromethyl-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,5-Dimethyl-phenyl)-2-oxo-6-trifluoromethyl-1,2-dihydro-indol-3-ylidene]-hydrazino}-5'-fluoro-2'-hydroxy-biphenyl-3-carboxylic acid;

3'-{N'-[1-(3,4-Dimethyl-phenyl)-2-oxo-6-trifluoromethyl-1,2-dihydro-indol-3-ylidene]-hydrazino}-4,5'-difluoro-2'-hydroxy-biphenyl-3-carboxylic acid;

3'-{N'-[1-(3,5-Dimethyl-phenyl)-2-oxo-6-trifluoromethyl-1,2-dihydro-indol-3-ylidene]-hydrazino}-4,5'-difluoro-2'-hydroxy-biphenyl-3-carboxylic acid;

4,5'-Difluoro-2'-hydroxy-3'-{N'-[2-oxo-6-trifluoromethyl-1-(4-trifluoromethyl-phenyl)-1,2-dihydro-indol-3-ylidene]-hydrazino}-biphenyl-3-carboxylic acid;

3'-{N'-[1-(4-Fluoro-3,5-dimethyl-phenyl)-2-oxo-6-trifluoromethyl-1,2-dihydro-indol-3-ylidene]-hydrazino}-2'-hydroxy-biphenyl-3-carboxylic acid;

2'-Hydroxy-3'-{N'-[1-(4-methoxy-phenyl)-2-oxo-6-trifluoromethyl-1,2-dihydro-indol-3-ylidene]-hydrazino}-biphenyl-3-carboxylic acid;

3'-{N'-[1-(4-Fluoro-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,5-Dimethoxy-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,4-Dimethoxy-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,5-Difluoro-phenyl)-2-oxo-6-trifluoromethyl-1,2-dihydro-indol-3-ylidene]-hydrazino}-2'-hydroxy-biphenyl-3-carboxylic acid;

5'-Fluoro-3'-{N'-[1-(4-fluoro-3,5-dimethyl-phenyl)-2-oxo-6-trifluoromethyl-1,2-dihydro-indol-3-ylidene]-hydrazino}-2'-hydroxy-biphenyl-3-carboxylic acid;

4,5'-Difluoro-3'-{N'-[1-(4-fluoro-3,5-dimethyl-phenyl)-2-oxo-6-trifluoromethyl-1,2-dihydro-indol-3-ylidene]-hydrazino}-2'-hydroxy-biphenyl-3-carboxylic acid;

2'-Hydroxy-3'-{N'-[1-(4-methoxy-3,5-dimethyl-phenyl)-2-oxo-6-trifluoromethyl-1,2-dihydro-indol-3-ylidene]-hydrazino}-biphenyl-3-carboxylic acid;

2'-Hydroxy-3'-{N'-[1-(4-hydroxy-3,5-dimethyl-phenyl)-2-oxo-6-trifluoromethyl-1,2-dihydro-indol-3-ylidene]-hydrazino}-biphenyl-3-carboxylic acid;

3'-{N'-[1-(4-Cyclohexyl-phenyl)-2-oxo-1,2-dihydro-indol-3-ylidene]-hydrazino}-2'-hydroxy-biphenyl-3-carboxylic acid;

2'-Hydroxy-3'-[N'-(2-oxo-1-pyridin-2-yl-1,2-dihydro-indol-3-ylidene)-hydrazino]-biphenyl-3-carboxylic acid;

2'-Hydroxy-3'-[N'-(2-oxo-1-pyridin-3-yl-1,2-dihydro-indol-3-ylidene)-hydrazino]-biphenyl-3-carboxylic acid;

3'-{N'-[1-(4-Ethyl-phenyl)-2-oxo-6-trifluoromethyl-1,2-dihydro-indol-3-ylidene]-hydrazino}-2'-hydroxy-biphenyl-3-carboxylic acid;

3'-{N'-[1-(4-Ethyl-phenyl)-4-fluoro-2-oxo-6-trifluoromethyl-1,2-dihydro-indol-3-ylidene]-hydrazino}-2'-hydroxy-biphenyl-3-carboxylic acid;

3-[(3'-Carboxy-2-hydroxy-biphenyl-3-yl)-hydrazono]-1-(3,5-dimethyl-phenyl)-2-oxo-2,3-dihydro-1-H-indole-5-carboxylic acid methyl ester;

3'-{N'-[1-(3-Chloro-4-methyl-phenyl)-2-oxo-6-trifluoromethyl-1,2-dihydro-indol-3-ylidene]-hydrazino}-2'-hydroxy-biphenyl-3-carboxylic acid;

2'-Hydroxy-3'-(N'-{2-oxo-1-[4-(4,4,4-trifluoro-butyl)-phenyl]-1,2-dihydro-indol-3-ylidene}-hydrazino)-biphenyl-3-carboxylic acid;

3'-{N'-[1-(3,5-Dimethyl-phenyl)-4-fluoro-2-oxo-6-trifluoromethyl-1,2-dihydro-indol-3-ylidene]-hydrazino}-2'-hydroxy-biphenyl-3-carboxylic acid;

3'-{N'-[1-(4-tert-Butyl-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,4-Dimethyl-phenyl)-2-oxo-6-trifluoromethyl-1,2-dihydro-indol-3-ylidene]-hydrazino}-2'-hydroxy-biphenyl-4-carboxylic acid;

3'-{N'-[1-(3,4-Dimethyl-phenyl)-2-oxo-6-bromo-1,2-dihydro-indol-3-ylidene]-hydrazino}-2'-hydroxy-biphenyl-3-carboxylic acid;

3'-{N'-[1-(3,4-Dimethyl-phenyl)-2-oxo-6-trifluoromethyl-1,2-dihydro-indol-3-ylidene]-hydrazino}-3-fluoro-2'-hydroxy-biphenyl-4-carboxylic acid;

3'-{N'-[1-(3,5-Bis-trifluoromethyl-phenyl)-2-oxo-6-trifluoromethyl-1,2-dihydro-indol-3-ylidene]-hydrazino}-2'-hydroxy-biphenyl-3-carboxylic acid;

3'-{N'-[1-(3,4-Dichloro-phenyl)-2-oxo-6-trifluoromethyl-1,2-dihydro-indol-3-ylidene]-hydrazino}-2'-hydroxy-biphenyl-3-carboxylic acid;

2'-Hydroxy-3'-[N'-(2-oxo-7-phenyl-1,2-dihydro-indol-3-ylidene)-hydrazino]-biphenyl-3-carboxylic acid;

3'-{N'-[1-(3,4-Dimethyl-phenyl)-2-oxo-6-trifluoromethoxy-1,2-dihydro-indol-3-ylidene]-hydrazino}-2'-hydroxy-biphenyl-3-carboxylic acid;

3'-{N'-[1-(3,4-Dimethyl-phenyl)-2-oxo-6-(1,1,2,2-tetrafluoro-ethoxy)-1,2-dihydro-indol-3-ylidene]-hydrazino}-2'-hydroxy-biphenyl-3-carboxylic acid;

3'-{N'-[1-(3,4-Dimethyl-phenyl)-5-methyl-2-oxo-1,2-dihydro-indol-3-ylidene]-hydrazino}-2'-hydroxy-biphenyl-3-carboxylic acid;

3'-{N'-[1-(4-Isopropyl-phenyl)-5-methyl-2-oxo-1,2-dihydro-indol-3-ylidene]-hydrazino}-2'-hydroxy-biphenyl-3-carboxylic acid;

3'-{N'-[1-(3,4-Dimethyl-phenyl)-6-phenyl-2-oxo-1,2-dihydro-indol-3-ylidene]-hydrazino}-2'-hydroxy-biphenyl-3-carboxylic acid;

3'-{N'-[1-(3-Trifluoromethyl-phenyl)-6-trifluoromethyl-2-oxo-1,2-dihydro-indol-3-ylidene]-hydrazino}-2'-hydroxy-biphenyl-3-carboxylic acid;

3'-{N'-[1-(4-Trifluoromethoxy-phenyl)-5-trifluoromethoxy-2-oxo-1,2-dihydro-indol-3-ylidene]-hydrazino}-2'-hydroxy-biphenyl-3-carboxylic acid;

3'-{N'-[1-(3,5-Dimethyl-phenyl)-6-trifluoromethyl-2-oxo-1,2-dihydro-indol-3-ylidene]-hydrazino}-2'-hydroxy-biphenyl-3-carboxylic acid;

3'-{N'-[1-(3-Trifluoromethyl-phenyl)-4,6-dimethyl-2-oxo-1,2-dihydro-indol-3-ylidene]-hydrazino}-2'-hydroxy-biphenyl-3-carboxylic acid;

3'-{N'-[1-(3-Trifluoromethyl-phenyl)-5,6-dimethyl-2-oxo-1,2-dihydro-indol-3-ylidene]-hydrazino}-2'-hydroxy-biphenyl-3-carboxylic acid;

3'-{N'-[1-(3,5-Dimethyl-phenyl)-6-trifluoromethyl-2-oxo-1,2-dihydro-indol-3-ylidene]-hydrazino}-2'-hydroxy-5'-chloro-4-fluoro-biphenyl-3-carboxylic acid;

3'-{N'-[1-(3,5-Dimethyl-phenyl)-6-trifluoromethyl-2-oxo-1,2-dihydro-indol-3-ylidene]-hydrazino}-2'-hydroxy-4-fluoro-biphenyl-3-carboxylic acid;

3'-{N'-[6-Chloro-1-(3,4-dimethyl-phenyl)-2-oxo-1,2-dihydro-indol-3-ylidene]-hydrazino}-2'-hydroxy-biphenyl-3-carboxylic acid;

3'-{N'-[5-Fluoro-2-oxo-1-(4-propyl-phenyl)-1,2-dihydro-indol-3-ylidene]-hydrazino}-2'-hydroxy-biphenyl-3-carboxylic acid;

3'-{N'-[5-Cyano-1-(3,4-dimethyl-phenyl)-2-oxo-1,2-dihydro-indol-3-ylidene]-hydrazino}-2'-hydroxy-biphenyl-3-carboxylic acid;

3'-{N'-[6-Chloro-1-(3,5-dimethyl-phenyl)-2-oxo-1,2-dihydro-indol-3-ylidene]-hydrazino}-2'-hydroxy-biphenyl-3-carboxylic acid;

4-Fluoro-3'-{N'-[1-(3-fluoro-4-methyl-phenyl)-2-oxo-6-trifluoromethyl-1,2-dihydro-indol-3-ylidene]-hydrazino}-2'-hydroxy-biphenyl-3-carboxylic acid; and a pharmaceutically acceptable sale ester, and amide thereof.

5. The compound of claim 1 selected from:

3'-{N'-[1-(4-Chloro-3,5-dimethylphenyl)-2-oxo-6-trifluoromethyl-1,2-dihydroindol-3-ylidene]hydrazino}-2'-hydroxy-biphenyl-3-carboxylic acid;

3'-{N'-[1-(3,5-Dimethylphenyl)-4-fluoro-2-oxo-6-trifluoromethyl-1,2-dihydroindol-3-ylidene]hydrazino}-2'-hydroxybiphenyl-4-fluoro-3-carboxylic acid;

3'-{N'-[1-Benzo[1,3]dioxo-5-yl-2-oxo-6-trifluoromethyl-1,2-dihydroindol-3-ylidene]hydrazino}-2'-hydroxybiphenyl-3-carboxylic acid;

3'-{N'-[1-Benzo[1,3]dioxo-5-yl-2-oxo-6-trifluoromethyl-1,2-dihydroindol-3-ylidene]hydrazino}-2'-hydroxybiphenyl-2-fluoro-3-carboxylic acid;

3'-{N'-[1-(3,5-Dimethylphenyl)-2-oxo-6-trifluoromethyl-1,2-dihydroindol-3-ylidene]hydrazino}-2'-hydroxybiphenyl-2-hydroxy-3-carboxylic acid;

3'-{N'-[1-(3-Methoxycarbonylphenyl)-2-oxo-6-trifluoromethyl-1,2-dihydroindol-3-ylidene]hydrazino}-2'-hydroxybiphenyl-3-carboxylic acid;

3'-{N'-[1-(3-Methoxycarbonylphenyl)-2-oxo-1,2-dihydroindol-3-ylidene]hydrazino}-2'-hydroxybiphenyl-3-carboxylic acid;

3'-{N'-[1-(3,5-Dimethylphenyl)-2-oxo-1,2-dihydroindol-6-trifluoromethyl-3-ylidene]hydrazino}-2'-hydroxybiphenyl-3-(2-methyl-2-propionic acid); and a pharmaceutically acceptable salt, ester, and amide thereof.

6. A compound of claim 1 that is a selective TPO modulator.

7. A compound of claim 6 that is a TPO mimic.

8. A compound of claim 6 that is a selective TPO receptor agonist.

9. A compound of claim 6 that is a selective TPO receptor partial agonist.

10. A compound of claim 6 that is a selective TPO receptor antagonist.

11. A compound of claim 1 that is a selective TPO receptor binding compound.

12. A method for modulating a TPO activity in a cell comprising contacting a cell with a compound of claim 1.

13. A method of treating thrombocytopenia in a patient in need thereof with a compound of claim 1.

14. The method of claim 13 wherein the thrombocytopenia results from radiation or chemotherapy.

15. The method of claim 13 further comprising harvesting cells from the patient.

16. A pharmaceutical composition comprising a physiologically acceptable carrier, diluent, or excipient; and a compound of claim 1.

17. The pharmaceutical composition of claim 16 for use in treating a condition thrombocytopenia.

18. The compound of claim 1, wherein:
$R^1$ is $CO_2R^{10}$;
$R^2$ and $R^3$ are each null;
$R^4$ is hydrogen;
$R^5$ is $OR^{10}$;
$R^6$ is hydrogen;
$R^7$ is phenyl substituted with alkyl;
$R^8$ is hydrogen, F, Cl, or Br;
$R^9$ is F, Cl, Br, or $C_1$-$C_4$ haloalkyl;
$R^{10}$ is hydrogen; and
n is 0.

19. The compound of claim 18, selected from 3'-{N'-[6-Chloro-1-(4-isopropyl-phenyl)-2-oxo-1,2-dihydro-indol-3-ylidene]-hydrazino}-2'-hydroxy-biphenyl-3-carboxylic acid, and a pharmaceutically acceptable salt thereof.

20. The compound of claim 18, selected from 3'-{N'-[1-(4-Propyl-phenyl)-6-chloro-2-oxo-1,2-dihydro-indol-3-ylidene]-hydrazino}-2'-hydroxy-biphenyl-3-carboxylic acid, and a pharmaceutically acceptable salt thereof.

21. The compound of claim 18, selected from 3'-{N'-[1-(3,4-Dimethyl-phenyl)-4-fluoro-2-oxo-6-trifluoromethyl-1,2-dihydro-indol-3-ylidene]-hydrazino}-2'-hydroxy-biphenyl-3-carboxylic acid, and a pharmaceutically acceptable salt thereof.

22. The compound of claim 18, selected from 3'-{N'-[1-(3,4-Dimethyl-phenyl)-6-fluoro-2-oxo-1,2-dihydro-indol-3-ylidene]-hydrazino}-2'-hydroxy-biphenyl-3-carboxylic acid, and a pharmaceutically acceptable salt thereof.

23. The compound of claim 18, selected from 3'-{N'-[6-Fluoro-1-(4-isopropyl-phenyl)-2-oxo-1,2-dihydro-indol-3-ylidene]-hydrazino}-2'-hydroxy-biphenyl-3-carboxylic acid, and a pharmaceutically acceptable salt thereof.

24. The compound of claim 18, selected from 3'-{N'-[6-Fluoro-2-oxo-1-(4-propyl-phenyl)-1,2-dihydro-indol-3-ylidene]-hydrazino}-2'-hydroxy-biphenyl-3-carboxylic acid, and a pharmaceutically acceptable salt thereof.

25. The compound of claim 18, selected from 2'-Hydroxy-3'-{N'-[1-(4-isopropyl-phenyl)-2-oxo-6-trifluoromethyl-1,2-dihydro-indol-3-ylidene]-hydrazino}-biphenyl-3-carboxylic acid, and a pharmaceutically acceptable salt thereof.

26. The compound of claim 18, selected from 2'-Hydroxy-3'-{N'-[2-oxo-1-(4-propyl-phenyl)-6-trifluoromethyl-1,2-dihydro-indol-3-ylidene]-hydrazino}-biphenyl-3-carboxylic acid, or a pharmaceutically acceptable salt thereof.

27. The compound of claim 18, selected from 3'-{N'-[1-(3,4-Dimethyl-phenyl)-2-oxo-6-trifluoromethyl-1,2-dihydro-indol-3-ylidene]-hydrazino}-2'-hydroxy-biphenyl-3-carboxylic acid, and a pharmaceutically acceptable salt thereof.

28. The compound of claim 18, selected from 3'-{N-[1-(4-Ethyl-phenyl)-2-oxo-6-trifluoromethyl-1,2-dihydro-indol-3-ylidene]-hydrazino}-2'-hydroxy-biphenyl-3-carboxylic acid, and a pharmaceutically acceptable salt thereof.

29. The compound of claim 18, selected from 3'-{N'-[1-(4-Ethyl-phenyl)-4-fluoro-2-oxo-6-trifluoromethyl-1,2-dihydro-indol-3-ylidene]-hydrazino}-2'-hydroxy-biphenyl-3-carboxylic acid, and a pharmaceutically acceptable salt thereof.

30. The compound of claim 18, selected from 3-{N'-[1-(3,5-Dimethyl-phenyl)-4-fluoro-2-oxo-6-trifluoromethyl-1,2-dihydro-indol-3-ylidene]-hydrazino}-2-hydroxy-biphenyl-3-carboxylic acid, and a pharmaceutically acceptable salt thereof.

31. The compound of claim 18, selected from 3'-{N-[1-(3,5-Dimethyl-phenyl)-6-trifluoromethyl-2-oxo-1,2-dihydro-indol-3-ylidene]-hydrazino}-2'-hydroxy-biphenyl-3-carboxylic acid, and a pharmaceutically acceptable salt thereof.

32. The compound of claim 18, selected from 3'-{N'-[6-Chloro-1-(3,4-dimethyl-phenyl)-2-oxo-1,2-dihydro-indol-3-ylidene]-hydrazino}-2'-hydroxy-biphenyl-3-carboxylic acid, and a pharmaceutically acceptable salt thereof.

33. The compound of claim 18, selected from 3'-{N'-[6-Chloro-1-(3,5-dimethyl-phenyl)-2-oxo-1,2-dihydro-indol-3-ylidene]-hydrazino}-2'-hydroxy-biphenyl-3-carboxylic acid, and a pharmaceutically acceptable salt thereof.

34. The compound of claim 1 wherein:
R is selected from $CO_2R^{10}$, $CONR^{10}R^{11}$, $SO_3R^{10}$, and a carboxylic acid bioisostere selected from tetrazole, $NHSO_2R^{15}$, $OC(S)NR^{10}R^{11}$, $SC(O)NR^{10}R^{11}$, and

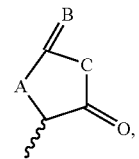

wherein A, B, and C are each independently selected from O, S, and N;
$R^2$ and $R^3$ are each independently selected from hydrogen, $OR^{12}$, $NR^{12}R^{13}$, an optionally substituted $C_1$-$C_4$ alkyl, an optionally substituted $C_1$-$C_4$ haloalkyl, an optionally substituted $C_1$-$C_4$ heteroalkyl, and $(CH_2)_mR^{14}$;
$R^4$ is selected from hydrogen, F, Cl, Br, $C_1$-$C_4$ alkyl, $C_1$-$C_4$ haloalkyl, and $C_1$-$C_4$ heteroalkyl;
$R^5$ is selected from $OR^{10}$, $SR^{10}$, $NHR^{11}$, and $CO_2H$;
$R^7$ is selected from hydrogen, an optionally substituted $C_1$-$C_8$ alkyl, an optionally substituted $C_1$-$C_8$ haloalkyl, an optionally substituted $C_1$-$C_8$ heteroalkyl, an optionally substituted $C_1$-$C_8$ heterohaloalkyl, an optionally substituted aromatic ring, and $(CH_2)_mR^{14}$;
$R^8$ and $R^9$ are each independently selected from hydrogen, F, Cl, Br, $CO_2R^{10}$, $NO_2$, CN, $SO_2R^{10}$, $(CH_2)_mR^{14}$, $C_1$-$C_4$ alkyl, $C_1$-$C_4$ haloalkyl, $C_1$-$C_4$ heteroalkyl, and $C_1$-$C_4$ heterohaloalkyl;
$R^{10}$ is selected from hydrogen, an optionally substituted $C_1$-$C_4$ alkyl, $C_1$-$C_4$ haloalkyl, and $C_1$-$C_4$ heteroalkyl;
$R^{11}$ is selected from hydrogen, $SO_2R^{15}$, $C_1$-$C_4$ alkyl, $C_1$-$C_4$ haloalkyl, and $C_1$-$C_4$ heteroalkyl;
$R^{12}$ and $R^{13}$ are each independently selected from hydrogen, an optionally substituted $C_1$-$C_4$ alkyl, an optionally substituted $C_1$-$C_4$ haloalkyl, an optionally substituted $C_1$-$C_4$ heteroalkyl, and $(CH_2)_mR^{14}$; and
$R^{15}$ is selected from hydrogen, $C_1$-$C_3$ alkyl, $C_1$-$C_3$ haloalkyl, and aryl.

35. The compound of claim 1, wherein:
$R^1$ is selected from $CO_2R^{10}$;
$R^2$ and $R^3$ are each independently selected from null and $C_1$-$C_4$ aliphatic;
$R^4$ is selected from hydrogen, F, Cl, Br, and $C_1$-$C_4$ aliphatic;
$R^5$ is $OR^{10}$;
$R^6$ is selected from hydrogen, $OR^{12}$, F, Cl, Br, and $C_1$-$C_4$ alkyl;

$R^7$ is selected from hydrogen, a $C_1$-$C_8$ aliphatic, an optionally substituted ring, and $(CH_2)_m R^{14}$;

$R^8$ and $R^9$ are each independently selected from hydrogen, F, Cl, Br, $CO_2R^{10}$, $NO_2$, CN, $SO_2R^{10}$, $C_1$-$C_4$ aliphatic, $C_1$-$C_4$ haloaliphatic, $C_1$-$C_4$ heteroaliphatic, and $C_1$-$C_4$ heterohaloaliphatic;

$R^{10}$ is selected from hydrogen and methyl;

$R^{12}$ is hydrogen;

$R^{14}$ is an optionally substituted aryl;

m is 1; and n is 0.

36. The compound of claim 35, wherein:

$C_1$-$C_4$ aliphatic is $C_1$-$C_4$ alkyl;

$C_1$-$C_4$ haloaliphatic is $C_1$-$C_4$ haloalkyl;

$C_1$-$C_4$ heteroaliphatic is $C_1$-$C_4$ heteroalkyl; and $C_1$-$C_4$ heterohaloaliphatic is $C_1$-$C_4$ heterohaloalkyl.

37. The compound of claim 35, wherein $R^7$ is selected from hydrogen, a $C_1$-$C_8$ alkyl, an optionally substituted phenyl, an optionally substituted $C_2$-$C_5$ heterocycle, a $C_3$-$C_7$ alicylic ring, and $(CH2)_m R^{14}$, wherein $R^{14}$ is phenyl.

* * * * *